US008561870B2

(12) United States Patent
Baxter, III et al.

(10) Patent No.: US 8,561,870 B2
(45) Date of Patent: Oct. 22, 2013

(54) SURGICAL STAPLING INSTRUMENT

(75) Inventors: Chester O. Baxter, III, Loveland, OH (US); Adam R. Dunki-Jacobs, Cincinnati, OH (US); James J. Bedi, Cincinnati, OH (US); Venkataramanan Mandakolathur Vasudevan, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 287 days.

(21) Appl. No.: 13/036,647

(22) Filed: Feb. 28, 2011

(65) Prior Publication Data

US 2011/0226837 A1   Sep. 22, 2011

Related U.S. Application Data

(63) Continuation-in-part of application No. 12/855,351, filed on Aug. 12, 2010, now Pat. No. 8,453,908, which is a continuation-in-part of application No. 12/725,993, filed on Mar. 17, 2010, now Pat. No. 8,540,133, which is a continuation-in-part of application No. 12/234,149, filed on Sep. 19, 2008, now Pat. No. 7,905,381, application No. 13/036,647, which is a continuation-in-part of application No. 12/622,099, filed on Nov. 19, 2009, now Pat. No. 8,348,129, and a continuation-in-part of application No. 12/843,436, filed on Jul. 26, 2010, now Pat. No. 8,540,129, which is a continuation of application No. 12/030,424, filed on Feb. 13, 2008, now Pat. No. 7,766,209.

(60) Provisional application No. 61/250,377, filed on Oct. 9, 2009.

(51) Int. Cl.
*A61B 17/068* (2006.01)

(52) U.S. Cl.
USPC .......................................... 227/175.1; 227/19

(58) Field of Classification Search
USPC ................ 227/180.1, 175.1, 176.1, 179.1, 19
See application file for complete search history.

(56) References Cited

U.S. PATENT DOCUMENTS

| 3,490,675 A | 1/1970 | Green et al. |
| 3,499,591 A | 3/1970 | Green |

(Continued)

FOREIGN PATENT DOCUMENTS

| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Brian D Nash

(57) ABSTRACT

A surgical stapler can comprise an anvil comprising a staple pocket formed in a tissue contacting surface. The staple pocket can comprise a midline or centerline, a first forming cup, and a second forming cup. The first forming cup can comprise a first interior sidewall comprising a first vertical portion which is substantially perpendicular to the tissue contacting surface. The second forming cup can comprise a second interior sidewall comprising a second vertical portion which is substantially perpendicular to the tissue contacting surface. The first vertical portion and the second vertical portion can extend through the centerline, wherein the first interior sidewall and the second interior sidewall can comprise a trap for deforming a first staple leg of a staple to a first side of the centerline and for deforming a second staple leg of the staple to a second side of the centerline.

21 Claims, 94 Drawing Sheets

(56) References Cited

U.S. PATENT DOCUMENTS

| | | |
|---|---|---|
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| RE28,932 E | 8/1976 | Noiles et al. |
| 4,198,982 A | 4/1980 | Fortner et al. |
| 4,296,881 A | 10/1981 | Lee |
| 4,304,236 A | 12/1981 | Conta et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,527,724 A | 7/1985 | Chow et al. |
| 4,530,453 A | 7/1985 | Green |
| 4,566,620 A | 1/1986 | Green et al. |
| 4,573,468 A * | 3/1986 | Conta et al. ............... 227/179.1 |
| 4,573,622 A | 3/1986 | Green et al. |
| 4,580,712 A | 4/1986 | Green |
| 4,605,001 A | 8/1986 | Rothfuss et al. |
| 4,605,004 A | 8/1986 | Di Giovanni et al. |
| 4,608,981 A | 9/1986 | Rothfuss et al. |
| 4,610,383 A | 9/1986 | Rothfuss et al. |
| 4,629,107 A | 12/1986 | Fedotov et al. |
| 4,632,290 A | 12/1986 | Green et al. |
| 4,633,874 A | 1/1987 | Chow et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,805,823 A * | 2/1989 | Rothfuss ........................ 227/19 |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,892,244 A | 1/1990 | Fox et al. |
| 4,930,674 A | 6/1990 | Barak |
| 4,938,408 A | 7/1990 | Bedi et al. |
| 4,941,623 A | 7/1990 | Pruitt |
| 4,944,443 A | 7/1990 | Oddsen et al. |
| 4,978,049 A | 12/1990 | Green |
| 5,027,834 A | 7/1991 | Pruitt |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,614 A | 10/1992 | Green et al. |
| 5,158,567 A | 10/1992 | Green |
| 5,173,133 A | 12/1992 | Morin et al. |
| 5,211,649 A | 5/1993 | Kohler et al. |
| 5,219,111 A | 6/1993 | Bilotti et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,263,629 A | 11/1993 | Trumbull et al. |
| 5,282,806 A | 2/1994 | Haber et al. |
| 5,282,829 A | 2/1994 | Hermes |
| 5,285,945 A | 2/1994 | Brinkerhoff et al. |
| 5,304,204 A | 4/1994 | Bregen |
| 5,309,927 A | 5/1994 | Welch |
| 5,333,772 A | 8/1994 | Rothfuss et al. |
| 5,342,395 A | 8/1994 | Jarrett et al. |
| 5,342,396 A | 8/1994 | Cook |
| 5,350,400 A * | 9/1994 | Esposito et al. ............... 606/219 |
| 5,366,133 A | 11/1994 | Geiste |
| 5,366,479 A | 11/1994 | McGarry et al. |
| 5,395,034 A | 3/1995 | Allen et al. |
| 5,397,324 A | 3/1995 | Carroll et al. |
| 5,405,072 A | 4/1995 | Zlock et al. |
| 5,413,272 A | 5/1995 | Green et al. |
| 5,417,361 A | 5/1995 | Williamson, IV |
| 5,425,745 A | 6/1995 | Green et al. |
| 5,445,304 A | 8/1995 | Plyley et al. |
| 5,447,265 A | 9/1995 | Vidal et al. |
| 5,452,837 A | 9/1995 | Williamson, IV et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A * | 1/1996 | Blewett ...................... 227/175.1 |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,507,426 A | 4/1996 | Young et al. |
| 5,509,596 A | 4/1996 | Green et al. |
| 5,511,564 A | 4/1996 | Wilk |
| 5,520,700 A | 5/1996 | Beyar et al. |
| 5,529,235 A | 6/1996 | Boiarski et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,551,622 A | 9/1996 | Yoon |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,571,285 A | 11/1996 | Chow et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |

(56) References Cited

U.S. PATENT DOCUMENTS

| | | |
|---|---|---|
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,690,269 A | 11/1997 | Bolanos et al. |
| 5,692,668 A | 12/1997 | Schulze et al. |
| 5,695,524 A | 12/1997 | Kelley et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,743,456 A | 4/1998 | Jones et al. |
| 5,752,644 A | 5/1998 | Bolanos et al. |
| 5,752,965 A | 5/1998 | Francis et al. |
| 5,758,814 A | 6/1998 | Gallagher et al. |
| 5,762,255 A | 6/1998 | Chrisman et al. |
| 5,762,256 A | 6/1998 | Mastri et al. |
| 5,772,578 A | 6/1998 | Heimberger et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,787,897 A | 8/1998 | Kieturakis |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,855,583 A | 1/1999 | Wang et al. |
| 5,865,361 A | 2/1999 | Milliman et al. |
| 5,868,760 A * | 2/1999 | McGuckin, Jr. ............... 606/139 |
| 5,871,135 A | 2/1999 | Williamson, IV et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,937,951 A | 8/1999 | Izuchukwu et al. |
| 5,941,442 A | 8/1999 | Geiste et al. |
| 5,954,259 A | 9/1999 | Viola et al. |
| 5,988,479 A | 11/1999 | Palmer |
| 6,003,517 A | 12/1999 | Sheffield et al. |
| 6,010,054 A | 1/2000 | Johnson et al. |
| 6,032,849 A | 3/2000 | Mastri et al. |
| 6,045,560 A | 4/2000 | McKean et al. |
| 6,050,472 A | 4/2000 | Shibata |
| 6,053,390 A | 4/2000 | Green et al. |
| 6,079,606 A | 6/2000 | Milliman et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| 6,126,058 A | 10/2000 | Adams et al. |
| 6,131,789 A | 10/2000 | Schulze et al. |
| 6,155,473 A | 12/2000 | Tompkins et al. |
| 6,171,330 B1 | 1/2001 | Benchetrit |
| 6,193,129 B1 | 2/2001 | Bittner et al. |
| 6,202,914 B1 | 3/2001 | Geiste et al. |
| 6,234,178 B1 | 5/2001 | Goble et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,338,737 B1 | 1/2002 | Toledano |
| 6,387,113 B1 | 5/2002 | Hawkins et al. |
| RE37,814 E | 8/2002 | Allgeyer |
| 6,436,107 B1 | 8/2002 | Wang et al. |
| 6,439,446 B1 | 8/2002 | Perry et al. |
| 6,443,973 B1 | 9/2002 | Whitman |
| 6,450,391 B1 | 9/2002 | Kayan et al. |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,510,854 B2 | 1/2003 | Goble |
| 6,517,565 B1 | 2/2003 | Whitman et al. |
| 6,517,566 B1 | 2/2003 | Hovland et al. |
| 6,543,456 B1 | 4/2003 | Freeman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,297 B1 | 10/2003 | Huitema |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |

(56) References Cited

U.S. PATENT DOCUMENTS

| | | | |
|---|---|---|---|
| 6,716,233 B1 | 4/2004 | Whitman |
| 6,722,552 B2 | 4/2004 | Fenton, Jr. |
| 6,755,338 B2 | 6/2004 | Hahnen et al. |
| 6,769,590 B2 | 8/2004 | Vresh et al. |
| 6,769,594 B2 | 8/2004 | Orban, III |
| 6,773,438 B1 | 8/2004 | Knodel et al. |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,866,178 B2 | 3/2005 | Adams et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,939,358 B2 | 9/2005 | Palacios et al. |
| 6,945,444 B2 | 9/2005 | Gresham et al. |
| 6,953,138 B1 * | 10/2005 | Dworak et al. ............ 227/175.1 |
| 6,953,139 B2 | 10/2005 | Milliman et al. |
| 6,959,851 B2 | 11/2005 | Heinrich |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,331 B2 * | 6/2006 | Adams et al. ............ 128/898 |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,097,089 B2 | 8/2006 | Marczyk |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,131,445 B2 | 11/2006 | Amoah |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,147,139 B2 * | 12/2006 | Schwemberger et al. . 227/181.1 |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 * | 4/2007 | Wukusick et al. ......... 227/181.1 |
| 7,210,609 B2 | 5/2007 | Leiboff et |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 * | 2/2008 | Arad et al. ............ 227/176.1 |
| 7,334,717 B2 | 2/2008 | Rethy et al. |
| 7,334,718 B2 | 2/2008 | McAlister et al. |
| 7,343,920 B2 | 3/2008 | Toby et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 * | 7/2008 | Racenet et al. ............ 227/176.1 |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,563 B2 | 6/2009 | Mather et al. |
| 7,549,564 B2 | 6/2009 | Boudreaux |
| 7,552,854 B2 | 6/2009 | Wixey et al. |
| 7,556,185 B2 | 7/2009 | Viola |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |

(56) References Cited

U.S. PATENT DOCUMENTS

| | | |
|---|---|---|
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,641,095 B2 | 1/2010 | Viola |
| 7,644,848 B2 | 1/2010 | Swayze et al. |
| 7,651,017 B2 | 1/2010 | Ortiz et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,708,180 B2 | 5/2010 | Murray et al. |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,780,055 B2 | 8/2010 | Scirica et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,938,307 B2 * | 5/2011 | Bettuchi .................... 227/179.1 |
| 7,942,303 B2 | 5/2011 | Shah |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,967,180 B2 | 6/2011 | Scirica |
| 7,997,469 B2 | 8/2011 | Olson et al. |
| 8,002,795 B2 | 8/2011 | Beetel |
| 8,011,551 B2 | 9/2011 | Marczyk et al. |
| 8,011,555 B2 | 9/2011 | Tarinelli et al. |
| 8,016,177 B2 | 9/2011 | Bettuchi et al. |
| 8,025,199 B2 | 9/2011 | Whitman et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| D650,074 S | 12/2011 | Hunt et al. |
| 8,083,119 B2 | 12/2011 | Prommersberger |
| 8,091,756 B2 | 1/2012 | Viola |
| 8,097,017 B2 | 1/2012 | Viola |
| 8,100,310 B2 | 1/2012 | Zemlok |
| 8,123,103 B2 | 2/2012 | Milliman |
| 8,152,041 B2 | 4/2012 | Kostrzewski |
| 8,157,152 B2 | 4/2012 | Holsten et al. |
| 8,167,895 B2 | 5/2012 | D'Agostino et al. |
| 8,201,721 B2 | 6/2012 | Zemlok et al. |
| 8,210,414 B2 | 7/2012 | Bettuchi et al. |
| 8,225,799 B2 | 7/2012 | Bettuchi |
| 8,245,898 B2 | 8/2012 | Smith et al. |
| 8,245,901 B2 | 8/2012 | Stopek |
| 8,256,654 B2 | 9/2012 | Bettuchi et al. |
| 8,276,802 B2 | 10/2012 | Kostrzewski |
| 8,360,296 B2 | 1/2013 | Zingman |
| 8,393,514 B2 | 3/2013 | Shelton, IV et al. |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0093024 A1 | 5/2004 | Lousararian et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0145675 A1 | 7/2005 | Hartwick et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085032 A1 * | 4/2006 | Viola ........................ 606/219 |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |

(56) References Cited

U.S. PATENT DOCUMENTS

| | | |
|---|---|---|
| 2006/0124688 A1* | 6/2006 | Racenet et al. ............ 227/175.1 |
| 2006/0173470 A1 | 8/2006 | Oray et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0073341 A1 | 3/2007 | Smith et al. |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0270884 A1 | 11/2007 | Smith et al. |
| 2007/0278277 A1* | 12/2007 | Wixey et al. ............... 227/175.2 |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082125 A1 | 4/2008 | Murray et al. |
| 2008/0082126 A1* | 4/2008 | Murray et al. ................ 606/221 |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0185419 A1 | 8/2008 | Smith et al. |
| 2008/0197167 A1 | 8/2008 | Viola et al. |
| 2008/0237296 A1 | 10/2008 | Boudreaux et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0078736 A1 | 3/2009 | Van Lue |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0308907 A1 | 12/2009 | Nalagatla et al. |
| 2010/0001036 A1 | 1/2010 | Marczyk et al. |
| 2010/0012704 A1 | 1/2010 | Tarinelli Racenet et al. |
| 2010/0023024 A1 | 1/2010 | Zeiner et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072254 A1 | 3/2010 | Aranyi et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096431 A1 | 4/2010 | Smith et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147922 A1 | 6/2010 | Olson |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0237132 A1 | 9/2010 | Measamer et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |

(56) References Cited

U.S. PATENT DOCUMENTS

| | | |
|---|---|---|
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0011916 A1 | 1/2011 | Levine |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0036890 A1 | 2/2011 | Ma |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0087279 A1 | 4/2011 | Shah et al. |
| 2011/0095068 A1* | 4/2011 | Patel .......................... 227/180.1 |
| 2011/0101065 A1 | 5/2011 | Milliman |
| 2011/0108604 A1* | 5/2011 | Adams et al. ............. 227/179.1 |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174861 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0233258 A1 | 9/2011 | Boudreaux |
| 2011/0253766 A1 | 10/2011 | Baxter, III et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138658 A1 | 6/2012 | Ullrich et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |

(56) References Cited

U.S. PATENT DOCUMENTS

| | | |
|---|---|---|
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Vasudevan et al. |
| 2012/0241497 A1 | 9/2012 | Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2012/0325892 A1 | 12/2012 | Kostrzewski |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0037596 A1 | 2/2013 | Bear et al. |
| 2013/0041371 A1 | 2/2013 | Yates et al. |
| 2013/0048697 A1 | 2/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0105551 A1 | 5/2013 | Zingman |

FOREIGN PATENT DOCUMENTS

| | | |
|---|---|---|
| CA | 2514274 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EM | 0392547 B1 | 12/1995 |
| EM | 0873089 B1 | 10/2003 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0277959 B1 | 10/1993 |
| EP | 0233940 B1 | 11/1993 |
| EP | 0261230 B1 | 11/1993 |
| EP | 0639349 42 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0685204 A1 | 12/1995 |
| EP | 0364216 91 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 81 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |

(56) References Cited

FOREIGN PATENT DOCUMENTS

| | | |
|---|---|---|
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 B1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B11 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1897502 A1 | 3/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 2005894 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 A1 | 6/2009 |
| EP | 1550413 B1 | 6/2009 |
| EP | 2090237 A1 | 8/2009 |
| EP | 2090241 A1 | 8/2009 |
| EP | 2090244 A2 | 8/2009 |
| EP | 2090245 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |

(56) References Cited

FOREIGN PATENT DOCUMENTS

| | | | |
|---|---|---|---|
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 2286738 A2 | 2/2011 |
| EP | 1690502 B1 | 3/2011 |
| EP | 1769755 B1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 1785102 B1 | 1/2012 |
| EP | 2090253 B1 | 3/2012 |
| EP | 2005895 B1 | 8/2012 |
| EP | 2090248 B1 | 8/2012 |
| ER | 1344498 B1 | 11/2005 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | S 58500053 A | 1/1983 |
| JP | 61-98249 A | 5/1986 |
| JP | S 61502036 A | 9/1986 |
| JP | 63-203149 | 8/1988 |
| JP | 3-12126 A | 1/1991 |
| JP | 5-212039 A | 8/1993 |
| JP | 6007357 A | 1/1994 |
| JP | H 6-30945 A | 2/1994 |
| JP | H 6-121798 A | 5/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | 2000-14632 | 1/2000 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-521301 A | 7/2003 |
| JP | 2004-329624 A | 11/2004 |
| JP | 2004-344663 | 12/2004 |
| JP | 2005-028147 A | 2/2005 |
| JP | 2005-028149 A | 2/2005 |
| JP | 2005-505309 A | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-218297 A | 8/2006 |
| JP | 2006-281405 A | 10/2006 |
| JP | 2007-117725 A | 5/2007 |
| JP | 2008-283459 A | 11/2008 |
| RU | 2008830 C1 | 3/1994 |
| RU | 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 2004/078050 A2 | 0/2004 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18693 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/93743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | Wo 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |

(56) References Cited

FOREIGN PATENT DOCUMENTS

| | | |
|---|---|---|
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12467 A1 | 3/1999 |
| WO | WO 99/12468 A1 | 3/1999 |
| WO | WO 99/12483 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/008302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A1 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044378 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |

(56) References Cited

FOREIGN PATENT DOCUMENTS

| WO | WO 2008/070763 A1 | 6/2008 |
|---|---|---|
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/137761 A2 | 11/2009 |
| WO | WO 2010/030434 A1 | 3/2010 |
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/dol/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aspetic Battery Transfer Kit, Sodem System, 2000, 3 pages.

"Biomedical Coating," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

U.S. Appl. No. 13/040,604, filed Mar. 4, 2011.

Partial European Search Report, U.S. Appl. No. 09250355.6, dated Jun. 2, 2009 (6 pages).

International Search Report for PCT/US2011/047353, dated Sep. 14, 2011 (5 pages).

Written Opinion for PCT/US2011/047353, dated Sep. 14, 2011 (6 pages).

European Search Report, Application No. 09250355.6, dated Aug. 18, 2009 (11 pages).

International Search Report for PCT/US2012/026531, dated Oct. 25, 2012 (6 pages).

Written Opinion for PCT/US2012/026531, dated Oct. 25, 2012 (9 pages).

International Preliminary Report on Patentability for PCT/US2011/047353, dated Feb. 12, 2013 (6 pages).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

U.S. Appl. No. 12/846,986, filed Jul. 30, 2010.

\* cited by examiner

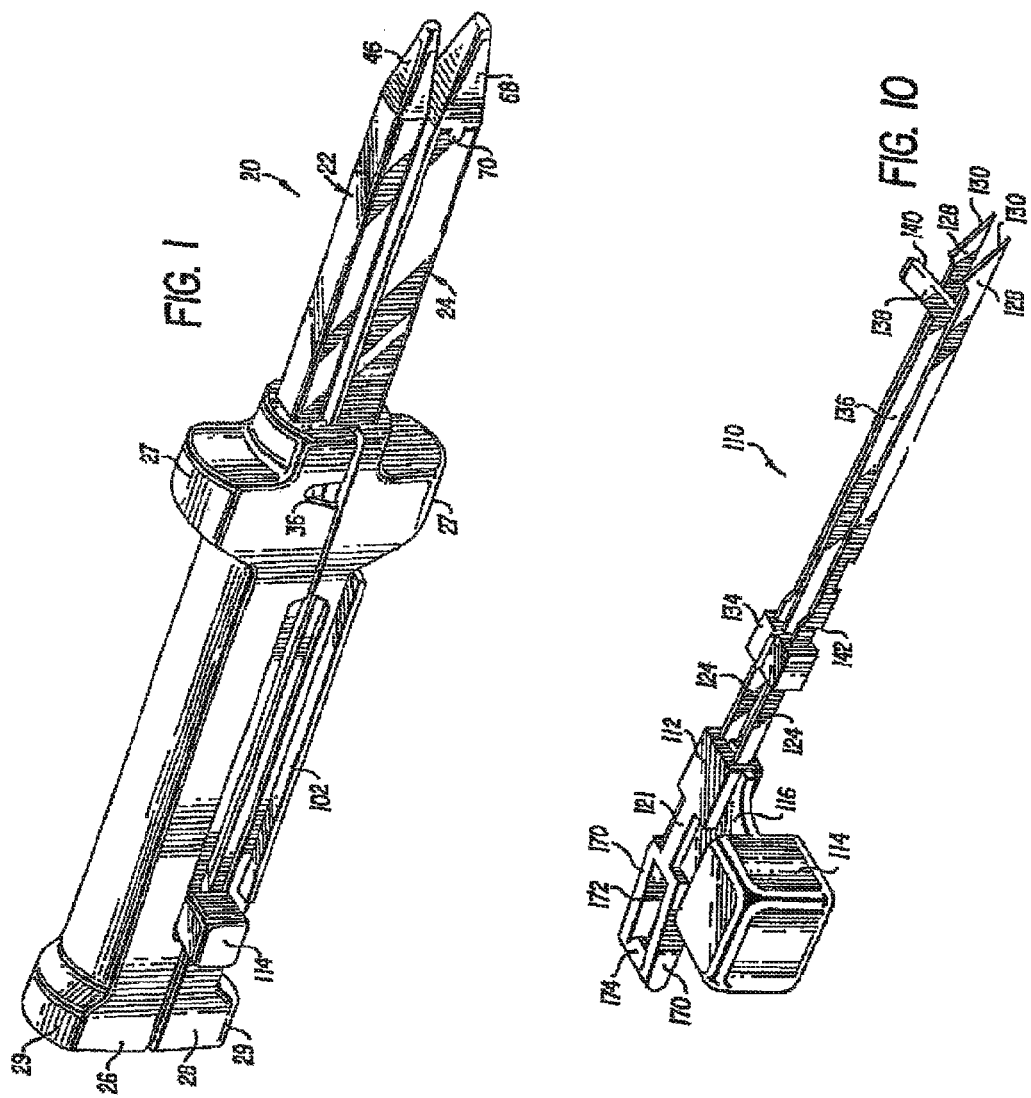

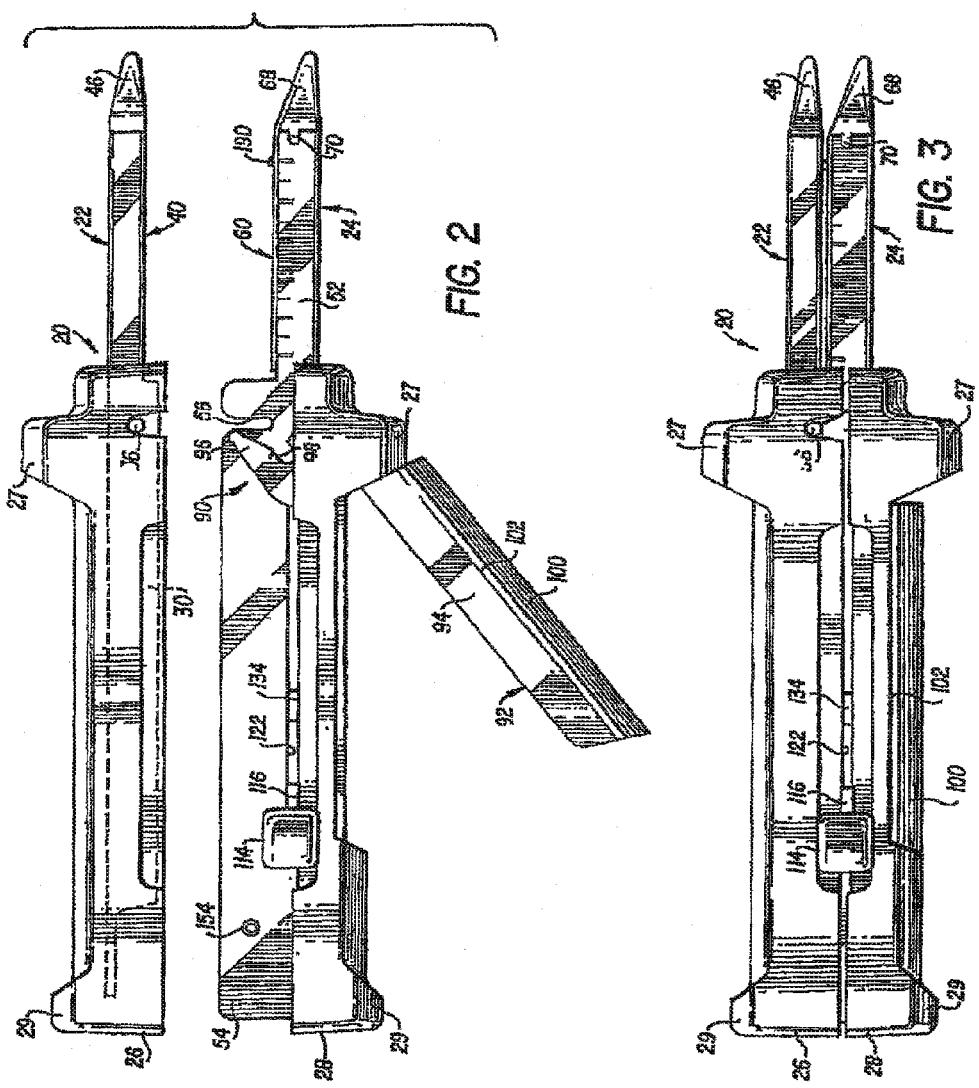

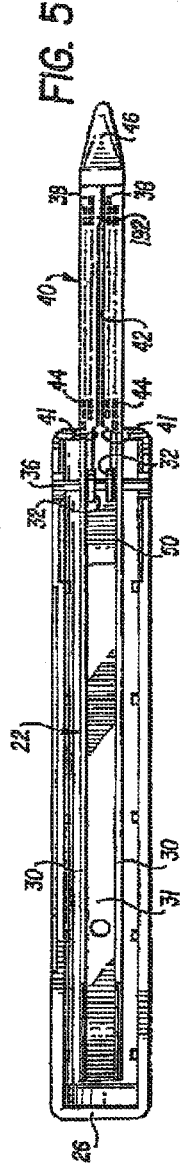
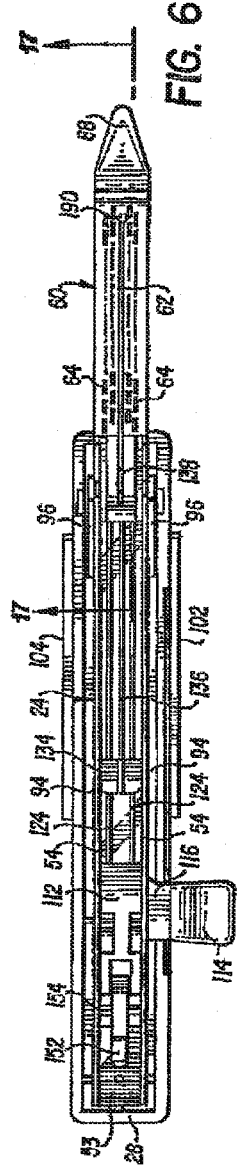
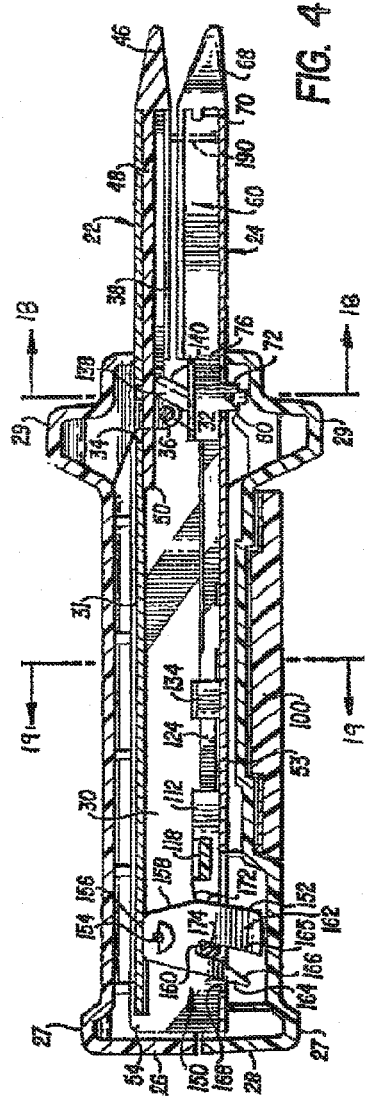

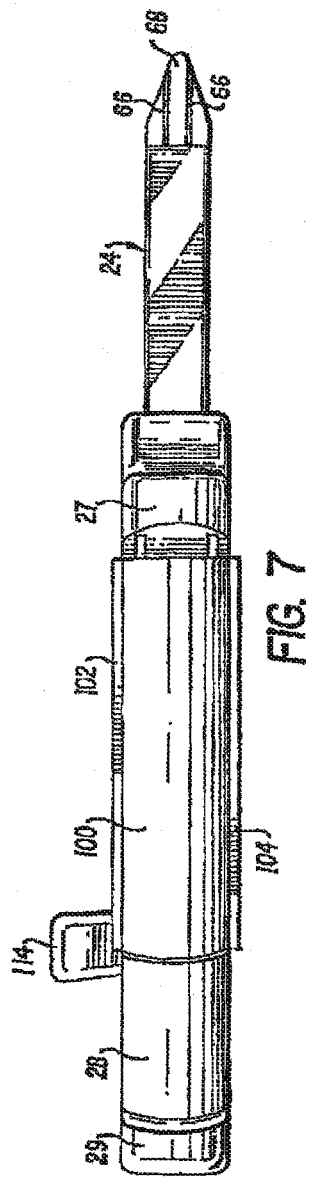
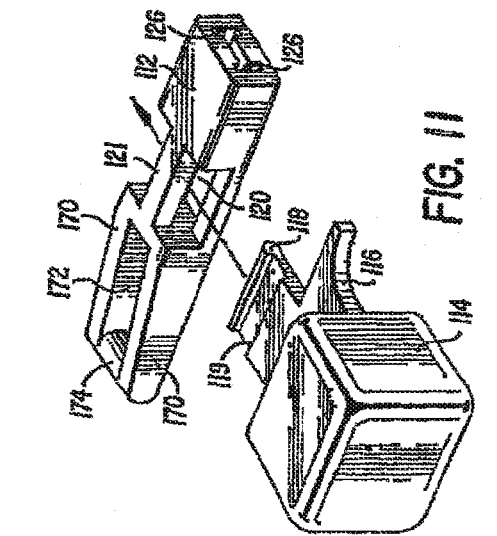
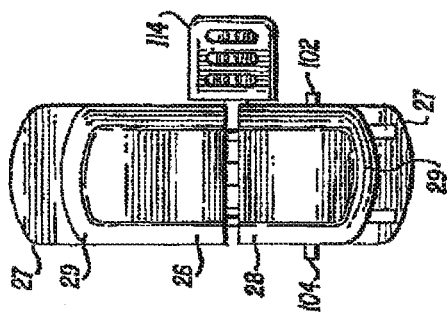
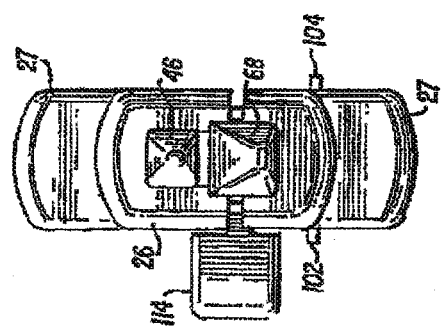

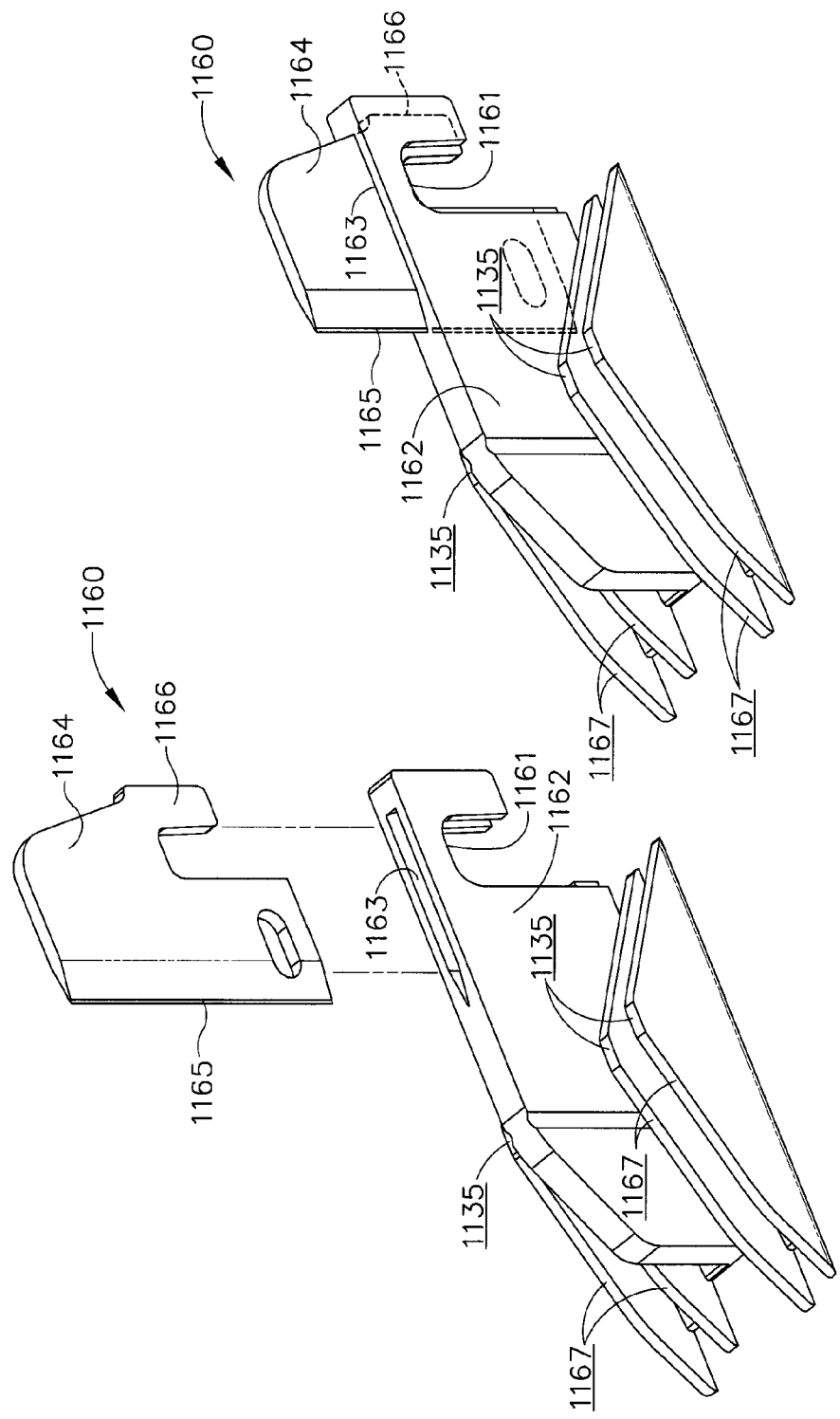

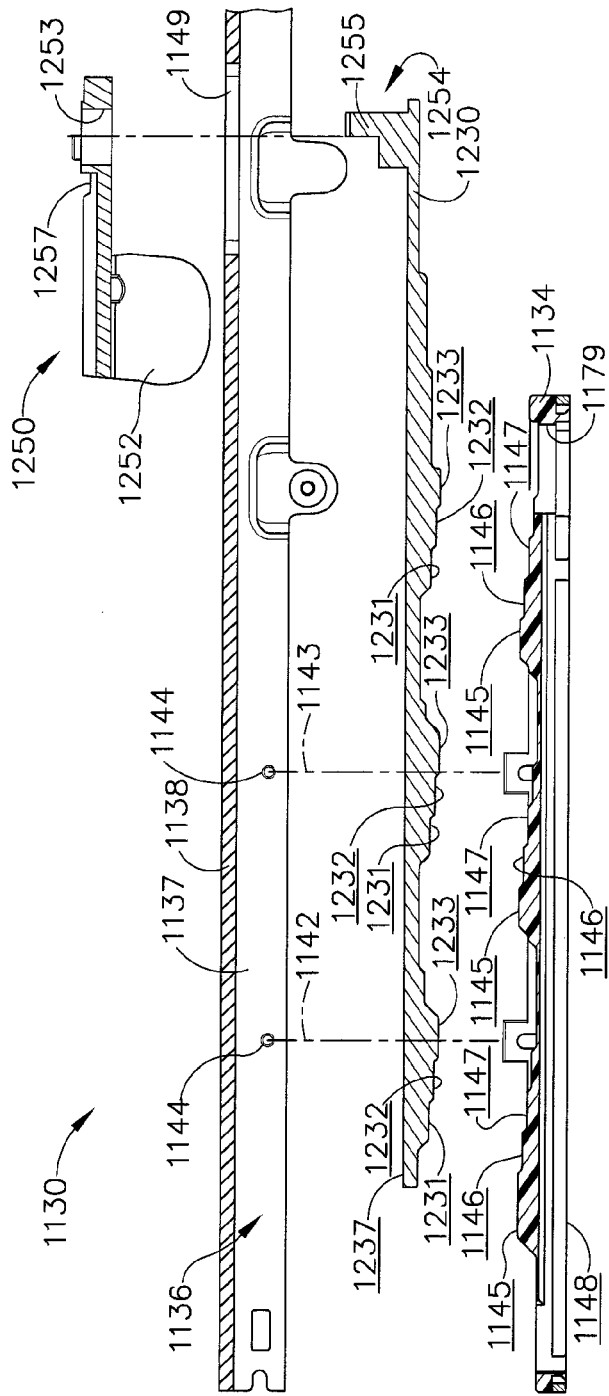
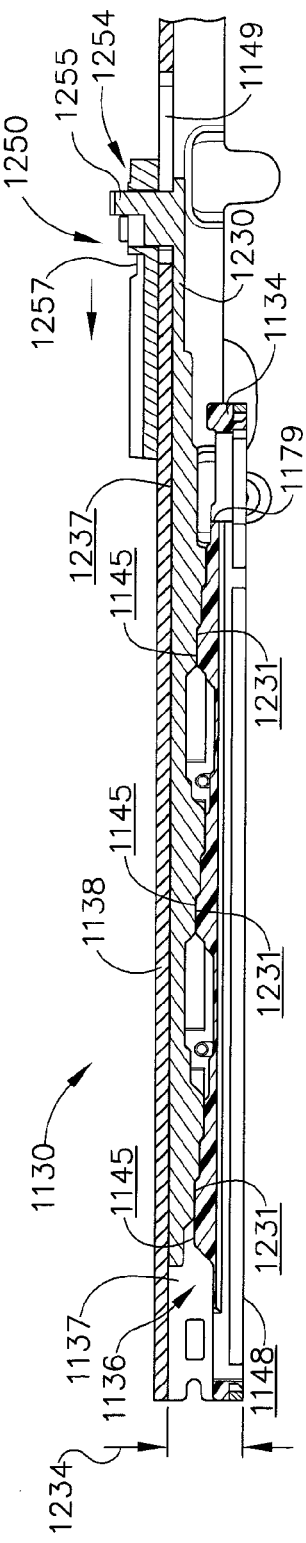
FIG. 53
FIG. 54

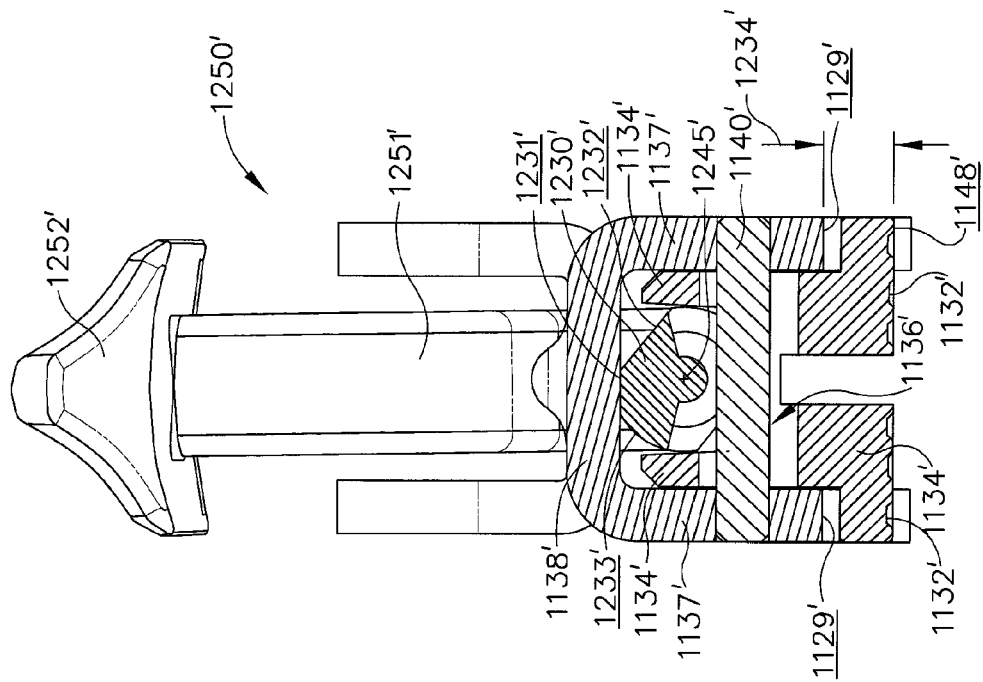
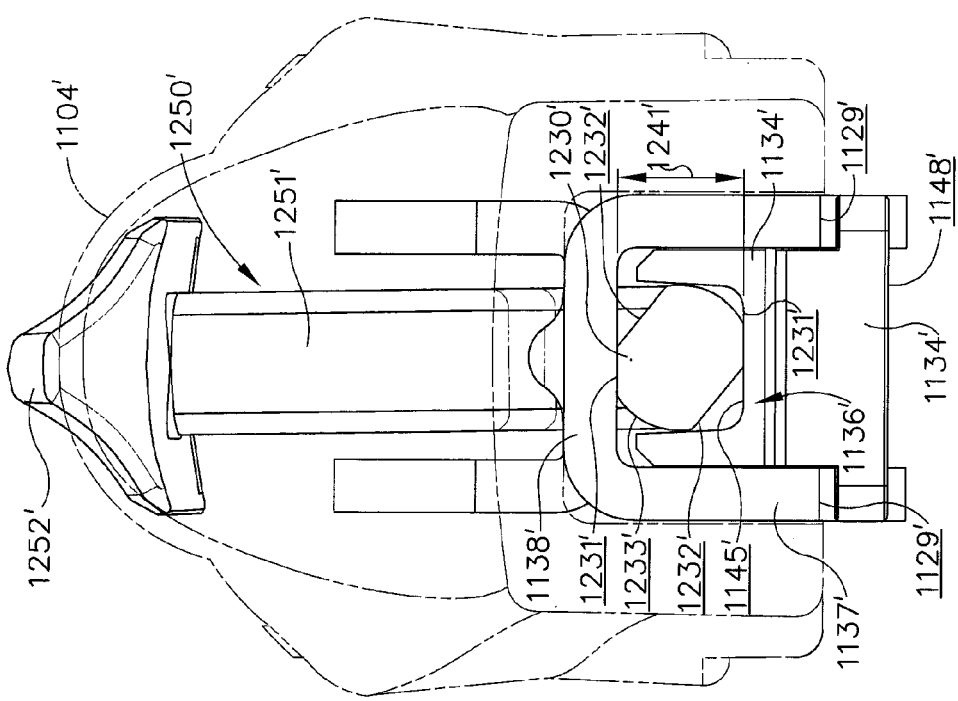

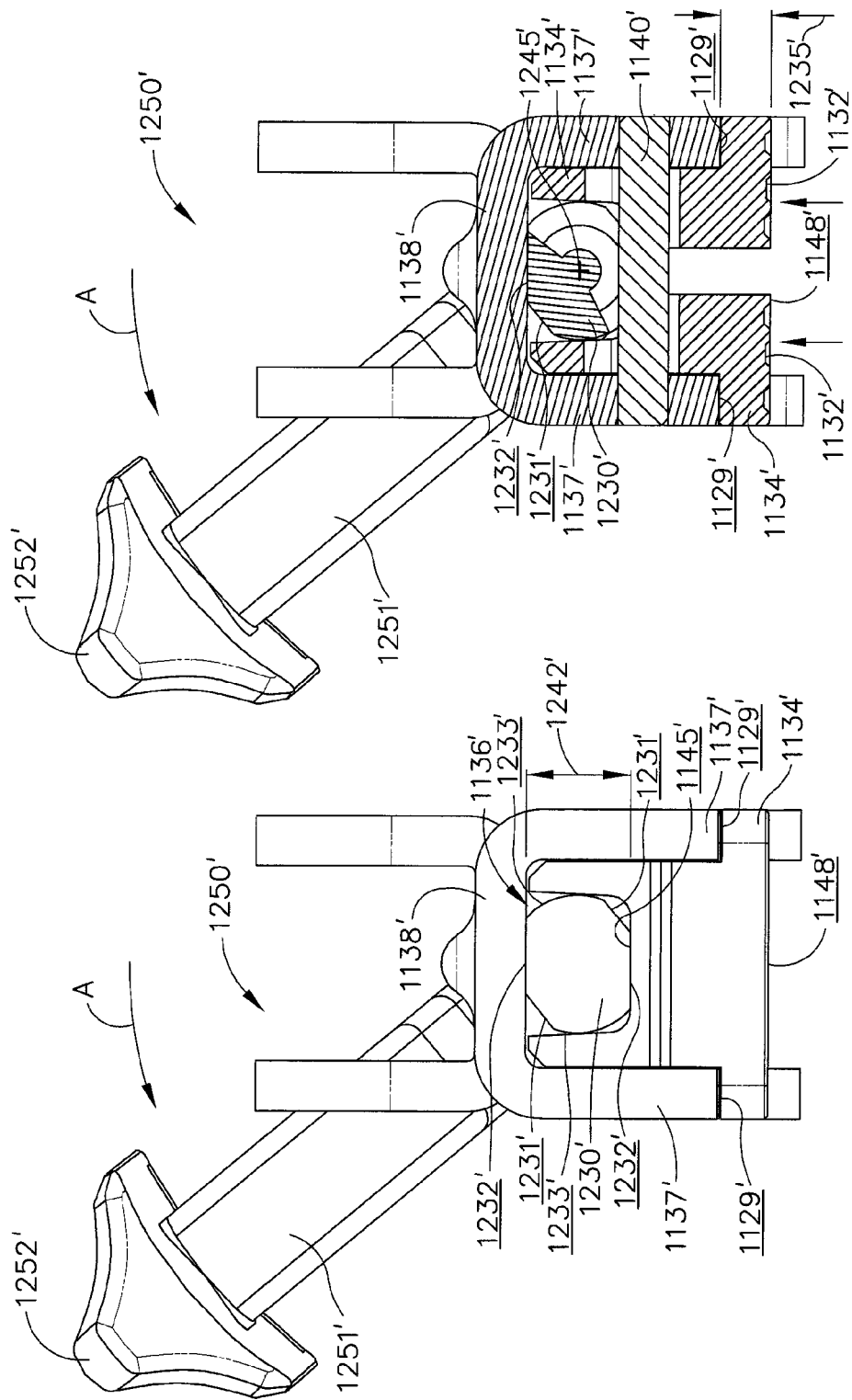

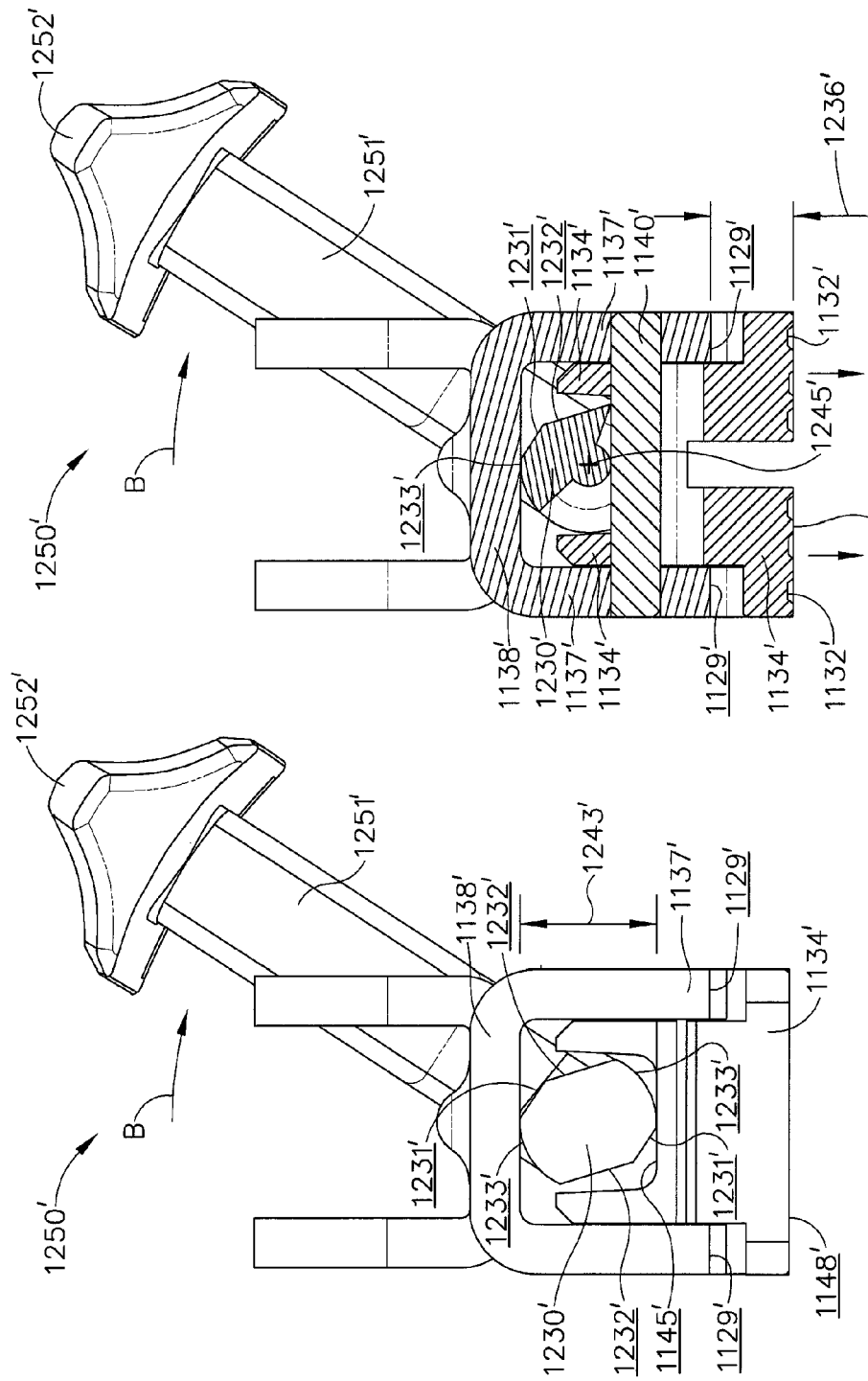

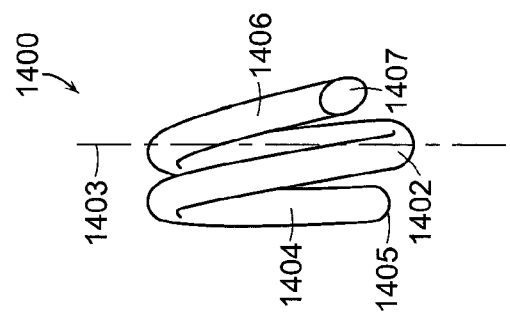
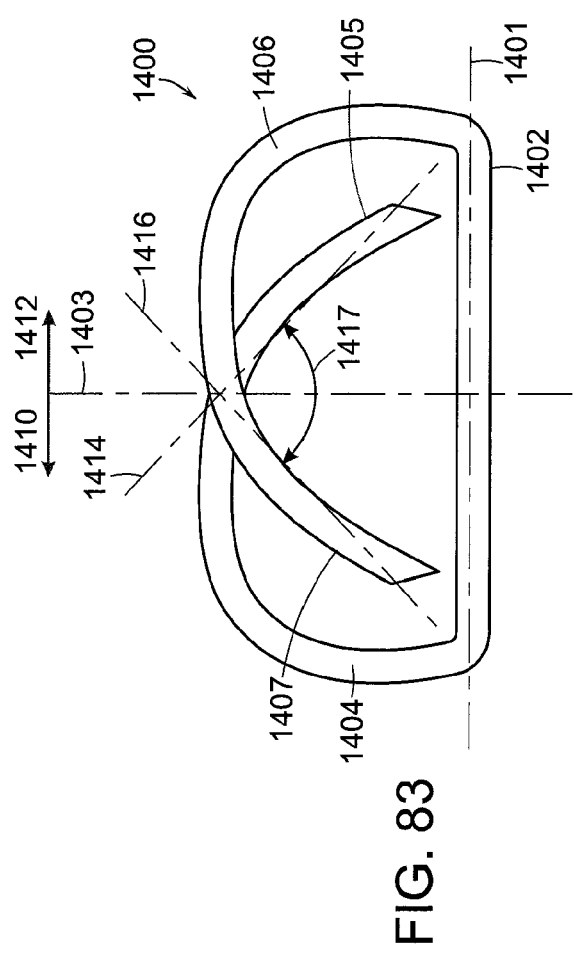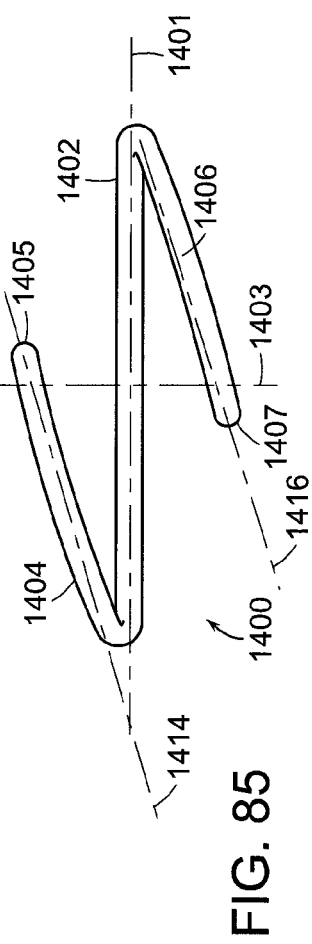

SURGICAL STAPLING INSTRUMENT

CROSS-REFERENCE TO RELATED APPLICATIONS

This non-provisional patent application is a continuation-in-part application under 35 U.S.C. §120 of U.S. patent application Ser. No. 12/855,351, entitled SURGICAL STAPLING INSTRUMENT WITH IMPROVED FIRING TRIGGER ARRANGEMENT, filed on Aug. 12, 2010, now U.S. Pat. No. 8,453,908, which is a continuation-in-part application under 35 U.S.C. §120 of U.S. patent application Ser. No. 12/725,993, entitled STAPLE CARTRIDGE, filed on Mar. 17, 2010, now U.S. Pat. No. 8,540,133, which is a continuation-in-part application under 35 U.S.C. §120 of U.S. patent application Ser. No. 12/234,149, entitled SURGICAL STAPLING INSTRUMENT WITH CUTTING MEMBER ARRANGEMENT, filed on Sep. 19, 2008, now U.S. Pat. No. 7,905,381, the entire disclosures of which are hereby incorporated by reference herein. This non-provisional patent application is a continuation-in-part application under 35 U.S.C. §120 of U.S. patent application Ser. No. 12/622,099, entitled SURGICAL STAPLER HAVING A CLOSURE MECHANISM, filed on Nov. 19, 2009, now U.S. Pat. No. 8,348,129, which claims the benefit under 35 U.S.C. §119(e) of U.S. Provisional Patent Application No. 61/250,377, entitled SURGICAL STAPLER, filed on Oct. 9, 2009, the entire disclosures of which are hereby incorporated by reference herein. This non-provisional patent application is a continuation-in-part application under 35 U.S.C. §120 of U.S. patent application Ser. No. 12/843,436, entitled SURGICAL STAPLING INSTRUMENT WITH IMPROVED FIRING TRIGGER ARRANGEMENT, filed on Jul. 26, 2010, now U.S. Pat. No. 8,540,129, which is a continuation application under 35 U.S.C. §120 of U.S. patent application Ser. No. 12/030,424, now U.S. Pat. No. 7,766,209, entitled SURGICAL STAPLING INSTRUMENT WITH IMPROVED FIRING TRIGGER ARRANGEMENT, filed on Feb. 13, 2008, the entire disclosures of which are hereby incorporated by reference herein.

BACKGROUND i. Technical Field

The present invention relates to stapling instruments and, in various embodiments, to a surgical stapling instrument for producing one or more rows of staples.

ii. Background of the Related Art

In recent years, there has been an increasing tendency for surgeons to use stapling instruments to suture body tissues such as a lung, an esophagus, a stomach, a duodenum and/or other organs in the intestinal tract. The use of an appropriate stapling instrument in many instances may perform a better job in less time and simplify previously difficult surgical procedures such as gastrointestinal anastomoses. Previous linear two and four row cutting staplers comprised cartridge-less instruments into which staples were individually hand-loaded. Other previous devices have included a presterilized disposable staple loading unit and a cutting member which could be utilized for dividing the tissue and forming the rows of staples simultaneously. An example of such a surgical stapler is disclosed in U.S. Pat. No. 3,499,591, entitled INSTRUMENT FOR PLACING LATERAL GASTROINTESTINAL ANASTOMOSES, which issued on Mar. 10, 1970, the entire disclosure of which is hereby incorporated by reference herein.

A stapling instrument can include a pair of cooperating elongate jaw members, wherein each jaw member can be adapted to be inserted into an internal, tubular body organ to be anastomosed. In various embodiments, one of the jaw members can support a staple cartridge with at least two laterally spaced rows of staples, and the other jaw member can support an anvil with staple-forming pockets aligned with the rows of staples in the staple cartridge. Generally, the stapling instrument can further include a pusher bar and knife blade which are slidable relative to the jaw members to sequentially eject staples from the staple cartridge via camming surfaces on the pusher bar. In at least one embodiment, the camming surfaces can be configured to activate a plurality of staple drivers carried by the cartridge and associated with the individual staples to push the staples against the anvil and form laterally spaced rows of deformed staples in the tissue gripped between the jaw members. In typical stapling instruments, however, the anvil is unmovable relative to the staple cartridge once the jaw members have been assembled together and the formed height of the staples cannot be adjusted. In at least one embodiment, the knife blade can trail the pusher bar and cut the tissue along a line between the staple rows. Examples of such stapling instruments are disclosed in U.S. Pat. No. 4,429,695, entitled SURGICAL INSTRUMENTS, which issued on Feb. 7, 1984, the entire disclosure of which is hereby incorporated by reference herein.

SUMMARY

In at least one form, a surgical stapler can comprise a curved anvil assembly comprising a tissue contacting surface and a plurality of staple pockets formed in the tissue contacting surface, wherein the staple pockets are positioned along a curve. Each staple pocket can comprise a staple pocket centerline, wherein a staple pocket centerline of a first staple pocket is neither parallel to nor collinear with a staple pocket centerline of a second staple pocket. Each staple pocket can further comprise a first forming cup including a first inside portion, a first outside portion, and a first interior sidewall extending between the first outside portion and the first inside portion, wherein the first interior sidewall comprises a first vertical portion which is substantially perpendicular to the tissue contacting surface. Each staple pocket can further comprise a second forming cup including a second inside portion, a second outside portion, wherein the first inside portion is positioned in close relation to the second inside portion, wherein the first inside portion and the second inside portion are positioned offset with respect to the staple pocket centerline, wherein the first outside portion and the second outside portion are positioned on opposite sides of the first inside portion and the second inside portion, and wherein the first outside portion and the second outside portion are oriented in a direction which is transverse to the staple pocket centerline, and a second interior sidewall extending between the second outside portion and the second inside portion, wherein the second interior sidewall comprises a second vertical portion which is substantially perpendicular to the tissue contacting surface.

In at least one form, a surgical stapler can comprise a curved anvil assembly comprising a tissue contacting surface and a plurality of staple pockets formed in the tissue contacting surface, wherein the staple pockets are positioned along a curved path, wherein each staple pocket comprises a staple pocket midline, and wherein a staple pocket midline of a first staple pocket is neither parallel to nor collinear with a staple pocket midline of a second staple pocket. Each staple pocket can further comprise a first forming cup including a first inside portion, a first outside portion, and a first interior sidewall extending between the first outside portion and the first inside portion, wherein the first interior sidewall comprises a first vertical portion which is substantially perpendicular to the tissue contacting surface. Each staple pocket can further comprise a second forming cup including a second inside portion, a second outside portion, wherein the first inside portion is positioned in close relation to the second inside portion, wherein the first inside portion and the second inside portion are positioned offset with respect to the staple pocket midline, and wherein the first outside portion and the second outside portion are positioned on opposite sides of the first inside portion and the second inside portion, and a second interior sidewall extending between the second outside portion and the second inside portion, wherein the second interior sidewall comprises a second vertical portion which is substantially perpendicular to the tissue contacting surface, wherein the first vertical portion and the second vertical portion extend through the staple pocket midline, and wherein the first interior surface and the second interior surface comprise a trap for deforming a first staple leg of a staple to a first side of the staple pocket midline and for deforming a second staple leg of the staple to a second side of the staple pocket midline.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is a perspective view of a linear anastomotic stapling instrument;

FIG. 2 is a side elevational view showing the anastomotic stapling instrument of FIG. 1 partially disassembled with its upper anvil carrying jaw member detached from its lower staple cartridge carrying jaw member;

FIG. 3 is a side elevational view showing the anastomotic stapling instrument of FIG. 1 in its assembled configuration;

FIG. 4 is a cross-sectional view of the anastomotic stapling instrument of FIG. 1 showing a cam mechanism for urging the rear portions of the upper and lower jaw members apart;

FIG. 5 is a bottom view of the anvil carrying jaw member of the anastomotic stapling instrument of FIG. 1;

FIG. 6 is a top view of the staple cartridge carrying jaw member of the anastomotic stapling instrument of FIG. 1;

FIG. 7 is a bottom view of the anastomotic stapling instrument of FIG. 1;

FIG. 8 is a front end view of the anastomotic stapling instrument of FIG. 1;

FIG. 9 is a rear end view of the anastomotic stapling instrument of FIG. 1;

FIG. 10 is a perspective view of a pusher bar and knife blade assembly of the anastomotic stapling instrument of FIG. 1;

FIG. 11 is a perspective view of a pusher block and an actuator knob which are components of the pusher bar and knife blade assembly of FIG. 10;

FIG. 44 is an exploded view of a staple sled and cutting member assembly of the staple cartridge assembly of FIG. 41;

FIG. 45 is a perspective view of the staple sled and cutting member assembly of FIG. 44;

FIG. 53 is an exploded cross-sectional elevational view of the anvil assembly of FIG. 50;

FIG. 54 is a cross-sectional assembly view of the anvil assembly of FIG. 50 illustrating an anvil adjustment member in a first position;

FIG. 63 is an end view of the surgical stapling instrument of FIG. 57 with some components removed and others shown in dashed lines illustrating the rotatable anvil adjustment member in the first orientation of FIG. 61;

FIG. 64 is a cross-sectional end view of the surgical stapling instrument of FIG. 57 taken along line 64-64 in FIG. 57;

FIG. 65 is an end view of the surgical stapling instrument of FIG. 57 illustrating the rotatable anvil adjustment member of FIG. 61 rotated in a first direction into a second orientation;

FIG. 66 is a cross-sectional end view of the surgical stapling instrument of FIG. 57 illustrating the anvil adjustment member in the second orientation of FIG. 65;

FIG. 67 is an end view of the surgical stapling instrument of FIG. 57 illustrating the rotatable anvil adjustment member of FIG. 61 rotated in a second direction into a third orientation;

FIG. 68 is a cross-sectional end view of the surgical stapling instrument of FIG. 57 illustrating the anvil adjustment member in the third orientation of FIG. 67;

FIG. 83 is an elevational view of the surgical staple of FIG. 82 in a deformed shape in accordance with at least one embodiment of the present invention;

FIG. 84 is a side view of the surgical staple of FIG. 82 in the deformed shape of FIG. 83;

FIG. 85 is a plan view of the surgical staple of FIG. 82 in the deformed shape of FIG. 83;

FIG. 118 is an elevational view of another deformed staple in accordance with at least one embodiment of the present invention;

FIG. 119 is a partial face view of an anvil in accordance with at least one embodiment of the present invention; and FIG. 120 is a partial perspective view of a surgical stapling instrument comprising a curved anvil and a curve piece of compressible material positioned thereon.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Figure 12:
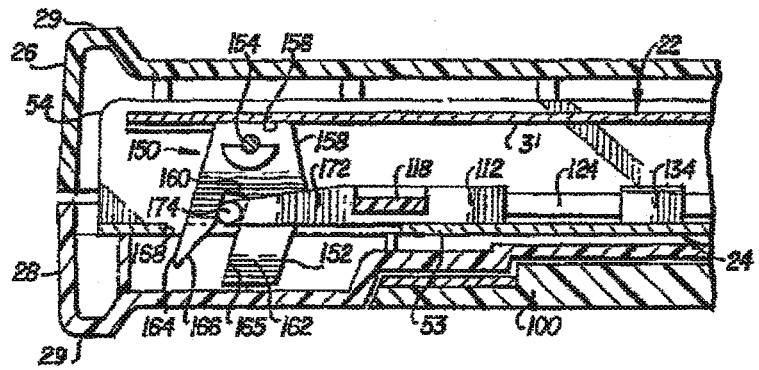
FIG. 12 is a partial cross-sectional view of the rear portion of the anastomotic stapling instrument of FIG. 1 illustrating the cam mechanism in its inoperative position.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The entire disclosures of the following United States patent applications are hereby incorporated by reference herein:

U.S. patent application Ser. No. 12/725,993, entitled STAPLE CARTRIDGE, filed on Mar. 17, 2010;

U.S. patent application Ser. No. 12/234,149, entitled SURGICAL STAPLING INSTRUMENT WITH CUTTING MEMBER ARRANGEMENT, filed on Sep. 19, 2008;

U.S. patent application Ser. No. 12/234,143, entitled SURGICAL STAPLER HAVING AN INTERMEDIATE CLOSING POSITION, filed on Sep. 19, 2008;

U.S. patent application Ser. No. 12/234,133, entitled SURGICAL STAPLER WITH APPARATUS FOR ADJUSTING STAPLE HEIGHT, filed on Sep. 19, 2008;

U.S. patent application Ser. No. 12/234,113, entitled LOCKOUT ARRANGEMENT FOR A SURGICAL STAPLER, filed on Sep. 19, 2008;

U.S. patent application Ser. No. 12/622,099, entitled SURGICAL STAPLER HAVING A CLOSURE MECHANISM, filed on Nov. 19, 2009;

U.S. patent application Ser. No. 12/622,130, entitled METHOD FOR FORMING A STAPLE, filed on Nov. 19, 2009;

U.S. patent application Ser. No. 12/622,113, entitled SURGICAL STAPLER COMPRISING A STAPLE POCKET, filed on Nov. 19, 2009;

U.S. patent application Ser. No. 12/843,436, entitled SURGICAL STAPLING INSTRUMENT WITH IMPROVED FIRING TRIGGER ARRANGEMENT, filed on Jul. 26, 2010;

U.S. patent application Ser. No. 12/030,424, entitled SURGICAL STAPLING INSTRUMENT WITH IMPROVED FIRING TRIGGER ARRANGEMENT, filed on Feb. 13, 2008; and U.S. Provisional Patent Application No. 61/250,377, entitled SURGICAL STAPLER, filed on Oct. 9, 2009.

Referring to FIGS. 1 and 2, a linear anastomotic stapling instrument, generally 20, can comprise an upper elongated anvil carrying jaw member 22 and a lower elongated staple cartridge carrying jaw member 24. Upper anvil carrying jaw member 22 can be supported by a handle 26 with a front portion of the jaw member extending forwardly therefrom. Lower staple cartridge carrying jaw member 24 can be supported by a handle 28 with a front portion of the jaw member extending forwardly therefrom. As shown in FIG. 3, upper handle 26 and lower handle 28 can be suitably shaped to form a hand grip to facilitate the handling and operation of the stapling instrument by a surgeon. An enlarged front protrusion 27 and a small rear protrusion 29 can be provided on each handle for this purpose. In various embodiments, handles 26 and 28 can be made of plastic of other lightweight materials, for example, while jaw members 22 and 24 can be made of stainless steel or other similar materials, for example.

As shown in FIG. 5, upper jaw member 22 can comprise a one-piece elongated channel-shaped frame including a pair of opposed, elongated side walls 30 connected by a top wall 31. Upper handle 26 can include a pair of depending ears 32 located inside the upper handle adjacent to its front end. Upper jaw member 22 can include a slot 34 (FIG. 4) formed at an intermediate position along its top wall 31 through which depending ears 32 can project downwardly. A latch pin 36 can extend through circular holes formed in side walls 30 of upper jaw member 22 and through circular holes formed in depending ears 32 to pivotally connect the upper jaw member to upper handle 26.

Referring to FIG. 5, the front portion of upper jaw member 22 can be provided with a pair of elongated inwardly extending flanges 38 which can define an anvil 40 of the stapling instrument. Flanges 38 can be separated by a central longitudinal slot 42 which extends along the entire length of anvil 40. At the proximal end of central slot 42, the flanges 38 can be provided with inwardly sloped guide surfaces 41. Each flange 38 can also provided with two longitudinal rows of uniformly spaced staple-forming pockets 44. Referring to FIGS. 4 and 5, a tapered anvil tip 46 can be mounted at the front of anvil carrying jaw member 22 to facilitate the insertion of the jaw member into hollow, tubular body organs, for example. Anvil tip 46 can include an elongated body 48 (FIG. 4) which can be inserted through the longitudinal passageway above anvil 40 defined by side walls 30 and flanges 38 of the upper jaw member. This elongated body 48 can extend between depending ears 32 above latch pin 36 and can include an enlarged rear portion 50 located behind ears 32 to hold anvil tip 46 in place on upper jaw member 22.

Referring to FIGS. 2 and 6, lower cartridge carrying jaw member 24 can comprise a one-piece elongated channel-shaped frame including a pair of opposed, elongated side walls 52 connected by a bottom wall 53. Along the rearward portion of lower jaw member 24, a pair of spaced, elongated upstanding side flanges 54 (FIG. 2) can extend upward from its opposed side walls 52. As shown in FIGS. 5 and 6, the width of lower jaw member 24 between its side flanges 54 can be greater than the width of upper jaw member 22 between its side walls 30 to permit the rear portion of the upper jaw member to be received between side flanges 54 of the lower jaw member when the stapling instrument is assembled for operation. As shown in FIG. 2, each side flange 54 of lower jaw member 24 can include a vertical notch 56 located in alignment with latch pin 36 on upper jaw member 22. When upper jaw member 22 and lower jaw member 24 are assembled, the opposite ends of latch pin 36 can be received in notches 56.

Figure 15:
FIG. 15 is a top view of the staple cartridge of the anastomotic stapling instrument of FIG. 1.
Figure 16:
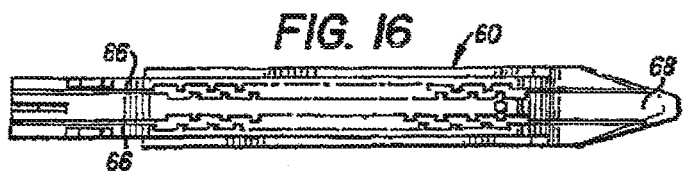
FIG. 16 is a bottom view of the staple cartridge of the anastomotic stapling instrument of FIG. 1.

As shown in FIGS. 2 and 6, lower jaw member 24 can support a staple cartridge 60 which is adapted to receive a plurality of surgical staples 61 (FIG. 17) arranged in at least two laterally spaced longitudinal rows. Staple cartridge 60 can be mounted at the front portion of lower jaw member 24 between its side walls 52. Staple cartridge 60 can be divided longitudinally by a central, elongated slot 62 (FIG. 6) which extends from the proximal end of the cartridge toward its distal end. In various embodiments, a plurality of staple openings 64 formed in staple cartridge 60 can be arranged in two pairs of laterally spaced rows, with each pair of rows disposed on opposite sides of central longitudinal slot 62. A plurality of surgical staples 61 (FIG. 17) can be mounted within openings 64 of cartridge 60. As shown in FIG. 6, the staple openings 64 in adjacent rows can be staggered to provide more effective stapling of the tissue when the instrument is operated. Referring to FIGS. 15 and 16, staple cartridge 60 can include a pair of longitudinal slots 66 located on opposite sides of elongated central slot 62 and disposed between the staggered rows of openings 64 on each side of the central slot. Each longitudinal slot 66 can extend from the proximal end of cartridge 60 towards its distal end.

Figure 17:
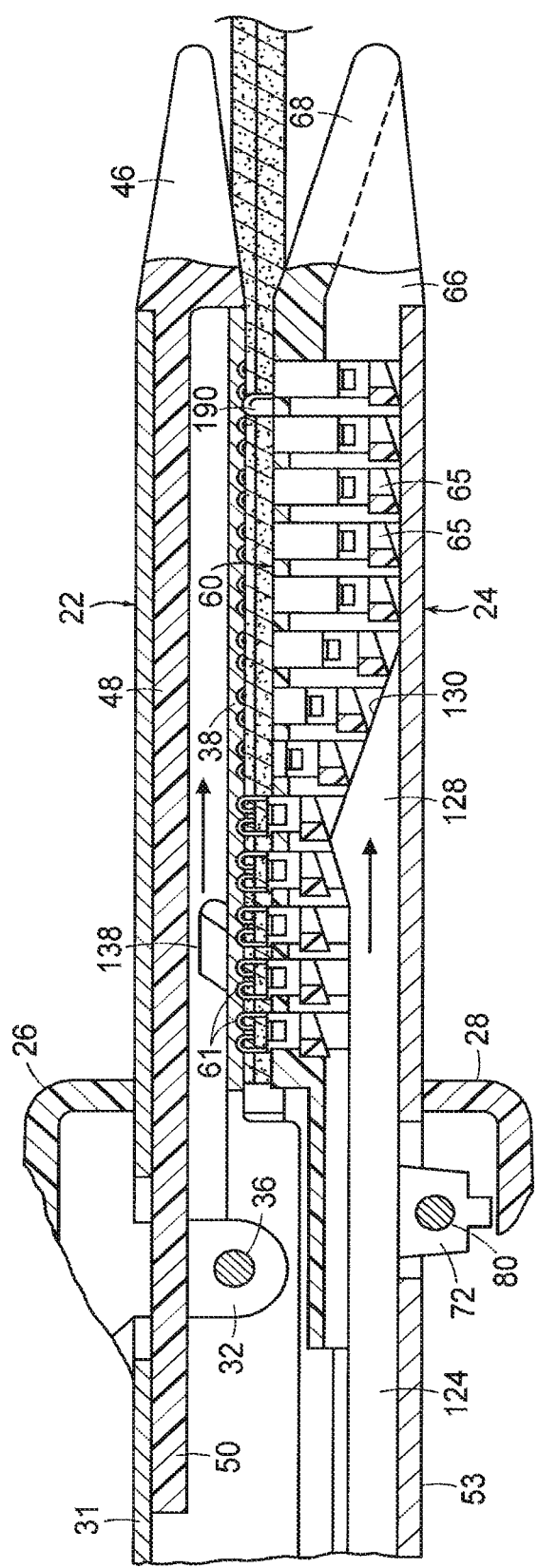
FIG. 17 is a partial cross-sectional view of the anvil and staple cartridge carrying jaw members of FIGS. 5 and 6 illustrating the operation of the pusher bar and knife blade assembly of FIG. 10.

As shown in FIG. 17, a plurality of staple drivers 65 can be slidably mounted in staple openings 64 for actuating the staples 61 which are loaded into staple cartridge 60. Referring to FIG. 6, each staple driver 65 can be designed to simultaneously actuate two staples 61 located in the adjacent rows provided in staple cartridge 60. Thus, in various embodiments, a first set of staple drivers 65 can be provided for actuating the staples 61 in the staggered rows located on one side of central longitudinal slot 62, and a second set of staple drivers 65 can be provided for actuating the staples 61 in the pair of adjacent rows located on the other side of central longitudinal slot 62.

Figure 14:
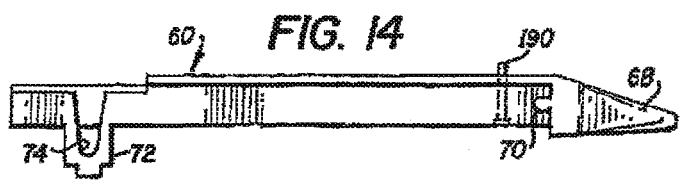
FIG. 14 is a side view of the staple cartridge of the anastomotic stapling instrument of FIG. 1.
Figure 18:
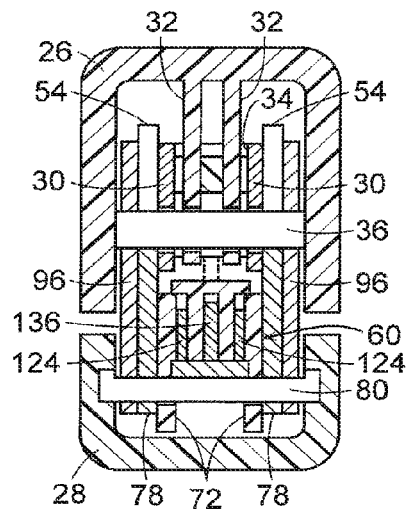
FIG. 18 is a cross-sectional view of the anastomotic stapling instrument of FIG. 1 taken along line 18-18 in FIG. 4.

As shown in FIGS. 2 and 3, similar to the above, the front or distal end of staple cartridge 60 can include a tapered tip 68 to facilitate the insertion of lower jaw member 24 into a hollow, tubular body organ, for example. Immediately behind its tapered tip 68, staple cartridge 60 can be provided with a pair of rearwardly extending protrusions 70 (one shown in FIG. 14) which can be received in corresponding notches provided in side walls 52 of lower jaw member 24. At the rear of staple cartridge 60, a pair of depending arms 72 can extend downwardly from the cartridge. Each arm 72 can be notched to provide a side opening 74. When cartridge 60 is assembled on lower jaw member 24, its protrusions 70 can be received in corresponding notches provided at the front ends of side walls 52 and its depending arms 72 extend downwardly through an opening 76 (FIG. 4) formed in bottom wall 53 of jaw member 24. Lower jaw member 24 can include a pair of depending ears 78 (FIG. 18) extending downwardly from its side walls 52 on opposite sides of opening 76. A pivot pin 80 can extend through holes formed in depending ears 78 of lower jaw member 24 and through side openings 74 of depending arms 72 on staple cartridge 60 to fasten the staple cartridge to the lower jaw member.

Referring to FIG. 2, the stapling instrument 20 can include a latching mechanism, generally 90, for latching upper jaw member 22 and lower jaw member 24 together at an intermediate position along the jaw members. In various embodiments, jaw members 22 and 24 can be latched together at a position adjacent to the proximal ends of anvil 40 and staple cartridge 60. In at least one embodiment, latching mechanism 90 can comprise a latch arm 92 (FIG. 2) pivotally connected to lower jaw member 24 via pivot pin 80 (FIG. 4). Latch arm 92 can be channel-shaped in configuration and can include a pair of opposed, elongated side walls 94 (FIG. 6) which are spaced apart by a distance sufficient to span side walls 52 of lower jaw member 24. Each side wall 94 of latch arm 92 can include an upwardly and forwardly extending hook member 96 provided with a forwardly facing slot 98 for receiving latch pin 36. A shroud 100 can be mounted on the lower surface of latch arm 92. When latch arm 92 is closed, as shown in FIG. 3, shroud 100 can be aligned with the bottom of lower handle 28 to facilitate the handling and operation of stapling instrument 20 by the surgeon. In various embodiments, shroud 100 can be made of plastic or other lightweight materials, for example, while latch arm 92 can be made of stainless steel, for example. As shown in FIG. 7, shroud 100 can include elongated flanges 102 and 104 extending outwardly from its opposite sides which can serve as fingergrips to enable latch arm 92 to be pivoted downwardly from its latched to its unlatched position. When latch arm 92 is moved to its closed or latched position, the surfaces of slots 98 of hook members 96 can cooperate with latch pin 36 which can act as an over-center latch to maintain latch arm 92 in its latched position.

Referring to FIGS. 6 and 10, the preferred embodiment of stapling instrument 20 can include an improved pusher bar and knife blade assembly, generally 110, which can be slidably mounted for longitudinal movement relative to upper and lower jaw members 22 and 24, respectively, for driving staples 61 from staple cartridge 60 into tissue gripped between the jaw members, forming staples 61 against anvil 40, and cutting the tissue along a line between the rows of staples formed in the tissue. Pusher bar and knife blade assembly 110 can include a pusher block 112 (FIG. 6) which can be slidably received within the lower channel-shaped jaw member 24 between its upstanding side flanges 54. As shown in FIG. 11, pusher block 112 can be attached to an actuator knob 114 by a flange 116 which includes a laterally projecting finger 118 provided with a longitudinally extending notch 119 on its top surface. Finger 118 can be snap-fitted into a lateral slot 120 formed in pusher block 112 to locate notch 119 underneath a longitudinal locking bar 121 to secure pusher block 112 and actuator knob 114 together. Flange 116 of actuator knob 114 can extend through and rids along an elongated slot 122 (FIG. 2) formed in one side flange 54 of lower jaw member 24.

Figure 21:
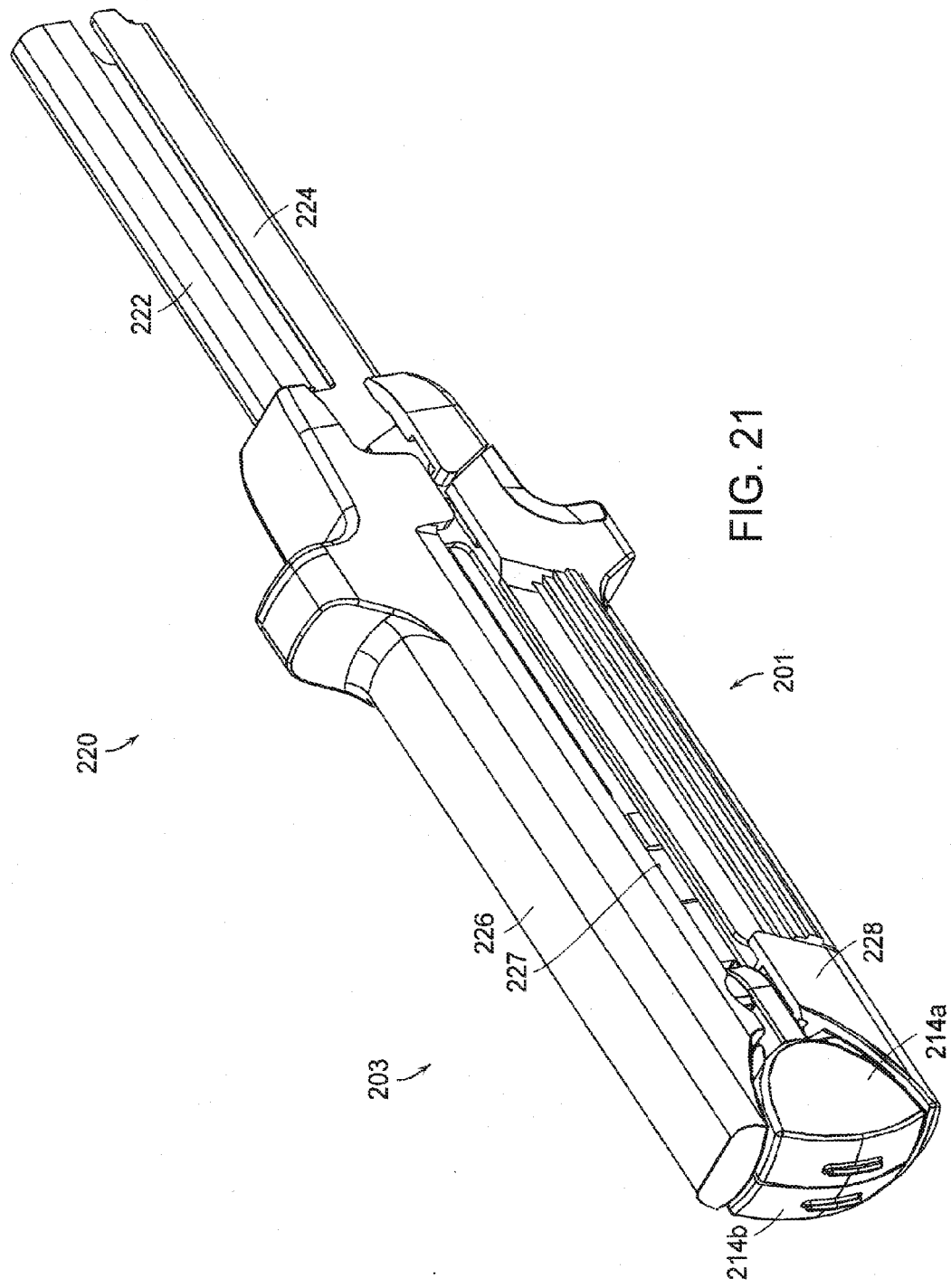
FIG. 21 is a perspective view of a stapling instrument in accordance with one non-limiting embodiment of the present invention.

The pusher bar and knife blade assembly 110 can include a pair of staple pusher bars 124 (FIG. 10) projecting forwardly from pusher block 112 and slidably received in elongated slots 66 (FIG. 16) of staple cartridge 60. Pusher block 112 can be provided with a pair of vertical slots 126 (FIG. 11) in which pusher bars 124 are secured. As shown in FIG. 10, the front end of each staple pusher bar 124 can be provided with a wedge-shaped tip 128 which defines an inclined cam surface 130 for engaging staple drivers 65 as pusher bars 124 are advanced into staple cartridge 60. As shown in FIG. 21, each staple driver 65 can be provided with a sloped surface 132 oriented at the same angle as cam surface 130 of each staple pusher bar 124 to provide a flat, sliding contact between the surfaces.

Referring to FIGS. 6 and 10, the pusher bar and knife blade assembly 110 can include a knife block 134 which is slidably mounted for longitudinal movement along lower jaw member 24 between its upstanding side flanges 54. Knife block 134 can include a knife support bar 136 which extends forwardly into central longitudinal slot 62 of staple cartridge 60. An inclined knife blade 138 provided with a beveled cutting edge 140 can be located at the front end of knife support bar 136. The beveled cutting edge of knife blade 138 can be oriented at an angle relative to elongate jaw members 22 and 24 and can be slidably received in central longitudinal slot 62 of staple cartridge 60.

Figure 19:
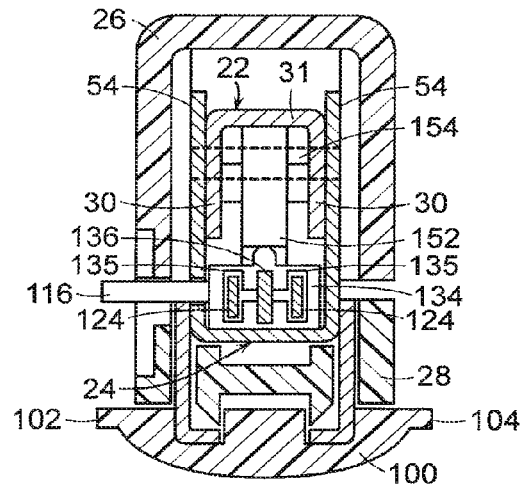
FIG. 19 is a cross-sectional view of the anastomotic stapling instrument of FIG. 1 taken along line 19-19 in FIG. 4.
Figure 20:
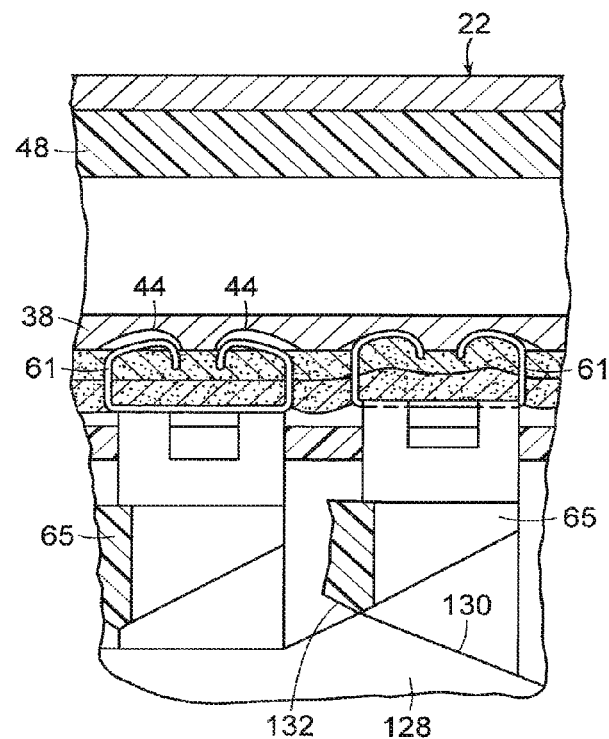
FIG. 20 is a detail view of a portion of the anvil and staple cartridge shown in FIG. 18.

In various embodiments, knife block 134 can include a pair of longitudinal slots 135 (FIG. 19) extending therethrough which slidably receive staple pusher bars 124 to permit pusher block 112 to slide relative to the knife block. Accordingly, when pusher block 112 is advanced toward staple cartridge 60 by actuator knob 114, staple pusher bars 124 can slide through knife block 134 which remains stationary until the pusher block moves into engagement with the knife block. After knife block 134 is engaged by pusher block 112, the knife block and pusher block can advance simultaneously toward staple cartridge 60. As shown in FIG. 17, knife blade 138 can be advanced through staple cartridge 60 along with staple pusher bars 124, forming staples 61 in the tissue gripped between the jaw members and cutting the tissue between the staple rows. Thereafter, when actuator knob 114 is retracted, pusher block 112 can initially slide staple pusher bars 124 backward through knife block 134 which can remain stationary. Each staple pusher bar 124 can include an offset portion 142 which can move into engagement with knife block 134 after staple pusher bars 124 are withdrawn by a predetermined distance. With offset portions 142 of staple pusher bars 124 engaging knife block 134, pusher block 112 and knife block 134 can be simultaneously retracted by actuator knob 114 to return pusher bars 124 and knife blade 138 to the start position.

In accordance with various embodiments of the invention, stapling instrument 20 can be provided with jaw clamping means for applying clamping forces to the jaw members to urge staple cartridge 60 and anvil 40 together during the formation of staples 61. The jaw clamping means can include means for urging the jaw members apart at a position remote from the latching mechanism to resist the forces exerted on staple cartridge 60 and anvil 40 when staples 61 are formed. In at least one embodiment, a cam means can be mounted on one of the jaw members and can be engageable with the other jaw member for moving said jaw members apart at the remote position to urge staple cartridge 60 and anvil 40 together. In various embodiments, a cam member can be pivotally mounted on one of the jaw members at a position remote from the latching mechanism. The cam member can be pivotable from a first inoperative position to a second operative position to move the remote ends of the jaw members apart. The cam member can be operable by pusher block 112 of pusher bar and knife blade assembly 110 to move to its operative position when the pusher block is advanced and to return to its inoperative position when the pusher block is retracted.

In various embodiments, a cam mechanism, generally 150, can be located adjacent to the rear end of lower jaw member 24, as shown in FIG. 4. Cam mechanism 150 can include a cam member 152 pivotally mounted on a transverse pivot pin 154 extending between upstanding side flanges 54 of lower jaw member 24. Cam member 152 can include a first lower cam surface 156 for engaging top wall 31 of upper jaw member 22 with cam 152 in its first inoperative position (FIG. 12) and a second higher cam surface 158 for engaging the top wall 31 of upper jaw member 22 with cam 152 disposed in its second operative position (FIG. 13). First cam surface 156 can be arranged to maintain upper and lower jaw members substantially parallel with cam 152 in its inoperative position. Second cam surface 158 can be arranged to raise the rear end of upper jaw member 22 by approximately 0.125 inch (3.2 mm), for example, when cam 152 pivots from its inoperative position to its operative position. In addition, upper jaw member 22 can be sufficiently flexible to permit the rear portion of upper jaw member 22 to bend upward away from lower jaw member 24 when cam member 152 is moved from its inoperative position to its operative position.

As shown in FIG. 4, cam member 152 can include a radially extending notch 160 which divides the cam into a large front finger 162 and a small rear finger 164. Front cam finger 162 can include a flat, rearwardly facing surface 165, and rear cam finger 164 can include a sloped, forwardly facing surface 166. With cam 152 in its inoperative position, front cam finger 162 and rear cam finger 164 can extend downwardly through an elongated slot 168 formed in bottom wall 53 of lower jaw member 24.

In various embodiments, cam member 152 can be operable by pusher block 112 to move from its inoperative position to its operative position when the pusher block is advanced. As shown in FIG. 11, pusher block 112 can include a pair of rearwardly extending arms 170 which are spaced apart to define a gap 172 therebetween. The rear ends of arms 170 can be connected by a cam actuator pin 174 which extends across gap 172. Referring to FIGS. 4 and 11, with cam member 152 disposed in its inoperative position, front cam finger 162 can extend through gap 172 between arms 170 of pusher block 112, while cam actuator pin 174 can be received in notch 160 between front finger 162 and rear finger 164 of the cam member.

Figure 13:
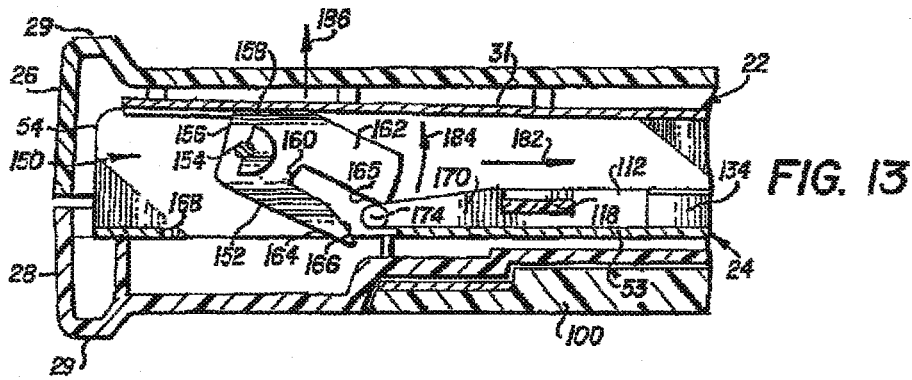
FIG. 13 is a partial cross-sectional view of the rear portion of the anastomotic stapling instrument of FIG. 1 illustrating the cam mechanism in its operative position.

As shown in FIG. 12, with cam member 152 disposed in its first inoperative position, top wall 31 of upper jaw member 22 can rest on first cam surface 156 of the cam member. With cam member 152 in its inoperative position, top wall 31 of upper jaw member 22 can be substantially parallel to bottom wall 53 of lower jaw member 24. In addition, pusher block 112 can be located in its start position spaced rearwardly from knife block 134. When pusher block 112 is advanced, as indicated by arrow 182 (FIG. 13), cam actuator pin 174 can engage rear surface 165 of front cam finger 162 to rotate cam member 152 in a counter-clockwise direction, as indicated by arrow 184, to pivot the cam member to its second operative position and move its second cam surface 158 into engagement with top wall 31 of upper jaw member 22. With cam member 152 pivoted to its operative position, the top wall 31 of upper jaw member 22 can be bent upwardly, as indicated by arrow 186, away from bottom wall 53 of lower jaw member 24. The cam member can apply forces to upper jaw member 22 and lower jaw member 24 which bend the rear portions of the jaw members apart. As a result of the bending the rear portions of upper jaw member 22 and lower jaw member 24 apart, additional clamping forces can be applied to the front portions of upper jaw member 22 and lower jaw member 24 to clamp anvil 40 and staple cartridge 60 against the tissue gripped between the jaw members. Thus, anvil 40 and staple cartridge 60 can be urged together to resist the forces exerted on the anvil and staple cartridge when pusher bar and knife blade assembly 110 is advanced to form staples 61 and cut the tissue.

Referring to FIG. 13, when pusher block 112 is retracted after staples 61 are formed, cam actuator pin 174 can engage sloped surface 166 of rear cam finger 164 to pivot cam member 152 in a clockwise direction. As cam actuator pin 174 moves along sloped surface 166 into notch 160, cam member 152 can pivot in a clockwise direction and return to its first inoperative position (FIG. 12) with its first cam surface 156 in engagement with top wall 31 of upper jaw member 22. As a result, the forces exerted on the rear portions of upper jaw member 22 and lower jaw member 24 by cam 152 can be released and top wall 31 of upper jaw member 22 can return to a substantially parallel relationship with bottom wall 53 of lower jaw member 24. Similarly, the clamping forces applied to the front portions of jaw members 22 and 24 can be released to unclamp anvil 40 and staple cartridge 60.

In various embodiments, stapling instrument 20 can include spacer means mounted on one of the jaw members for maintaining a predetermined gap between staple cartridge 60 and anvil 40 of the stapling instrument. Referring to FIGS. 4 and 6, this spacer means can be embodied as a spacer pin 190 mounted adjacent to the distal end of staple cartridge 60. Spacer pin 190 can extend vertically upward from bottom wall 53 of lower jaw member 24 through staple cartridge 60 and project upwardly from the top of the staple cartridge by a predetermined distance. As shown in FIG. 5, one flange 38 of anvil 40 can include a flange section 192 adjacent to its distal end for engaging spacer pin 190. With the stapling instrument assembled for operation (FIG. 4), spacer pin 190 can engage flange section 192 to maintain a predetermined gap between anvil 40 and staple cartridge 60.

In the operation of stapling instrument 20, the tissue to be stapled and cut can be initially placed between jaw members 22 and 24 and clamped by the jaw members. Thus, handles 26 and 28 can be unlatched by pivotal movement of latch arm 92 downward to its unlatched position (FIG. 2). As a result, the opposite ends of latch pin 36 can be disengaged from slots 98 formed in hook members 96 of latching arm 92. Thereafter, upper and lower jaw members 22 and 24 can be separated by disengaging latch pin 36 from slots 56 formed in side flanges 54 of the lower jaw member.

Next, the tissue to be stapled and cut can be placed on jaw members 22 and 24. For example, as shown in FIG. 17, a piece of tubular, intestinal tissue may be slipped onto the front portion of each jaw member. After the tissue is placed on the jaw member, stapling instrument 20 can be reassembled. The reassembly can be accomplished by aligning latch pin 36 with vertical slots 56 formed in upstanding side flanges 54 of lower jaw member 24. Thereafter, side flanges 54 of lower jaw member 24 can be positioned inside upper handle 26, spanning side walls 30 of upper jaw member 22, while the opposite ends of latch pin 36 can be inserted into vertical slots 56. Finally, latch arm 92 can be pivoted upward to its latched position (FIG. 3) with its cover 100 flush with the bottom of lower handle 28. As a result, hook members 92 can be pivoted over latch pin 36 and slots 98 can receive the opposite ends of the latch pin. Thus, upper jaw member 22 and lower jaw member 24 can be latched together at an intermediate position therealong adjacent to anvil 40 and staple cartridge 60. In addition, spacer pin 190 can engage flange section 192 of anvil 40 through the body tissue to maintain a predetermined gap between anvil 40 and staple cartridge 60.

After the tissue is clamped between the jaw members, stapling instrument 20 can be fired by advancing actuator knob 114 to actuate the pusher bar and knife blade assembly 110. Initially, in the actuation of cam mechanism 150, pusher block 112 and pusher bars 124 (FIG. 4) can be advanced, while knife block 134 can remain stationary. Since only pusher block 112 and its pusher bars 124 are advanced to actuate cam member 152, the initial force required to operate stapling instrument 20 can be minimized.

Referring to FIG. 12, during the initial advance of pusher block 112, pusher bars 124 can slide through knife block 134 and the wedge-shaped tips 128 of the pusher bars can begin to advance through slots 66 of staple cartridge 60. As pusher block 112 advances toward knife block 134, its cam actuator pin 174 can engage rear surface 165 of front cam finger 162 to pivot cam 152 counter-clockwise, as indicated by arrow 184 of FIG. 13, to move the second cam surface 158 of the cam member into engagement with top wall 31 of upper jaw member 22. Cam member 152 can apply forces to upper jaw member 22 and lower jaw member 24 which bend the rear portions of the jaw members apart. As a result, the rear end of top wall 31 of upper jaw member 22 can be bent upward by approximately 0.125 inch (3.2 mm), for example, relative to the rear end of bottom wall 53 of lower jaw member 24. The bending of the rear ends of jaw members 22 and 24 apart can result in additional clamping forces on the front portions of the jaw members to clamp anvil 40 and staple cartridge 60 against the tissue gripped between the jaw members. These additional clamping forces tend to resist the forces exerted on anvil 40 and staple cartridge 60, while the tissue is cut and staples 61 are formed against anvil 40, to maintain the desired spacing between anvil 40 and staple cartridge 60 to produce formed staples 61 which are substantially uniform in height.

Referring to FIG. 13, after cam mechanism 150 is actuated, pusher block 112 can subsequently engage knife block 134 to begin the longitudinal movement of knife block 134 toward staple cartridge 60. In various embodiments, the initial spacing between pusher block 112 and knife block 134 can be arranged such that pusher block 112 engages knife block 134 slightly before cam member 152 arrives at its operative position. Alternatively, the initial spacing between pusher block 112 and knife block 134 can be arranged such that pusher block 112 initially engages knife block 134 after the movement of cam member 152 to its operative position is completed. When pusher block 112 engages knife block 134, the advance of knife blade 138 along central longitudinal slots 42 and 62 of anvil 40 and staple cartridge 60, respectively, can be initiated. Thereafter, staple pusher bars 124 and knife blade 138 can be advanced simultaneously to staple and cut the tissue gripped between anvil 40 and staple cartridge 60.

As pusher block 112 is advanced, staple pusher bars 124 can be moved longitudinally along slots 66 provided in staple cartridge 60. The two wedge-like cam surfaces 130 of staple pusher bars 124 can move through slots 66 into engagement with the sloped surfaces of staple drivers 65 to sequentially drive staples 61 from cartridge 60 and to form staples 61 into B-shaped configuration against anvil flanges 38. The cam surfaces 130 can be located at the same distance from pusher block 112 to simultaneously actuate staple drivers 65 located on opposite sides of central longitudinal slot 62. At the same time, knife block 134 can be advanced to move knife blade 138 through central longitudinal slot 42 of anvil 40 and through central longitudinal slot 62 of staple cartridge 60 to cut the tissue gripped between the jaw members. The additional clamping forces applied to the front portions of upper jaw member 22 and lower jaw member 24 via cam mechanism 150 can tend to resist the forces exerted on anvil 40 and staple cartridge 60 when staples 61 are formed.

After pusher block 112 is fully advanced to form all of the staples in cartridge 60, the pusher block can be retracted toward its start position by retraction of actuator knob 114. Initially, only pusher block 112 can move backward from staple cartridge 60 because staple pusher bars 124 slide through knife block 134 which remains stationary. When offset portions 142 of staple pusher bars 124 engage the front of knife block 134, the knife block can be moved backward from staple cartridge 60 along with pusher block 112. As a result, staple pusher bars 124 and knife blade 138 can be simultaneously retracted from staple cartridge 60 and anvil 40.

As pusher block 112 returns toward its start position, cam actuator pin 174 can engage sloped surface 166 of rear cam finger 164 to pivot cam member 152 in a clockwise direction toward its inoperative position. Cam actuator pin 174 can move along sloped surface 166 into slot 160 between cam fingers 162 and 164 to return cam member 152 to its inoperative position. As a result, second cam surface 158 of cam member 152 can be disengaged from the top wall of upper jaw member 22 and rear end of top wall 31 of upper jaw member 22 and move downwardly into engagement with first cam surface 156. At the same time, front cam finger 162 can pivot downwardly into gap 172 between fingers 170 on pusher block 112, and both cam fingers 162 and 164 can pivot downwardly into slot 168 formed in bottom wall 53 of lower jaw member 24. Thereafter, with cam member 152 in its inoperative position, latching arm 92 can be pivoted downward, as shown in FIG. 2, to permit upper jaw member 22 and lower jaw member 24 to be disassembled. At this point, the cut and stapled tissue can be removed from the jaw members.

As outlined above, a surgical stapling instrument can include an actuator knob, such as actuator knob 114 (FIG. 1), for example, which can be configured to advance a pusher bar assembly, such as pusher bar assembly 110 (FIG. 10), within a staple cartridge of the surgical stapling instrument. In various embodiments, actuator knob 114 can be configured to be grasped by a surgeon such that the surgeon can apply a force thereto. In various circumstances, actuator knob 114 can come into contact with or abut tissue surrounding the surgical site when it is advanced distally. In at least one circumstance, as a result, the surgeon may have to reposition the stapling instrument such that actuator knob 114 can pass by the tissue. In other circumstances, the surgeon may have to force actuator knob 114 by the tissue. In either event, such circumstances may be unsuitable and, as a result, there exists a need for a stapling instrument having an actuator knob which can be manipulated to reduce the possibility that the actuator knob may impinge on the surrounding tissue.

Figure 22:
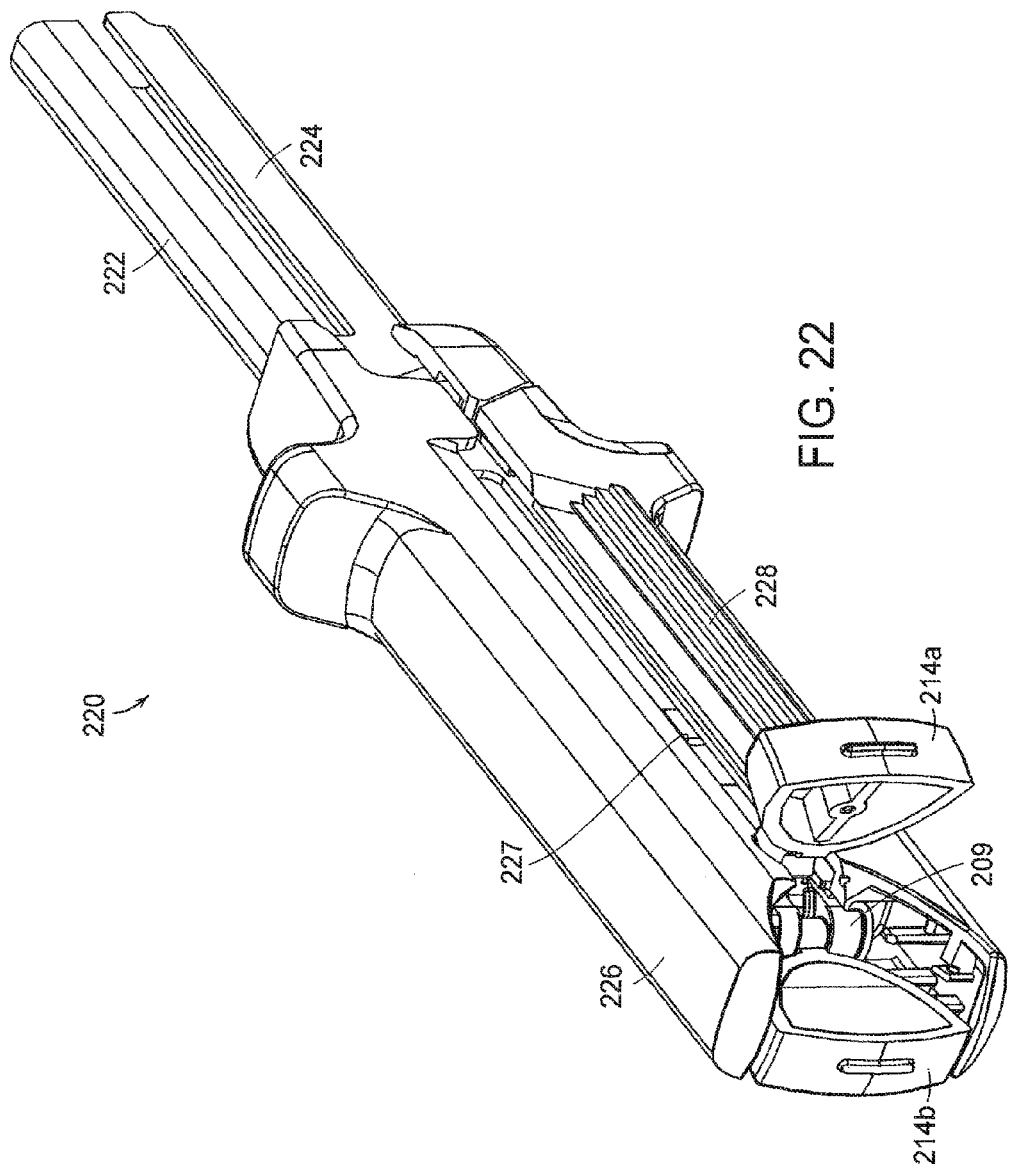
FIG. 22 is a perspective view of the stapling instrument of FIG. 21 illustrating a first actuator knob in an extended position.
Figure 24:
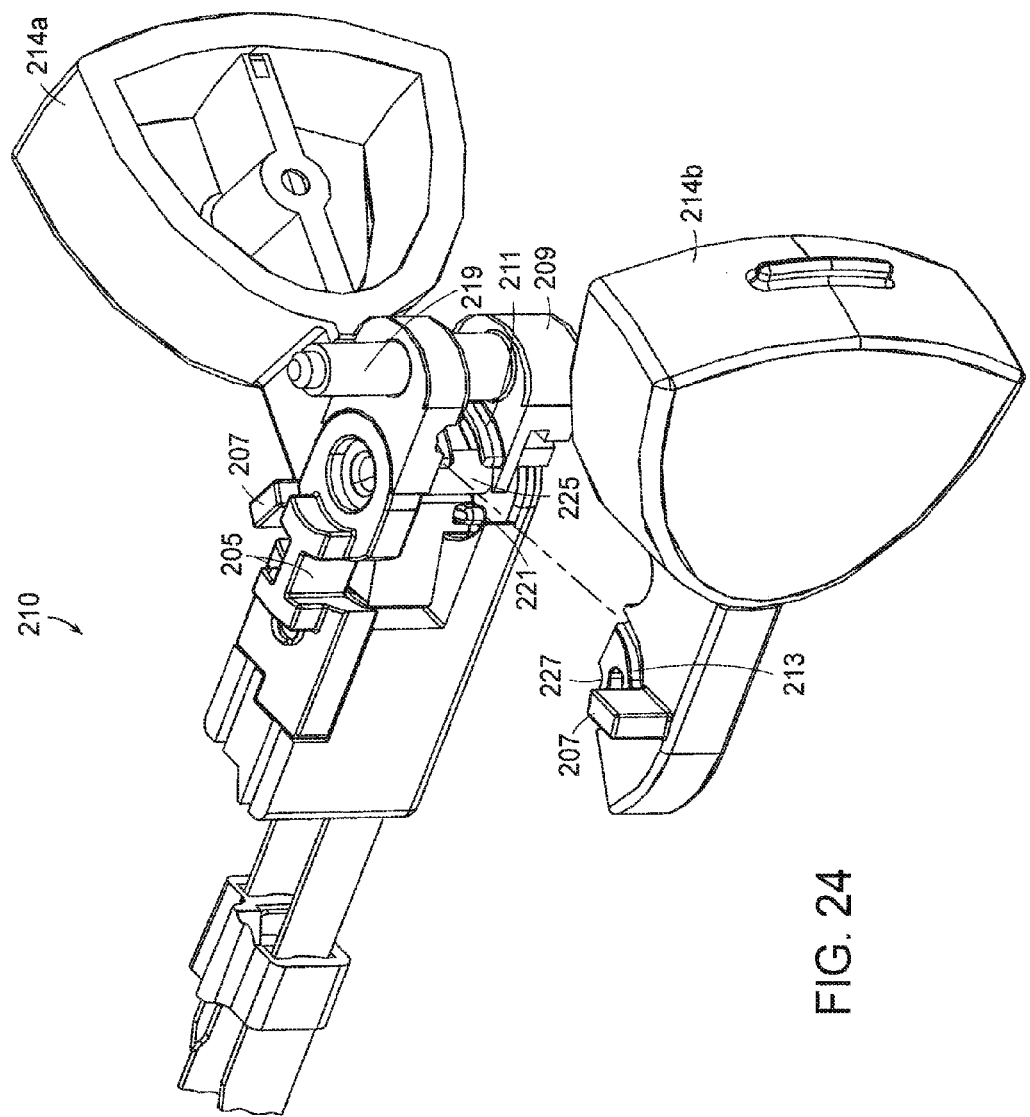
FIG. 24 is an exploded view of a clutch mechanism for operably engaging one or more actuator knobs with a pusher bar of the stapling instrument of FIG. 21.

In various embodiments of the present invention, referring to FIG. 21, stapling instrument 220 can include anvil carrying jaw member 222 extending from upper handle 226, staple cartridge carrying jaw member 224 extending from lower handle 228, and actuator knobs 214a and 214b which can be operably engaged with a pusher bar assembly, such as pusher bar assembly 210 as illustrated in FIG. 24, for example. In various embodiments, a staple cartridge can be removably attached to staple cartridge carrying jaw member 224, for example, such that, after the staple cartridge has been expended, it can be replaced with another staple cartridge. In at least one embodiment, pusher bar assembly 210 can include a staple driver integrally-formed with or operably mounted thereto which can be moved through the staple cartridge as outlined above. In at least one other embodiment, the staple cartridge can include a staple driver contained therein which can be engaged with and pushed distally by the pusher bar assembly. In any event, first actuator knob 214a, for example, can be rotated between a first position (FIG. 21) in which it is operably disengaged from pusher bar assembly 210 and a second position (FIG. 22) in which it is operably engaged with pusher bar assembly 210. Similarly, second actuator knob 214b can be configured to be rotated between first and second positions in which it is operably disengaged and engaged, respectively, with pusher bar assembly 210.

Figure 23:
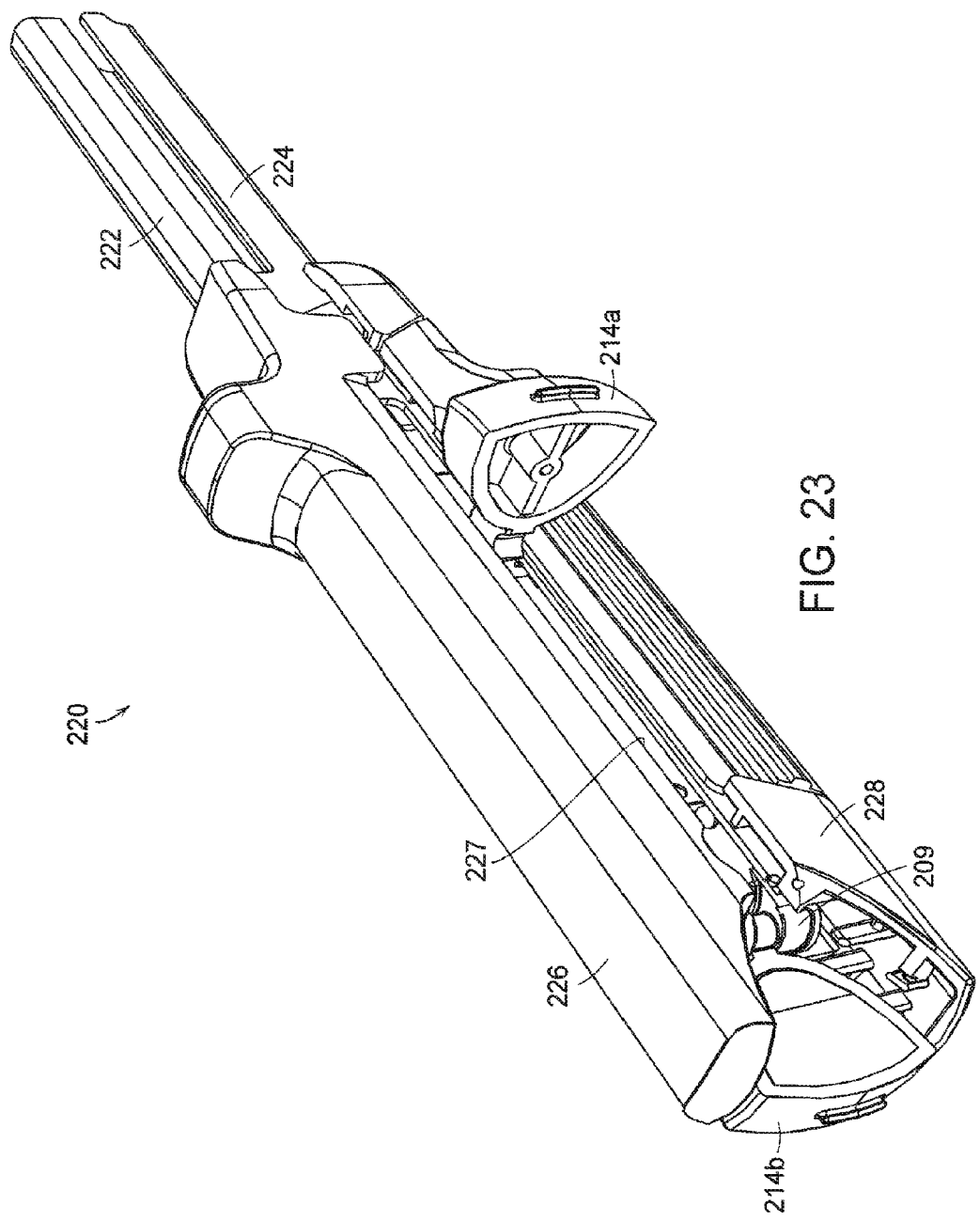
FIG. 23 is a perspective view of the stapling instrument of FIG. 21 illustrating the extended actuator knob of FIG. 22 after it has been advanced distally.
Figure 28:
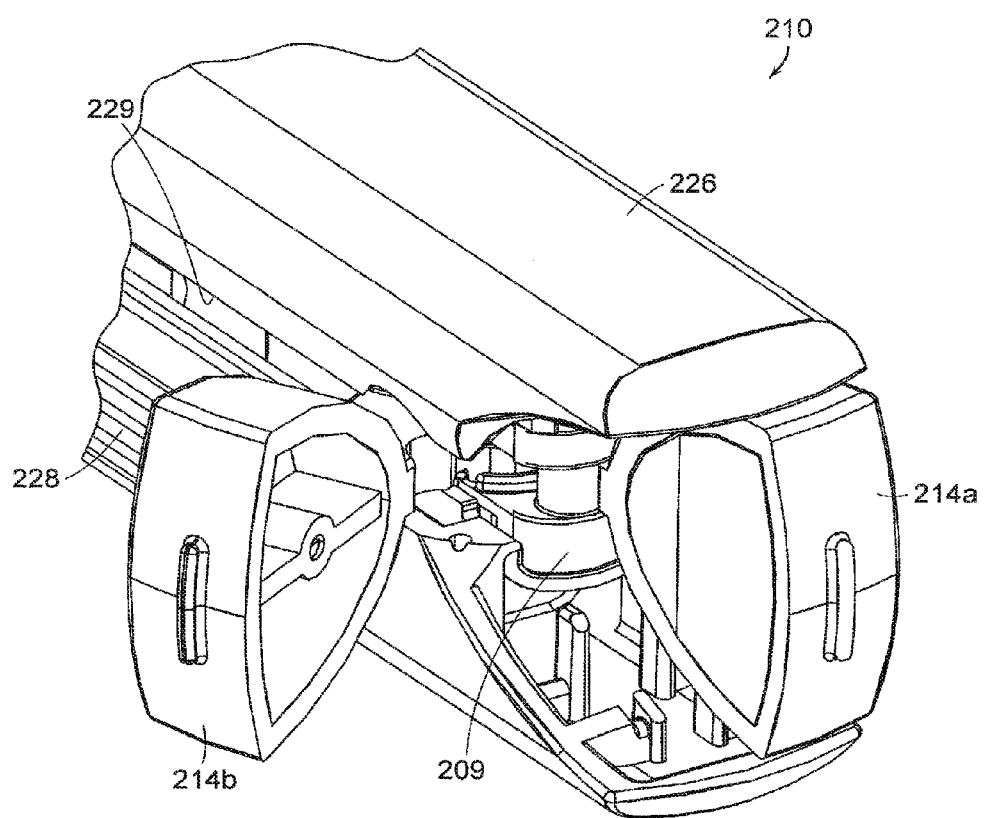
FIG. 28 is a perspective view of the stapling instrument of FIG. 21 illustrating the first actuator knob in a retracted position and a second actuator knob in an extended position.

In various embodiments, as a result of the above, the actuator knobs of a stapling instrument can be selectively engaged with a pusher bar assembly such that, in the event that an actuator knob may come into contact with or abut tissue surrounding the surgical site when it is advanced, that actuator knob can remain in its retracted position while another actuator knob can be extended to advance the pusher bar assembly distally. In at least one such embodiment, referring to FIG. 22, first actuator knob 214a can be rotated into its second position such that it can be operably engaged with pusher bar assembly 210 while second actuator knob 214b can remain in its retracted position. Thereafter, referring to FIG. 23, first actuator knob 214a can be advanced distally relative to upper handle 226 and lower handle 228 along first side 201 of surgical stapler 210 in order to motivate pusher assembly 210. In at least one embodiment, first actuator knob 214a can be slid within first slot 227 defined between, or within, upper handle 226 and lower handle 228. In various other circumstances, referring to FIG. 28, first actuator knob 214a can remain in its retracted position while second actuator knob 214b can be rotated into its extended position. Similar to the above, second actuator knob 214b can be advanced distally along second side 203 of stapling instrument 210 to advance pusher bar assembly 210 within second slot 229, for example. In at least one embodiment, both actuator knobs 214 can be extended to advance pusher bar assembly 210 distally. In various alternative embodiments, although not illustrated, a stapling instrument can include more than two actuator knobs which can be selectively utilized to motivate a pusher bar and/or knife blade assembly. In effect, as a result of the above, the actuator knobs of a surgical instrument can be engaged with a pusher bar assembly independently of each other.

Figure 25:
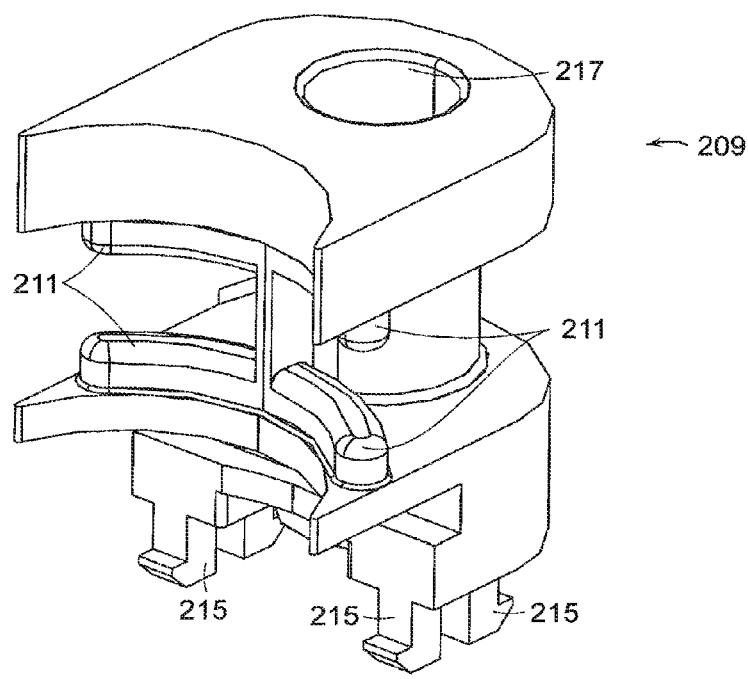
FIG. 25 is a perspective view of a guide member of the clutch mechanism of FIG. 24.
Figure 26:
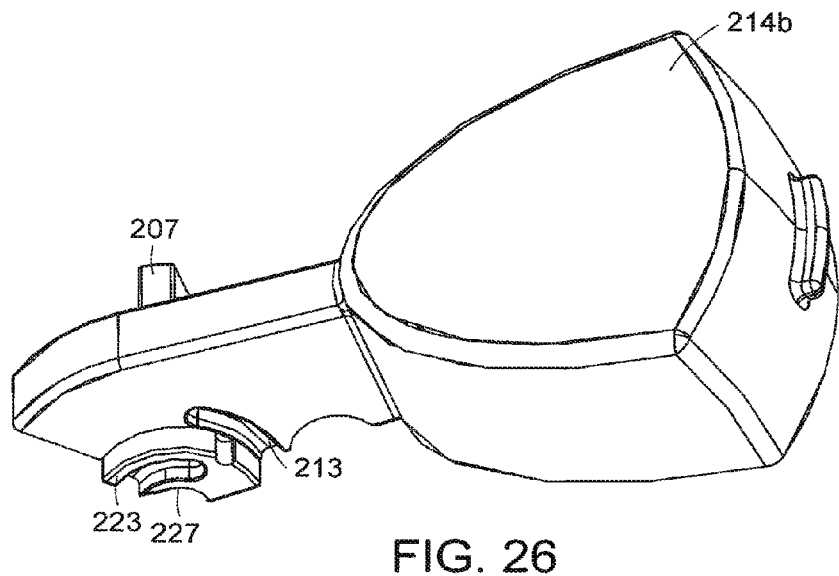
FIG. 26 is a perspective view of an actuator knob of the stapling instrument of FIG. 21.
Figure 27:
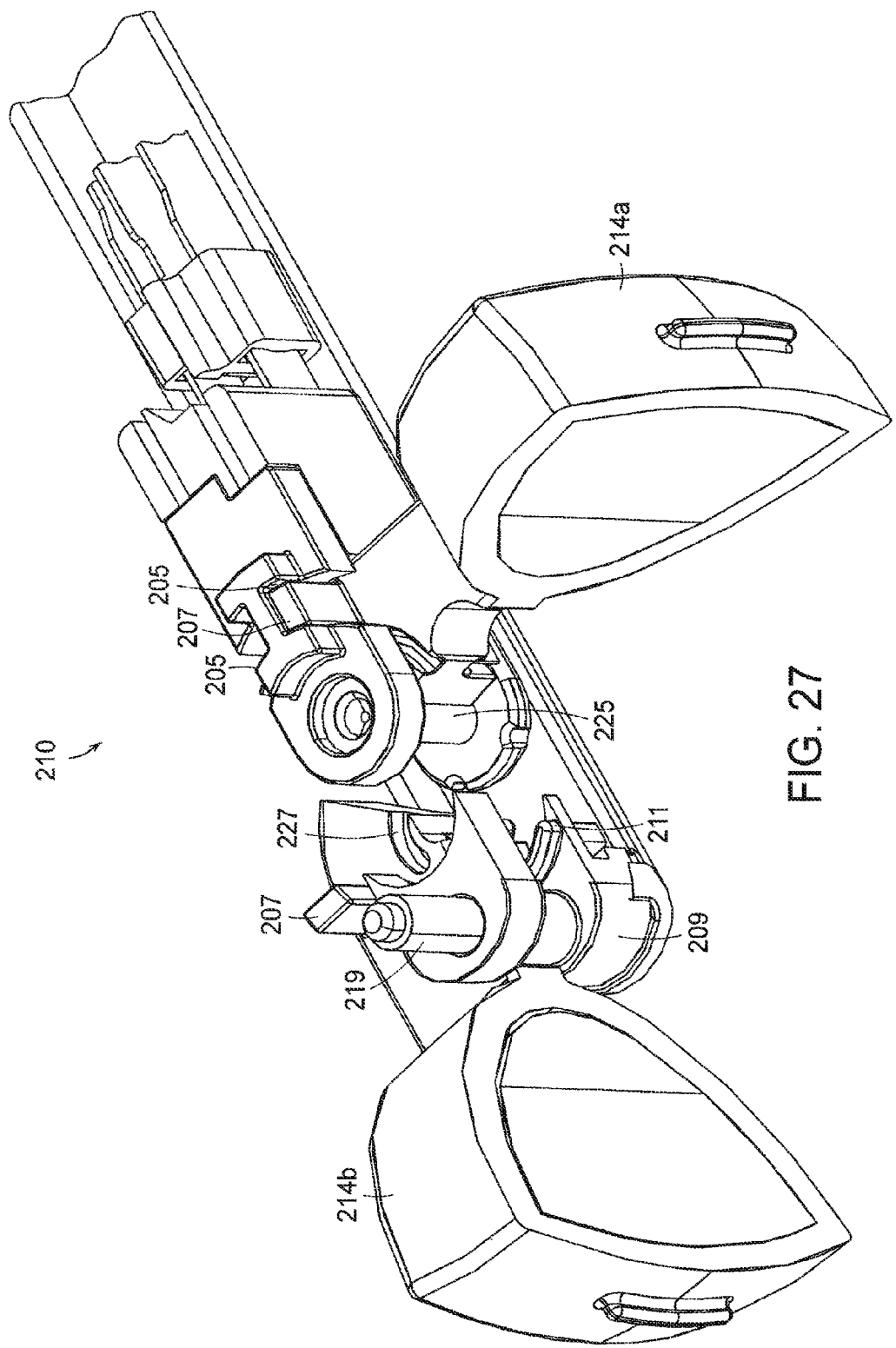
FIG. 27 is another perspective view of the clutch mechanism of FIG. 24.

In various embodiments, further to the above, the actuator knobs of a stapling instrument can be situated in a first position in which they can be held in position and held out of operative engagement with a pusher bar assembly. In at least one embodiment, referring to FIG. 24, stapling instrument 201 can further include guide member 209 which can be configured to guide actuator knobs 214 as they are rotated between their first and second positions. In various embodiments, referring to FIGS. 24-26, guide member 209 can include guide rails 211 which can be slidably received within grooves 213 of actuator knobs 214 such that, when actuator knobs 214 are rotated, guide member 209 can dictate the path along which the actuator knobs 214 are moved. Furthermore, guide rails 211 and grooves 213 can comprise interlocking features which can cooperatively prevent actuator knobs 214 from being unintentionally displaced proximally and/or distally, for example. In at least one such embodiment, guide member 209 can prevent one or more of actuator knobs 214 from being translated along with pusher bar assembly 210 when pusher bar assembly 210 is advanced distally as described above. In various embodiments, a slight friction or interference fit can be present between guide rails 211 and grooves 213 such that the possibility that actuator knobs 214 may be unintentionally rotated into their extended positions can be reduced. Although not illustrated, the actuator knobs can include guide rails extending therefrom which can be slidably received in grooves within the guide member, for example. In any event, referring to FIG. 25, guide member 209 can include one or more retention members 215 which can be configured to retain guide member 209 in position intermediate upper handle 226 and lower handle 228. Furthermore, referring to FIGS. 24 and 25, guide member 209 can include aperture 217 which can be configured to receive retention pin 219 extending therethrough wherein retention pin 219 can be configured to be engaged with upper handle 226 and/or lower handle 228 to retain guide member 209 in position.

In various embodiments, as actuator knobs 214 are rotated between their first and second positions as described above, grooves 213 can be rotated out of engagement with guide rails 211 and actuator knobs 214 can be operatively engaged with pusher bar assembly 210. In at least one embodiment, referring primarily to FIG. 24, pusher bar assembly 210 can include a first clutch feature, such as slots or grooves 205, for example, and actuator knobs 214 can each include a second clutch feature, such as projections 207, for example, wherein the first and second clutch features can be operatively engaged with each other in order to operatively engage one or more of actuator knobs 214 with pusher bar assembly 210. In at least one such embodiment, projections 207 can be closely received within slots 205 such that, when a force is applied to one or more of actuator knobs 214, the force can be transmitted to pusher bar assembly 210 through projections 207 and the sidewalls of slots 205. In at least one embodiment, similar to the above, a slight friction or interference fit can be present between projections 207 and slots 205 to hold actuators 214 in their extended position. In any event, although not illustrated, the first clutch feature can include projections extending from the pusher bar assembly which can be configured to be received within recesses or slots within the actuator knobs. In addition to or in lieu of the above, referring to FIG. 24, pusher bar assembly 210 can further include second guide rails 221 which can be configured to be slidably received within slots or grooves 223 within actuator knobs 214, wherein rails 221 and grooves 223 can be configured to guide actuator knobs 214 into their second position and/or transmit forces from actuator knobs 214 to pusher bar assembly 210 once they are in their second position. Similar to guide rails 211, guide rails 221 can be configured to create a slight friction or interference fit with grooves 223 to hold actuator knobs 214 in position. Further to the above, in various embodiments, actuator bar 210 can include post 225 about which actuator knobs 214 can be rotated. In at least one embodiment, actuator knobs 214 can include recesses 227 which can be contoured such that the sidewalls of recesses 227 can closely receive and slide around post 225 and, as a result, post 225 can guide actuator knobs 214 as they are rotated between their first and second positions, for example.

Figure 30:
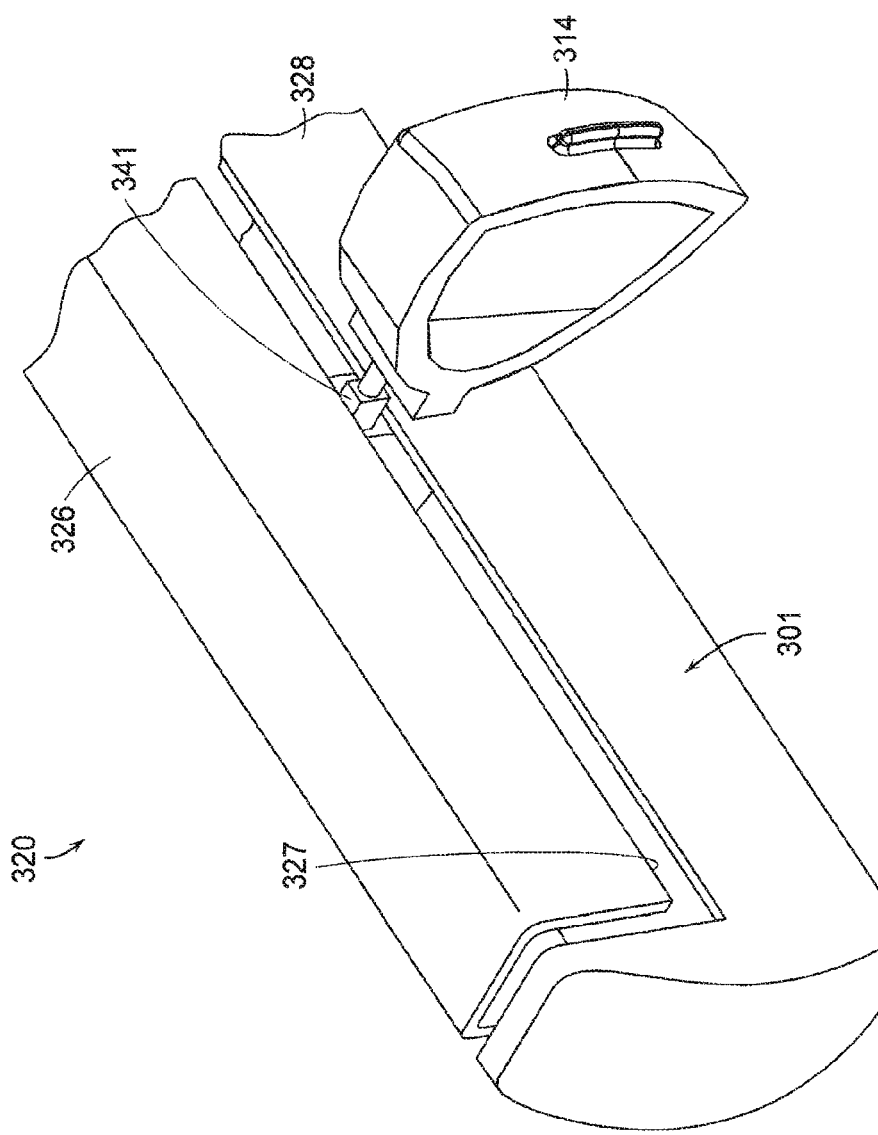
FIG. 30 is a partial perspective view of the stapling instrument of FIG. 29 illustrating an actuator knob after it has been advanced distally along a first side of the stapling instrument.
Figure 31:
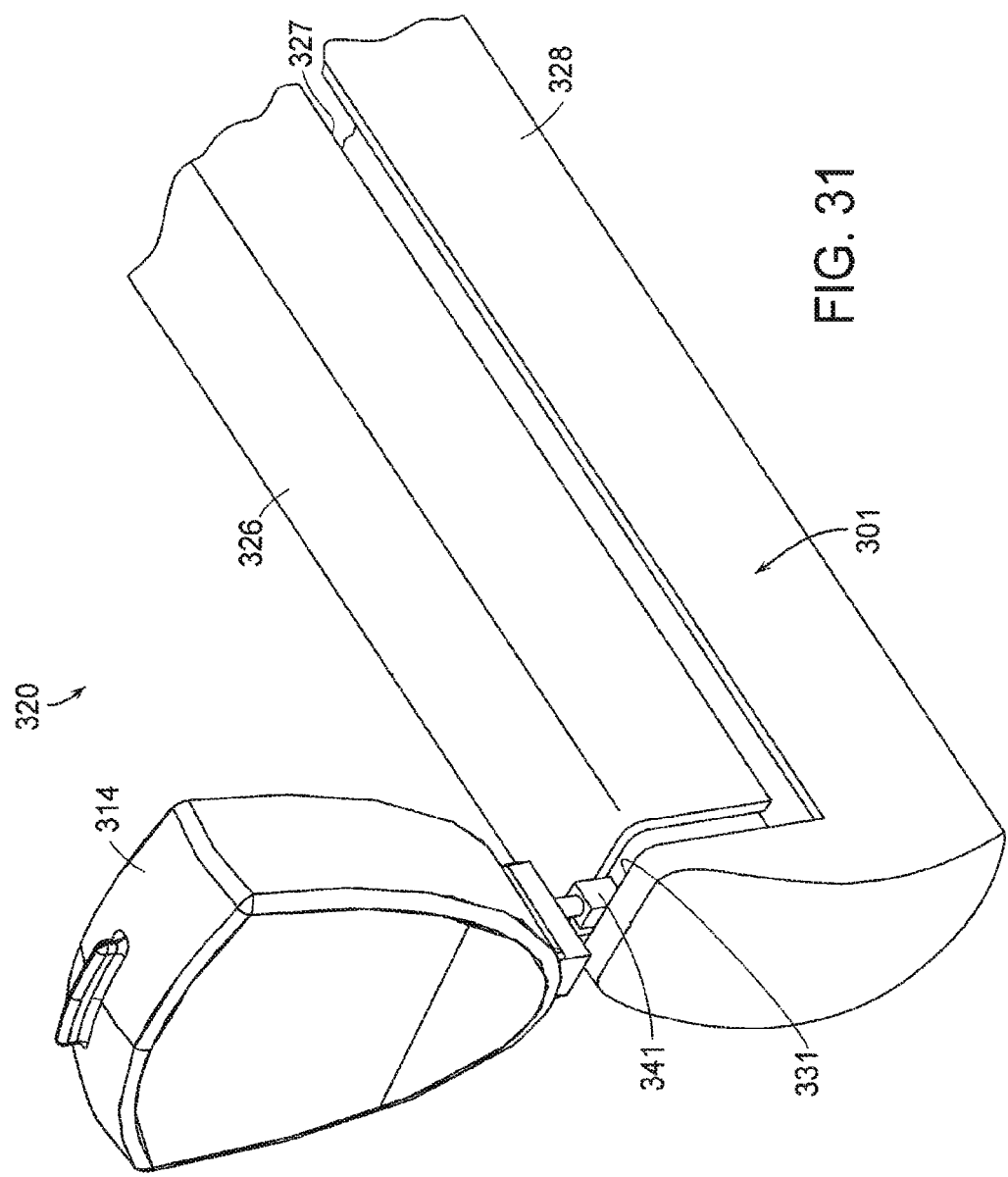
FIG. 31 is a partial perspective view of the stapling instrument of FIG. 29 illustrating the actuator knob of FIG. 30 being rotated between a first position and a second position.
Figure 32:
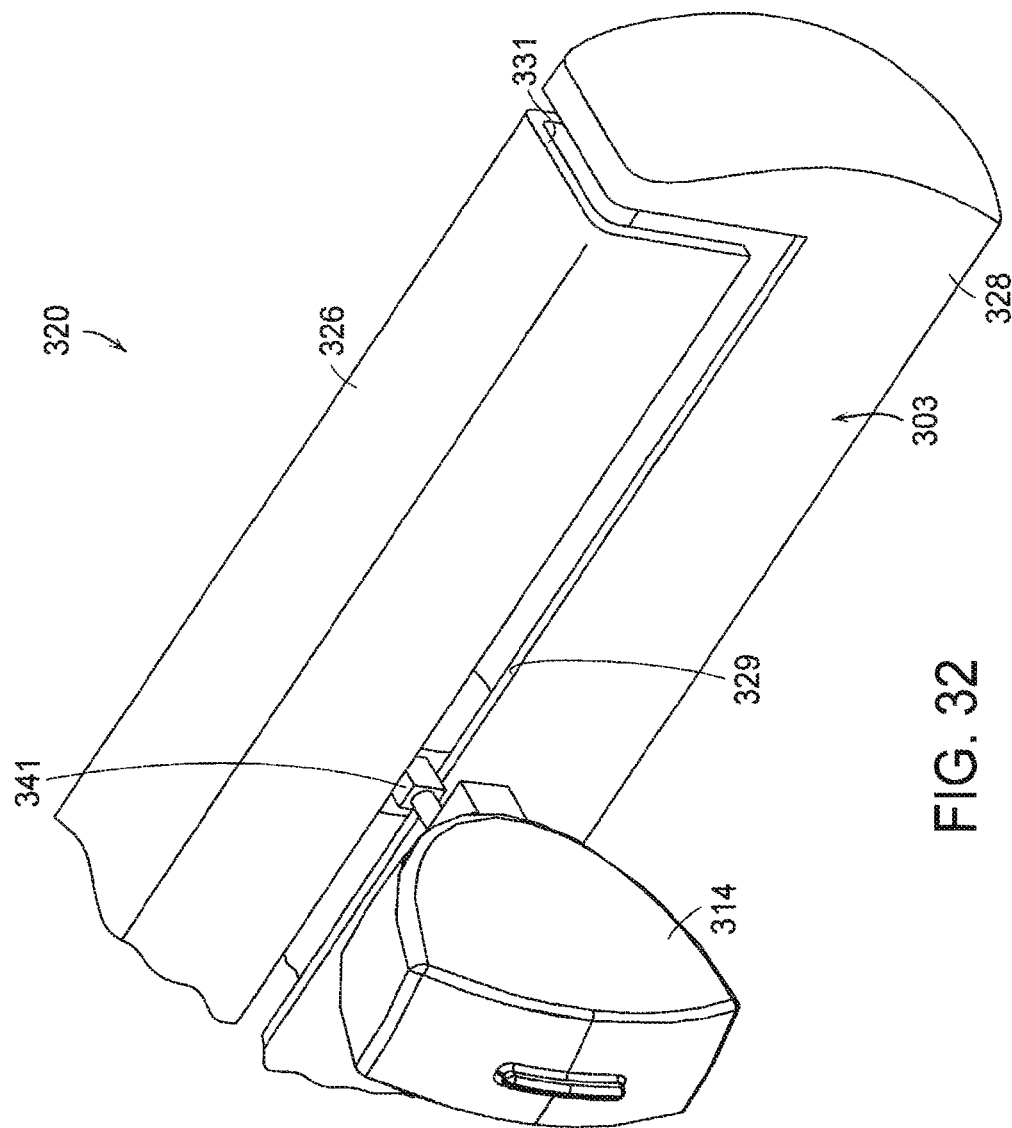
FIG. 32 is a partial perspective view of the stapling instrument of FIG. 29 illustrating the actuator knob of FIG. 30 after it has been advanced distally along a second side of the stapling instrument.

In various embodiments of the present invention, a stapling instrument can include an actuator knob which can be configured to be selectively advanced along a first side of the stapling instrument and a second side of the stapling instrument. In at least one embodiment, referring to FIGS. 29 and 30, stapling instrument 320 can include an upper handle 326, a lower handle 328, and an actuator knob 314, wherein actuator knob 314 can, similar to the above, be configured to advance a pusher bar assembly within a staple cartridge. In at least one embodiment, upper handle 326 and lower handle 328 can define first slot 327 and second slot 329 therebetween, wherein slots 327 and 329 can both be configured to permit actuator knob 314 to slide therethrough. More particularly, in various embodiments, actuator knob 314 can be configured such that it can be selectively slid through first slot 327 along first side 301 or, alternatively, through second slot 329 along second side 303. In various embodiments, referring to FIG. 31, stapling instrument 320 can further include third slot 331 which can be configured to allow actuator knob 314 to be moved from one side of the stapling instrument to the other. In at least one such embodiment, as a result, a surgeon can selectively position actuator knob 314 such that, if it appears that actuator knob 314 may impinge on tissue if it is advanced distally on one side of the stapling instrument, actuator knob 314 can rotated over to the other side of the stapling instrument before it is advanced. Although the first and second sides of the illustrated embodiment are located on opposite sides of surgical instrument 320, other embodiments are envisioned where the first and second slots, for example, are located on adjacent sides and/or sides which are not directly opposite to each other. Furthermore, other embodiments are envisioned in which the sides of a stapling instrument are not readily discernable, such as instruments having round and/or arcuate portions.

Figure 29:
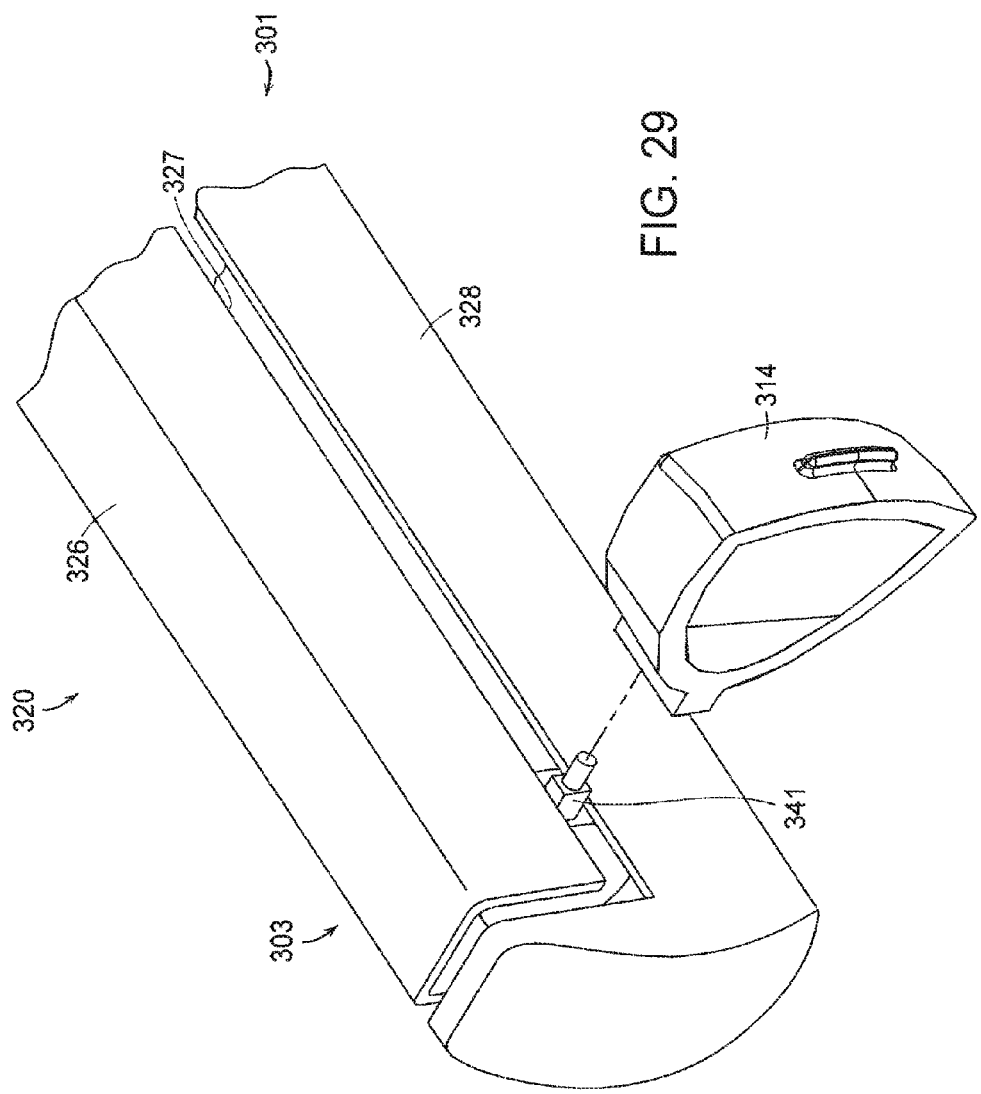
FIG. 29 is a partial exploded view of a stapling instrument in accordance with one non-limiting embodiment of the present invention.

In various embodiments, referring primarily to FIG. 29, first slot 327 can be configured such that it defines a path for actuator knob 314 which is parallel to, or at least substantially parallel to, a path defined by second slot 329. In at least one embodiment, third slot 331 can be configured to connect first slot 327 and second slot 329 such that it can define a path for actuator knob 314 which is perpendicular to, or at least substantially perpendicular to, the paths defined by slots 327 and 329. In such embodiments, actuator knob 314 can be rotated over the top of the surgical instrument to move actuator knob 314 from first side 301 to second side 303. In the event that a surgeon decides to reposition actuator knob on first side 301, the surgeon can move actuator knob 314 back through slot 311 until it is positioned within first slot 327 once again. In various alternative embodiments, although not illustrated, a third slot can define a path for actuator knob 314 which is parallel to, or at least substantially parallel to, and/or co-planar with, or at least substantially co-planar with, the paths defined by slots 327 and 329. In further various embodiments, a third slot can define a path which is skew with respect to the paths defined by slots 327 and 329. In any event, a third slot can be configured connect first and second slots such that an actuator knob can be slid therewithin.

Figure 33:
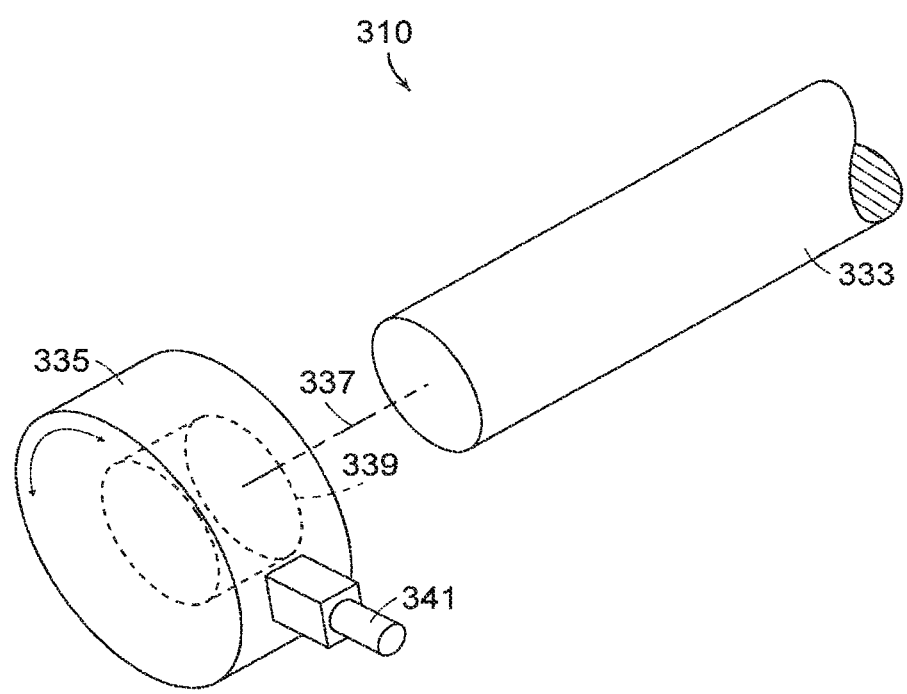
FIG. 33 is an exploded view of a pusher bar assembly of the stapling instrument of FIG. 29 configured to allow the actuator knob of FIG. 30 to be rotated between its first and second positions.

As outlined above, stapling instrument 320 can include a pusher bar assembly which can be operably engaged with actuator knob 314, for example, such that actuator knob 314 can be configured to advance the pusher bar assembly distally. In various embodiments, referring to FIG. 33, stapling instrument 320 can include pusher bar assembly 310 which can include a first portion 333 operably engaged with a knife assembly, for example, and, in addition, a second portion 335 which can be rotatably mounted to first portion 333. In at least one embodiment, first portion 333 can define an axis 337 about which second portion 335 can be rotated. In at least one such embodiment, second portion 335 can include aperture 339 defined therein which can be configured to closely receive first portion 333. In at least one embodiment, although not illustrated, pusher bar assembly 310 can further include one or more retaining members, such as set screws, for example, configured to extend into a groove in first portion 333, for example, for retaining second portion 335 to first portion 333. In various embodiments, second portion 335 can include mount 341 extending therefrom which can be configured to retain actuator knob 314 to second portion 335. In order to move actuator knob from a first side of stapling instrument 320 to the another side, as described above, actuator knob 314 and second portion 335 can be rotated relative to first portion 333 such that actuator knob 314 can be selectively positioned within first slot 327 and second slot 329. In at least one embodiment, although not illustrated, a stapling instrument can have more than two slots for receiving an actuator knob when it is advanced within a staple cartridge. In any event, in various alternative embodiments, first portion 333 and second portion 335 can be fixedly mounted together such that they are rotated together about axis 337. In at least one such embodiment, first portion 333 can be configured to rotate relative to a substantially non-rotatable portion of pusher bar assembly 310.

Figure 34:
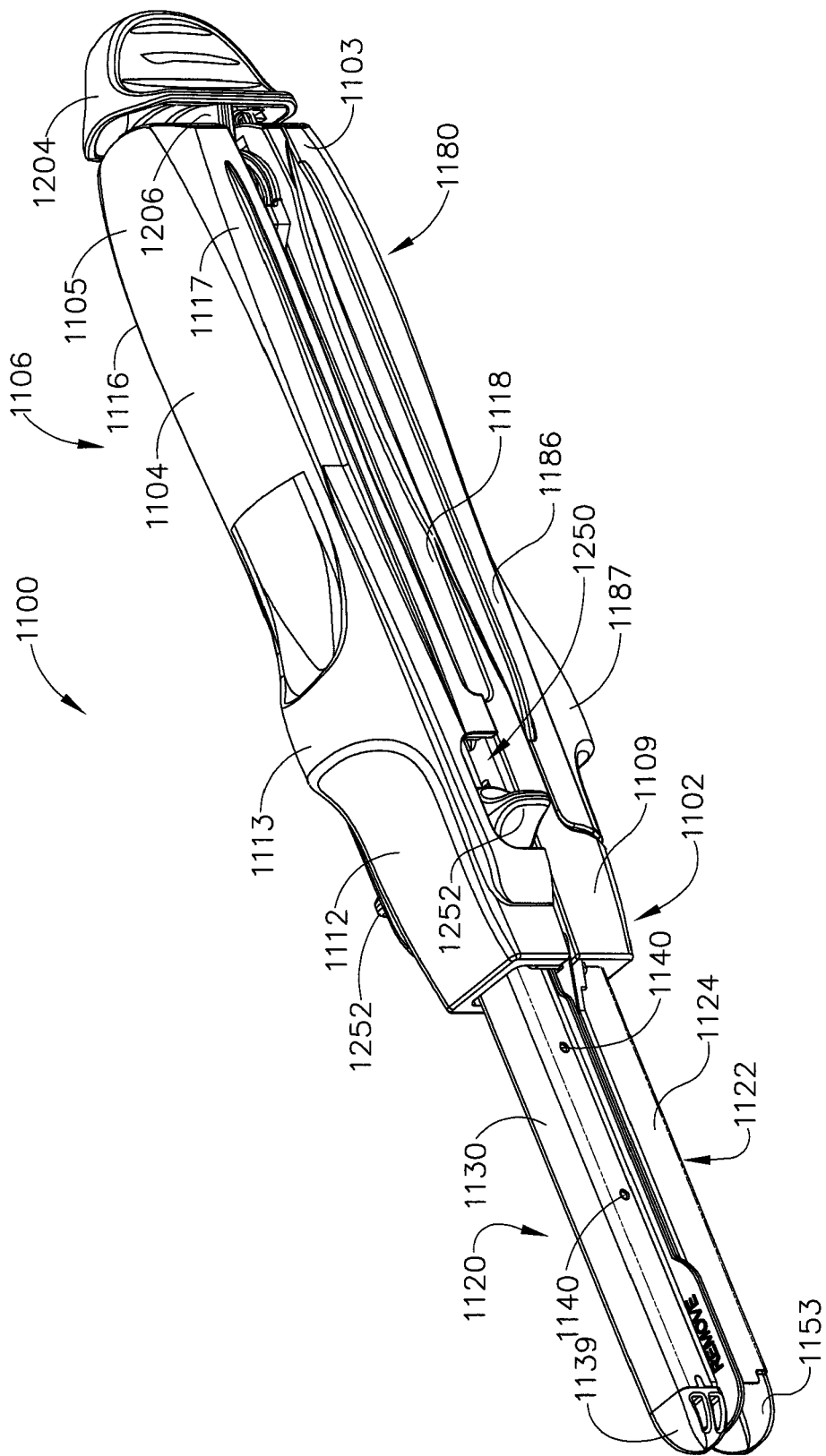
FIG. 34 is a perspective view of a surgical stapling instrument in accordance with at least one embodiment of the present invention.

Referring to FIG. 34, a surgical stapling instrument, generally 1100, can comprise a first handle portion 1102 and a second handle portion 1104. In various embodiments, first handle portion 1102 and second handle portion 1104 can be configured to be grasped by a surgeon, for example, and can comprise hand grip portion 1106. In at least one embodiment, first handle portion 1102, referring to FIGS. 35 and 36, can include a first cover 1108 attached to a first frame 1110 and, similarly, second handle portion 1104 can include a second cover 1112 attached to a second frame 1114. Covers 1108 and 1112 can be ergonomically contoured, or otherwise suitably contoured, to assist a surgeon in manipulating stapling instrument 1100 within a surgical site. In various embodiments, handle covers 1108 and 1112, for example, can include enlarged protrusions 1109 and 1113, respectively, which can facilitate the insertion of stapling instrument 1100 into a surgical site. In various embodiments, handle covers 1108 and 1112 can be made of plastic, lightweight materials, and/or any other suitable material, for example, while handle frames 1110 and 1114 can be made of stainless steel, titanium, and/or any other suitable material, for example.

Figure 35:
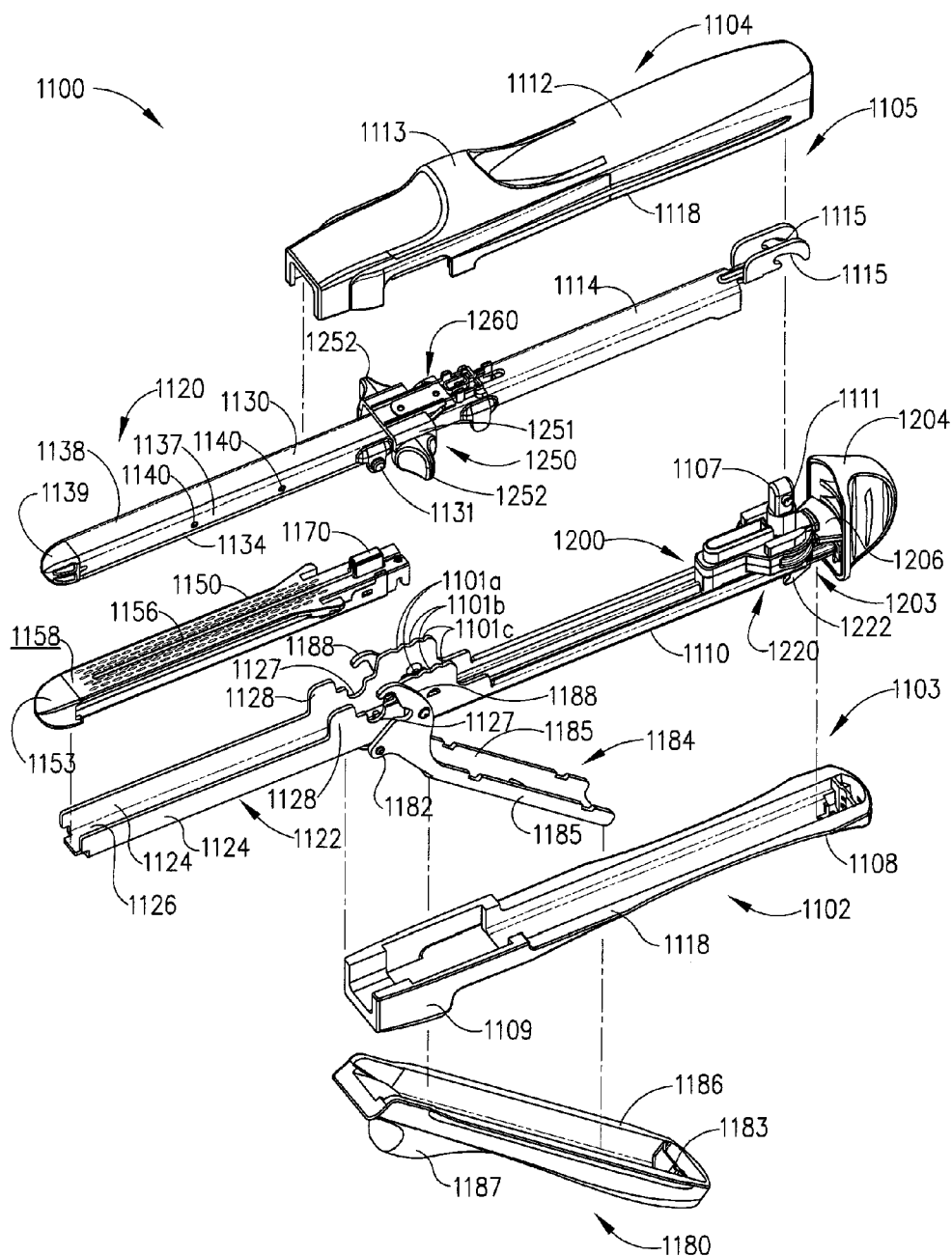
FIG. 35 is an exploded perspective view of the surgical stapling instrument of FIG. 34.

In various embodiments, referring again to FIGS. 34-37, the distal ends of handle portions 1102 and 1104 can comprise an end-effector 1120 which can be configured to treat tissue within a surgical site, for example. In at least one such embodiment, end-effector 1120 can include a staple cartridge channel 1122 configured to receive and/or retain a staple cartridge as described in greater detail further below. In certain embodiments, staple cartridge channel 1122 can comprise a one-piece elongated channel-shaped frame extending from first handle portion frame 1110. In at least one embodiment, staple cartridge channel 1122 can include a pair of opposed, elongated side walls 1124 connected by a bottom wall 1126. Along the rearward, or proximal, portion of staple cartridge channel 1122, a pair of spaced, upstanding side flanges 1128 can extend upwardly from opposed side walls 1124. In various embodiments, the width of staple cartridge channel 1122 between side flanges 1128 can be greater than the width of the upper jaw member, or anvil, 1130 extending from second handle portion 1104. In at least one embodiment, the distance between flanges 1128 can be configured to permit at least a portion of anvil 1130 to be received between side flanges 1128 when the stapling instrument is assembled for operation. As shown in FIG. 35, each side flange 1128 of can include a notch, or recess, 1127, for example, which can be configured to receive one or more latch projections 1131, for example, extending from anvil 1130, and/or any other suitable portion of second handle portion 1104, as described in greater detail further below.

Figure 42:
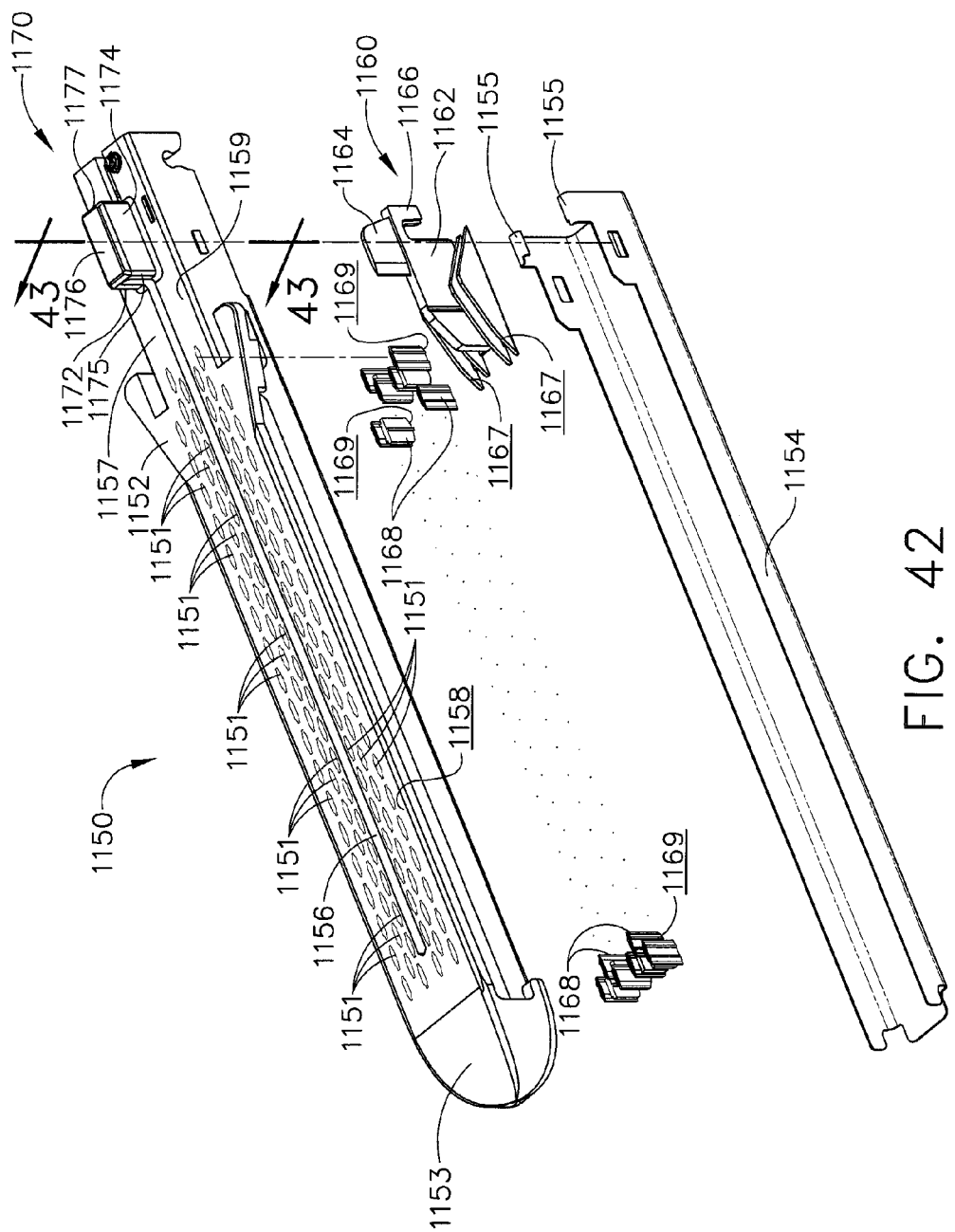
FIG. 42 is an exploded view of the staple cartridge assembly of FIG. 41.
Figure 43:
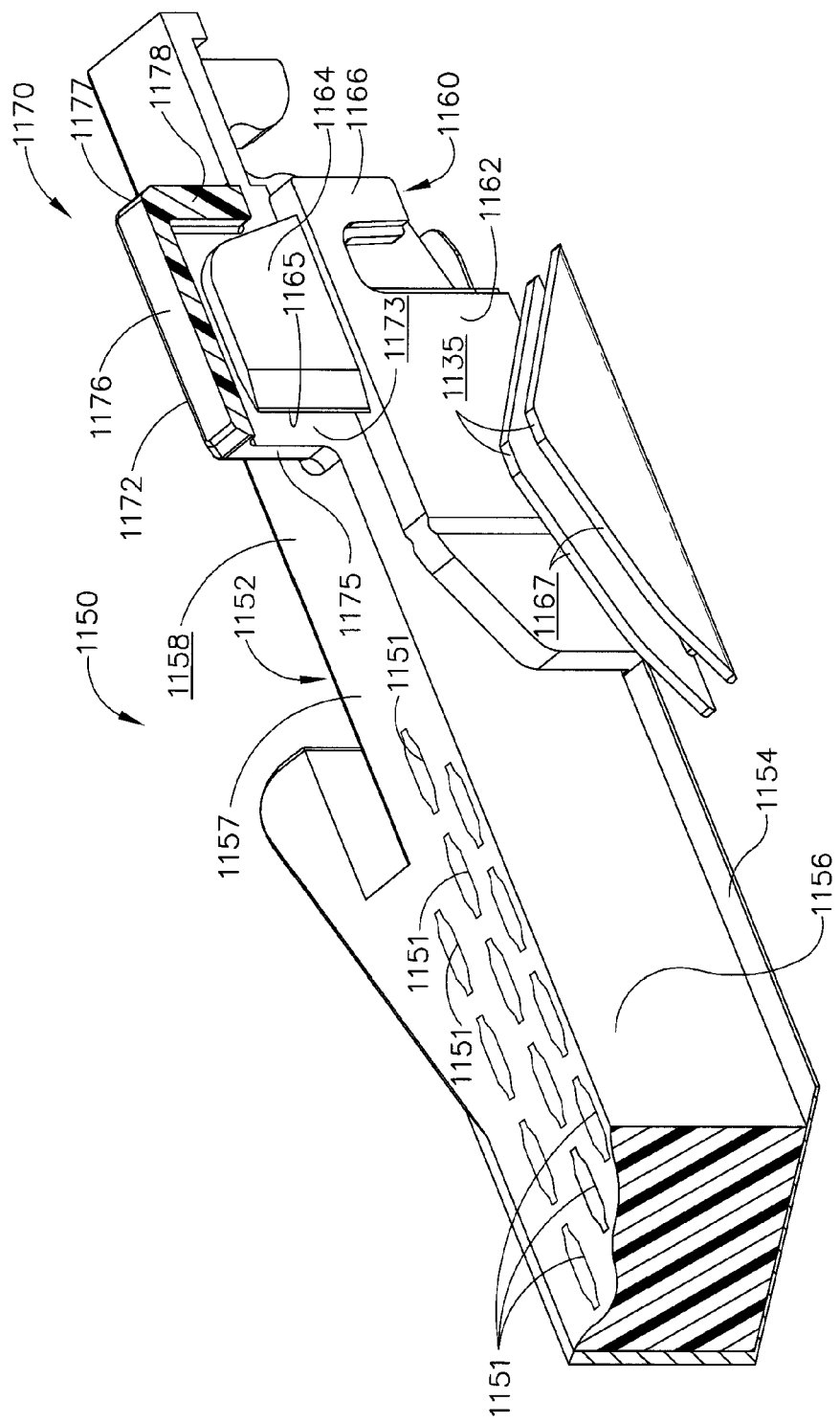
FIG. 43 is a cross-sectional view of the staple cartridge assembly of FIG. 41 taken along line 43-43 in FIG. 42.

As indicated above, referring once again to FIGS. 34-37, staple cartridge channel 1122 can be configured to support and/or retain a staple cartridge, such as staple cartridge 1150, for example, within end-effector 1120, wherein the staple cartridge can include one or more staples (not illustrated) removably stored therein. In various embodiments, referring to FIGS. 41-43, staple cartridge 1150 can include one or more staple cavities 1151 which can be configured to store staples in any suitable arrangement, such as in at least two laterally-spaced longitudinal rows, for example. In at least one embodiment, referring to FIGS. 42 and 43, staple cartridge 1150 can include staple cartridge body 1152 and pan, or retainer, 1154, wherein staple cartridge body 1152 and/or pan 1154 can be configured to define a channel, or path, for slidably receiving a staple sled and/or cutting member therein. In at least one embodiment, pan 1154 can include flexible arms 1155, for example, which can be configured to engage staple cartridge body 1152 in a snap-fit and/or press-fit arrangement. Referring to FIGS. 43-45, staple cartridge 1150 can further include staple sled assembly 1160 which can include staple sled portion 1162 and, in addition, cutting member 1164. In various embodiments, cutting member 1164 can include cutting edge 1165 and lock arm 1166, for example, wherein lock arm 1166 can be configured to be press-fit and/or snap-fit into aperture 1163 in staple sled 1162 when cutting member 1164 is assembled to staple sled portion 1162. In other various embodiments, staple sled portion 1162 can be integrally molded to cutting member 1164.

Figure 41:
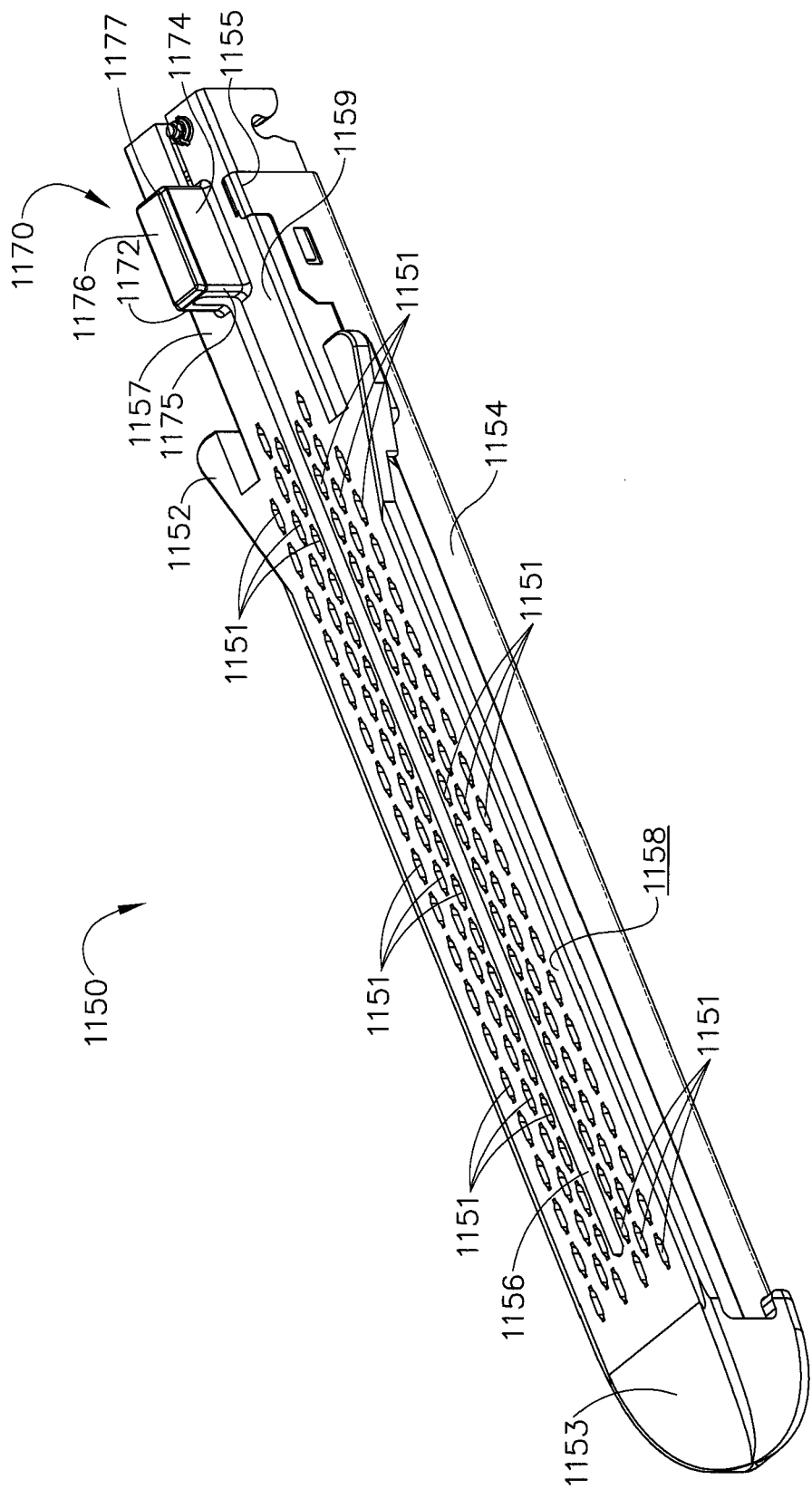
FIG. 41 is a perspective view of a staple cartridge assembly of the surgical stapling instrument of FIG. 34.

Further to the above, referring to FIGS. 41-43, staple cartridge body 1152 can include a slot, such as slot 1156, for example, which can be configured to receive at least a portion of cutting member 1164 therein, and/or any other portion of staple sled assembly 1160 and pusher bar assembly 1200 (discussed below), wherein slot 1156 can be configured to permit cutting member 1164 to be moved between first and second positions within staple cartridge 1150. In various embodiments, slot 1156 can be configured to permit cutting member 1164 to be moved between a proximal position (FIG. 43) and a distal position in order to incise tissue positioned intermediate staple cartridge 1150 and anvil 1130, for example. Referring again to FIGS. 43-45, staple sled portion 1162 can include cam, ramp, or actuator, surfaces 1167 which can be configured to engage staple drivers positioned within staple cartridge 1150. In various embodiments, referring to FIG. 42, staple cartridge 1150 can include staple drivers 1168 which can be lifted, or slid, upwardly within staple cavities 1151 by sled portion 1162 such that the upward movement of staple drivers 1168 can eject, or deploy, staples at least partially positioned within staple cavities 1151. While staple drives 1168 can be, in fact, lifted vertically upwardly, the term upward, and the like, can mean that staple drivers 1168, for example, are moved toward the top surface, or deck, 1158 of the staple cartridge and/or toward anvil 1130, for example. In certain embodiments, as illustrated in FIG. 42, each staple driver 1168 can include one or more sloped surfaces 1169 oriented at the same angle as a cam surface 1167, and/or any other suitable angle, which can provide a relatively flat, or at least substantially flat, sliding contact surface between staple sled 1162 and staple drivers 1168. In various embodiments, a staple driver can be configured to deploy only one staple, while, in certain embodiments, a staple driver can be configured to simultaneously deploy two or more staples located in adjacent rows, for example. Other devices are disclosed in U.S. patent application Ser. No. 12/030,424, entitled SURGICAL STAPLING INSTRUMENT WITH IMPROVED FIRING TRIGGER ARRANGEMENT, which was filed on Feb. 13, 2008, the entire disclosure of which is incorporated by reference herein.

In various embodiments, as described above, a surgical stapling instrument can include a cutting member/staple sled assembly configured to incise tissue and deploy staples from a staple cartridge. In certain embodiments, though, a surgical stapling instrument may not require, or include, a cutting member. In at least one such embodiment, a staple cartridge can include a staple sled positioned therein and/or a surgical instrument can be configured to move a staple sled into a staple cartridge in order to staple tissue, for example, without otherwise dissecting it. In certain other embodiments, a staple cartridge can include a staple sled positioned therein where a surgical instrument can include a cutting member movable into, or relative to, the staple cartridge. In at least one such embodiment, the cutting member can be advanced into contact with the staple sled such that the cutting member and staple sled can be advanced together. Thereafter, the cutting member can be sufficiently retracted to allow the staple cartridge to be detached from the surgical instrument and replaced with a new staple cartridge having a new staple sled. Such embodiments may be useful when a staple sled may become worn or deformed during use. Other embodiments are envisioned where a staple cartridge can include a cutting member positioned therein where a surgical instrument can include a staple sled movable into, or relative to, the staple cartridge. In at least one such embodiment, similar to the above, the staple sled can be advanced into contact with the cutting member such that the cutting member and staple sled can be advanced together. Thereafter, the staple sled can be sufficiently retracted to allow the staple cartridge to be detached from the surgical instrument and replaced with a new staple cartridge having a new cutting member. Such embodiments may be useful when a cutting member may become worn or deformed during use. In various embodiments, as described in greater detail below, the staple cartridge can include a protective housing or cover configured to prevent, or at least reduce the possibility of, a surgeon or other clinician from touching the cutting member positioned within the staple cartridge while handling the staple cartridge, for example.

Figure 36:
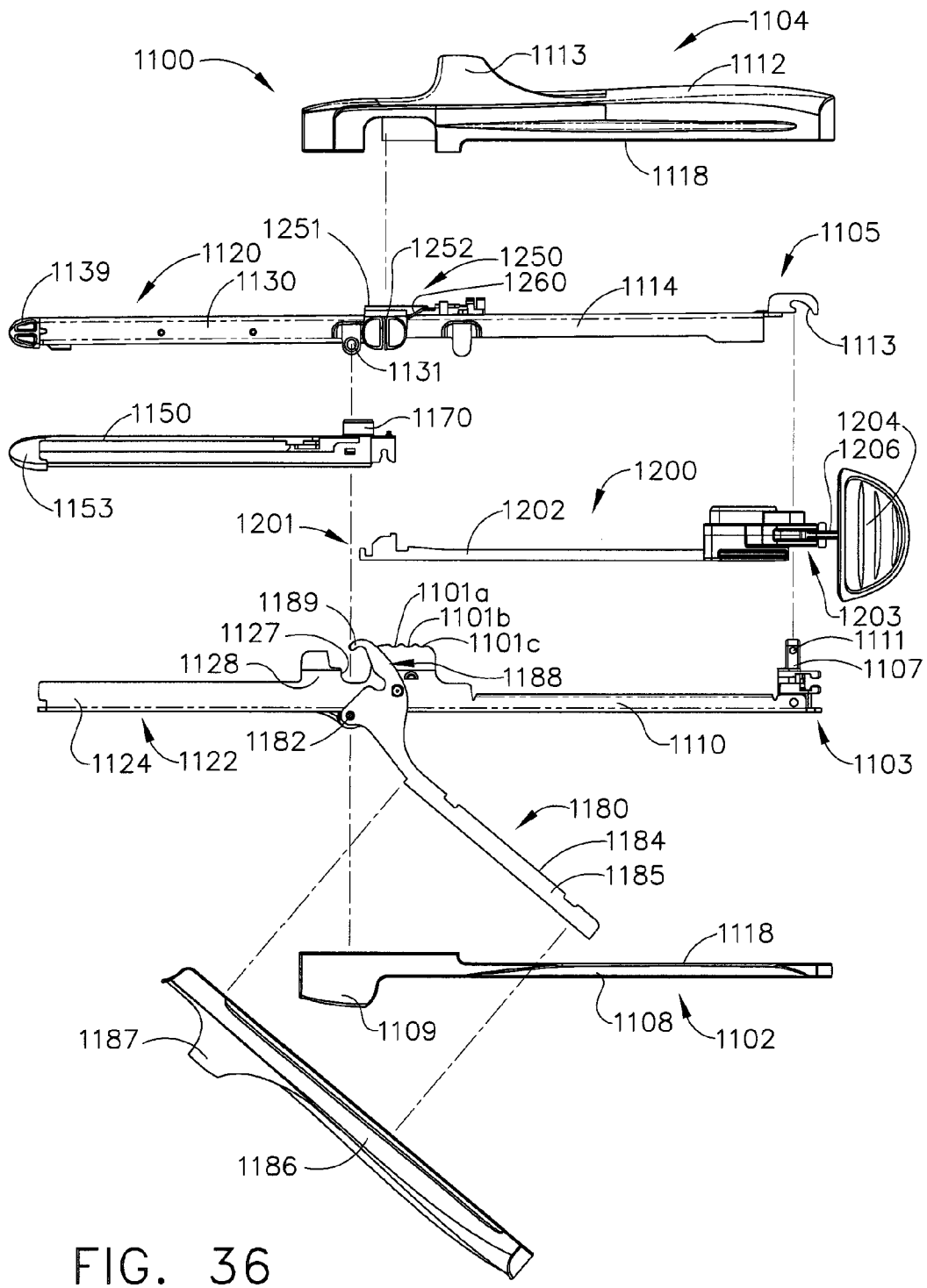
FIG. 36 is an exploded elevational view of the surgical stapling instrument of FIG. 34.

In various embodiments, further to the above, staple cartridge channel 1122 and/or staple cartridge 1150, for example, can include one or more co-operating projections and/or recesses, for example, which can be configured to removably retain staple cartridge 1150 within staple cartridge channel 1122. Once staple cartridge 1150 has been inserted into staple cartridge channel 1122, in various embodiments, the first handle portion 1102 can be assembled to the second handle portion 1104. In other various embodiments, the staple cartridge may be inserted into the staple cartridge channel after the first and second handle portions have been assembled together. In either event, referring to FIGS. 34-41, first handle portion 1102 and second handle portion 1104 can include proximal ends 1103 and 1105, respectively, which can be assembled together such that the first and second handle portions can be rotatably or pivotably coupled to one another. In various embodiments, referring to FIGS. 35 and 36, first handle portion 1102 can include one or more pins, or projections, 1111 extending therefrom which can be configured to be slidably received within one or more grooves, channels, or slots 1115 in second handle portion 1104. In certain embodiments, slots 1115 can be defined in second handle frame 1114 and projections 1111 can extend from a proximal end post 1107 extending from first handle frame 1110, for example. In order to assemble first handle portion 1102 and second handle portion 1104, referring to FIG. 37, the open ends of slots 1115 can be aligned with projections 1111 such that second handle portion 1104, for example, can be translated relative to first handle portion 1102 and projections 1111 can be slid within slots 1115. In at least one embodiment, as illustrated in FIGS. 35 and 36, the open ends of slots 1115 can be located proximally with respect to their closed ends. In at least one such embodiment, proximal end 1105 of second handle portion 1104 can be positioned distally with respect to proximal end 1103 of first handle portion 1102 such that second handle portion 1104 can be moved proximally in order to position projections 1111 within slots 1115. In various other circumstances, first handle portion 1102 can be positioned proximally with respect to second handle portion 1104 and slid distally in order to position projections 1111 within slots 1115.

Figure 38:
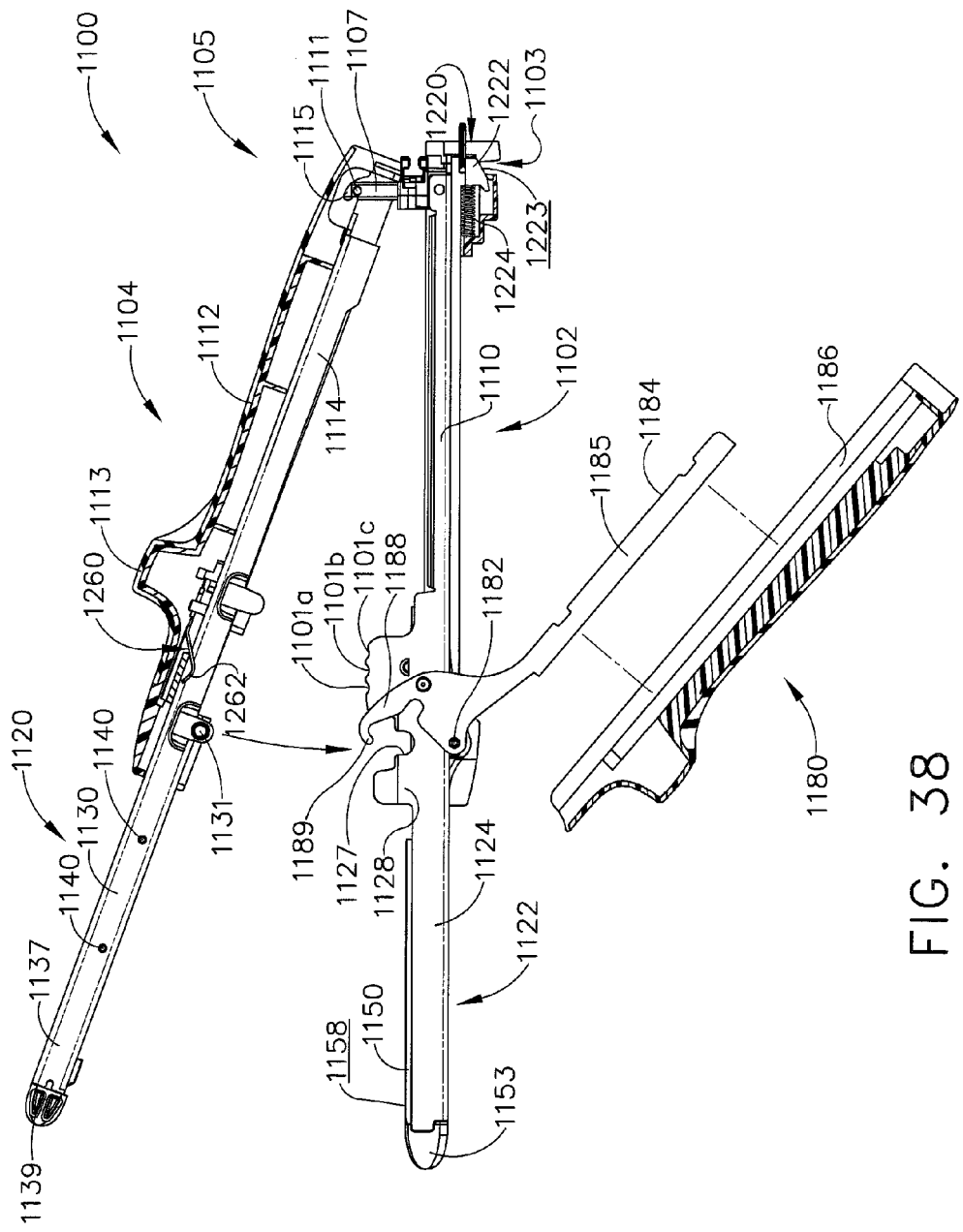
FIG. 38 is a partial cross-sectional view of the surgical stapling instrument of FIG. 34 illustrating the proximal end of the first portion of FIG. 37 being locked to the proximal end of the second portion of FIG. 37 and illustrating the second portion being rotated toward the first portion.

In various embodiments, referring to FIG. 38, second handle portion 1104 can be rotated toward first handle portion 1102 such that anvil 1130 can be moved into position relative to staple cartridge 1150 and/or staple cartridge channel 1122. In certain embodiments, first handle portion 1102 can be rotated toward second handle portion 1104 and/or the first and second handle portions can be rotated toward each other. In any event, projections 1111 and slots 1115, when engaged with one another, can comprise a pivot about which one or both of the first and second handle portions can be moved relative to each other. In various embodiments, second handle portion 1104 can be moved relative to first handle portion 1102 such that anvil 1130 is moved into close opposition to staple cartridge 1150. In certain embodiments, referring to FIG. 39, second handle portion 1104 can be moved relative to first handle portion 1102 such that latch projections 1131 extending from second handle portion 1104 can be aligned with and/or inserted into recesses 1127 within first handle portion 1102. In various embodiments, referring primarily to FIGS. 35 and 36, first handle portion 1102 can further include latching mechanism 1180 rotatably mounted thereto which can be utilized to engage latch projections 1131 extending from second handle portion 1104 and secure the first and second handle portions together. Although not illustrated, other embodiments are envisioned in which a latching mechanism is rotatably mounted to the second handle portion and latch projections can extend from the first handle portion. In any event, in at least one embodiment, latching mechanism 1180 can be mounted to first frame 1110 by one or more pivot pins 1182 which can be configured to define an axis about which latch 1180 can be rotated.

Figure 37:
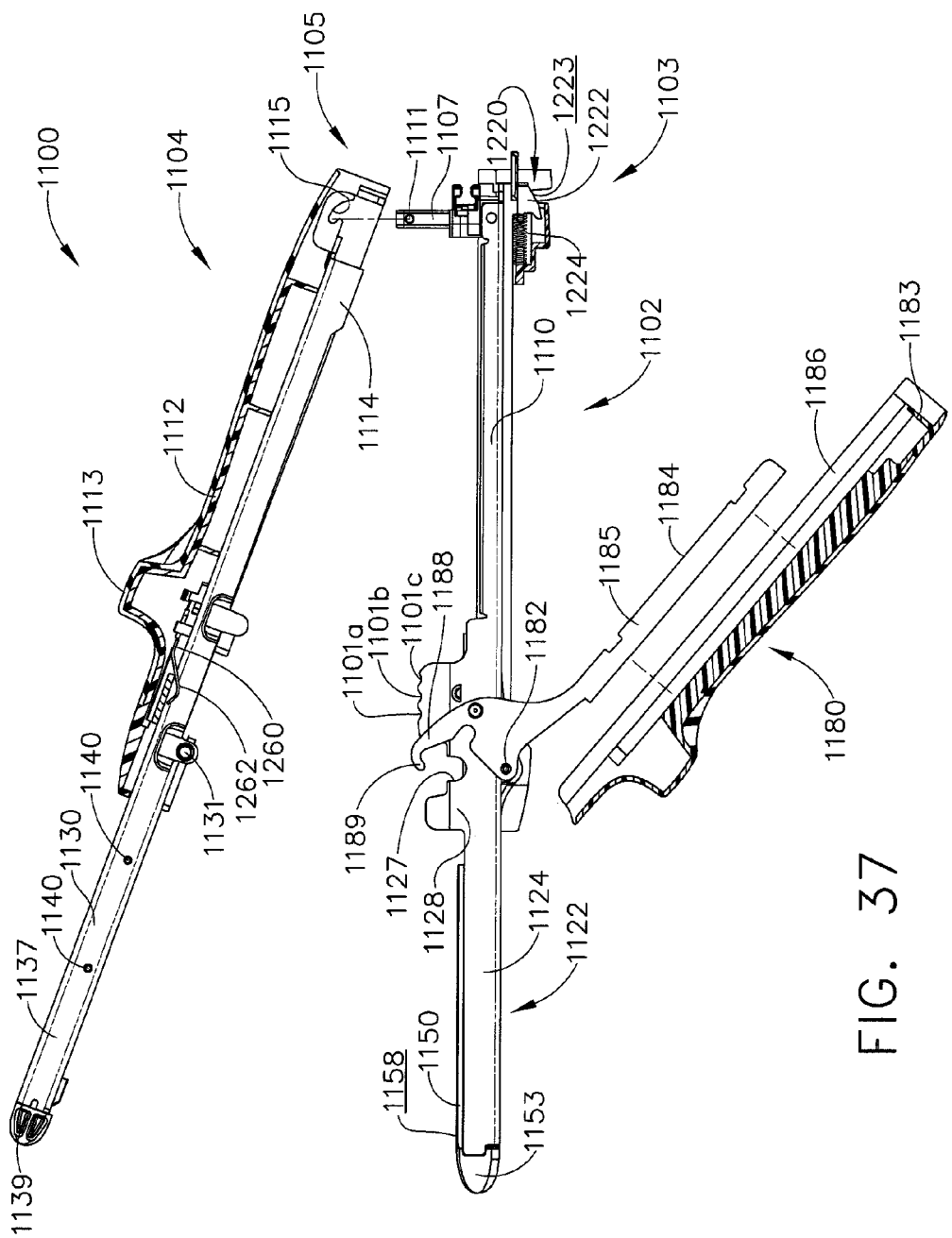
FIG. 37 is a partial cross-sectional view of the surgical stapling instrument of FIG. 34 illustrating first and second portions being assembled together.
Figure 39:
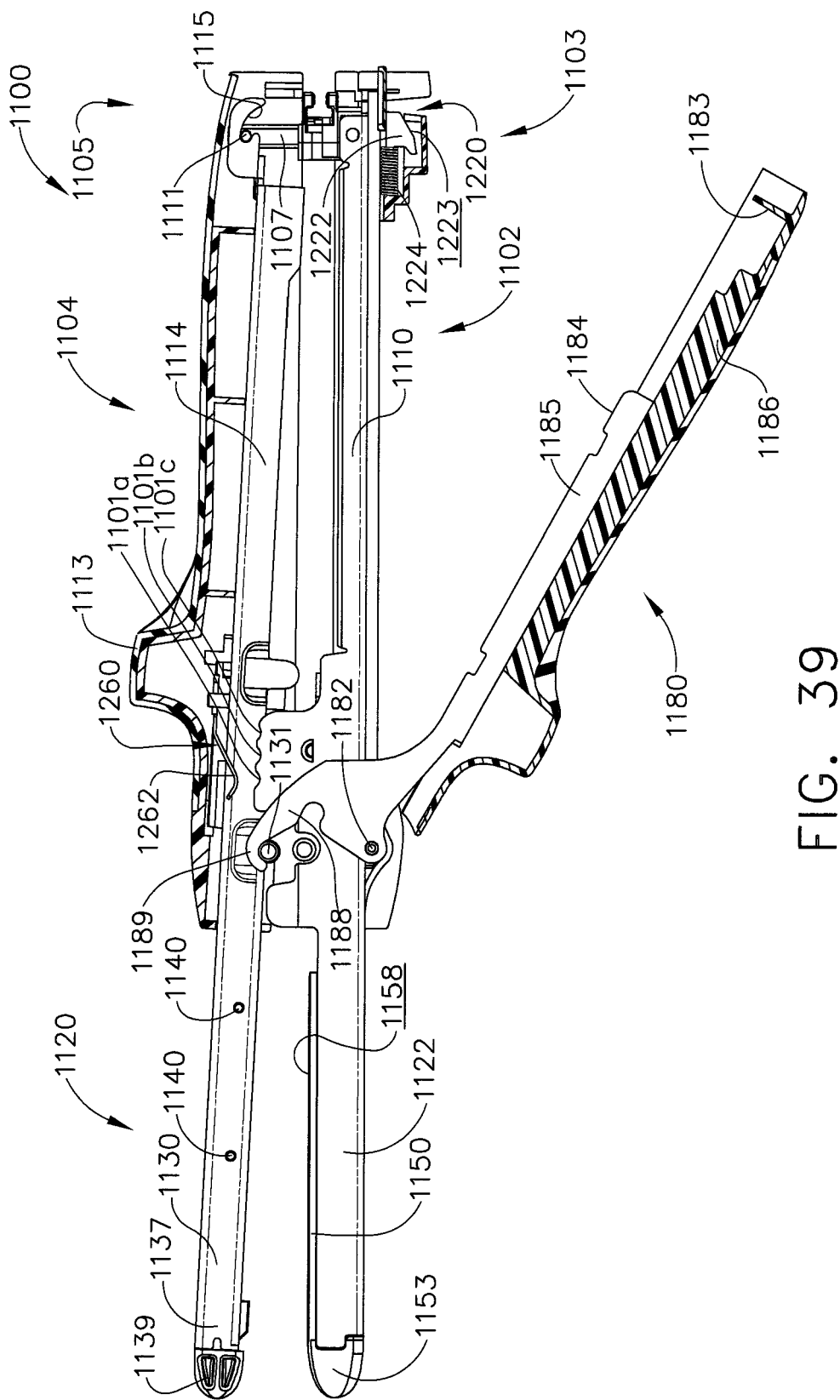
FIG. 39 is a partial cross-sectional view of the surgical stapling instrument of FIG. 34 illustrating a latch rotatably mounted to the first portion, wherein the latch is engaged with the second portion and wherein the latch has been rotated into a partially-closed position.
Figure 40:
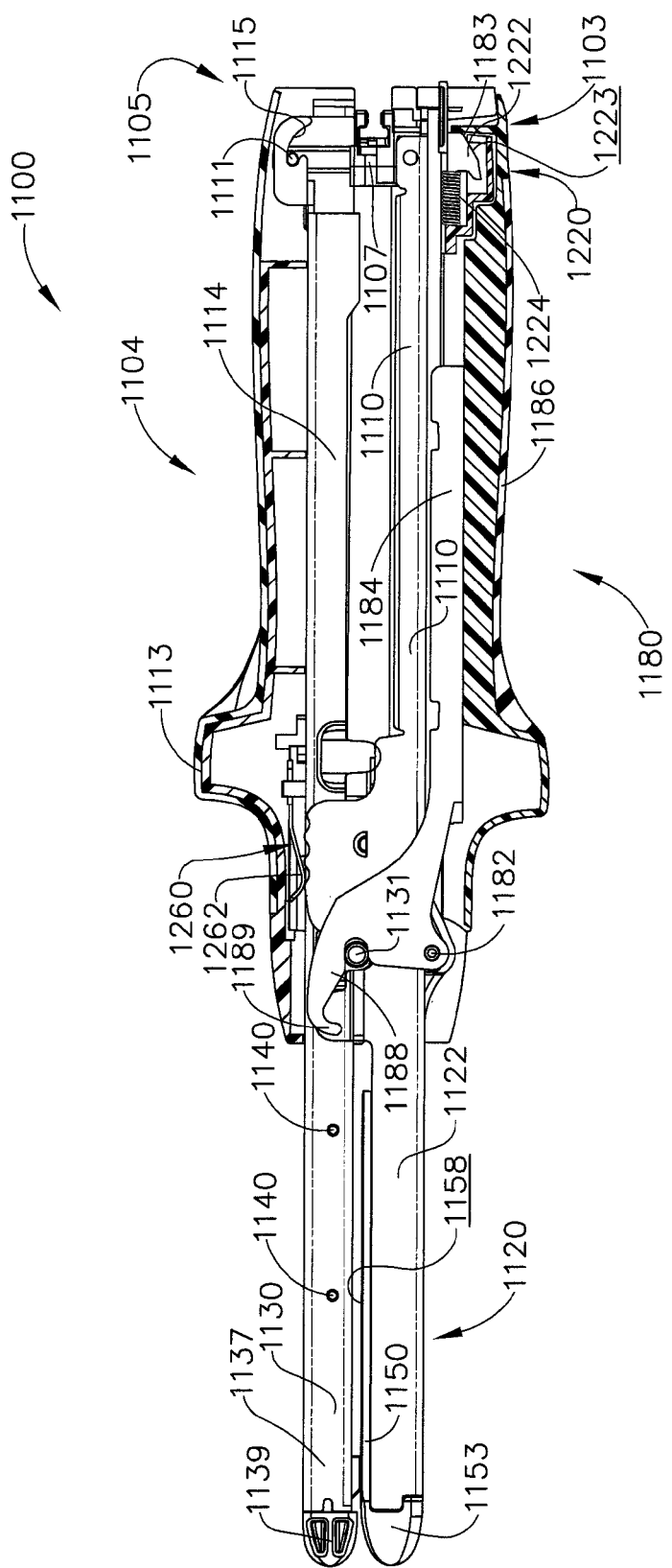
FIG. 40 is a partial cross-sectional view of the surgical stapling instrument of FIG. 34 illustrating the latch of FIG. 39 in a closed position.

In certain embodiments, referring now to FIGS. 37 and 38, latching mechanism 1180 can include latch frame 1184 and, in addition, latch cover 1186 assembled to latch frame 1184. In other various embodiments, the latch cover and the latch frame can comprise an integral unit or, in certain embodiments, the latching mechanism may not even include a cover. In certain embodiments, latch frame 1184 can be channel-shaped and can include a pair of opposed, elongated side walls 1185 which are spaced apart by a distance sufficient to span first frame portion 1110. In at least one embodiment, latch cover 1186 can be made of plastic, lightweight materials, and/or any other suitable materials, for example, while latch frame 1184 can be made of stainless steel and/or any other suitable material, for example. In certain embodiments, when latching mechanism 1180 is closed, as illustrated in FIG. 40, latch cover 1186 can be aligned with first handle cover 1108. Latch cover 1186 can include contoured portion 1187 which can be configured to assist a surgeon in manipulating surgical instrument 1100 wherein, in at least one embodiment, contoured portion 1187 can be aligned with, or at least substantially aligned with, protrusion 1109 extending from first handle cover 1108. Latching mechanism 1180 can further include one or more latch arms 1188 extending therefrom which can be configured to engage one or more latch projections 1131 extending from second handle portion 104 and pull and/or secure projections 1131 within recesses 1127 as illustrated in FIG. 40. In at least one embodiment, at least one of latch arms 1188 can be integrally-formed with latch frame 1184. In certain embodiments, referring to FIG. 39, at least one of latch arms 1188 can include a distal hook 1189 which can be configured to wrap around at least a portion of projections 1131 so as to encompass or surround, or at least partially encompass or surround, projections 1131. In at least one embodiment, latch arms 1188 can act as an over-center latch to maintain latching mechanism 1180 in its latched, or closed, position.

In use, in various circumstances, one of the first handle portion 1102 and the second handle portion 1104 can be positioned on a first side of tissue within a surgical site and the other handle portion can be rotated into position on the opposite side of the tissue. In such embodiments, staple cartridge 1150 can be positioned on one side of the tissue and anvil 1130 can be positioned on the other side of the tissue. Thereafter, as also outlined above, latching mechanism 1180 can be actuated such that it can be moved between an open position and a closed position in order to latch second handle portion 1104 to first handle portion 1102 and apply a clamping force to the tissue positioned between staple cartridge 1150 and anvil 1130. In certain circumstances, latching mechanism 1180 can be moved between an open position (FIG. 38), a partially-closed, or intermediate, position (FIG. 39), and a closed position (FIG. 40). In at least one such embodiment, referring to FIGS. 38 and 39, latching mechanism 1180 can be moved between an open position in which latch arms 1188 are not engaged with projections 1131 and a partially-closed position in which latch arms 1188 are engaged with projections 1131 such that, although anvil 1130 has been at least partially brought into opposition to staple cartridge 1150, a sufficient gap can remain between anvil 1130 and staple cartridge 1150 which can allow end-effector 1120 to be repositioned relative to the tissue, for example. Once the anvil 1130 and staple cartridge 1150 have been sufficiently positioned relative to the tissue, latching mechanism 1180 can be moved between its partially-closed position and a closed position, as illustrated in FIG. 40.

In various embodiments, further to the above, a surgical stapling instrument can further include a biasing member which can be configured to bias the first handle portion of a stapling instrument away from a second handle portion. In at least one embodiment, as described in greater detail further below, a spring, and/or any suitably resilient material, can be positioned intermediate the first and second handle portions such that the anvil and staple cartridge of the stapling instrument can be biased away from each other. In certain embodiments, the spring can be configured to at least partially separate the first and second handle portions such that a gap exists between the anvil and the staple cartridge, wherein the gap can be sufficient to allow tissue to be positioned therebetween. In use, a surgeon can position such a surgical stapling instrument without having to separate and hold the first and second handle portions apart from each other. Such an instrument may be especially useful when the stapling instrument is in a partially-closed configuration and the surgeon is manipulating the instrument within a surgical site. After the surgeon is satisfied with the positioning of the stapling instrument, the surgeon can compress and/or disengage the spring and place the stapling instrument in a closed configuration.

In various circumstances, as outlined above, the distal end of first handle portion 1102 can be moved relative to the distal end of second handle portion 1104, especially when latching mechanism 1180 is not engaged with, or only partially engaged with, projections 1131 of second handle portion 1104. In such circumstances, projections 1111 and slots 1115 at the proximal ends of the first and second handle portions can be configured to retain at least the proximal ends of the first and second handle portions together when the distal ends of the first and second handle portions are being moved relative to each other, for example. Stated another way, projections 1111 and slots 1115 can cooperate to prevent, or at least inhibit, first handle portion 1102 from becoming completely detached from second handle portion 1104. In certain embodiments, a first handle portion can include a first lock portion and a second handle portion can include a second lock portion, wherein the first and second lock portions can be configured to be engaged with one another and prevent the first handle portion from becoming completely detached from the second handle portion. In at least one embodiment, projections 1111 can comprise the first lock portion and slots 1115 can comprise the second lock portion. Previous stapling instruments lacked such lock portions and instead relied on a sole latching mechanism to keep the first and second handle portions together. In circumstances where the latching mechanisms of these previous stapling instruments were not fully engaged with both of the first and second handle portions, the first and second handle portions could become completely detached from one another, thereby requiring a surgeon, for example, to reposition and reassemble the handle portions. In certain circumstances, a complete detachment of the first and second handle portions of these previous staples could expose at least a portion of a cutting member.

In various embodiments, as outlined above, latching mechanism 1180 can be configured to be moved between an open position, a partially-closed position, and a closed position. When latching mechanism 1180 is in its open position, as also outlined above, projections 1111 can be inserted into and/or removed from slots 1115. When latching mechanism 1180 is in its partially-closed position, referring to FIG. 39, latch arms 1188 can be configured to engage latch projections 1131 such that projections 1111 cannot be removed from slots 1115. In at least one such embodiment, latch arms 1188 and latch projections 1131 can be configured to prevent, or at least inhibit, second handle portion 1104 from being moved distally with respect to first handle portion 1102 and, as a result, prevent, or at least inhibit, projections 1111 from being disengaged from slots 1115. Correspondingly, latch arms 1188 and latch projections 1131 can be configured to prevent first handle portion 1102 from being moved proximally with respect to second handle portion 1104. Similar to the above, in various embodiments, latch arms 1188 and latch projections 1131 can also be configured to prevent, or at least inhibit, projections 1111 from being removed from slots 1115 when latching mechanism 1180 is in its closed position (FIG. 40). In certain embodiments, further to the above, latch projections 1131 can extend from second handle portion 1104 at a location which is intermediate its proximal and distal ends. In at least one such embodiment, projections 1111 and slots 1115 can be configured to hold the first and second handle portions together at their proximal ends while latching mechanism 1180 can be utilized to hold the first and second handle portions together at an intermediate location. In any event, in certain embodiments, the first and second handle portions cannot be disengaged from one another unless latching mechanism 1180 is moved into its fully open position. In at least one such embodiment, projections 1111 and slots 1115 cannot be disengaged from one another when latching mechanism 1180 is in a closed and/or partially-closed position.

Once anvil 1130 and staple cartridge 1150 have been sufficiently positioned, the tissue positioned intermediate anvil 1130 and staple cartridge 1150 can be stapled and/or incised. In various embodiments, referring to FIG. 36, surgical stapling instrument 1100 can further include pusher bar assembly 1200 which can be configured to advance and/or retract staple sled assembly 1160 within staple cartridge 1150, for example. In at least one embodiment, pusher bar assembly 1200 can include pusher bar 1202 and firing actuator 1204, wherein firing actuator 1204 can be configured to move pusher bar 1202 and staple sled assembly 1160 distally to deploy staples from staple cartridge 1150 and deform the staples against anvil 1130 as described above. In at least one embodiment, referring to FIGS. 44 and 45, staple sled 1162 can include a groove, channel, or slot 1161 which can be configured to receive, and can be operably connected to, a distal end 1201 (FIG. 36) of pusher bar 1202. In certain embodiments, staple sled assembly 1160 can be operably engaged with pusher bar 1202 when staple cartridge 1150 is inserted into staple cartridge channel 1122. In at least one embodiment, distal end 1201 and slot 1161 can include cooperating features which can allow distal end 1201 and slot 1161 to be assembled in a transverse direction but prevent, or at least inhibit, distal end 1201 and slot 1161 from being disassembled from one another in a proximal direction and/or distal direction. In other embodiments, pusher bar 1202 can be advanced distally before contacting and engaging staple sled assembly 1160. In at least one such embodiment, the staple sled assembly 1160 can remain stationary until contacted by pusher bar 1202. In any event, as outlined above, actuator 1204 can be operably connected to pusher bar 1202 such that a pushing and/or pulling force can be applied to actuator 1204 and transmitted to pusher bar 1202. In certain embodiments, as described in greater detail below, actuator 1204 can be pivotably connected to a proximal end 1203 of pusher bar 1202 such that actuator 1204 can be selectively rotated between at least first and second positions.

Figure 46:
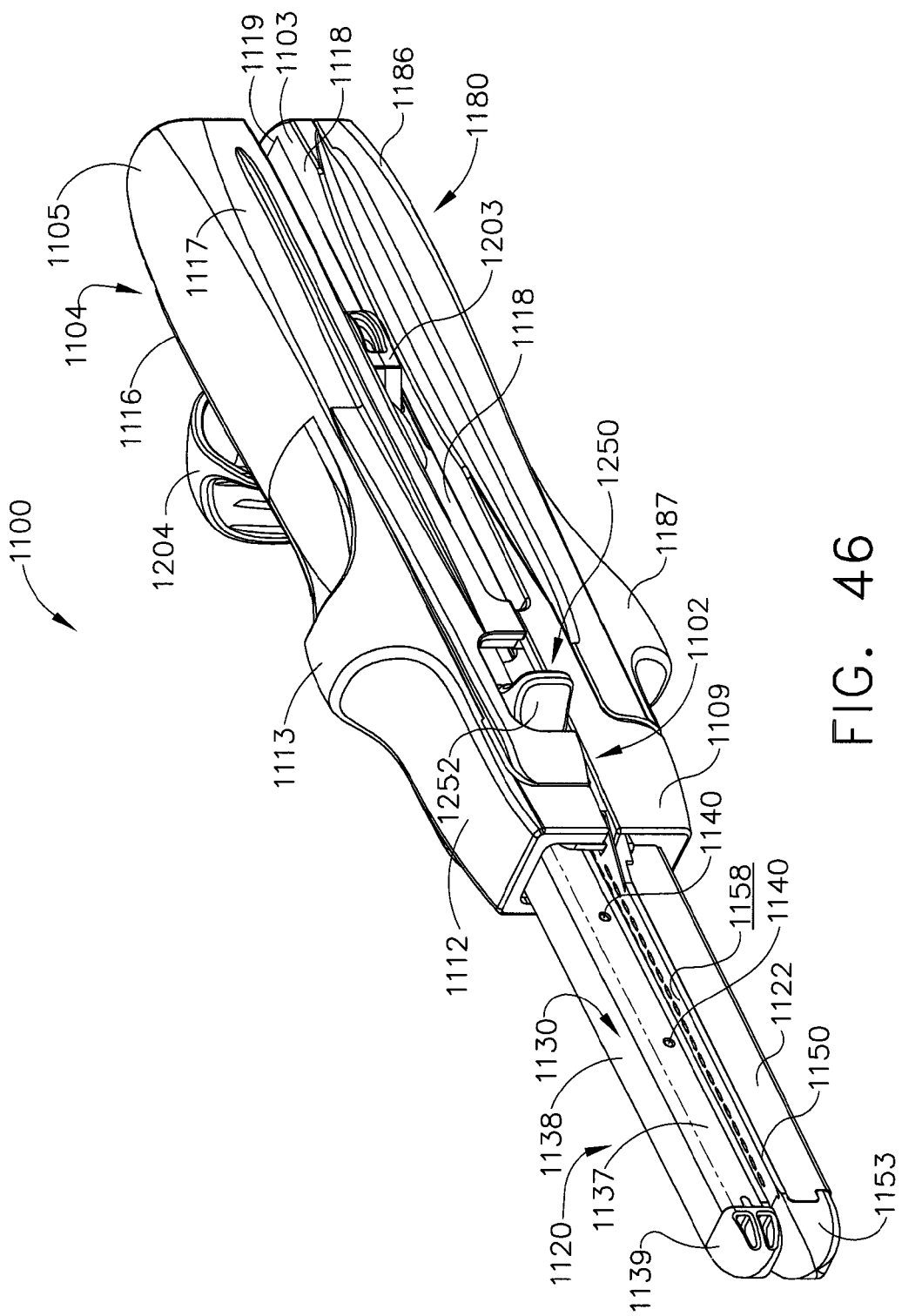
FIG. 46 is a perspective view of the surgical stapling instrument of FIG. 34 illustrating a firing actuator moved distally along a first side of the surgical stapling instrument.
Figure 47:
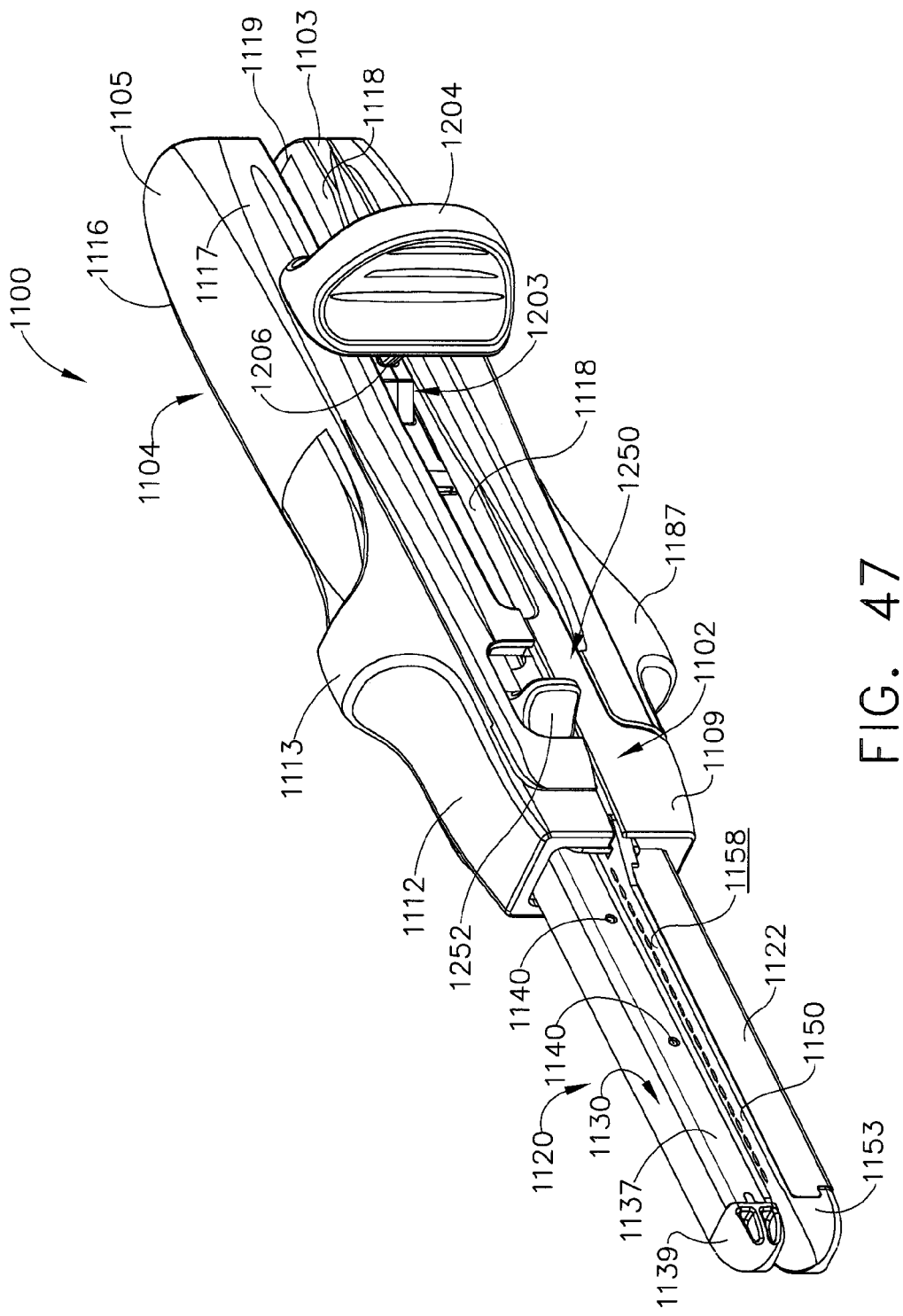
FIG. 47 is a perspective view of the surgical stapling instrument of FIG. 34 illustrating the firing actuator of FIG. 46 moved distally along a second side of the surgical stapling instrument.

Further to the above, referring to FIGS. 34, 46, and 47, actuator 1204 can be movable between a first position on a first side 1116 of surgical stapling instrument 1100 (FIG. 46), a second position on a second side 1117 (FIG. 47), and an intermediate position (FIG. 34) located at the proximal ends 1103 and 1105 of the first and second handle portions 1102 and 1104. Once actuator 1204 has been rotated into position on one of the first and second sides 1116, 1117, actuator 1204 can be advanced distally. In various circumstances, as a result, a surgeon may select whether to move actuator 1204 distally along first side 1116 or second side 1117. Such circumstances may arise when it is more likely that actuator 1204 may impinge on tissue surrounding the surgical site, for example, when actuator 1204 is moved distally along one side of the surgical instrument as compared to the other. In various embodiments, referring to FIGS. 35 and 36, actuator 1204 can include arm 1206 extending therefrom where arm 1206 can be pivotably mounted to proximal end 1203 of pusher bar 1202. In certain embodiments, referring once again to FIGS. 34, 46, and 47, surgical instrument 1100 can include a first slot (not illustrated) extending along first side 1116 and a second slot 1118 extending along second side 1117, wherein the first and second slots can be configured to slidably receive at least a portion of actuator 1204. In at least one embodiment, the sidewalls of the first and second slots can confine, or at least assist in confining, the movement of actuator 1204 such that it can be moved along a predetermined path. Referring to FIG. 47, second slot 1118, for example, can be defined between first handle portion 1102 and second handle portion 1104 such that, when actuator 1204 is moved distally along second side 1117, arm 1206 of actuator 1204 can be slid intermediate the first and second handle portions. Similar to the above, the first slot can also be defined intermediate the first and second handle portions. In various embodiments, referring again to FIGS. 46 and 47, surgical instrument 1100 can further include intermediate slot 1119 which can also be configured to allow arm 1206, and/or any other suitable portion of actuator 1204, to slide therein. In at least one such embodiment, intermediate slot 1119 can connect the first and second slots such that, when actuator 1204 is positioned in its intermediate position, actuator 1204 can be moved into either one of its first and second positions. In certain embodiments, the first slot, second slot 1117, and intermediate slot 1119 can be parallel, or at least substantially parallel, to one another and/or lie in the same plane, although other embodiments are envisioned in which one or more of the slots is not parallel to the others and/or lies in a different plane. Furthermore, although the first and second sides of the illustrated embodiment are located on opposite sides of surgical instrument 1100, other embodiments are envisioned where the first and second slots, for example, are located on adjacent sides and/or sides which are not directly opposite to each other. Furthermore, other embodiments are envisioned in which the sides of a stapling instrument are not readily discernable, such as instruments having round and/or arcuate portions.

In various embodiments, further to the above, surgical stapling instrument 1100 can further include a locking mechanism which can prevent, or at least inhibit, actuator 1204 and, correspondingly, staple sled assembly 1160, from being advanced prematurely. In at least one embodiment, the locking mechanism can be configured to prevent, or at least inhibit, actuator 1204 from being advanced distally prior to latching mechanism 1180 being moved into a closed, or an at least partially-closed, position. In certain embodiments, generally referring to FIG. 38, surgical stapling instrument 1100 can further including locking mechanism 1220 which can be engaged with actuator 1204 and can remain engaged with actuator 1204 while latching mechanism 1180 is in a fully open position (FIG. 38) and/or an at least substantially-open position. In various embodiments, locking mechanism 1220 can include lock 1222 which can be biased into engagement with actuator 1204 by a biasing force applied thereto by lock spring 1224, for example. In at least one such embodiment, actuator 1204 can include one or more grooves, channels, or slots (not illustrated) which can be configured to receive at least a portion of lock 1222. In use, locking mechanism 1220 can hold actuator 1204 in position until latching mechanism 1180 is moved into its fully closed position (FIG. 40) and/or an at least substantially closed position. In such circumstances, in at least one embodiment, latching mechanism 1180 can be configured to engage locking mechanism 1220 and disengage lock 1222 from actuator 1204. In at least one such embodiment, referring to FIGS. 38-40, latching mechanism 1180 can further include cam 1183 which can be configured to engage cam surface 1223 on lock 1222 when latching mechanism 1180 is moved into its closed position and, as a result, slide, and/or otherwise move, lock 1222 away from actuator 1204. In various embodiments, cam 1183 can comprise a wall, rib, and/or ridge extending from latch cover 1186 and/or latch frame 1184. In any event, once lock 1222 has been sufficiently disengaged from actuator 1204, in at least one embodiment, actuator 1204 can be moved from its intermediate position, illustrated in FIG. 34, into one of its first and second positions, as illustrated in FIGS. 46 and 47.

Figure 48:
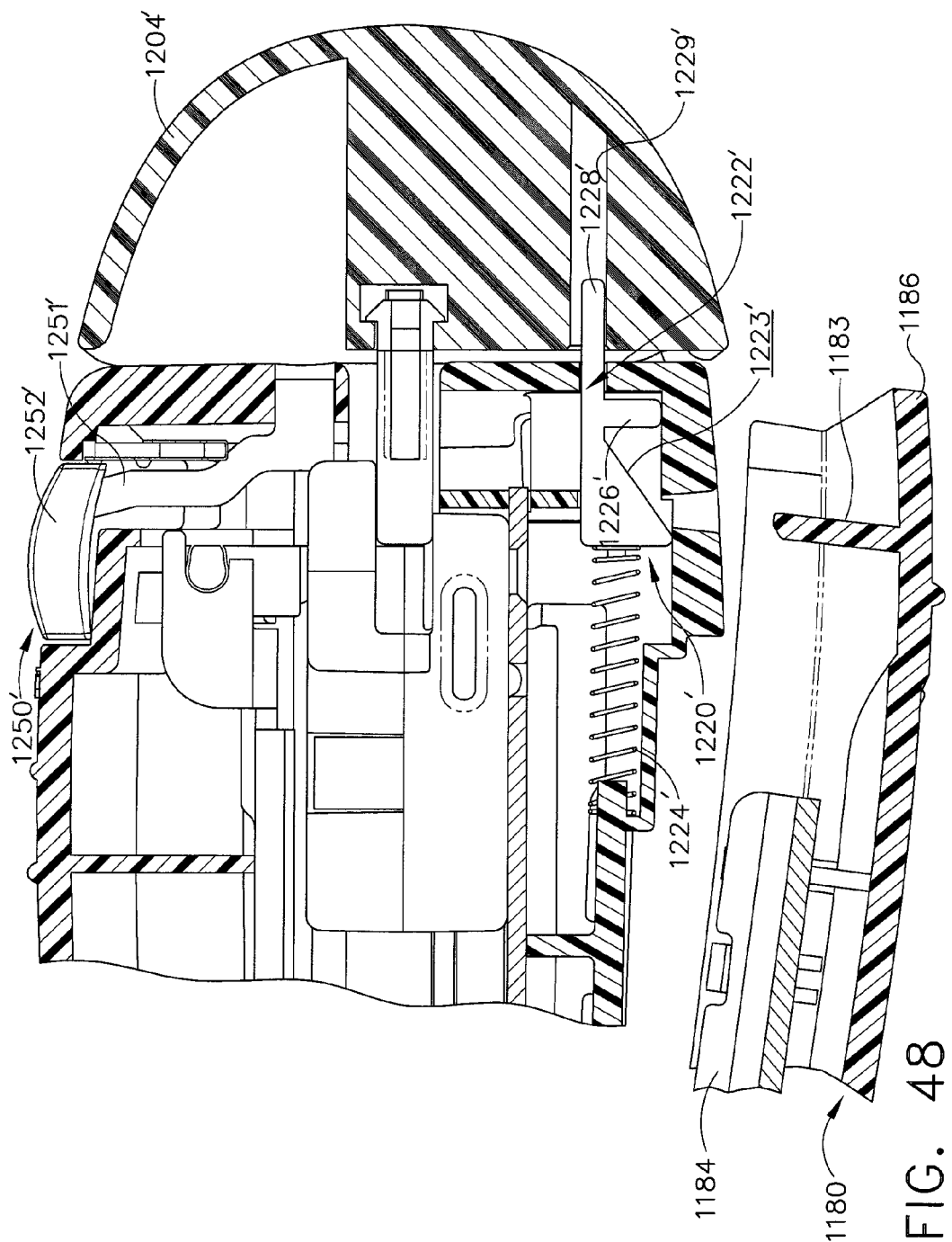
FIG. 48 is a cross-sectional view of a surgical stapling instrument in accordance with at least one alternative embodiment of the present invention illustrating a latch in a partially-closed position and a locking mechanism engaged with a firing actuator.
Figure 49:
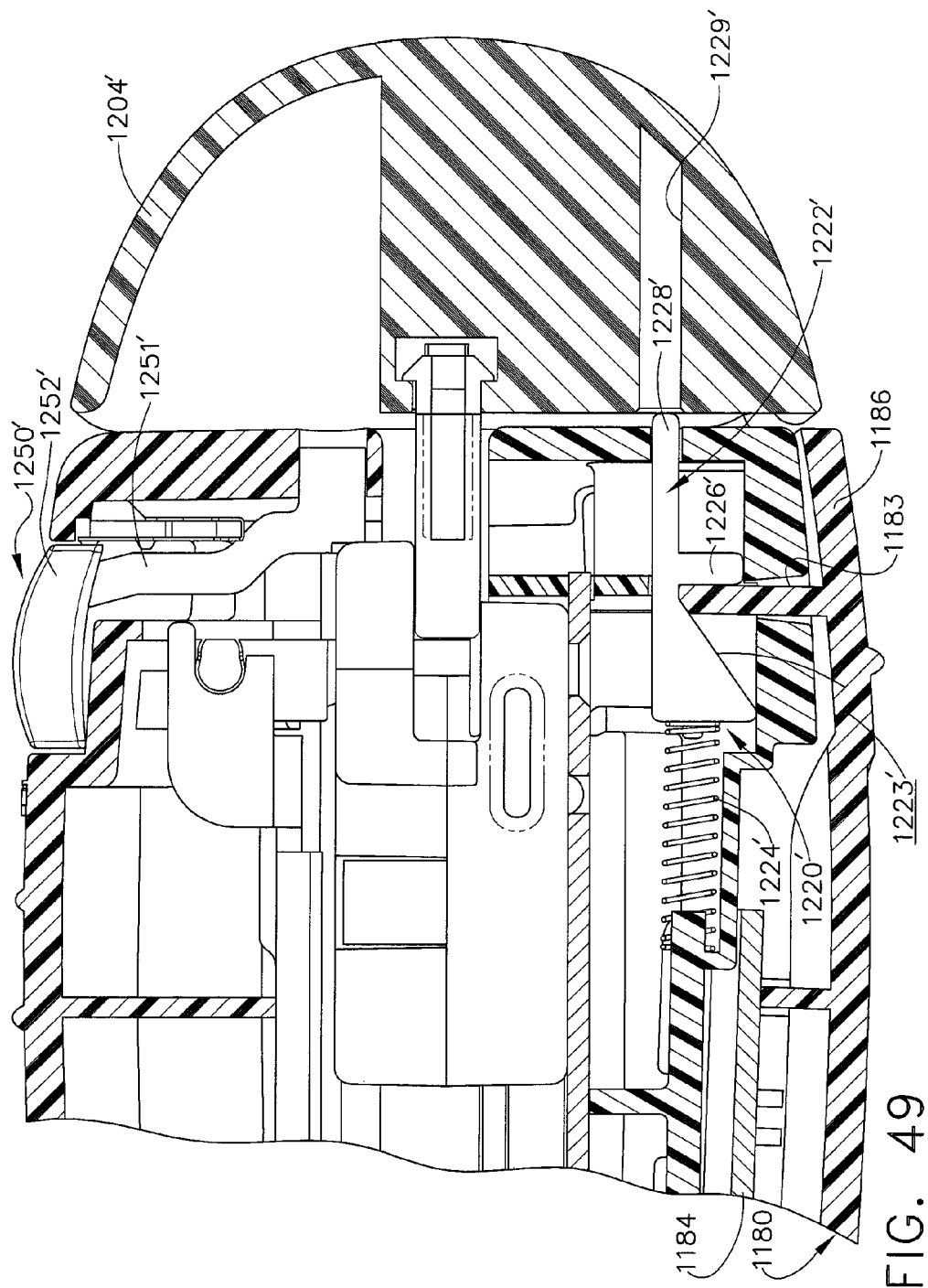
FIG. 49 is a cross-sectional view of the surgical stapling instrument of FIG. 48 wherein the latch has been moved into a closed position and has disengaged the locking mechanism from the firing actuator.

As described above, locking mechanism 1220 can be configured to prevent, or at least inhibit, drive bar 1202 from being advanced distally prior to latching mechanism 1180 being moved into a predetermined position, such as, for example, a closed position and/or partially-closed position. Advantageously, locking mechanism 1220 may also prevent, or at least inhibit, staple sled assembly 1160 from being advanced prior to the first handle portion 1102 and the second handle portion 1104 being assembled together. In effect, locking mechanism 1220 can prevent tissue positioned intermediate anvil 1130 and staple cartridge 1150 from being cut and/or stapled prior to anvil 1130 and staple cartridge 1150 being properly positioned relative to the tissue. Also, in effect, locking mechanism 1220 can prevent staples from being deployed into the tissue prior to an appropriate clamping force being applied to the tissue. In any event, when latching mechanism 1180 is returned to its fully open position, and/or a partially-open position, cam 1183 can be moved away from lock 1222 such that lock spring 1124 can bias lock 1222 into engagement with actuator 1204 once again. In various other embodiments, referring to FIGS. 38 and 39, locking mechanism 1220' can include a lock 1222' comprising a cam surface 1223' and, in addition, a stop 1226' which can limit the relative movement of lock 1222'. In at least one embodiment, cam 1183, for example, can be configured to contact cam surface 1223' and, owing to the contoured, beveled, and/or angled surface of cam surface 1223', cam 1183 can be configured to drive lock 1222' distally as illustrated in FIG. 49. Lock 1222' can be driven distally such that pin 1228', which extends from lock 1222', can be moved between a first position (FIG. 48) in which it is positioned within aperture 1229' in actuator 1204' and a second position (FIG. 49) in which pin 1228' has been sufficiently removed from aperture 1229'. In various embodiments, stop 1226' can be configured such that, as lock 1222' is driven distally, stop 1226' can come into contact with cam 1183 once lock 1222' has been sufficiently displaced. In such embodiments, stop 1226' can be configured to control the second, or displaced, position of lock 1222'. Similar to the above, as actuator 1180 is moved out of its closed position and cam 1183 is disengaged from locking mechanism 1220', lock spring 1224' can move lock 1222' into engagement with actuator 1204' once again.

In various embodiments, as described above, a firing actuator can be utilized to move a pusher bar, staple sled, and/or cutting member between first and second positions. As also described above, pusher bar assembly 1200, for example, can be utilized to move a staple sled assembly, such as staple sled assembly 1160, for example, between a proximal position (FIG. 43) and a distal position. In certain embodiments, a staple cartridge, such as staple cartridge 1150, for example, can include a staple sled assembly 1160 contained therein, wherein staple sled assembly 1160 can be positioned in a proximal position, as illustrated in FIG. 43, when the staple cartridge is assembled to or inserted into staple cartridge channel 1122. In at least one such embodiment, referring to FIGS. 41-43, staple cartridge 1150 can include further housing 1170 which can be configured to cover at least a portion of cutting member 1164 when staple sled assembly 1160 is in its proximal position, for example. In various embodiments, housing 1170 can be configured to protect a surgeon, for example, when handling the staple cartridge, when inserting the staple cartridge into the surgical stapler, and/or assembling two or more portions of the surgical stapler together, for example. In at least one such embodiment, at least an upper portion of cutting edge 1165 can extend above deck, or top surface, 1158 of staple cartridge 1150 and, absent a protective housing, such as housing 1170, for example, the upper portion of cutting edge 1165 may be exposed.

In various embodiments, as described above, cutting member 1165 can be at least partially positioned within slot, or channel, 1156 and, as illustrated in FIG. 43, at least the upper, or top, portion of cutting member 1164 can extend above deck 1158. In at least one embodiment, referring to FIGS. 41-43, housing 1170 can include a first wall, or portion, 1172 extending from a first portion 1157 of staple cartridge body 1152, a second wall, or portion, 1174 extending from a second portion 1159 of staple cartridge body 1152, and a top wall, or portion, 1176 extending between first wall 1172 and second wall 1174. In certain embodiments, a housing may comprise only one support wall, or support portion, extending from a staple cartridge body and, in addition, a top wall, or top portion, extending therefrom. In other embodiments, a housing may comprise one or more side walls, or portions, and no top wall. In at least one such embodiment, the side walls of the housing can be configured such that they extend above the top of the cutting member, or at least extend above a cutting edge of the cutting member, for example. In any event, as illustrated in FIG. 43, at least a portion of cutting member 1164 can be positioned underneath top wall 1176 and/or between side walls 1172 and 1174 when staple sled assembly 1160 is in its proximal position. In certain embodiments, cutting member 1164 can be entirely positioned underneath top wall 1176, and/or entirely positioned within housing 1170. In at least one embodiment, cutting member 1164 can be positioned underneath top wall 1176 such that cutting surface 1165 does not extend beyond the distal edge 1175 and/or the proximal edge 1177 of top wall 1176. In at least one embodiment, housing 1170 can include a rear wall 1178 which can be configured to limit the proximal movement of cutting member 1164 and/or any other portion of staple sled assembly 1160. In various embodiments, at least a portion of housing 1170, for example, can be integrally-formed with staple cartridge body 1152. In at least one such embodiment, first wall 1172, second wall 1174, top wall 1176, and/or rear wall 1178 can be formed when staple cartridge body 1152 is injection molded, for example. In certain embodiments, at least a portion of housing 1170 can be assembled to staple cartridge body 1152 via a snap-fit arrangement, press-fit arrangement, and/or any other suitable manner.

In various embodiments, further to the above, cutting member 1164 can be defined by a planar, or an at least substantially planar, body having a knife edge extending along at least one side of the cutting member body. In at least one such embodiment, first wall 1172 and/or second wall 1174 can be configured and arranged such that they can include planar, or at least substantially planar, interior surfaces 1173 which are parallel, or at least substantially parallel, to the side surfaces of cutting member 1164. In certain embodiments, cutting member 1164 can be closely received between the interior surfaces 1173 of walls 1172 and 1174. In at least one such embodiment, the distance between walls 1172 and 1174 may be the same as, or at least substantially the same as, the width of slot 1156. In any event, a housing can be configured such that at least a portion of the housing extends over at least a portion of slot 1156, for example. In certain embodiments, housing 1170 can completely enclose or surround a cutting member 1164 and/or cutting surface 1165. In at least one embodiment, although not illustrated, a housing can include a break-away and/or incisable portion which can be at least partially detached, separated, and/or otherwise deformed in order to permit a cutting member to exit the housing. In at least one such embodiment, the tissue cutting surface can be configured to contact the housing to break and/or incise a housing wall, for example. In various embodiments, the housing wall can include a thin portion, a reduced-thickness portion, score mark, and/or any other configuration to facilitate the deformation and/or incision of the housing wall. In certain embodiments, a cutting member can include one or more additional cutting surfaces and/or anvils, for example, which can be configured to deform and/or incise the housing. In at least one embodiment, the housing can include a movable and/or flexible portion, such as a hinged member and/or flexible flap, for example, which can be configured to sufficiently move and/or flex to allow the cutting member to pass thereby. In any event, embodiments are envisioned in which the cutting member can have any suitable configuration for incising tissue and the protective housing can have any suitable configuration for at least partially enclosing or surrounding the cutting member. Furthermore, although a cutting member can comprise a sharpened edge as described above, other suitable cutting members are envisioned, such as those supplied with an electrical current sufficient to dissect tissue, for example.

As described above, housing 1170 can be configured to at least partially cover, enclose, and/or surround a cutting member when it is in its proximal position. In various embodiments, the cutting member can be advanced distally to incise tissue, for example, and then retracted proximally in order to position the cutting member within housing 1170 once again. In such embodiments, the cutting member can be at least partially covered by housing 1170 when the staple cartridge is assembled to and removed from a surgical stapling instrument. In certain embodiments, a new, or unspent, staple cartridge can be inserted into the staple cartridge channel to replace the at least partially spent staple cartridge. In at least one such embodiment, the new staple cartridge can include a new cutting member and/or staple sled assembly positioned therein, although embodiments are envisioned in which the previously-used cutting member and/or staple sled assembly can be sufficiently withdrawn from the spent staple cartridge and advanced into the new staple cartridge in order to be reused once again. In embodiments where a new cutting member and/or staple sled assembly is provided with each new staple cartridge, a sharp cutting edge, for example, can be utilized with each staple cartridge.

In various embodiments, although not illustrated, a staple cartridge can include two or more housings configured to at least partially cover a cutting member when it is in two or more positions. In at least one embodiment, a staple cartridge can include a proximal housing configured to at least partially cover the cutting member when it is in a proximal position, for example, and, in addition, a distal housing configured to at least partially cover the cutting member when it is in a distal position, for example. In at least one such embodiment, the cutting member can be positioned within the proximal housing when the staple cartridge is assembled to a surgical stapling instrument and, in certain embodiments, the cutting member can be advanced into the distal housing after it has transected tissue positioned within the end-effector, for example. In such embodiments, as a result, the cutting member can be at least partially positioned within the distal housing when the staple cartridge is removed from the surgical stapler. Such embodiments may be particularly useful when a vessel, for example, is positioned intermediate the proximal housing and the distal housing of the staple cartridge. In various embodiments, although not illustrated, a cutting member can be moved proximally from a distal position to a proximal position, and/or any other suitable position.

Figure 92:
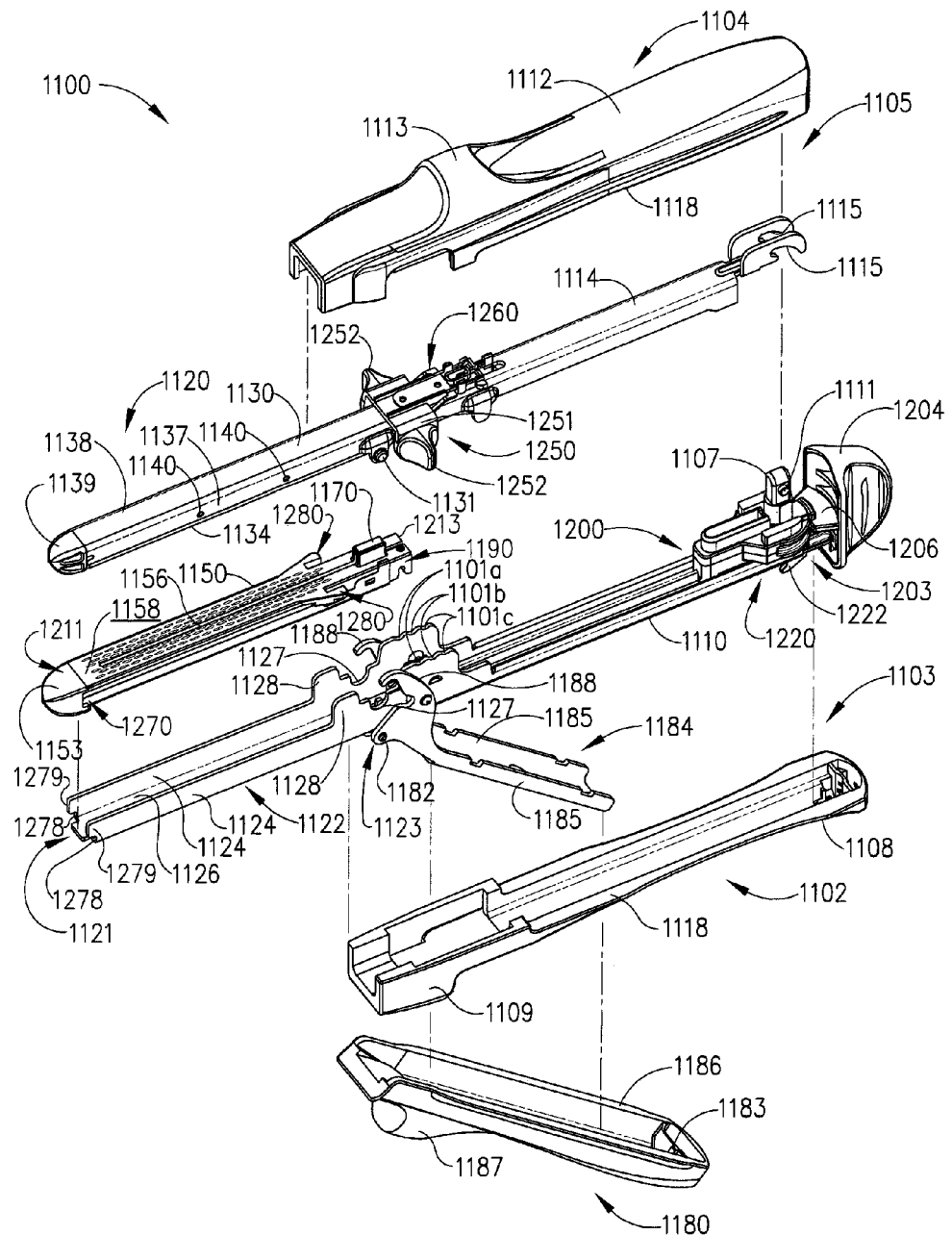
FIG. 92 is an exploded perspective view of the surgical stapling instrument of FIG. 34.

In various embodiments, as discussed above, staple cartridge 1150 can be inserted into staple cartridge channel 1122. Referring now to FIG. 92, a proximal end 1213 of staple cartridge 1150 can be positioned within a proximal end 1123 of staple cartridge channel 1122 while a distal end 1211 of staple cartridge 1150 can be positioned within a distal end 1121 of staple cartridge channel 1122. In at least one embodiment, the distal end 1121 of staple cartridge channel 1122 can comprise one or more projections and/or one or more recesses which can be correspondingly aligned with one or more projections and/or one or more recesses in the distal end 1211 of staple cartridge 1150, for example. In at least one such embodiment, each sidewall 1124 of staple cartridge channel 1122 can comprise a projection, or tab, 1279 and a recess, or slot, 1278, wherein each side of staple cartridge 1150 can comprise, referring to FIG. 95, a projection 1274 configured to be positioned within a recess 1278 and, in addition, a recess 1270 configured to receive a projection 1279. In various embodiments, each recess 1270 of staple cartridge 1150 can comprise opposing sidewalls 1272 and 1273 and a distal surface 1271, wherein the distal surface 1271 can be positioned against the projection 1279 positioned therein when the staple cartridge 1150 is positioned in staple cartridge channel 1122. In various circumstances, as discussed in greater detail below, the distal surfaces 1271 of recesses 1270 can serve as a datum surface from which certain features of the staple cartridge 1150 can be predetermined. In some circumstances, the distal end 1211 of staple cartridge 1150 can be aligned with and/or inserted into the distal end 1121 of staple cartridge channel 1122 before the proximal end 1213 of staple cartridge 1150 is inserted into the proximal end 1123 of staple cartridge channel 1122. For example, the distal end 1211 of staple cartridge channel 1150 can be aligned with the staple cartridge channel 1122 such that projections 1279 are positioned within recesses 1270 wherein, thereafter, the staple cartridge 1150 can be rocked, or rotated, toward staple cartridge channel 1122 such that proximal end 1213 of staple cartridge 1150 is inserted into the proximal end 1123 of staple cartridge channel 1122.

Figure 93:
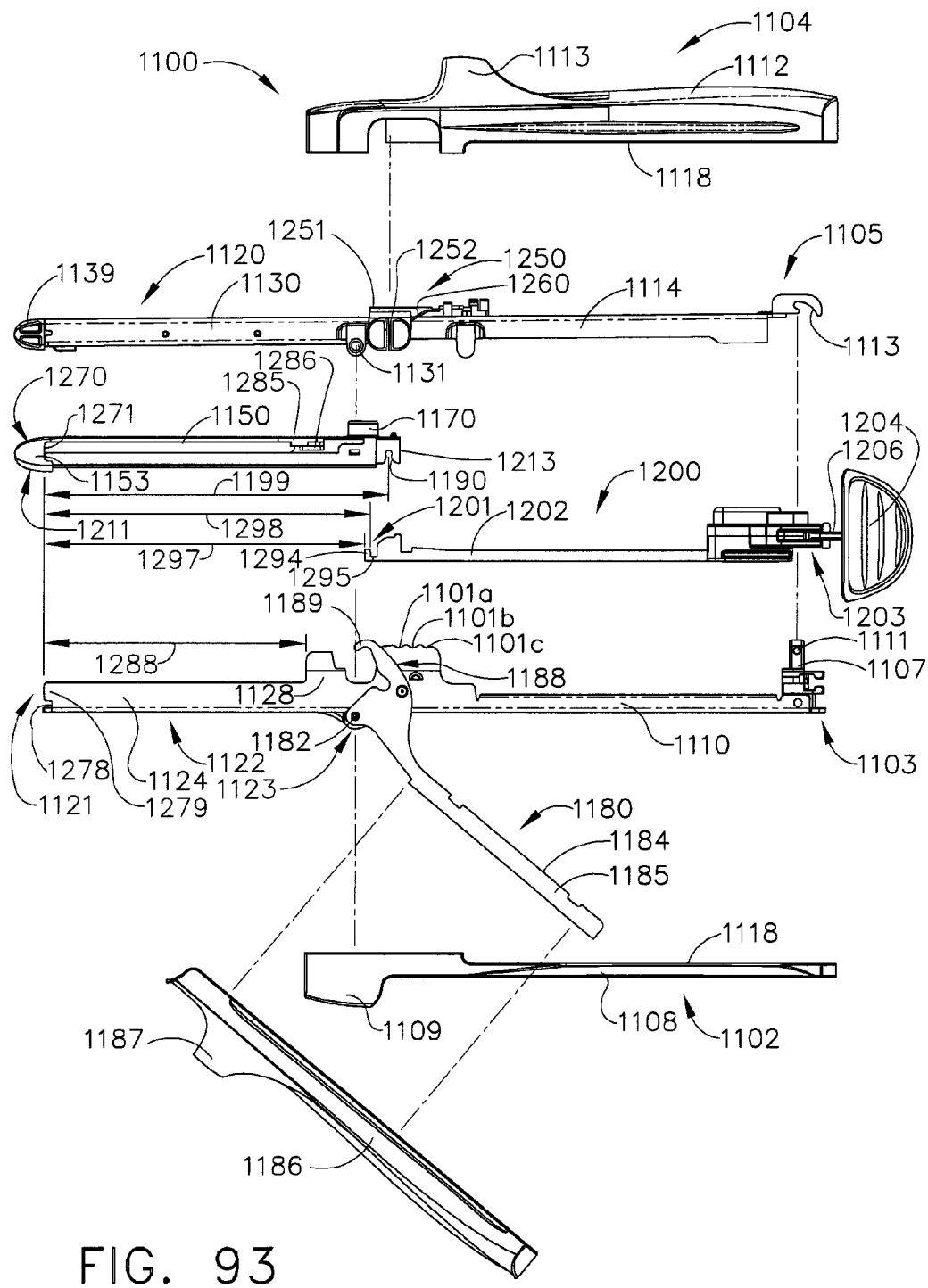
FIG. 93 is an exploded elevational view of the surgical stapling instrument of FIG. 34.
Figure 94:
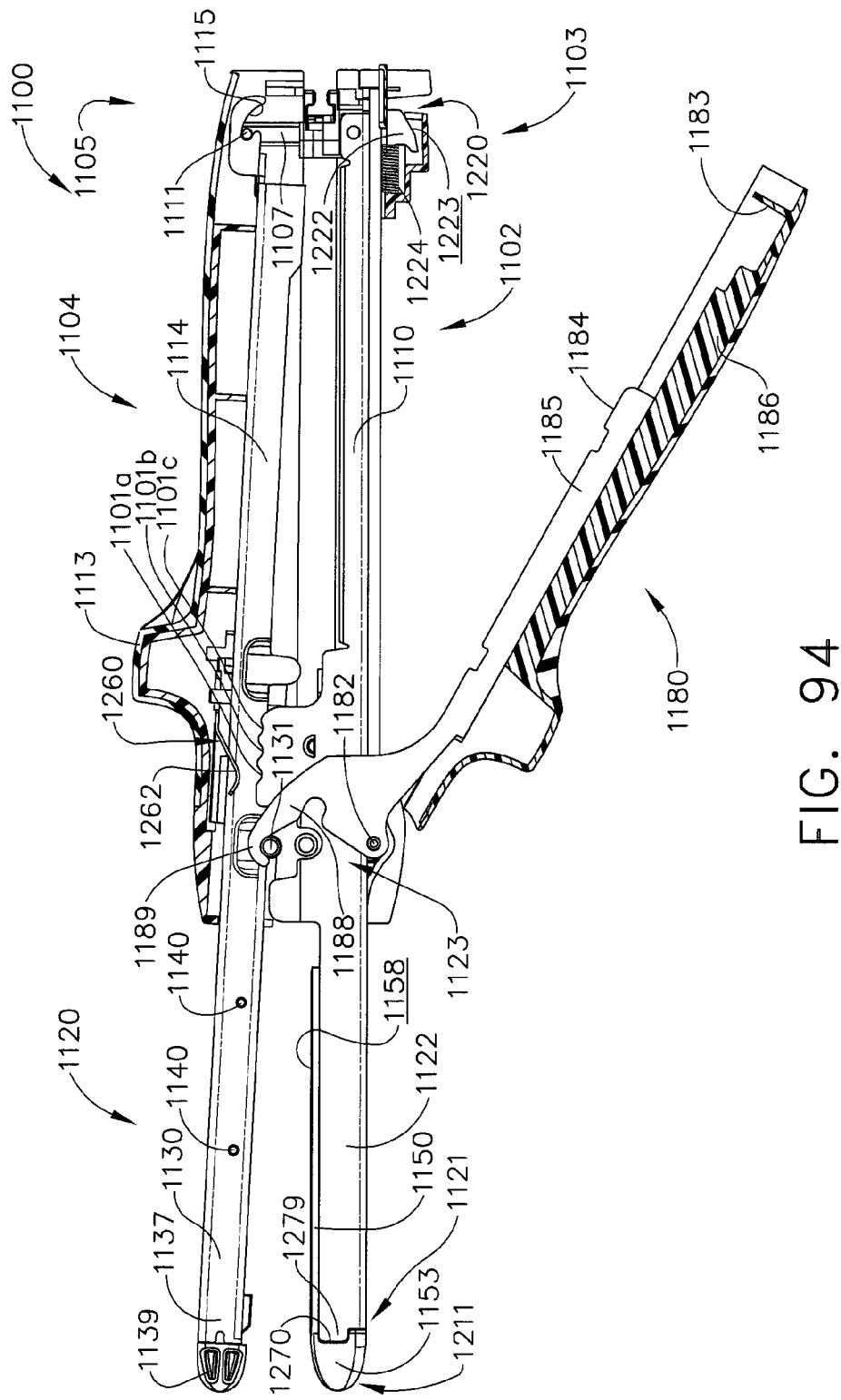
FIG. 94 is a partial cross-sectional view of the surgical stapling instrument of FIG. 34 illustrating a latch rotatably mounted to the first portion, wherein the latch is engaged with the second portion and wherein the latch has been rotated into a partially-closed position.
Figure 95:
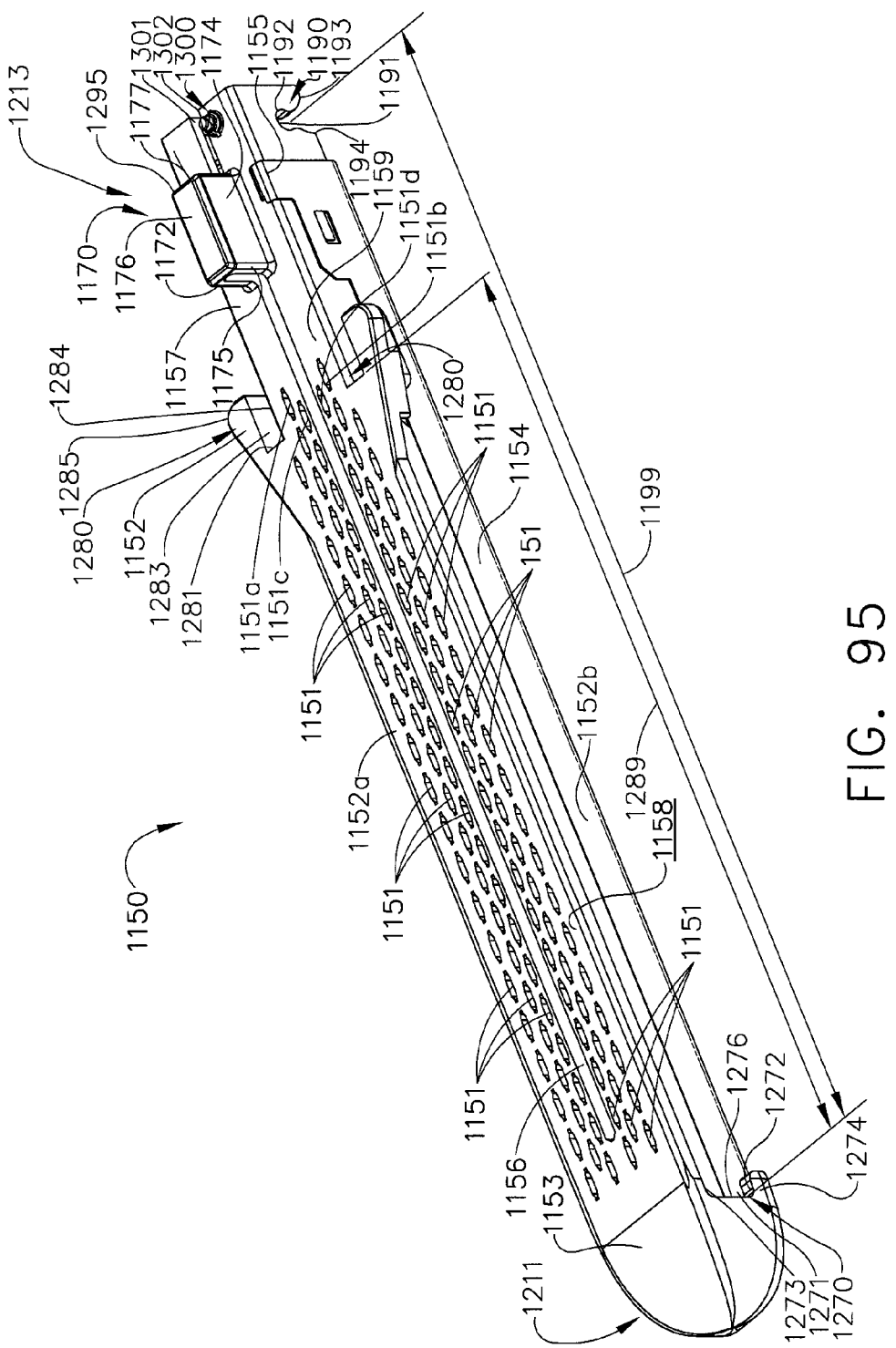
FIG. 95 is a perspective view of a staple cartridge assembly of the surgical stapling instrument of FIG. 34.

When distal end 1211 of staple cartridge 1150 is engaged with the distal end 1121 of staple cartridge channel 1122, as described above, the projections 1274 of staple cartridge 1150 can be inserted into the recesses 1279 of staple cartridge channel 1122 by hooking the projections 1274 underneath the projections 1278 of staple cartridge channel 1122. In such circumstances, the co-operation of projections 1274 and 1278 and recesses 1270 and 1279 can attach the distal end 1211 of staple cartridge 1150 to the distal end of staple cartridge 1122 and, in addition, align the staple cartridge 1150 with the staple cartridge channel 1122 such that the staple cartridge 1150 can be inserted between the sidewalls 1124 of staple cartridge channel 1122. Once the distal end 1211 of staple cartridge 1150 has been hooked to staple cartridge channel 1122, at least one of the staple cartridge 1150 and the staple cartridge channel 1122 can be rotated toward the other. In various circumstances, referring again to FIGS. 92 and 95, the staple cartridge 1150 can be pivoted toward the staple cartridge channel 1122 such that alignment slots 1280 in staple cartridge channel 1150 become aligned with side flanges 1128. In various embodiments, the staple cartridge 1150 can comprise alignment slots 1280 on opposite sides thereof which can each be configured to receive a side flange 1128. In at least one embodiment, each alignment slot 1280 can comprise lateral sidewalls 1283 and 1284 and a basewall 1281 extending between the sidewalls 1283 and 1284. Further to the above, a predetermined distance 1289 can be measured between the distal datum surfaces 1271 of recesses 1270 to the distal basewalls 1281 of alignment slots 1280. Referring now to FIGS. 93 and 95, the predetermined distance 1288 between the distal end of the projections 1279 and the distal end of the side flanges 1128 can be such that it is shorter than the distance 1289 between the distal surfaces 1271 of recesses 1270 and the basewalls 1281 of alignment slots 1280. Owing to the distance 1288 being shorter than the distance 1289, the staple cartridge 1150 can be rotated into position as described above such that side flanges 1128 can enter into alignment slots 1280. In various embodiments, alignment slots 1280 can be sized and configured such that the side flanges 1128 are closely received between the sidewalls 1283 and 1284 such that there is little, if any, relative movement between the side flanges 1128 and the sidewalls of the alignment slots 1280, for example.

In various alternative embodiments, further to the above, the proximal end 1213 of the staple cartridge 1150 can be inserted into the distal end 1121 of staple cartridge channel 1122 and slid proximally between sidewalls 1124 such that the proximal end 1213 of staple cartridge channel 1150 enters into the proximal end 1123 of staple cartridge channel 1122. During such sliding movement, the side flanges 1128 can enter into alignment slots 1280 and, in addition, the projections 1279 can enter into the recesses 1270. In certain embodiments, the staple cartridge 1150 can be both slid and rotated into the staple cartridge channel 1122. In any event, in various embodiments, the staple cartridge 1150 and the staple cartridge channel 1122 can be configured such that the staple cartridge 1150 can be removably secured within the staple cartridge channel 1122. In at least one embodiment, referring primarily now to FIGS. 95 and 100, the staple cartridge 1150 can comprise one or more retention features which can be configured to releasably engage one or more retention features in the staple cartridge channel 1122. More particularly, in at least one such embodiment, the staple cartridge 1150 can comprise one or more retention slots 1190 which can be configured to engage one or more retention keys 1195 in the staple cartridge channel 1122. In various embodiments, referring again to FIG. 95, each retention slot 1190 can comprise a first, or entrance, portion 1191 which can be configured to receive a retention key 1195 therein and, in addition, a second portion 1192 which can be configured to receive the retention key 1195 after it has passed through the entrance portion 1191. The entrance portion 1191, in certain embodiments, can define a first width between a proximal side 1193 and a distal side 1194 of retention slot 1190 and, in addition, the second portion 1192 can define a second width between the proximal side 1193 and the distal side 1194 which is wider than the first width of entrance portion 1191. In various embodiments, the first width of entrance portion 1191 can be narrower than the width of the retention key 1195 and the second width of second portion 1192 can be wider than the width of the retention key 1195. In at least one such embodiment, a retention slot 1190 can be configured to engage a retention key 1195 in at least one of a press-fit and/or a snap-fit manner. In certain embodiments, at least one of the proximal side 1193 and/or the distal side 1194 can be configured to flex or splay outwardly as the retention key 1195 is inserted into retention slot 1190. In at least one such embodiment, the proximal sides 1193 can be displaced proximally. In any event, referring to FIG. 100, once the retention slot 1190 has received the retention key 1195, the proximal side 1193 of retention slot 1190 can be positioned on a proximal side 1196 of retention key 1195 and the distal side 1194 of retention slot 1190 can be positioned on a distal side 1197 of retention key 1195.

As outlined above, the staple cartridge 1150 can be assembled into the staple cartridge channel 1122 by coupling the distal end 1211 of staple cartridge 1150 to the distal end 1121 of staple cartridge channel 1122 and then rotating the proximal end 1213 of staple cartridge 1150 into the proximal end 1123 of staple cartridge channel 1122. In at least one such embodiment, the retention slots 1190 can be configured to engage the retention keys 1195 as the staple cartridge 1195 is rotated into its seated position within staple cartridge channel 1122. Referring now to FIG. 93, a predetermined distance 1199 between the distal datum surfaces 1271 of recesses 1270 and the retention slots 1190 can be sized and configured such that the retention slots 1190 are aligned with the retention keys 1195 as the staple cartridge 1150 is rotated into position as described above. Correspondingly, in at least one embodiment, a distance between the distal ends of projections 1279 and retention keys 1195 can be such that it equals, or at least substantially equals, the distance 1199. In various circumstances, the above-mentioned distances can be measured to the center of the features comprising retention slots 1190 and retention keys 1195. For example, the distance 1199 can be measured to a position in the center of slot 1190 intermediate the proximal and distal sidewalls thereof, for example. In various embodiments, the retention slot 1190 can further comprise lead-in, beveled, and/or radiused surfaces, which can be configured to guide, or direct, the retention keys 1195 into the retention slots 1190. In at least one such embodiment, these lead-in surfaces can be wider than the first portions 1191.

Figure 101:
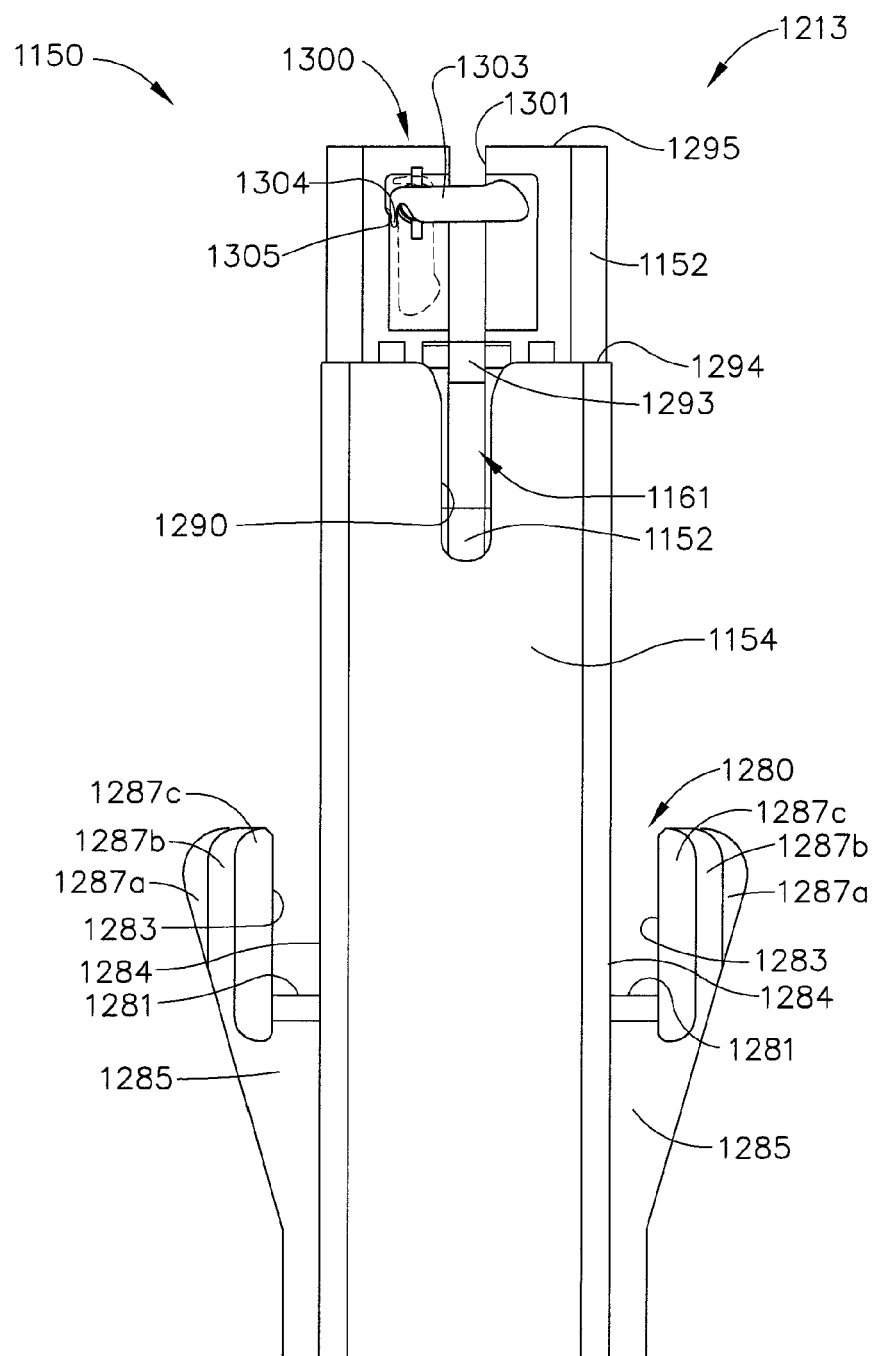
FIG. 101 is a partial bottom view of the staple cartridge assembly of FIG. 95.

As staple cartridge 1150 is rotated into staple cartridge 1122, a cutting member and/or staple deploying sled positioned within the staple cartridge 1150 can be operably engaged with the pusher bar 1202. More particularly, referring now to FIGS. 97-99, the staple cartridge 1150 can include a cutting member 1160 which can be operably coupled with pusher bar 1202 such that, after the staple cartridge 1150 has been seated within the staple cartridge channel 1122, the pusher bar 1202 and cutting member 1160 can be advanced together as described above. In at least one embodiment, the cutting member 1160 can comprise a slot 1161 which can be configured to receive a distal drive projection 1294 (FIG. 93) at the distal end of pusher bar 1202. More particularly, referring now to FIG. 101, the slot 1161 of cutting member 1160 can be aligned with an access slot 1290 in the bottom of the staple cartridge 1150 such that, as the proximal end 1213 of staple cartridge 1150 is seated in the proximal end 1123 of staple cartridge channel 1122, the drive projection 1294 of pusher bar 1200 can extend through the access slot 1290 into the slot 1161 of cutting member 1160. In various embodiments, the slot 1161 and the drive projection 1294 can be sized and configured such that there is little, if any, relative movement therebetween. More particularly, referring again to FIGS. 98 and 99, the slot 1161 can comprise a distal sidewall 1291 and a proximal sidewall 1292 wherein the drive projection 1294 can be securely received between the sidewalls 1291 and 1292. In various embodiments, referring again to FIGS. 93 and 101, the pusher bar 1202 can further comprise a recess, or slot, 1295 positioned proximally with respect to the drive projection 1294 wherein the slot 1295 can be configured to receive a proximal projection 1293 (FIG. 97) extending from the cutting member 1160. Similar to the above, the slot 1295 can be defined by sidewalls which can be configured to closely receive the proximal projection 1293 such that there is little, if any, relative movement therebetween.

Figure 96:
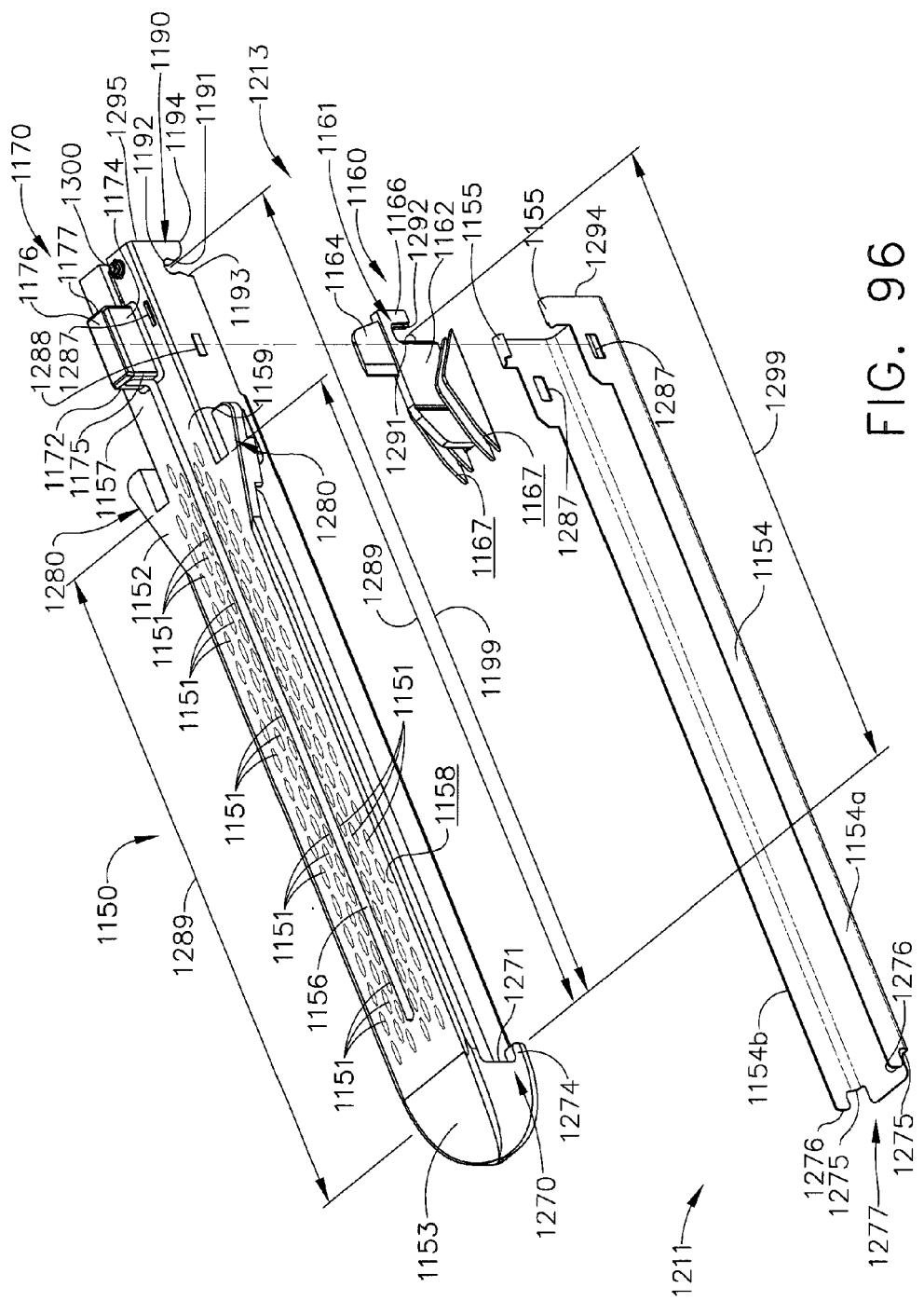
FIG. 96 is an exploded view of the staple cartridge assembly of FIG. 95.

As described above, the slot 1161 of cutting member 1160 can be positioned within the staple cartridge 1150 such that it is aligned with the drive projection 1294 of pusher bar 1202 when the staple cartridge 1150 is seated within the staple cartridge channel 1122. Referring now to FIG. 96, a predetermined distance 1299 can be defined between the distal surfaces 1271 of recesses 1270 and the slot 1161, wherein the distance 1299 can be equal to, or at least substantially equal to, a predetermined distance 1297 between the distal end of the projections 1279 and the drive projection 1294. In various circumstances, the cutting member 1160 can be moved through a range of positions between a proximal-most position, in which it is positioned in housing 1170, and a distal-most position after it has been advanced through the cutting slot 1156. In various embodiments, the distance 1299 can be measured with respect to the cutting member 1160 when it is in its proximal-most position. Similar to the above, the distances 1297 and 1299 can be measured to the center or midpoint of the drive projection 1297 and slot 1161, respectively. In various embodiments, the surgical instrument 1100 can further comprise a locking mechanism which can be configured to hold the pusher bar 1202 in position while the cutting member 1160 is engaged with the drive projection 1294.

Figure 100:
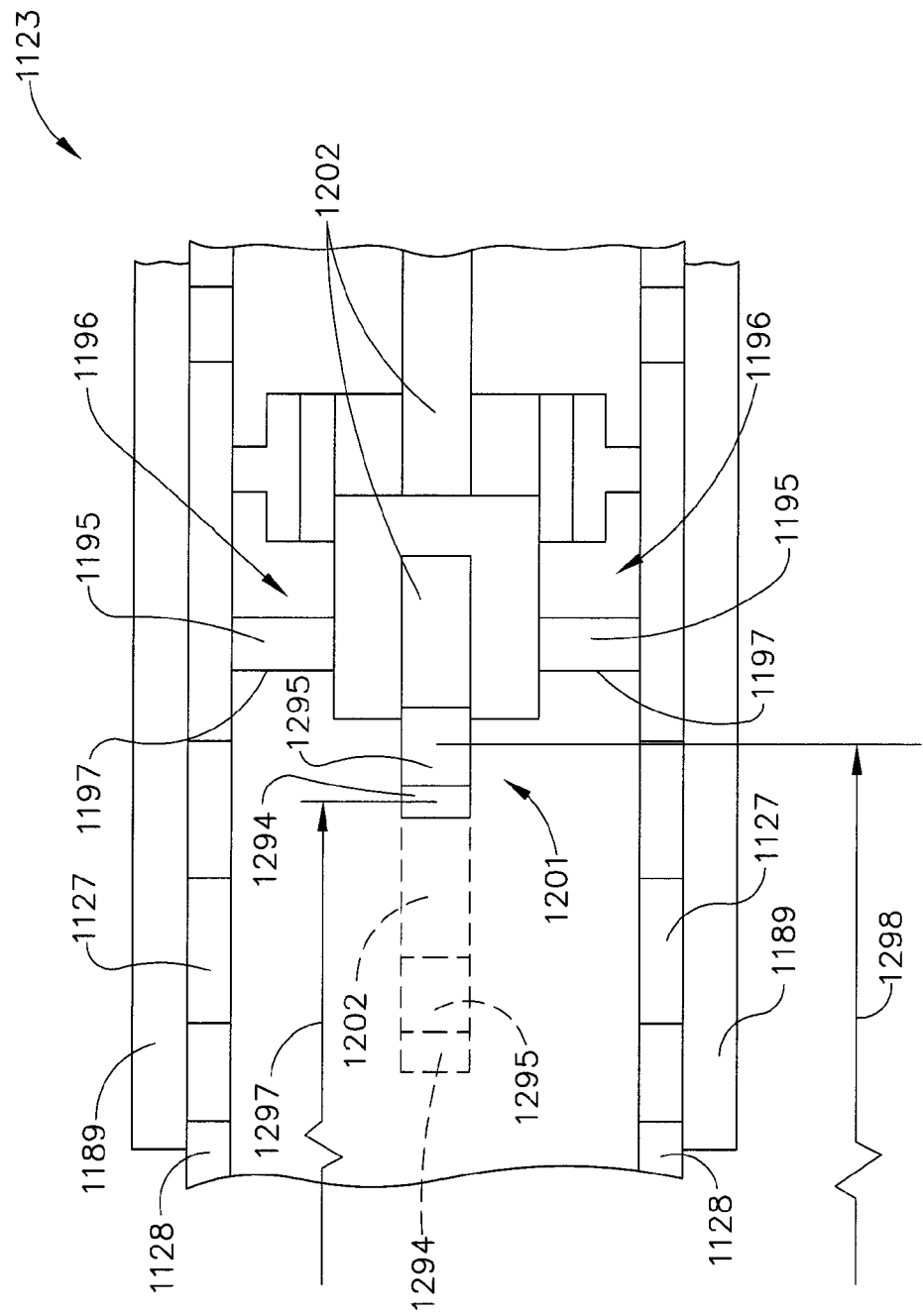
FIG. 100 is a detail view of a distal end of a drive bar configured to be operably connected to the staple sled and cutting assembly of FIG. 98, wherein the drive bar distal end is illustrated in a proximal position in solid lines a second, or distal, position in phantom lines.

Similar to the above, in certain embodiments, a distance 1298 can be defined between the distal end of projections 1279 and the recess 1295 of pusher bar 1202 wherein the distance 1298 can be equal to, or at least substantially equal to, the distance between the distal surface 1271 of recesses 1270 and the projection 1293 of cutting member 1160. In various embodiments, referring primarily now to FIGS. 97 and 100, the staple cartridge 1150 can comprise a clearance region defined between the proximal end 1295 of the staple cartridge body 1152 and the proximal end 1294 of the staple cartridge pan 1154, wherein such a clearance region can be configured to receive the pusher bar 1202 and/or a portion of the staple cartridge channel 1122 therein, for example. In any event, the pusher bar 1202 can be advanced distally once it has been engaged with cutting member 1160, wherein such movement is depicted in FIG. 100 which illustrates the distal end 1201 of pusher bar 1202 in a proximal position (illustrated with solid lines) and a second, distal position (illustrated with phantom lines), for example.

In various embodiments, as described above, the distal end 1211 of staple cartridge 1150 can be engaged with the distal end 1121 of the staple cartridge channel 1122 and then pivoted into staple cartridge channel 1122 such that the proximal end 1213 of staple cartridge 1150 can be seated in the proximal end 1123 of staple cartridge channel 1122. Such a process can comprise engaging the projections 1274 of staple cartridge 1150 underneath the projections 1276 of staple cartridge channel 1122 and then, as described above, rotating the staple cartridge 1150 until alignment slots 1280 are positioned adjacent to flanges 1182. At such point, in various embodiments, the cutting member 1160 may not be engaged with the pusher bar 1202 and, in addition, the retention slots 1190 may not be engaged with the retention keys 1195. As a result, the surgeon, or clinician, can adjust the position of the staple cartridge 1150 within the staple cartridge channel 1122 before the staple cartridge 1150 is locked into position. Once the side flanges 1182 have been at least partially positioned in alignment slots 1280, the proximal end 1213 can be further rotated toward the staple cartridge channel 1122. At such point, the cutting member 1160 can come into operable engagement with the pusher bar 1202 and, in addition, the retention slots 1190 can engage the retention keys 1195. In various embodiments, the cutting member 1160 can operably engage the pusher bar 1202 at the same time, or at least substantially the same time, as the retention slots engage retention keys 1195. More particularly, in at least one embodiment, the drive projection 1294 of pusher bar 1202 can enter slot 1161 of cutting member 1160 at the same time that the retention keys 1195 enter into, or snap into, the second portions 1192 of slots 1190. In at least one such embodiment, the cutting member 1160 may not be advanceable by the pusher bar 1202 until the staple cartridge 1150 is snapped into, or seated in, place. In certain alternative embodiments, the cutting member 1160 can be operably engaged with the pusher bar 1202 before the retention keys 1195 are fully seated within the retention slots 1190 when the proximal end 1213 of the staple cartridge 1150 is seated in the proximal end 1123 of the staple cartridge channel 1122. In various embodiments, the retention slots 1190 can be aligned with each other such that they engage the retention keys 1195 at the same time, or at least substantially the same time. In at least one such embodiment, the retention slots can be configured such that the retention keys 1195 enter into the second portions 1192 of the retention slots 1190 simultaneously. In at least one embodiment, the retention slots 1190 can be positioned along an axis which is transverse to or perpendicular to a longitudinal axis defined by the cutting slot 1156. In various embodiments, the retention slots 1190, and the axis defined therebetween, can be positioned proximally with respect to the cutting member 1160 regardless of the position of the cutting member 1160 including when the cutting member 1160 is in its proximal-most position, for example.

Figure 97:
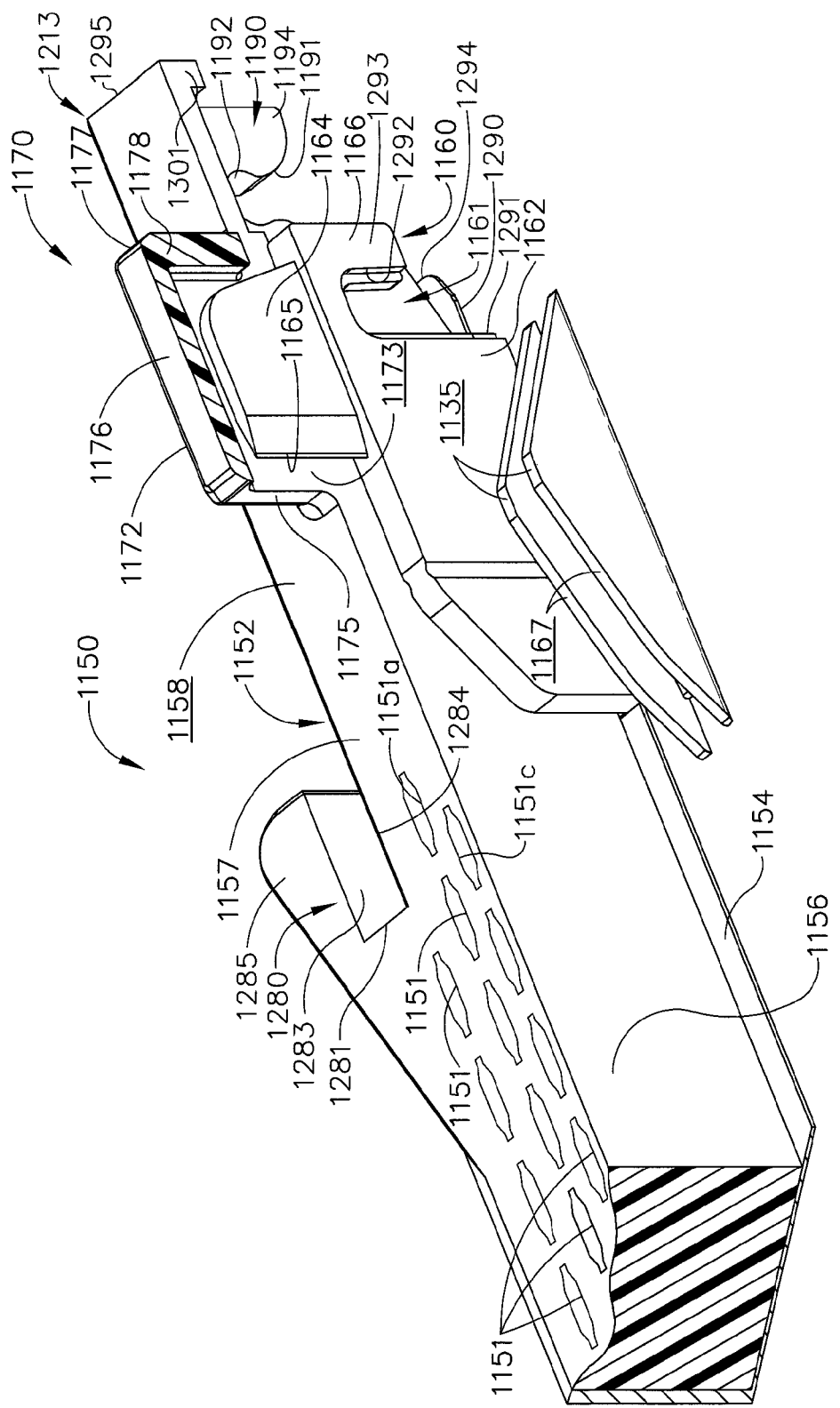
FIG. 97 is a cross-sectional view of the staple cartridge assembly of FIG. 95.
Figures 98, 99:
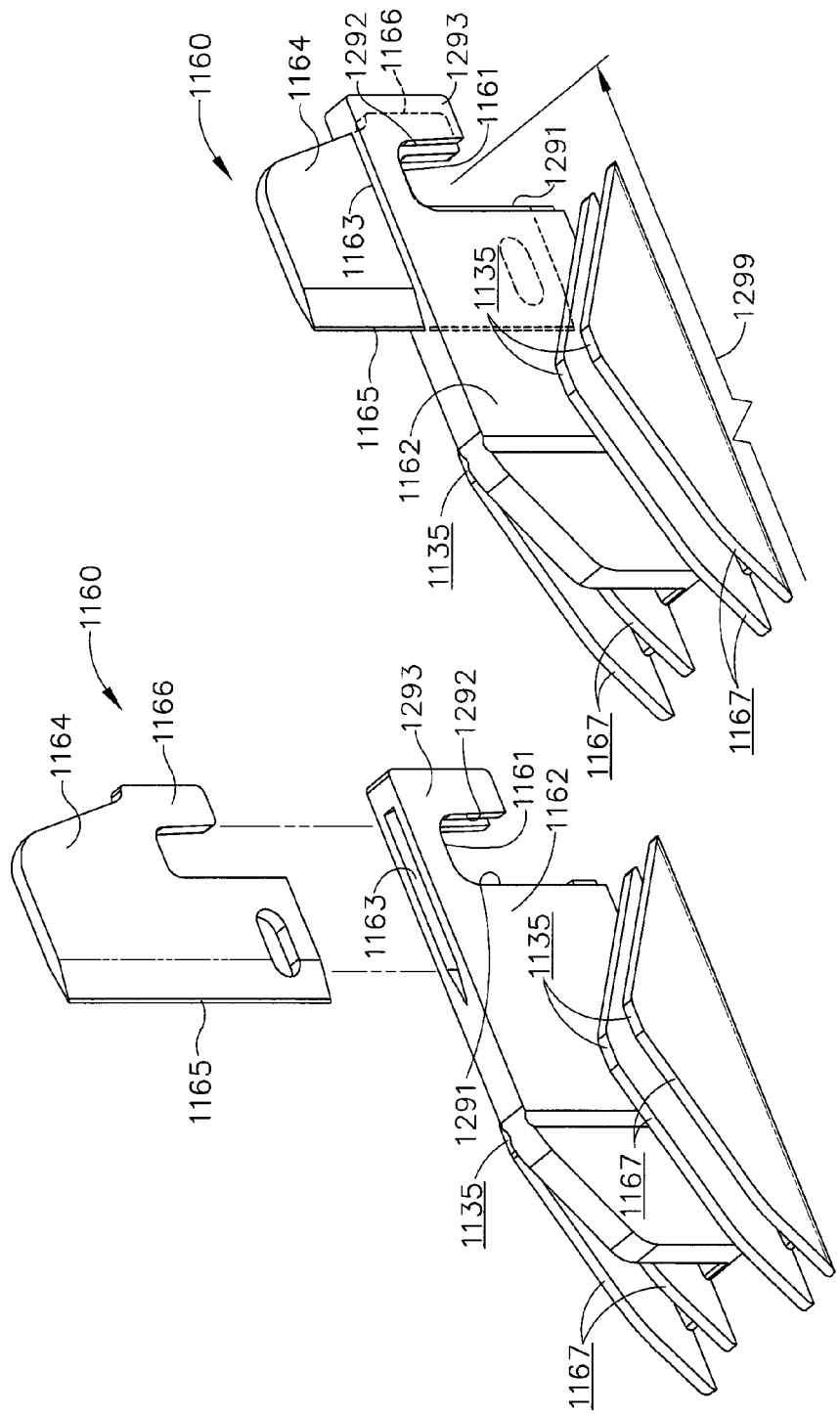
FIG. 98 is an exploded view of a staple sled and cutting member assembly of the staple cartridge assembly of FIG. 95.
FIG. 99 is a perspective view of the staple sled and cutting member assembly of FIG. 98.

In various embodiments, the cutting slot 1156 can define a first body portion 1152*a* on a first side thereof and a second body portion 1152*b* on a second, or opposite, side thereof. Referring to FIGS. 95 and 98, the first body portion 1152*a* can comprise a first plurality of staple cavities 1151 and, in addition, the second body portion 1152*b* can comprise a second plurality of staple cavities 1151. In at least one embodiment, the first body portion 1152*a* can comprise a proximal-most staple cavity 1151*a* which can be positioned proximally relative to the other staple cavities 1151 in first body portion 1152*a*. In at least one embodiment, the entirety of staple cavity 1151*a* can be positioned proximally relative to base wall 1281 of the alignment slot 1280 in first body portion 1152*a*, while, in other embodiments, at least a portion of staple cavity 1151*a* can be positioned proximally relative to the base wall 1281. As illustrated in FIG. 97, the alignment slot 1280 in the first body portion 1152*a* is positioned laterally with respect to the proximal-most staple cavity 1151*a* and, in addition, laterally with respect to the cutting slot 1156. Further to the above, the first body portion 1152*a* can comprise a second proximal-most staple cavity 1151*c* which can be positioned proximally relative to the other staple cavities 1151 in first body portion 1152*a* except for proximal-most staple cavity 1151*a*. In at least one embodiment, the entirety of staple cavity 1151*c* can be positioned proximally relative to base wall 1281 of the alignment slot 1280 in first body portion 1152*a*, while, in other embodiments, at least a portion of staple cavity 1151*c* can be positioned proximally relative to the base wall 1281. As illustrated in FIG. 97, the alignment slot 1280 is the first body portion 1152*a* is at least partially positioned laterally with respect to the second proximal-most staple cavity 1151*c*. Still referring to FIG. 97, the first body portion 1152*a* can comprise a retention slot 1190 therein which can be positioned proximally with respect to the staple cavities 1151 therein, including the staple cavities 151*a* and 1151*c*, for example.

Referring to FIG. 95, further to the above, the second body portion 1152*b* can comprise a proximal-most staple cavity 1151*b* which can be positioned proximally relative to the other staple cavities 1151 in second body portion 1152*b*. In at least one embodiment, the entirety of staple cavity 1151*b* can be positioned proximally relative to base wall 1281 of the alignment slot 1280 in second body portion 1152*b*, while, in other embodiments, at least a portion of staple cavity 1151*b* can be positioned proximally relative to the base wall 1281. As illustrated in FIG. 95, the alignment slot 1280 in the second body portion 1152*b* is positioned laterally with respect to the proximal-most staple cavity 1151*b* and the cutting slot 1156. Further to the above, the second body portion 1152*b* can comprise a second proximal-most staple cavity 1151*d* which can be positioned proximally relative to the other staple cavities 1151 in second body portion 1152*b* except for proximal-most staple cavity 1151*b*. In at least one embodiment, the entirety of staple cavity 1151*d* can be positioned proximally relative to base wall 1281 of the alignment slot 1280 in second body portion 1152*b*, while, in other embodiments, at least a portion of staple cavity 1151*d* can be positioned proximally relative to the base wall 1281. As illustrated in FIG. 95, the alignment slot 1280 in the second body portion 1152*b* is at least partially positioned laterally with respect to the second proximal-most staple cavity 1151*d*. Still referring to FIG. 95, the second body portion 1152*b* can comprise a retention slot 1190 therein which can be positioned proximally with respect to the staple cavities 1151 therein, including the staple cavities 1151*b* and 1151*d*, for example.

In various embodiments, further to the above, the staple cartridge body 1152 can be comprised of plastic and can be formed utilizing an injection molding process. Thereafter, in various embodiments, the staple drivers 1168 (FIG. 42) can be assembled into staple cavities 1151 and the cutting member 1160 can be positioned within the cartridge body 1152 such that the cutting member 1164 is located within housing 1170, as described above. The staple cartridge pan 1154 can then be assembled to the staple cartridge body 1152. In various embodiments, referring now to FIG. 96, the distal end 1277 of staple cartridge pan 1154 can be aligned with the proximal end 1295 of the staple cartridge body 1152 such that the staple cartridge body can be slid within the staple cartridge pan 1154 between opposing walls 1154*a* and 1154*b*, for example. The staple cartridge body 1152 and pan 1154 can be slid relative to one another until pan projections 1276 are positioned within recesses 1270 and projections 1274 are positioned within pan recesses 1275. At the same time, the lock projections 1288 extending from staple cartridge body 1152 can be received within the lock apertures 1287 in staple cartridge pan 1154 such that pan 1154 can be locked to staple cartridge body 1152. In various embodiments, the sidewalls 1154*a* and 1154*b* of pan 1154 can flex or splay outwardly as they pass over lock projections 1288 and then elastically return inwardly when lock apertures 1287 are aligned with lock projections 1288. At such point, the arms 1155 extending from pan 1154 can be aligned with and positioned within the retention slots 1287 in staple cartridge body 1152. In certain embodiments, referring now to FIG. 101, the staple cartridge 1150 can further comprise a retention member, such as retention member 1300, for example, which can be configured to selectively obstruct slot 1301 in staple cartridge body 1152, for example. In at least one embodiment, the retention member 1300 can comprise a pivotable arm 1303 which can be rotated between a first position in which it extends across slot 1301 (illustrated in solid lines) and a second position in which it is positioned adjacent to slot 1301 (illustrated in phantom lines). In at least one such embodiment, an integral pivot pin 1302 (FIG. 95) can extend from arm 1303 into an aperture in staple cartridge body 1152 which can define an axis about which the arm 1303 can be rotated. In certain embodiments, the arm 1303 can include a lock member 1304 extending therefrom which can be configured to be releasably engaged with a lock cavity 1305 in staple cartridge body 1152 in order to hold the arm 1303 in at least one of its first and second positions, for example. In certain embodiments, the positioning of arm 1303 across slot 1301 can prevent, or at least inhibit, the cutting member 1160, for example, from sliding out of the staple cartridge 1150.

In order to facilitate the insertion and removal of the staple cartridge 1150 from staple cartridge channel 1122, in various embodiments, the staple cartridge 1150 can comprise gripping portions positioned on opposite sides thereof, for example. In at least one embodiment, referring now to FIGS. 97 and 101, the staple cartridge body 1152 can comprise lateral portions 1285 positioned adjacent to alignment slots 1280 wherein the lateral portions 1285 can be gripped and/or pushed on by a clinician in order to seat the proximal end 1213 of staple cartridge 1150 in the proximal end of staple cartridge channel 1122, for example. Such a force can be applied to top, or tissue-contacting, surfaces of the lateral portions 1285 as the proximal end 1213 of staple cartridge 1150 is rotated into position as described above. In various embodiments, a lifting force can be applied to lateral portions 1285 in order to lift the proximal end 1213 of staple cartridge 1150 out of the staple cartridge channel 1122. In at least one such embodiment, referring primarily to FIG. 101, each lateral portion 1285 can comprise one or more steps, ridges, and/or elevations, such as elevations 1287a, 1287b, and/or 1287c, for example, which can be configured to improve the clinician's grip on the lateral portions 1285. In various embodiments, the elevations 1287a, 1287b, and/or 1287c can be positioned at different heights relative to one another. In any event, the staple cartridge 1150 can be removed from channel 1122 by lifting the proximal end 1213 of staple cartridge 1150 out of channel 1122 and then unhooking, or disengaging, the distal end 1211 of staple cartridge 1150 from the distal end 1121 of channel 1122, for example. As staple cartridge 1150 is removed from the channel 1122, the slot 1161 within cutting member 1160 can be moved away and disengaged from the drive projection 1294 of pusher bar 1202, for example.

Figure 102:
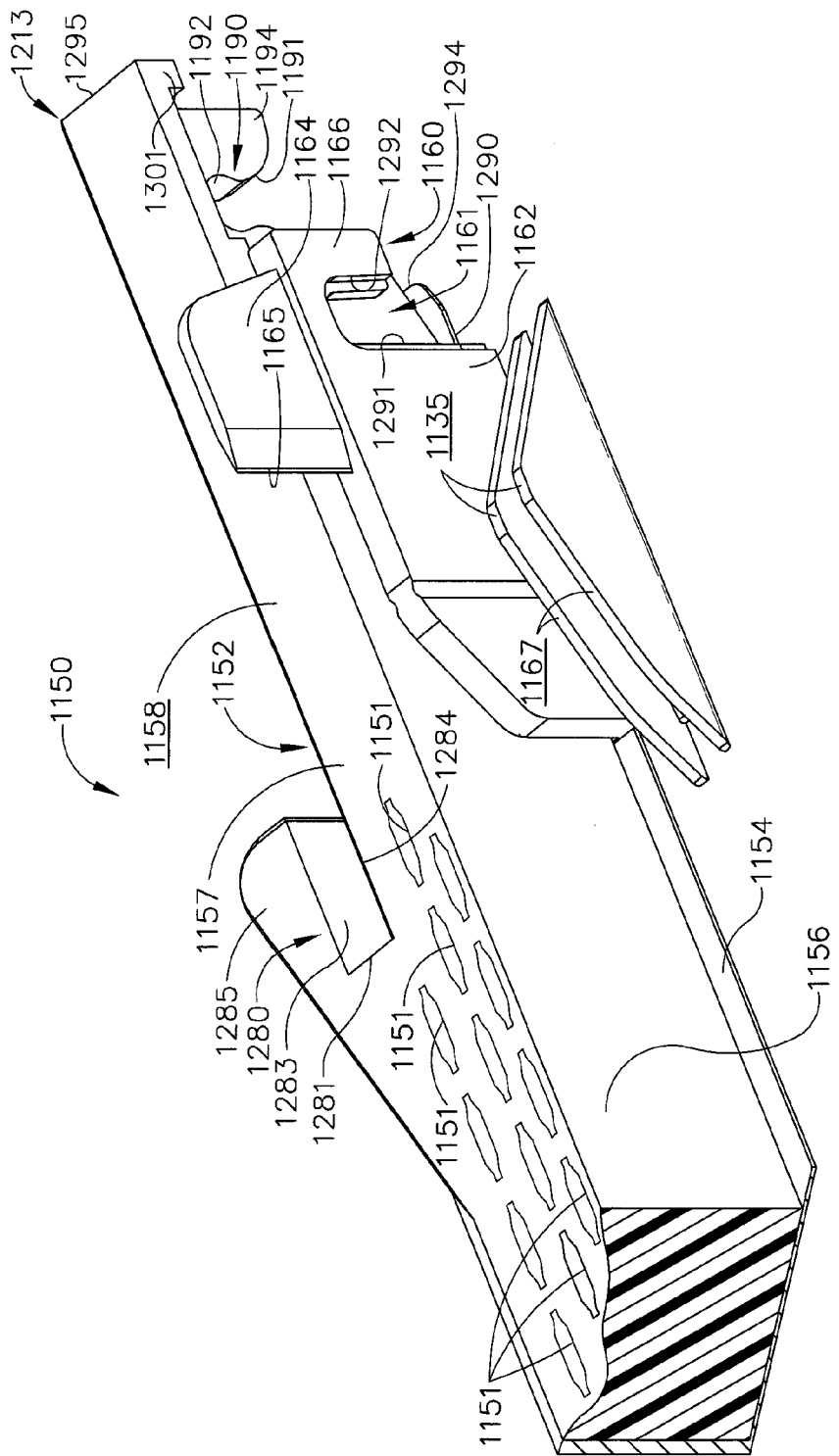
FIG. 102 is a cross-sectional view of a staple cartridge assembly in accordance with an alternative embodiment.
Figure 103:
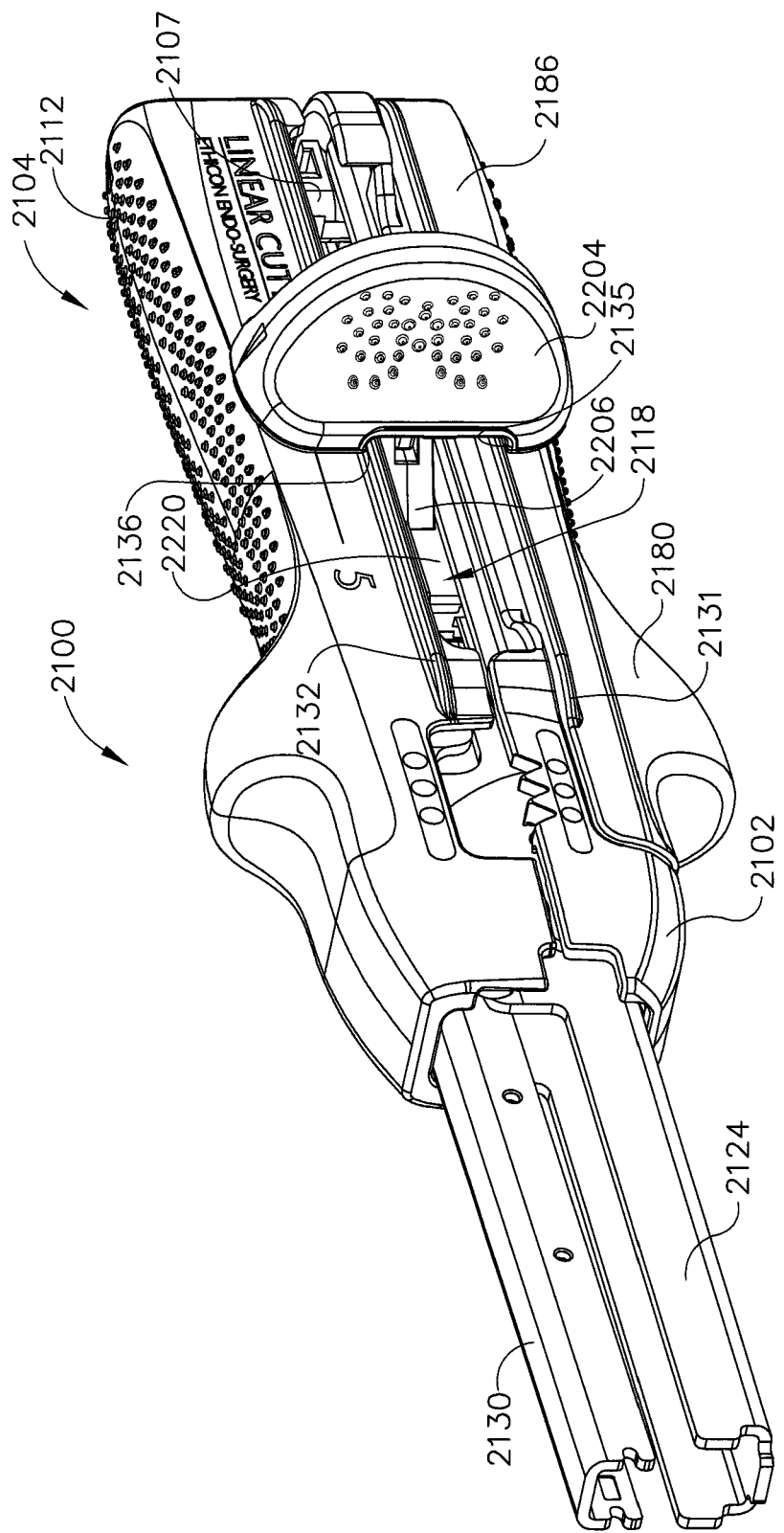
FIG. 103 is a perspective view of a surgical stapling instrument comprising a firing actuator in a partially-advanced position.

In various circumstances, further to the above, the pusher bar 1202 and cutting member 1160 can be returned to their proximal positions before the staple cartridge 1150 is removed from the staple cartridge channel 1122. In such a position, as described above, the cutting edge 1165 can be positioned within the housing 1170. In various embodiments, referring now to FIG. 102, an alternative embodiment of a staple cartridge 1150' is depicted without a housing 1170. In at least one such embodiment, the cutting edge 1165 can at least partially extend above the deck surface 1158 of the staple cartridge body 1152 in its proximal position and/or any other distally-advanced positions, for example.

Figure 50:
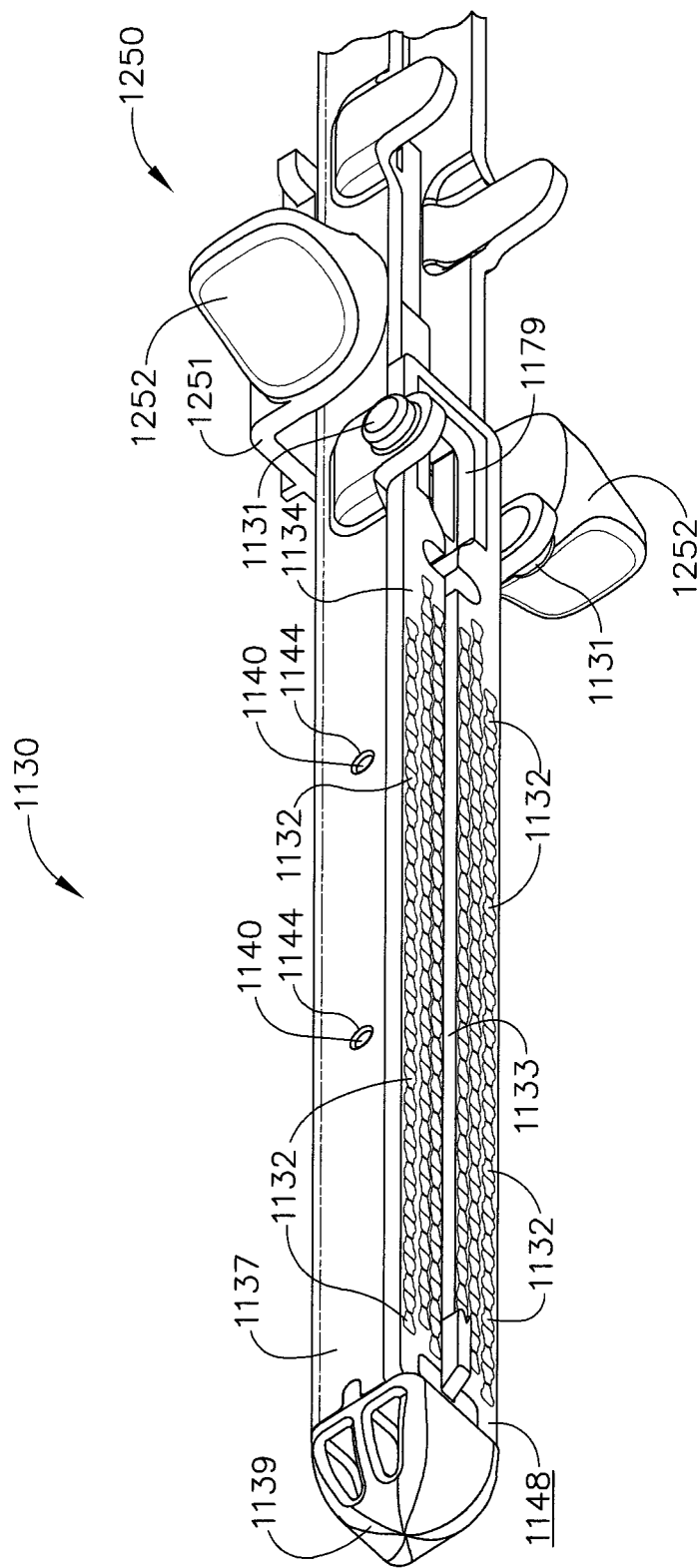
FIG. 50 is a perspective view of an anvil assembly of the surgical stapling instrument of FIG. 34.

In various embodiments, further to the above, anvil 1130 can include one or more apertures, slots, or recesses 1179 (FIG. 50) which can be configured to receive at least a portion of housing 1170 when anvil 1130 is brought into close opposition to staple cartridge 1150, for example. In at least one embodiment, sufficient clearance can be present between housing 1170 and recess 1179 such that anvil 1130 and staple cartridge 1150 can be moved relative to each other without interference, or at least substantial interference, therebetween. In embodiments having more than one cutting member housing as outlined above, an opposing anvil can have more than one corresponding aperture for receiving the housings. In various embodiments, an anvil can include a movable cutting member and at least one housing for at least partially covering, enclosing, and/or surrounding the cutting member. In certain embodiments, although not illustrated, both an anvil and a staple cartridge can comprise at least one movable cutting member and/or at least one housing configured to at least partially cover, surround, or enclose the cutting members when they are in a proximal position, for example.

Figure 51:
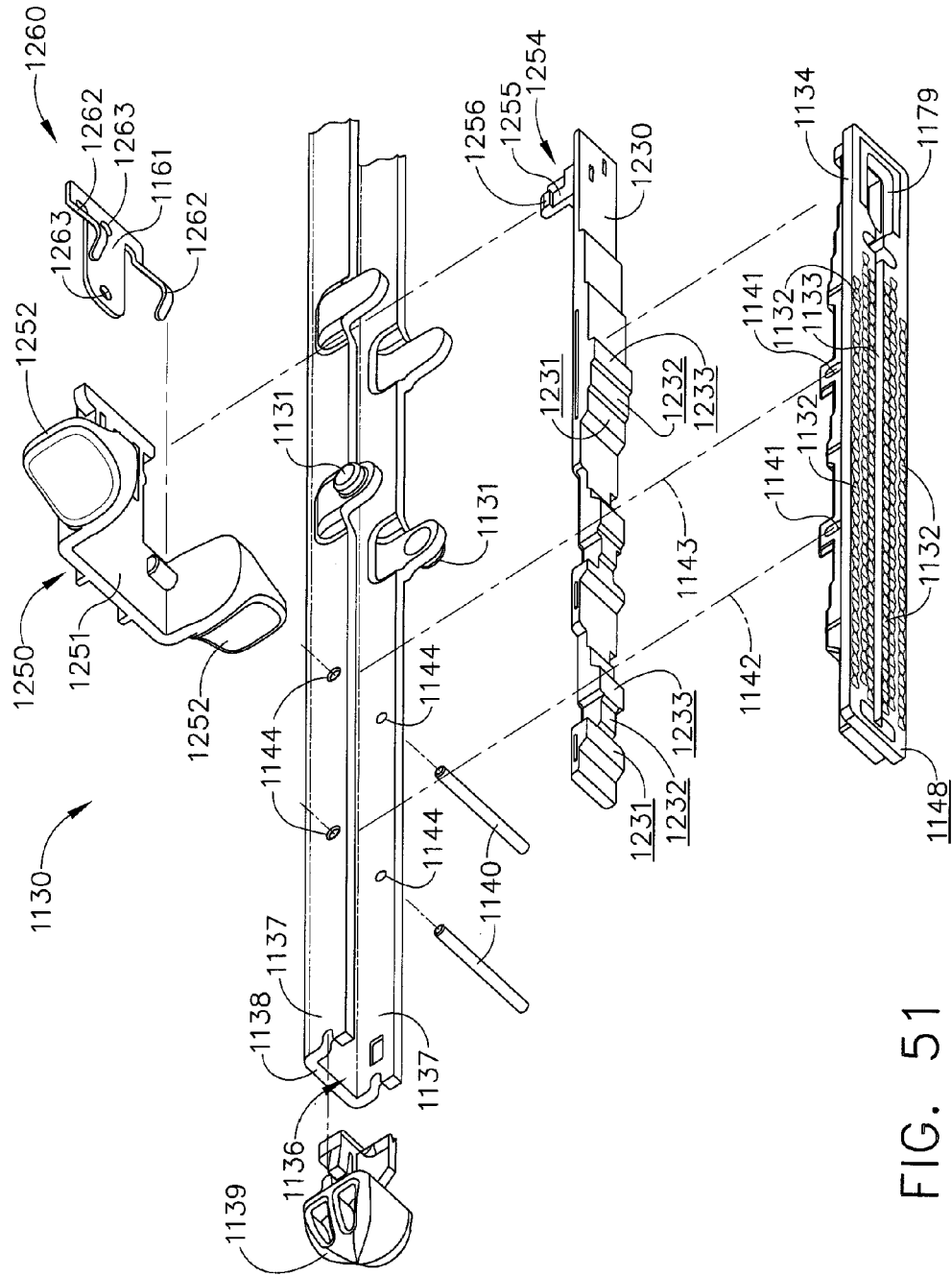
FIG. 51 is an exploded perspective view of the anvil assembly of FIG. 50.
Figure 52:
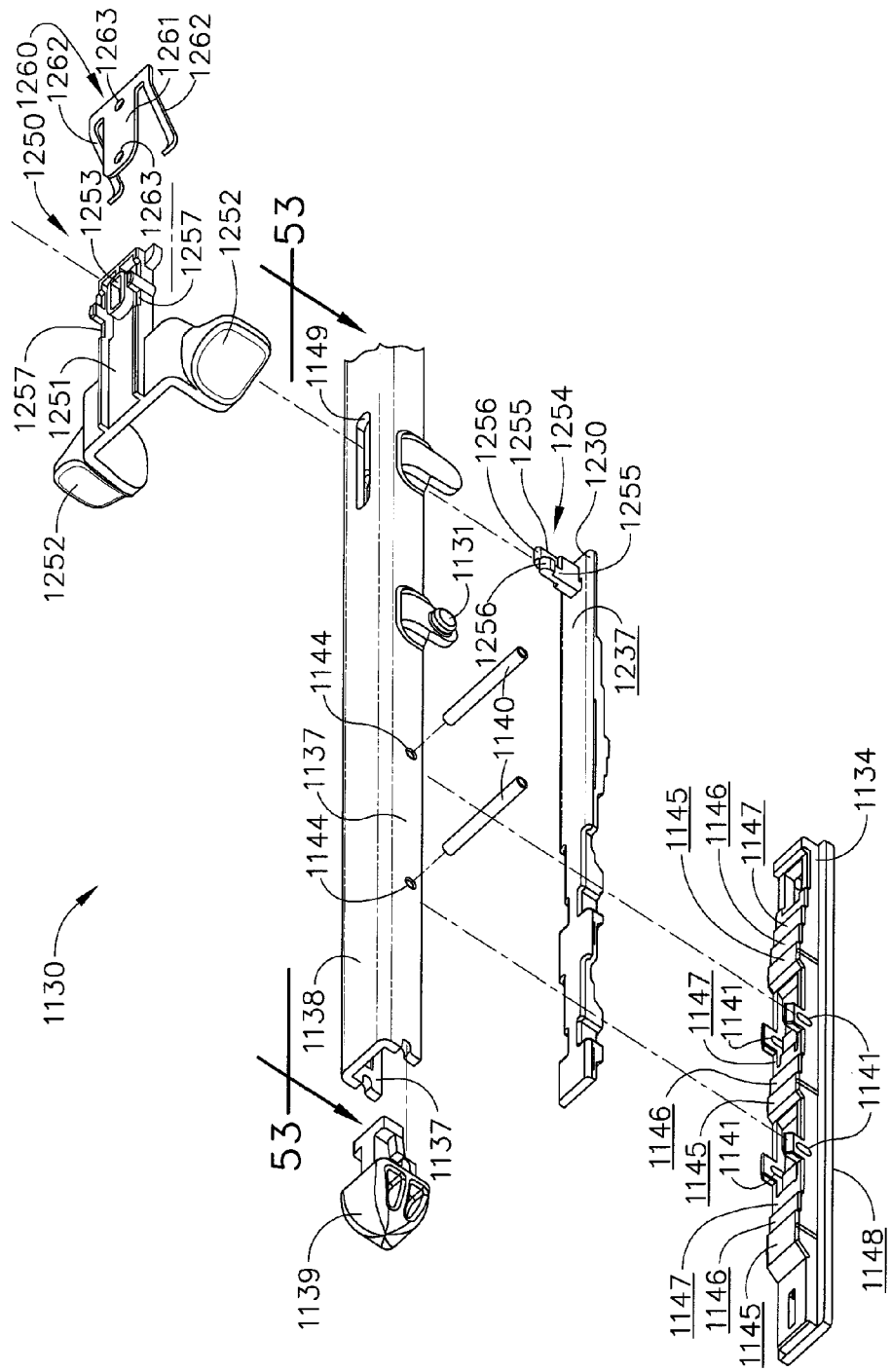
FIG. 52 is another exploded perspective view of the anvil assembly of FIG. 50.

As outlined above, pusher bar assembly 1200 can be advanced distally in order to move staple sled assembly 1160 within staple cartridge assembly 1150. In various embodiments, as also outlined above, the wedge-like cam surfaces 1167 of staple sled 1162 can be moved into engagement with the sloped surfaces 1169 on staple drivers 1168 to sequentially, and/or simultaneously, drive staples from staple cartridge 1150 against anvil 1130 and form the staples into any suitable configuration, such as B-shaped configurations, for example. In at least one such embodiment, referring to FIG. 50, anvil 1130 can include one or more staple forming surfaces, such as staple pockets 1132, for example, which can be configured to deform the staples. In certain embodiments, anvil 1130 can further include a slot, channel, or groove 1133 which can be configured to slidably receive at least a portion of staple sled 1162, cutting member 1164, and/or pusher bar 1202, for example. In at least one embodiment, although not illustrated, an anvil can include an anvil plate which can be securely and/or immovably positioned within an anvil channel defined within the anvil. In various other embodiments, as illustrated in FIGS. 51 and 52 and described in greater detail below, anvil 1130 can include an anvil plate 1134 movably positioned within anvil channel 1136. In certain embodiments, anvil channel 1136 can include opposite side walls 1137 and, in addition, a base 1138 extending between side walls 1137. In at least one embodiment, anvil 1130 can further include a distal nose portion 1139, for example, assembled thereto wherein nose portion 1139 can be configured to be press-fit and/or snap-fit into anvil channel 1136, for example, such that nose portion 1139 can be securely retained therein. In certain embodiments, nose portion 1139 can be comprised of a soft and/or pliable material, such as rubber, for example, and can comprise any suitable shape which can facilitate the insertion of anvil 1130 into a surgical site, for example. In some embodiments, referring to FIG. 51, a nose portion, such as nose portion 1139' can be retained to an anvil by one or more fasteners 1139a'. Similarly, referring to FIG. 34, a staple cartridge channel and/or staple cartridge, such as staple cartridge 1150, for example, can include a nose portion, such as nose portion 1153, for example, which can facilitate the insertion of staple cartridge 1150 into a surgical site, for example As indicated above, staples can be deployed from a staple cartridge and deformed against an anvil. In various circumstances, the distance between the staple forming surfaces on anvil 1130 and staple sled 1162 can determine the amount in which the staples are deformed. For example, if the distance between anvil pockets 1132 on anvil 1130 and top surfaces 1135 on staple sled 1162 (FIGS. 43-45) is relatively large, the staples will be deformed a lesser amount as compared to when the distance between anvil pockets 1132 and sled surfaces 1135 is relatively small. Correspondingly, if the distance between anvil pockets 1132 and sled surfaces 1135 is relatively small, the staples will be deformed a greater amount as compared to when the distance between anvil pockets 1132 and sled surfaces 1135 is relatively large. Often, the distance between anvil pockets 1132 and sled surfaces 1135 is referred to as the forming height of the staples. Sometimes the forming height of the staples can be measured between the top surface, or deck, of the staple cartridge and the staple forming surfaces on the anvil. For the purpose of this application, however, any reference to a staple forming height, or the like, can include one or both manners of measurement, where appropriate, and/or any other suitable manner of measurement. In any event, as described in greater detail below, a surgical stapling instrument, such as stapling instrument 1100, for example, can include means for adjusting the staple forming height.

In various embodiments, further to the above, an anvil can include one or more forming surfaces which can be moved toward and/or away from a staple cartridge in order to set the forming height of the staples. In at least one embodiment, referring to FIGS. 50-56, anvil 1130 can include anvil plate 1134 which can be movably and/or slidably positioned within anvil channel 1136. In certain embodiments, anvil 1130 can further include one or more retention, or guide, pins 1140, wherein anvil plate 1134 can include one or more retention, or guide, slots 1141 configured to slidably receive at least a portion of pins 1140. In at least one such embodiment, pins 1140 and/or slots 1141 can be configured to define a predetermined path along which anvil plate 1134 can be moved. Referring to FIG. 51, pins 1140 and slots 1141 can be structured and arranged such that anvil plate 1134 can be moved along a linear, or at least substantially linear, path, wherein the linear path can be at least partially defined by axes 1142 and 1143, for example. Other embodiments are envisioned in which an anvil plate can be moved along a non-linear path, such as a curved and/or curvi-linear path, for example. In certain embodiments, at least a portion of pins 1140 can be retained within apertures 1144 in side walls 1137 wherein, in at least one embodiment, pins 1140 can be press-fit within apertures 1144. In any event, as described herein, pins 1140 can guide anvil plate 1134 as it is moved toward and/or away from staple cartridge 1150, for example.

Figure 120:
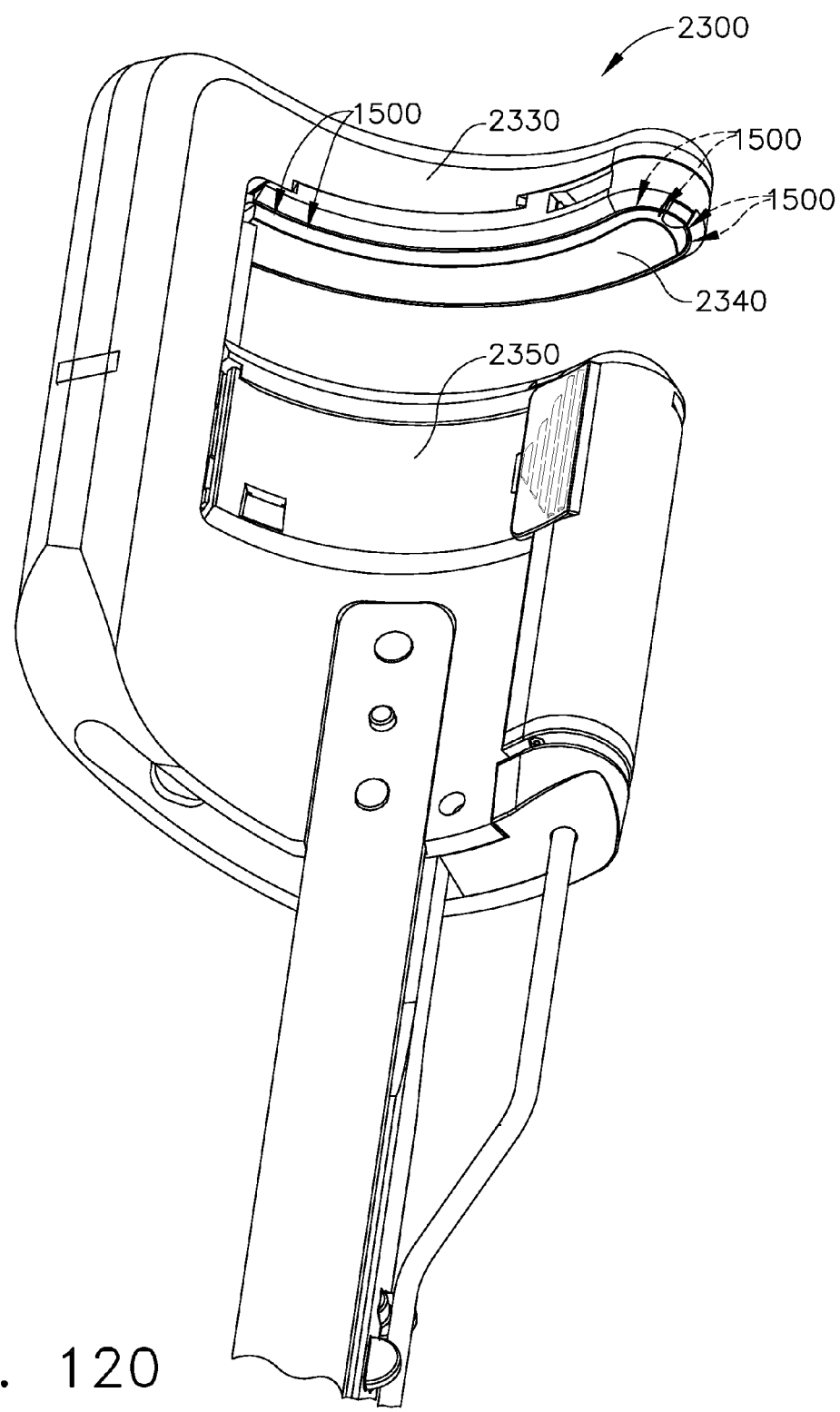

In various embodiments, further to the above, a surgical stapling instrument, such as stapling instrument 1100, for example, can include one or more adjustment members configured to position a portion of an anvil, such as anvil plate 1134, for example, relative to other portions of an anvil assembly and/or an opposing staple cartridge. In certain embodiments, referring to FIGS. 51 and 52, stapling instrument 1100 can include anvil plate adjustment member 1230 which can be configured to limit the range of motion of anvil plate 1134. In at least one such embodiment, referring to FIGS. 120 and 121, adjusting member 1230 can be positioned intermediate anvil plate 1134 in a first position in which first surface, or step, 1231 of adjusting member 1230 is positioned intermediate base 1138 of anvil channel 1136 and first positioning surface 1145 on anvil plate 1134. In such a first position, first step 1231 can define the amount of relative movement possible, or permitted, between anvil plate 1134 and anvil channel 1136. For example, when anvil 1130 is clamped against tissue as described above, anvil plate 1134 can contact the tissue and slide upwardly toward base 1138 until first positioning surface 1145 contacts first step 1231. Once surface 1145 and step 1231 are in contact, adjusting member 1230 can prevent, or at least inhibit, anvil plate 1134 from moving further toward base 1138. In at least one such embodiment, as a result, adjusting member 1230 can act as a stop such that the distance between base 1138 and tissue-contacting surface 1148 on anvil plate 1134 can be defined by a first distance 1234. While base 1138 is used as a reference datum in the present example, other portions of anvil 1130 and/or an opposing staple cartridge, for example, could be used as reference datums. When adjusting member 1230 is in its first position, as described above, second surface, or step, 1232 of adjusting member 1230 can be positioned intermediate base 1138 and second positioning surface 1146 on anvil plate 1134, and, in addition, third surface, or step, 1233 can be positioned intermediate base 1138 and third positioning surface 1147. Referring to FIG. 53, adjustment member 1230 can include two or more sets of steps, 1231, 1232, and/or 1233 and anvil plate 1134 can include two or more sets of positioning surfaces 1145, 1146, and/or 1147. While first step 1231 and first positioning surface 1145 are described above as being configured to control the position of anvil plate 1134, the second and third steps (1232, 1233) of adjustment member 1230 and the second and third positioning surfaces (1146, 1147) of anvil plate 1134, respectively, can also be configured to control the position of anvil plate 1134. For the sake of brevity, though, the present example will be described in reference to the first surface, or step 1231, as being the surface which controls the position of anvil plate 1134, although the reader will understand that the steps 1232 and 1233 can control the position of anvil plate 1134 as well.

In certain embodiments, the first position of adjustment member 1230 can provide for a relatively small, or short, staple forming height. In other embodiments, although not illustrated, the first position of an adjustment member can provide for an intermediate, a relatively large, and/or any other suitable staple forming height. In the event that the forming height associated with the first position of the adjustment member is suitable, a surgeon can proceed to use the surgical stapling instrument to staple and/or incise tissue as described above. In the event, however, that the staple forming height is unsuitable, a surgeon, or other clinician, can move adjustment member 1230 such that adjustment member 1230 can permit anvil plate 1134 to slide upwardly a different distance when anvil plate 1134 contacts tissue positioned intermediate anvil 1130 and staple cartridge 1150. In at least one such circumstance, the distance in which anvil plate 1134 is permitted to slide upwardly can be larger, thereby providing a larger forming height for the staples. Correspondingly, in other circumstances, the adjustment member can be moved such that anvil plate 1134 can slide upwardly a shorter distance when anvil plate 1134 contacts the tissue, for example, thereby providing a shorter staple forming height. While the term "upward", and the like, can mean vertically upward, the term is not so limited; rather, "upward" can mean any direction which is toward the base of the anvil and/or away from a staple cartridge, for example. In any event, adjustment member 1230 can be moved between its first position, illustrated in FIG. 54, and a second position, illustrated in FIG. 55, in order to increase the staple forming height. As indicated by arrow "P" in FIG. 55, adjustment member 1230 can be slid proximally in order to move adjustment member 1230 between its first and second positions, although embodiments are envisioned where an adjustment member can be slid distally and/or any other suitable direction in order to adjust adjustment member 1230. Once adjustment member 1230 has been moved into its second position, referring to FIG. 55, first surface, or step, 1231 can be positioned intermediate base 1138 and second positioning surface 1146 of anvil plate 1134. In such a second position, first step 1231 can once again define the amount of relative movement permitted between anvil plate 1134 and anvil channel 1136. In at least one embodiment, similar to the above, adjusting member 1230 can act as a stop such that the distance between base 1138 and tissue-contacting surface 1148 on anvil plate 1134 can be defined by a second distance 1235.

Figure 55:
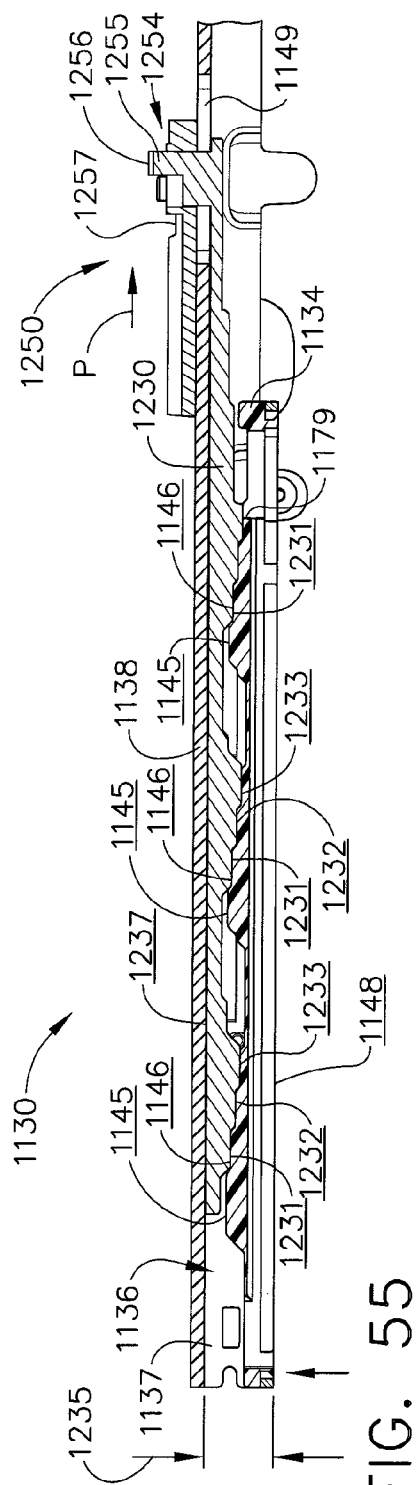
FIG. 55 is a cross-sectional assembly view of the anvil assembly of FIG. 50 illustrating the anvil adjustment member of FIG. 54 in a second position.
Figure 56:
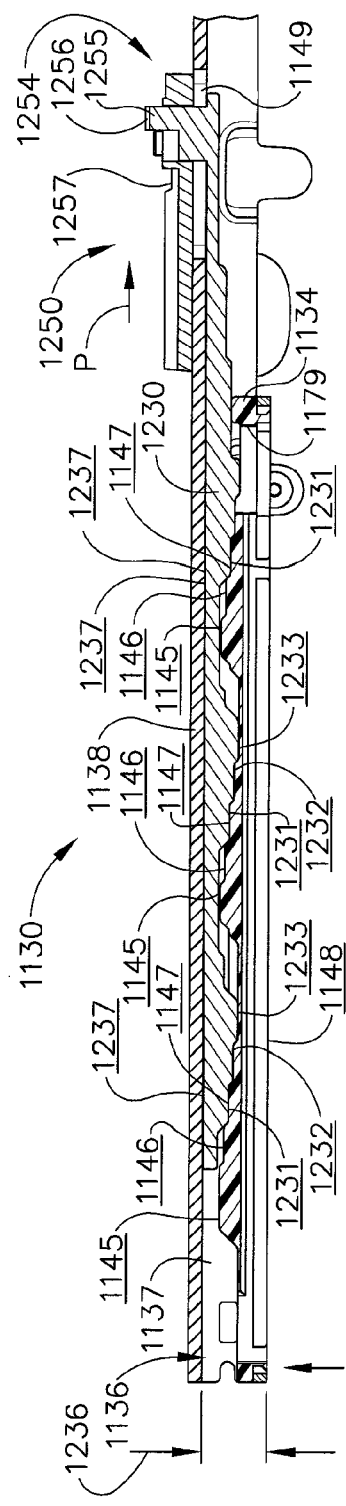
FIG. 56 is a cross-sectional assembly view of the anvil assembly of FIG. 50 illustrating the anvil adjustment member of FIG. 54 in a third position.
Figure 57:
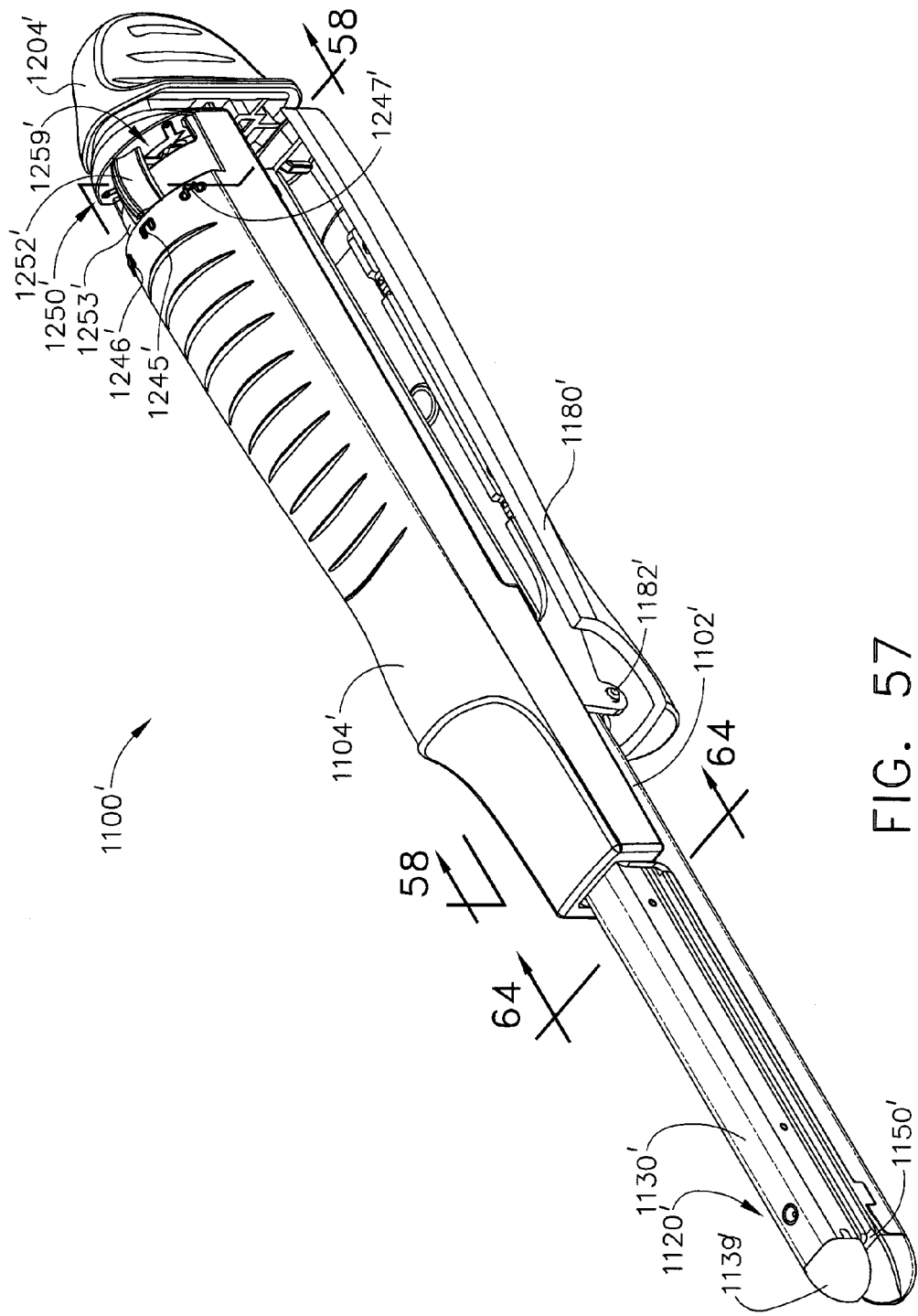
FIG. 57 is a perspective view of a surgical stapling instrument in accordance with at least one alternative embodiment of the present invention.

Further to the above, adjustment member 1230 can be moved between its second position, illustrated in FIG. 55, and a third position, illustrated in FIG. 56, in order to once again increase the staple forming height. As indicated by arrow "P" in FIG. 56, adjustment member 1230 can be slid proximally in order to move adjustment member 1230 between its second and third positions. Once adjustment member 1230 has been moved into its third position, referring to FIG. 56, first surface, or step, 1231 can be positioned intermediate base 1138 and third positioning surface 1147. In such a third position, first step 1231 can once again define the amount of relative movement between anvil plate 1134 and anvil channel 1136. In at least one embodiment, similar to the above, adjusting member 1230 can act as a stop such that the distance between base 1138 and tissue-contacting surface 1148 on anvil plate 1134 can be defined by a third distance 1236. While adjustment member 1230 can be selectively moved between three positions as described above to provide three different staple forming heights, other embodiments are envisioned which comprise an adjustment member which can be moved between more than three positions to provide more than three different staple forming heights. For example, an adjustment member can be movable between four positions in order to provide four staple forming heights. Further embodiments are envisioned which comprise an adjustment member which can be moved between two positions to provide two staple forming heights. Furthermore, while surfaces, or steps, 1231, 1232, and 1233 of adjustment member 1230 are arranged in a descending order, other arrangements are envisioned in which the surfaces, or steps, are arranged in an ascending order. Other arrangements are envisioned in which the surfaces, or steps, are not necessarily arranged in either an ascending or a descending order. Similarly, positioning surfaces 1145, 1146, and 1147 of anvil plate 1134 can be arranged in an ascending order, a descending order (FIG. 53), and/or any other suitable order. Furthermore, while adjustment member 1230 can be slid along an axis, other embodiments are envisioned where an adjustment member can be moved along any suitable path such as curved and/or curvilinear paths, for example.

As described above, referring to FIG. 54, adjustment member 1230 can comprise three surfaces, or steps, 1231, 1232, and 1233 while anvil plate 1134 can comprise three corresponding adjustment surfaces 1145, 1146, and 1147. When adjustment member 1230 is in its first position, for example, first surface 1231 can be positioned such that it abuts or is adjacent to first adjustment surface 1145, second surface 1232 can be positioned such that it abuts or is adjacent to second adjustment surface 1146, and third surface 1233 can be positioned such that it abuts or is adjacent to third adjustment surface 1147. As adjustment member 1230 is slid relative to anvil plate 1134, as described above and referring to FIGS. 55 and 56, surfaces 1231, 1232, and 1233 of adjustment member 1230 can be sequentially indexed relative to surfaces 1145, 1146, and 1147 of anvil plate 1134. In at least one such embodiment, an adjustment member can have the same number of steps as the number of positioning surfaces on an anvil plate. Other embodiments are envisioned where an adjustment member has more steps than positioning surfaces on the anvil plate. In at least one such embodiment, an anvil plate can include one positioning surface wherein the steps of an adjustment member can be selectively utilized to limit the upward movement of the anvil plate, for example. In various embodiments, referring generally to adjustment member 1230 and anvil plate 1134, an anvil plate may include one positioning surface, such as positioning surface 1145, for example, where steps 1231, 1232, and 1233 of adjustment member 1230, for example, can be selectively positioned intermediate base 1138 and positioning surface 1145. In such embodiments, first step 1231 can have a first thickness or height which can stop, or limit, the upward movement of anvil plate 1134 so as to define a first staple forming height, second step 1232 can have a second thickness or height which can stop, or limit, the upward movement of anvil plate 1134 so as to define a second staple forming height, and, in addition, third step 1233 can have a third thickness or height which can stop, or limit, the upward movement of anvil plate 1134 so as to define a third staple forming height. In at least one embodiment, the thickness or height of steps 1231, 1232, and/or 1233 can be measured between a back surface 1237 of adjustment member 1230 and a surface on the steps (1231, 1232, 1233) which will contact anvil plate 1134. In various embodiments, the difference in height, or thickness, between first step 1231 and second step 1232 can be the same, or at least substantially the same, as the difference in height, or thickness, between second step 1232 and third step 1233. In at least one such embodiment, as a result, the step heights can increase at a linear rate, or an at least substantially linear rate. In alternative embodiments, the difference in height, or thickness, between the first and second steps can be different than the difference in height, or thickness, between the second and the third steps. In at least one such embodiment, the first, second, and third steps may not increase or decrease in height, or thickness, at a linear rate; rather, although not illustrated, the steps may increase or decrease in height, or thickness, in a non-linear and/or geometric rate.

As described above, an adjustment member, such as adjustment member 1230, for example, can be movable between two or more positions. In various embodiments, a surgical stapling instrument can include an actuator configured to move the adjustment member. In at least one embodiment, referring to FIGS. 50-53, surgical stapling instrument 1100 can include actuator 1250 which can be operably attached to adjustment member 1230 such that a force can be applied to actuator 1250 and transmitted to adjustment member 1230. In certain embodiments, actuator 1250 can include grasping portions, or handles, 1252 which can be configured to be grasped by a surgeon, for example, in order to advance or retract adjustment member 1230 within anvil 1130 as described above. In certain embodiments, grasping portions 1252 can extend from actuator body 1251, wherein actuator body 1251 can include one or more apertures, slots, or cavities 1253 which can be configured to receive at least a portion of adjustment member 1230. In at least one such embodiment, referring to FIG. 52, adjustment member 1230 can include lock 1254 extending therefrom, wherein at least a portion of lock 1254 can be received within aperture 1253 so as to retain actuator body 1251 to adjustment member 1230. In various embodiments, lock 1254 can include one or more resilient, or flexible, legs 1255 which can be deflected when they are inserted into aperture 1253 but resiliently return, or at least partially return, to their unflexed position after feet 1256 of legs 1255 are sufficiently pushed through aperture 1253. In at least one such embodiment, feet 1256 can prevent, or at least inhibit, actuator body 1251 from being detached from adjustment member 1230.

In various embodiments, further to the above, surgical stapling instrument 1100 can further include a detent mechanism which can be configured to hold, or releasably hold, actuator 1250 and/or adjustment member 1230 in position. In at least one embodiment, referring to FIG. 52, detent member 1260 can be attached to actuator 1250 wherein, in at least some embodiments, actuator body 1251 can include one or more channels, grooves, or recesses 1257 which can be configured to receive and/or retain a detent body 1261 of detent member 1260 therein. In at least one embodiment, detent body 1261 can include one or more apertures 1263, and/or any other suitable channels, slots, or grooves, which can be configured to receive one or more fasteners for securing detent body 1261 to actuator 1251, for example. Detent member 1260 can further include detent legs 1262 which can be configured to engage one or more recesses, apertures, or grooves 1101 (FIGS. 35-40) in first frame portion 1110, for example. More particularly, referring to FIGS. 34 and 35, each side flange 1128 can include one or more recesses 1101 (1101*a*, 1101*b*, and 1101*c*) defined therein wherein detent legs 1262 can be biased into engagement with the top surfaces of side flanges 1128 such that detent legs 1262 can be slid into, and slid out of, recesses 1101. In the illustrated embodiment, each side flange can include three recesses 1101 which can be configured to removably hold actuator 1250 in a first, distal position, a second, intermediate position, and a third, proximal position, wherein the first, second, and third positions of actuator 1250 can respectively correspond with the first, second, and third positions of adjustment member 1230 described above. For example, when actuator 1250 is in its first, distal position, detent legs 1262 of detent member 1260 can be positioned within recess 1101*a* so as to removably retain actuator 1250 and adjustment member 1230 in their first positions. Upon the application of a sufficient force, actuator 1250 can be moved proximally into its second position such that detent legs 1162 are positioned within recess 1101*b* and actuator 1250 and adjustment member 1230 are retained in their second positions. Similarly, upon the application of a sufficient force, actuator 1250 can be moved proximally into its third position such that detent legs 1162 are positioned within recess 1101c and actuator 1250 and adjustment member 1230 are retained in their third positions. In various embodiments, detent legs 1162 can be configured such that actuator 1250 can be returned to its first and/or second positions.

As described above, adjustment member 1230 can be moved along a pre-determined path between two or more positions by actuator 1250. In various embodiments, surgical stapling instrument 1100, for example, can include one or more guides for controlling or limiting the movement of adjustment member 1230 and/or actuator 1250. In some embodiments, adjustment member 1230 can be closely received between side walls 1137 of anvil 1130 such that side walls 1137 can guide adjustment member 1230. In at least one such embodiment, side walls 1137 can be configured to control or limit the lateral or side-to-side movement of adjustment member 1230. In various embodiments, detent legs 1162 of detent member 1160 can comprise resilient members which can be configured to apply an upward biasing or pulling force on adjustment member 1230 so as to position adjustment member 1230 against, or at least adjacent to, base 1138 and intermediate side walls 1137. In certain embodiments, referring to FIG. 52, base 138 of anvil 1130 can further include guide slot 1149 which can be configured to receive at least a portion of adjustment member 1230 and/or actuator 1250 therein such that guide slot 1149 can limit the movement of adjustment member 1230 and actuator 1250. In at least one such embodiment, lock 1254 of adjustment member 1230 can be configured to extend through guide slot 1149 such that, when lock 1254 is inserted into aperture 1253 of actuator 1250 as described above, base 1138 of anvil 1130 can be captured intermediate adjustment member 1230 and actuator 1250. In certain embodiments, guide slot 1149 can be configured to limit the movement of lock 1254 such that adjustment member 1230 can be prevented, or at least inhibited, from being moved distally when adjustment member 1230 is in its first, or distal-most, position and/or, similarly, prevented, or at least inhibited, from being moved proximally when adjustment member 1230 is in its third, or proximal-most, position.

Figure 70:
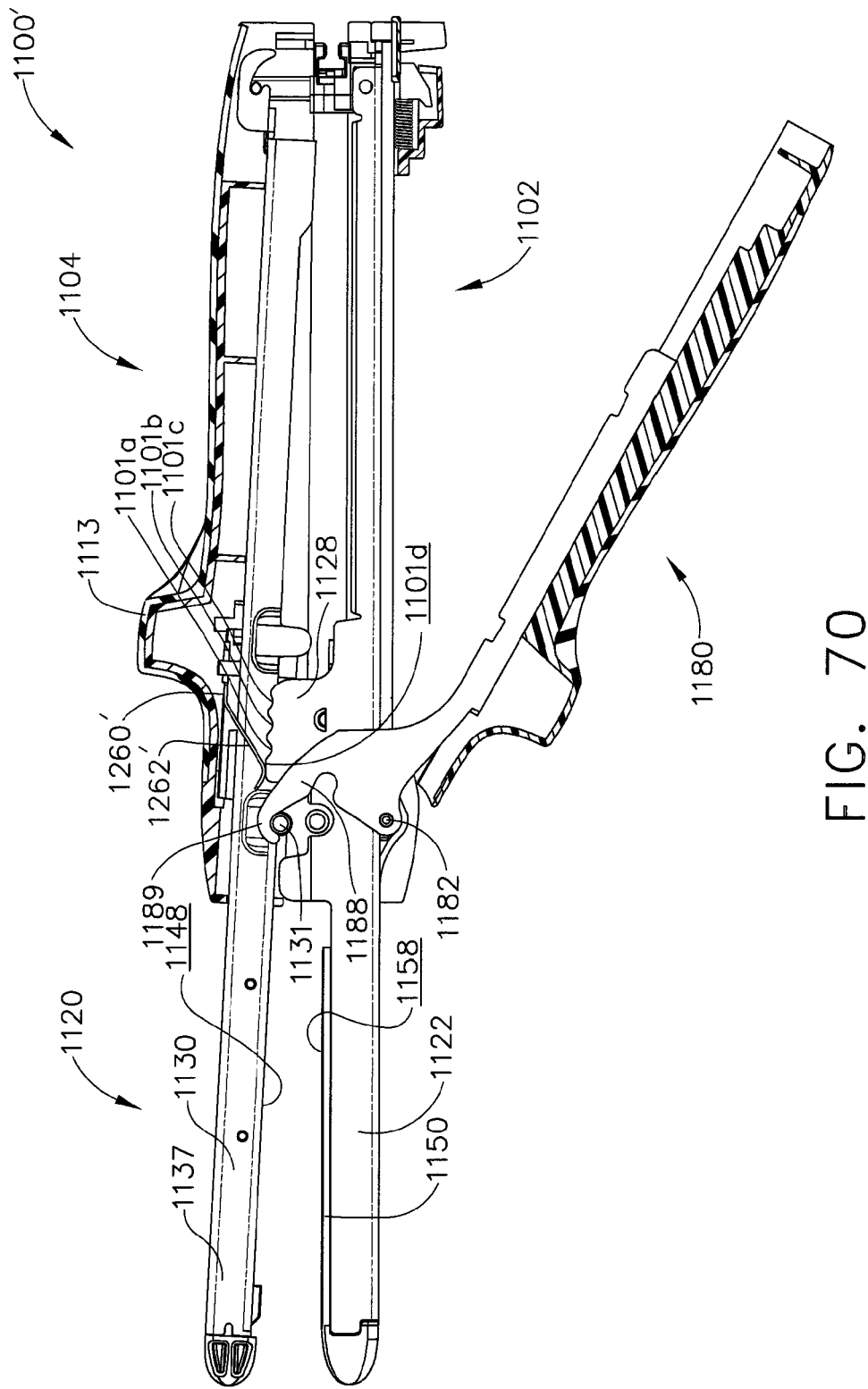
FIG. 70 is a partial cross-sectional view of a surgical stapling instrument including a spring configured to bias the distal end of a first handle portion away from the distal end of a second handle portion when the stapling instrument is in a partially-closed configuration.

In various embodiments, further to the above, a detent member, similar to detent member 1260, for example, can be utilized to bias first handle portion 1102 and second handle portion 1104 away from one another. In at least one embodiment, referring to FIG. 70, surgical stapling instrument 1100' can include a detent member 1260' configured to position first handle portion 1102 and second handle portion 1104 such that a gap exists between anvil 1130 and staple cartridge 1150. Such a feature, as outlined above, can allow a surgeon to easily manipulate the surgical instrument without having to hold the first and second handle portions apart from one another. In certain embodiments, detent member 1260' can be sufficiently mounted to second handle portion 1104 such that detent legs 1262' extending from detent member 1260' can contact flanges 1128 and, when compressed, apply a biasing force to the first and second handle portions. As seen in FIG. 70, legs 1262' can contact surfaces 1101d on flanges 1128. In order to compress detent legs 1262', latch mechanism 1180 can be moved into a partially-closed position such that latch arms 1188 can engage, and at least partially surround, latch projections 1131. In this configuration, a surgeon can manipulate the instrument and, when satisfied with its position, move latch mechanism 1180 into a closed position and further compress detent legs 1262'. Similar to the above, detent member 1260' can be affixed, or otherwise operably engaged with, actuator 1250 such that, when actuator 1250 is moved between its first, second, and third positions as described above, legs 1262' can engage recesses 1101a, 1101b, and 1101c, respectively. In at least one such embodiment, as a result, actuator 1250 can have a pre-staged position in which actuator 1250 is positioned distally with respect to its first position and, in addition, surfaces 1101d can comprise pre-stage surfaces against which legs 1262' can be positioned when actuator 1250 is in its pre-staged position.

As outlined above, an adjustment member can be slid, or translated, between first and second positions so as to adjust the forming height of staples deployed by a surgical stapling instrument. In various embodiments, although not illustrated, an adjustment member can be configured to positively displace an anvil plate toward and/or away from an opposing staple cartridge, for example. In at least one such embodiment, a surgical stapling instrument can include one or more biasing members, such as springs, for example, configured to position the anvil plate against the adjustment member such that, when the adjustment member is moved between its first and second positions, the adjustment member can displace the anvil plate between first and second positions in order to set first and second staple forming heights. In various embodiments, as a result of the above, an adjustment member can be configured to cam a portion of an anvil into position. In at least one such embodiment, an adjustment member can be slid along an axis in order to positively displace an anvil plate. In other embodiments, a rotatable adjustment member can be configured to positively displace an anvil plate toward and/or away from a staple cartridge, for example.

Figure 58:
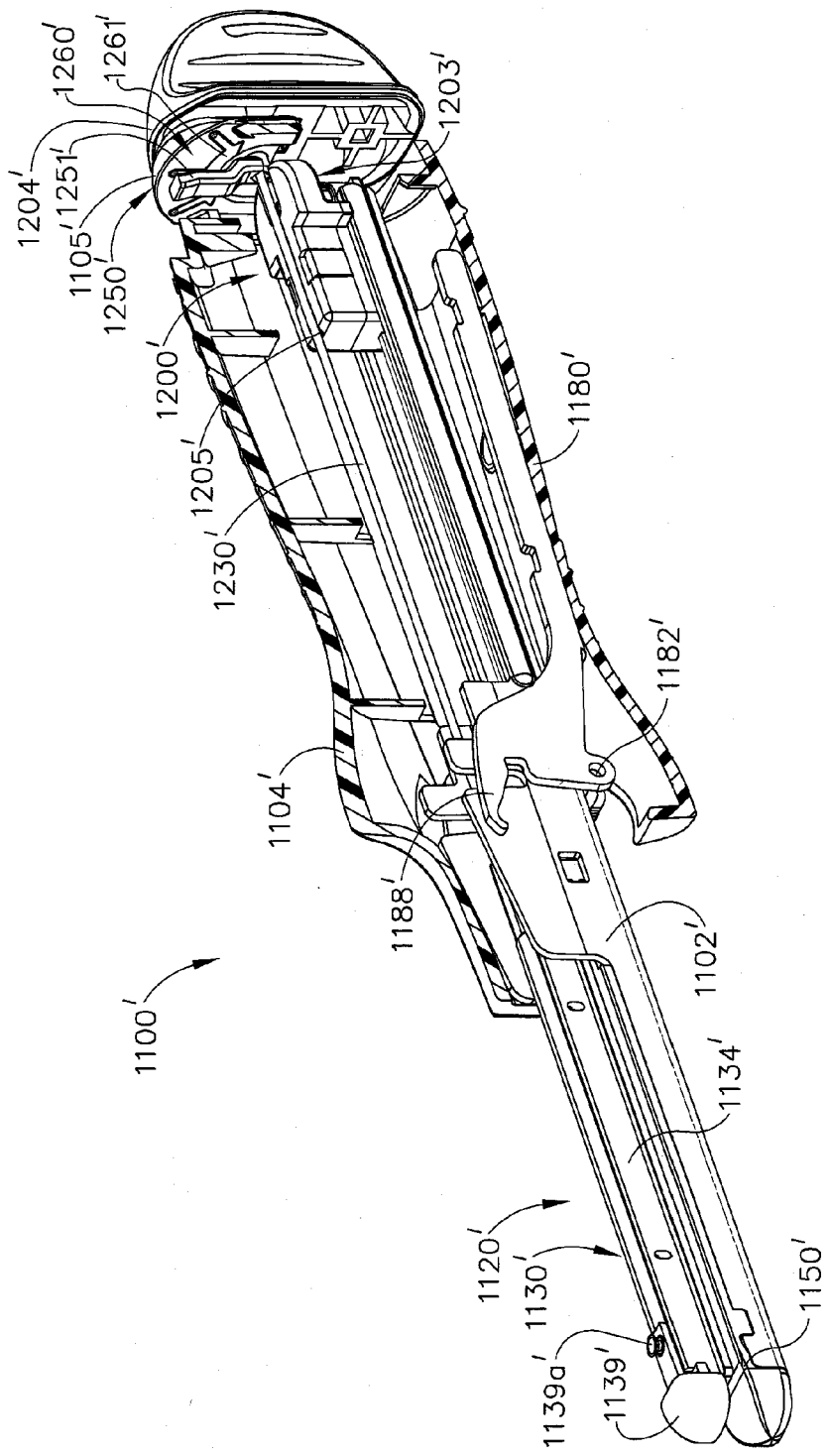
FIG. 58 is a cross-sectional view of the surgical stapling instrument of FIG. 57 taken along line 58-58 in FIG. 57.

Further to the above, as described in greater detail below, an adjustment member can be rotated to adjust the staple forming height. Referring to FIGS. 57-69, surgical instrument 1100' can include, similar to the above, a first handle portion 1102', a second handle portion 1104', and a latching mechanism 1180' which can be utilized to clamp tissue intermediate anvil 1130' and staple cartridge 1150'. Referring to FIG. 58, also similar to the above, latching mechanism 1180' can be pivotably coupled to first portion 1102' by one or more pivot pins 1182', wherein latching mechanism 1180' can include one or more latch arms 1188' which can be configured to engage second portion 1104' and latch the first and second handle portions together. Also similar to the above, referring to FIGS. 58 and 60, surgical instrument 1100' can further include pusher bar assembly 1200' which can be configured to advance a cutting member and/or staple sled within end-effector 1120'. In at least one such embodiment, pusher bar assembly 1200' can include a proximal end 1203' and an actuator 1204', wherein actuator 1204' can be rotatably mounted to proximal end 1203' and selectively positioned on first and second sides of stapling instrument 1100'. In various embodiments, surgical stapling instrument 1100' can comprise the same, or similar, features to those described in connection with surgical stapling instrument 1100 and can be operated in the same manner, or a similar manner, as instrument 1100 and, as a result, such details are not repeated herein.

Figure 60:
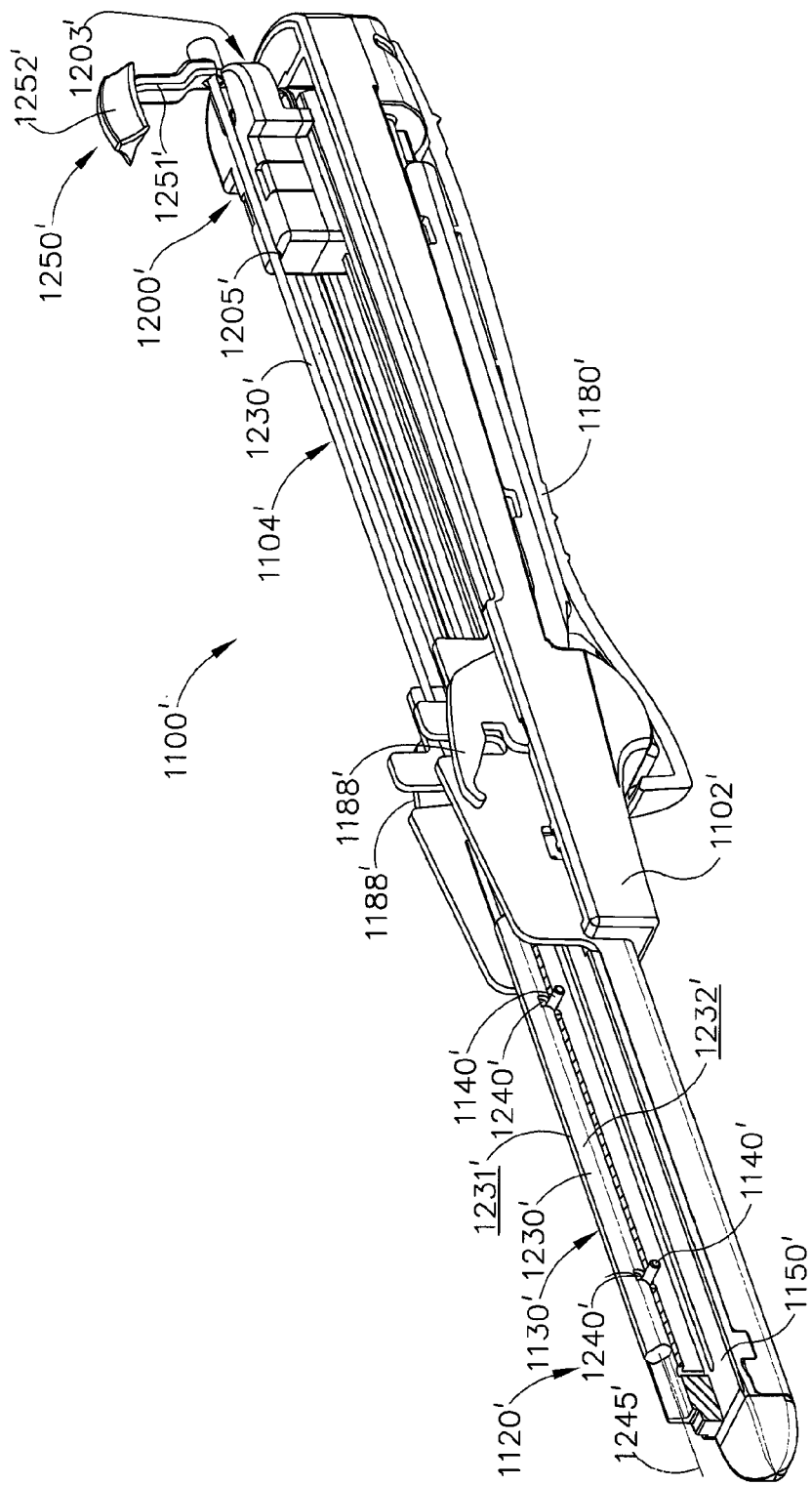
FIG. 60 is a perspective view of the surgical stapling instrument of FIG. 57 with some components removed and others shown in cross-section.
Figure 61:
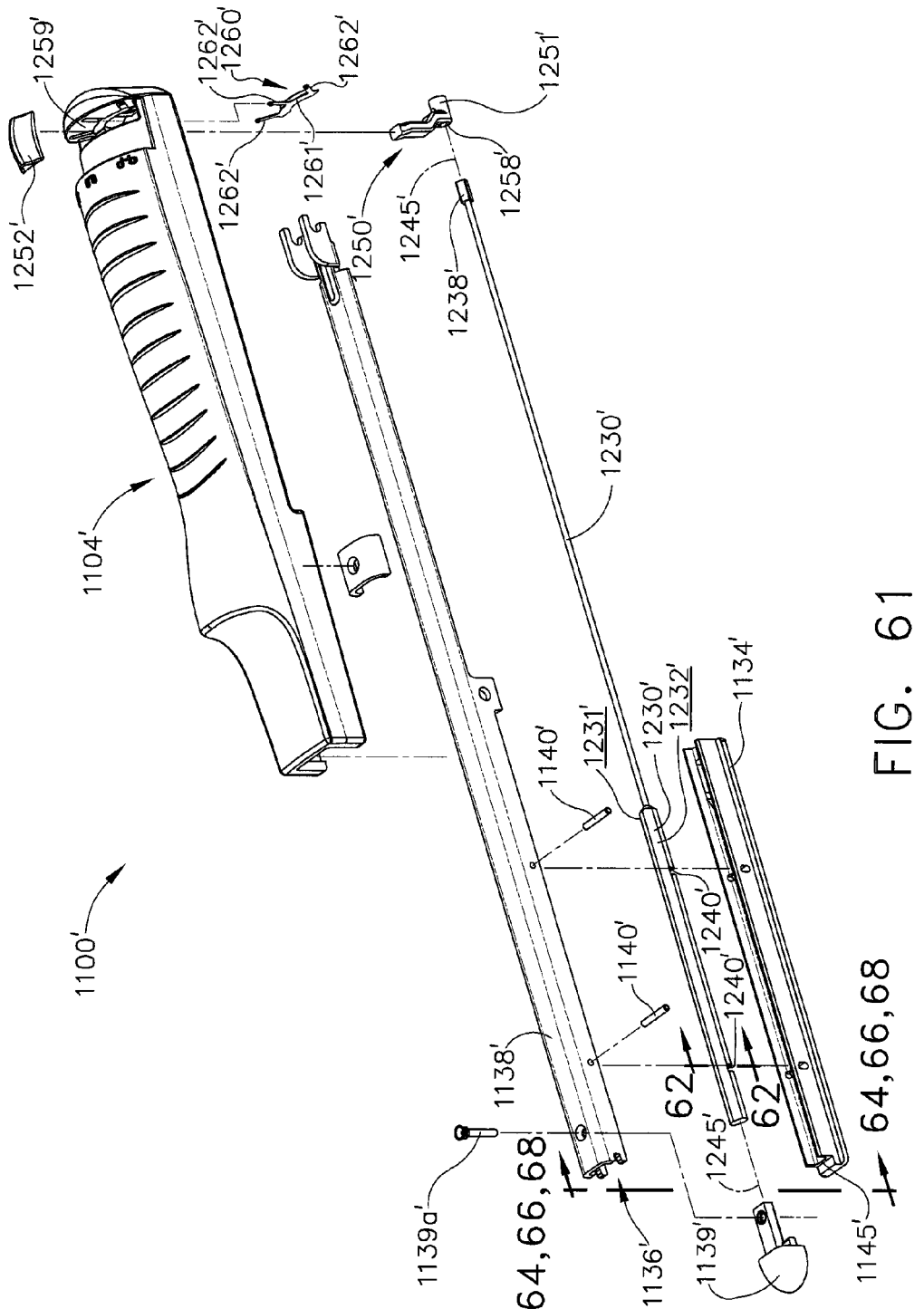
FIG. 61 is an exploded view of portions of the surgical stapling instrument of FIG. 57 illustrating a rotatable anvil adjustment member in a first orientation.
Figure 62:
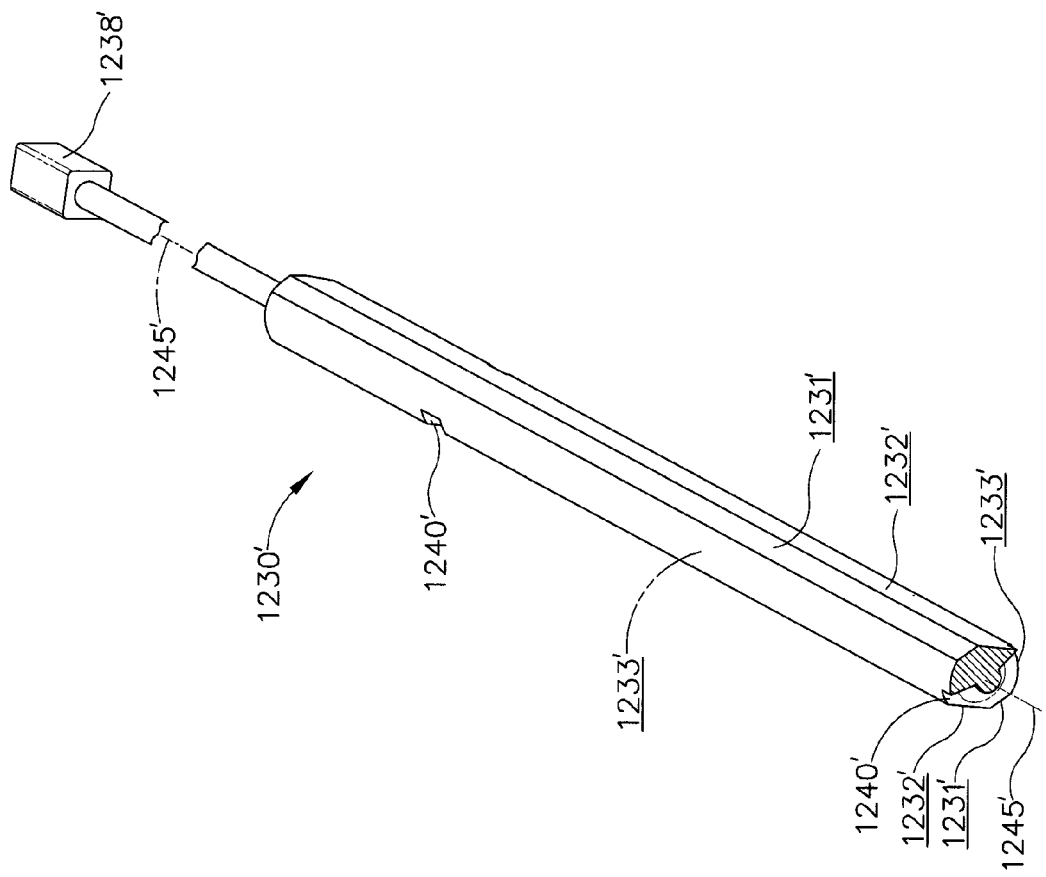
FIG. 62 is a perspective view of the rotatable anvil adjustment member of FIG. 61.
Figure 69:
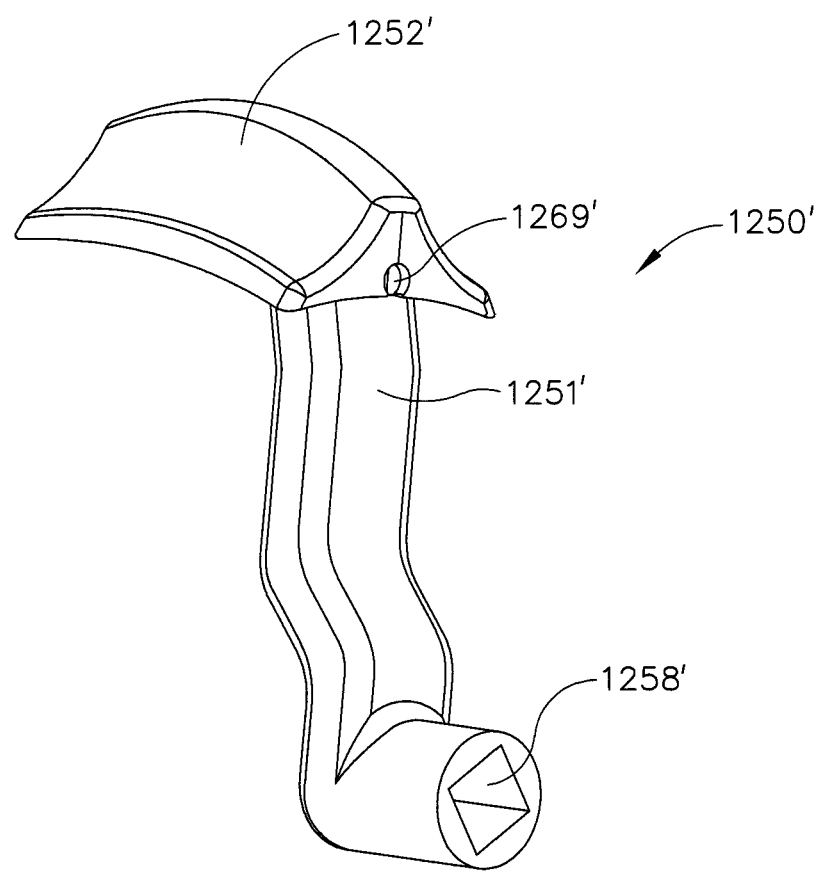
FIG. 69 is a perspective view of an actuator for rotating the anvil adjustment member of FIG. 61.

In various embodiments, referring to FIG. 60, surgical instrument 1100' can include a rotatable adjustment member 1230' which can be selectively positioned in at least first and second positions so as to provide different staple forming heights. In certain embodiments, surgical instrument 1100' can include an actuator 1250' which can be operably connected to adjustment member 1230' such that actuator 1250' can move adjustment member 1230' between at least its first and second positions. In at least one embodiment, referring to FIG. 61, actuator 1250' can include actuator body 1251' and grasping portion, or handle, 1252'. Actuator body 1251' can include an aperture 1258' which can be configured to receive a proximal end 1238' of adjustment member 1230' such that rotational motion, torque, and/or forces can be transmitted between actuator 1250' and adjustment member 1230'. In at least one such embodiment, referring to FIG. 69, aperture 1258' can comprise a non-circular profile and/or a profile which includes one or more flat drive surfaces configured to transmit rotational motion between actuator body 1251' and actuator 1230'. In certain embodiments, aperture 1258' can be sized and configured to closely receive proximal end 1238' of actuator 1230'. In at least one embodiment, aperture 1258' can be configured to receive proximal end 1238' in a press-fit and/or snap-fit arrangement. In various embodiments, referring again to FIG. 61, handle portion 1104' can include one or more slots 1259' which can be configured to permit at least a portion of actuator body 1251' to extend therethrough such that grasping portion 1252' can be assembled to actuator body 1251' with at least a portion of handle portion 1104' positioned therebetween. In at least one such embodiment, second handle portion 1104' can further include recess 1253' which can be configured such that at least a portion, if not all, of grasping portion 1252' is positioned within recess 1253'. In certain embodiments, recess 1253' can be configured such that grasping portion 1252' does not extend above the top surface of second handle portion 1104' although, in other embodiments, an upper portion of grasping portion 1252' can extend above second handle portion 1104, as illustrated in FIG. 63, such that grasping portion 1252' can be easily accessed by a surgeon.

In various embodiments, as outlined above, an adjustment member can be rotatable between at least first and second positions in order to adjust the forming height of staples deployed by a surgical stapler. In certain embodiments, referring to FIG. 61, a surgical stapling instrument can include an adjustment member rotatably positioned within an anvil wherein the adjustment member can be configured to limit the relative movement of a movable anvil portion. In at least one such embodiment, surgical stapling instrument 1100' can include an anvil plate 1134' which can be slidably retained within anvil channel 1136' by retention, or guide, pins 1140', wherein guide pins 1140' can be configured to allow anvil plate 1134' to slide upwardly when anvil plate 1134' comes into contact with tissue as described above. Referring to FIGS. 60, 63, and 64, adjustment member 1230' can be positionable in a first position, or orientation, such that it can limit the upward movement of anvil plate 1134' within anvil channel 1136' and dictate the staple forming height of the staples. In at least one such embodiment, referring to FIGS. 63 and 64, adjustment member 1230' can include opposing first surfaces 1231' which can be positioned intermediate base 1138' of anvil channel 1136' and positioning surface 1145' of anvil plate 1134' such that, when positioning surface 1145' contacts one of first surfaces 1231', tissue-contacting surface 1148' of anvil plate 1134' can be positioned a first distance 1234' away from a datum surface 1129' on anvil 1130', for example. Correspondingly, forming surfaces 1132' can be positioned a first distance away from a staple cartridge such that, when staples are deployed from the staple cartridge, the staples can be deformed to a first staple height. Further to the above, a first diameter 1241' can be defined between first surfaces 1231' wherein the first diameter 1241' can define the maximum upward position of anvil plate 1134' within anvil channel 1136'.

As indicated above, adjustment member 1230' can be rotated in order to adjust the forming height of the staples. In various embodiments, adjustment member 1230' can be rotated between its first position, or orientation, (FIGS. 63 and 64) and a second position, or orientation (FIGS. 65 and 66). In at least one embodiment, referring to FIGS. 65 and 66, handle 1252' can be rotated in a direction indicated by arrow "A" in order to move adjustment member 1230' between its first and second positions. Similar to the above, when actuator 1230' is in its second position, or orientation, actuator 1230' can limit the upward movement of anvil plate 1134' within anvil channel 1136' and dictate the staple forming height of the staples. In at least one such embodiment, referring to FIGS. 65 and 66, adjustment member 1230' can include opposing second surfaces 1232' which can be positioned intermediate base 1138' and positioning surface 1145' such that, when positioning surface 1145' contacts one of second surfaces 1232', tissue-contacting surface 1148' of anvil plate 1134' can be positioned a second distance 1235' away from datum surface 1129', for example. Correspondingly, forming surfaces 1132' can be positioned a second distance away from a staple cartridge such that, when staples are deployed from the staple cartridge, the staples can be deformed to a second staple height. In various embodiments, similar to the above, a second diameter 1242' can be defined between second surfaces 1232', wherein second diameter 1242' can define the maximum upward position of anvil plate 1134' within anvil channel 1136'. Although first surfaces 1231' and second surfaces 1232' can be defined by flat, or at least substantially flat, surfaces, other embodiments are envisioned in which the first and second surfaces 1231' and 1232' can include at least partially arcuate, or curved, contours. In any event, referring to FIG. 60, adjustment member 1230' may include one or more clearance slots 1240' which can be configured to provide clearance between actuator 1230' and retention pins 1140'. Clearance slots 1240' can be configured to provide clearance between actuator 1230' and retention pins 1140' when actuator 1230' is in its first position, second position, and/or any other suitable position.

In various embodiments, further to the above, adjustment member 1230' can be rotated between its first position, or orientation, (FIGS. 63 and 64) and a third position, or orientation (FIGS. 67 and 68). In at least one embodiment, referring to FIGS. 67 and 68, handle 1252' can be rotated in a direction indicated by arrow "B" in order to move adjustment member 1230' between its first and third positions. Similar to the above, when actuator 1230' is in its third position, or orientation, actuator 1230' can limit the upward movement of anvil plate 1134' within anvil channel 1136' and dictate the staple forming height of the staples. In at least one such embodiment, referring to FIGS. 67 and 68, adjustment member 1230' can include opposing third surfaces 1233' which can be positioned intermediate base 1138' and positioning surface 1145' such that, when positioning surface 1145' contacts one of third surfaces 1233', tissue-contacting surface 1148' of anvil plate 1134' can be positioned a third distance 1236' away from datum surface 1129', for example. Correspondingly, forming surfaces 1132' can be positioned a third distance away from a staple cartridge such that, when staples are deployed from the staple cartridge, the staples can be deformed to a third staple height. In various embodiments, similar to the above, a third diameter 1243' can be defined between third surfaces 1233', wherein third diameter 1243' can define the maximum upward position of anvil plate 1134' within anvil channel 1136'. Referring once again to FIGS. 67 and 68, third surfaces 1233' can be defined by an at least partially arcuate contour, although other embodiments are envisioned in which third surfaces 1233' can include flat, or at least substantially flat, contours. In at least one embodiment, adjustment member 1230' can be configured such that the largest distance, or diameter, between the arcuate third surfaces 1233' can be utilized to define the third staple height.

As described above, referring to FIGS. 63 and 64, adjustment member 1230' can be positioned in a first position, or orientation, to set a first forming height for the staples deployed by surgical stapling instrument 1100'. As also described above, referring to FIGS. 65 and 66, actuator 1250' can be utilized to move adjustment member 1230' into its second position, or orientation, to set a second forming height for the staples. To do this, in at least one embodiment, a force can be applied to handle 1252' which can cause handle 1252', and adjustment member 1230' attached thereto, to rotate in a direction indicated by arrow "A". In at least one embodiment, adjustment member 1230' and/or actuator 1250' can be sufficiently retained such that, when adjustment member 1230' is rotated, adjustment member 1230' can be rotated about an axis, such as axis 1245' (FIG. 60), for example. In at least one embodiment, referring to FIG. 58, the proximal end 1203' of pusher bar assembly 1200' can include one or more grooves, channels, or recesses 1205' which can be configured to receive and/or retain at least a portion of adjustment member 1230' and/or actuator 1250' therein. In any event, as illustrated in FIGS. 63-66, the second position, or orientation, of adjustment member 1230' can allow anvil plate 1134' to slide a larger distance within anvil channel 1136' as compared to when adjustment member 1230' is in its first position. In at least one embodiment, as a result, the second staple forming height can be larger than the first staple forming height. As also described above, referring to FIGS. 67 and 68, actuator 1250' can be utilized to move adjustment member 1230' into its third position, or orientation, to set a third forming height for the staples. To do this, in at least one embodiment, a force can be applied to handle 1252' which can cause handle 1252', and adjustment member 1230' attached thereto, to rotate in a direction indicated by arrow "B". As illustrated in FIGS. 63, 64, 67, and 68, the third position, or orientation, of adjustment member 1230' can allow anvil plate 1134' to slide a smaller distance within anvil channel 1136' as compared to when adjustment member 1230' is in its first position. In at least one embodiment, as a result, the first and second staple forming heights can be larger than the third staple forming height. In at least one such embodiment, the first position of adjustment member 1230', and actuator 1250', can represent an intermediate position, wherein adjustment member 1230' can be selectively moved into its second and third positions directly from its first position. In effect, the first position of adjustment member 1230' can represent an intermediate staple height, wherein the second and third staple positions of adjustment member 1230' can represent taller and shorter staple heights, respectively. In certain embodiments, referring to FIG. 57, surgical stapling instrument 1100' can include one or more indicia thereon which can be configured to convey the staple forming heights, or at least relative forming heights, that can be selected. For example, second handle portion 1104' can include a first indicium 1245' which can indicate an intermediate, or first, staple height, a second indicium 1246' which can indicate a taller, or second, staple height, and, in addition, a third indicium 1247' which can indicate a shorter, or third, staple height.

In various embodiments, further to the above, one or more of first surfaces 1231', second surfaces 1232', and third surfaces 1233' can comprise or define, or at least partially comprise or define, a perimeter, or circumference, of adjustment member 1230'. As discussed above, owing to the first, second, and third diameters (1241', 1242', and 1243') defined by the first, second, and third surfaces (1231', 1232', and 1233'), respectively, the perimeter, or circumference, of adjustment member 1230' may be non-circular. In certain embodiments, though, the perimeter, or circumference of adjustment member 1230', may be symmetrical, substantially symmetrical, and/or non-symmetrical. In various embodiments, further to the above, an adjustment member can comprise a cam rotatably positioned intermediate base 1138' of anvil 1130' and adjustment surface 1145' of anvil plate 1134', for example. In at least one such embodiment, one or more of first surfaces 1231', second surfaces 1232', and third surfaces 1233', for example, can comprise or define a cam profile which, similar to the above, can be configured to either positively position anvil plate 1134' and/or provide a stop against which anvil plate 1134' can be positioned. In any event, although not illustrated, various embodiments are envisioned in which an adjustment member can be slid and rotated in order to set two or more staple forming heights for staples deployed by a surgical stapling instrument. In at least one such embodiment, an adjustment member can comprise a cam profile which can be defined along the length of the adjustment member wherein longitudinal and/or rotational movement can be utilized to move the cam profile between at least first and second positions.

Figure 59:
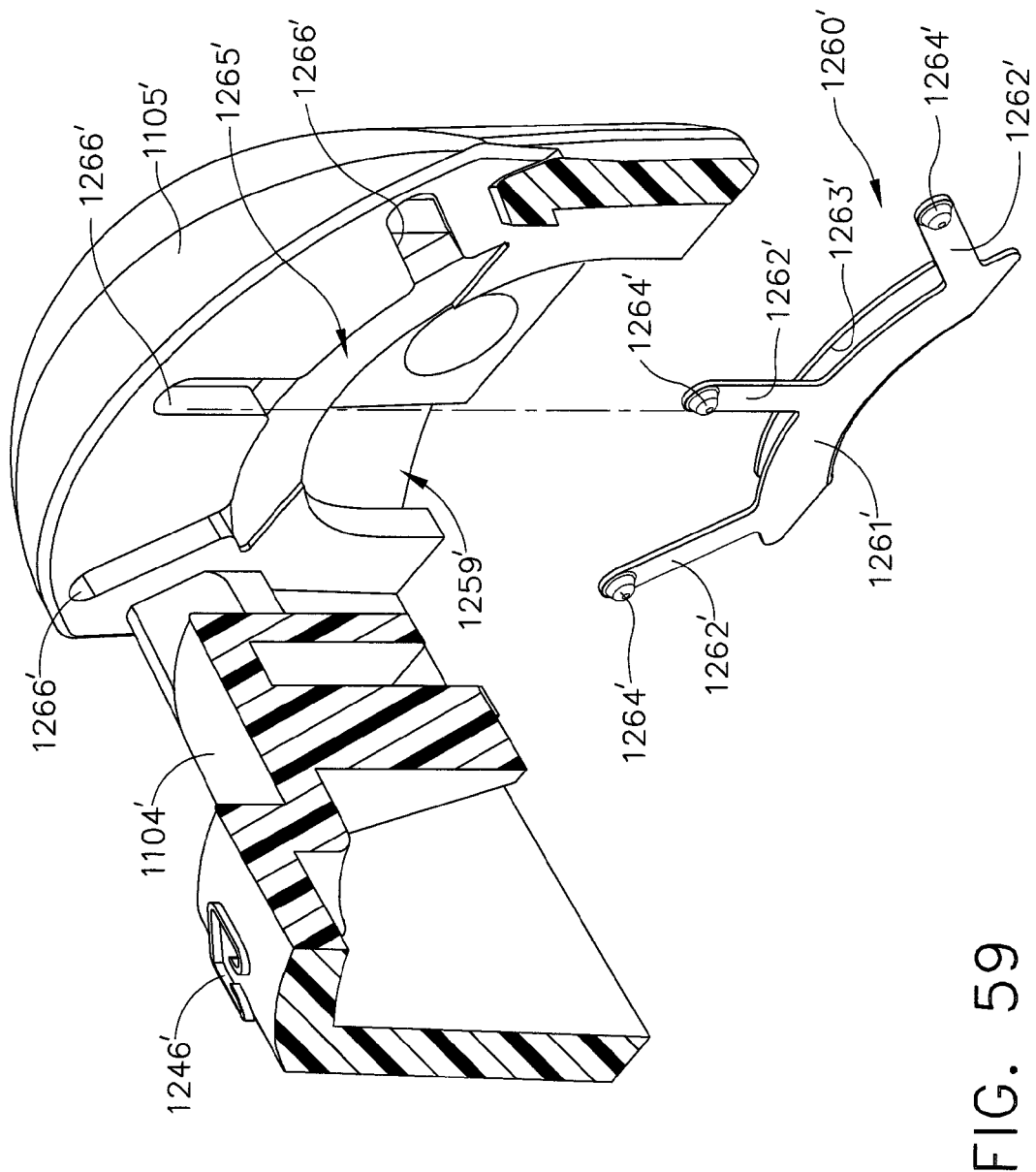
FIG. 59 is a partial exploded view of the proximal end of the surgical stapling instrument of FIG. 57 including a detent mechanism for releasably holding a rotatable anvil adjustment member in position.

In various embodiments, similar to the above, surgical instrument 1100' can further include a detent mechanism configured to hold, or at least releasably hold, actuator 1250' in position. In at least one embodiment, referring to FIGS. 58 and 59, surgical instrument 1100' can further include detent member 1260' comprising detent body 1261' and one or more detent legs 1262'. Referring to FIG. 59, detent body 1261' can include one or more grooves, recesses, or channels 1263' which can be configured to receive at least a portion of proximal end 1105' of second handle portion 1104' therein such that detent member 1260' can be retained in position. In at least one such embodiment, proximal end 1105' can further include one or more grooves, channels, or recesses 1265' which can be configured to closely receive detent member 1260'. In certain embodiments, at least a portion of detent body 1261', such as channel 1263', for example, can be press-fit, snap-fit, and/or otherwise suitably retained in recess 1265'. As also illustrated in FIG. 59, each detent leg 1262' of detent member 1260' can include one or more projections 1264' extending therefrom which can be configured to engage actuator body 1251' and releasably hold actuator 1250' in position. In at least one embodiment, referring to FIG. 69, actuator body 1251' can include one or more recesses, or holes, 1269' which can be configured to receive a projection 1264'. When a projection 1264' is positioned within recess 1269', the projection can be configured to hold actuator 1250' in its first position, for example, until a sufficient force is applied to actuator 1250' so as to cause the projection 1264' to be displaced out of recess 1269'. More particularly, the force applied to actuator 1250' can be transmitted to the projection 1264' and, owing to cooperating surfaces between the projection 1264' and recess 1269', the detent leg 1262' associated with the projection 1264' can be flexed or moved proximally to allow actuator body 1251' to be moved relative thereto. In order to accommodate such proximal movement, referring to FIG. 58, recess 1265' can include elongate portions 1266' which can each be configured to receive at least a portion of legs 1262' such that legs 1262' can move relative to handle portion 1104'. As actuator 1250' is moved into either its second or third position, actuator body 1251' can contact a projection 1264' extending from another leg 1262' and deflect the leg 1262' proximally such that, once actuator 1250' is in its second or third positions, the leg 1262' can spring forward, or distally, such that the projection 1264' can be secured within recess 1269'. In at least one embodiment, further to the above, the interaction between projections 1264' and the sidewalls of recess 1269' can be such that actuator 1250' can be securely held in one of its first, second, and third positions, for example, yet permit actuator 1250' to be moved upon a sufficient application of force. In such embodiments, the detent member 1260' can prevent, or at least inhibit, actuator 1250' and, correspondingly, adjustment member 1230' from being unintentionally displaced.

As discussed above and as shown in FIG. 35, each side flange 1128 of first handle portion 1102 can include a notch, or recess, 1127, for example, which can be configured to receive one or more latch projections 1131, for example, extending from anvil 1130, and/or any other suitable portion of second handle portion 1104. As also discussed above, referring primarily to FIGS. 35 and 36, first handle portion 1102 can further include latching mechanism 1180 rotatably mounted thereto which can be utilized to engage latch projections 1131 extending from second handle portion 1104 and secure the first and second handle portions 1102, 1104 together. Latching mechanism 1180 can include one or more latch arms 1188 extending therefrom which can be configured to engage latch projections 1131 and pull and/or secure projections 1131 within recesses 1127 as illustrated in FIG. 40. Referring to FIG. 39, at least one of latch arms 1188 can include a distal hook 1189 which can be configured to wrap around at least a portion of projections 1131 so as to encompass or surround, or at least partially encompass or surround, projections 1131. In at least one embodiment, latch arms 1188 can act as an over-center latch to maintain latching mechanism 1180 in its latched, or closed, position.

Figure 71:
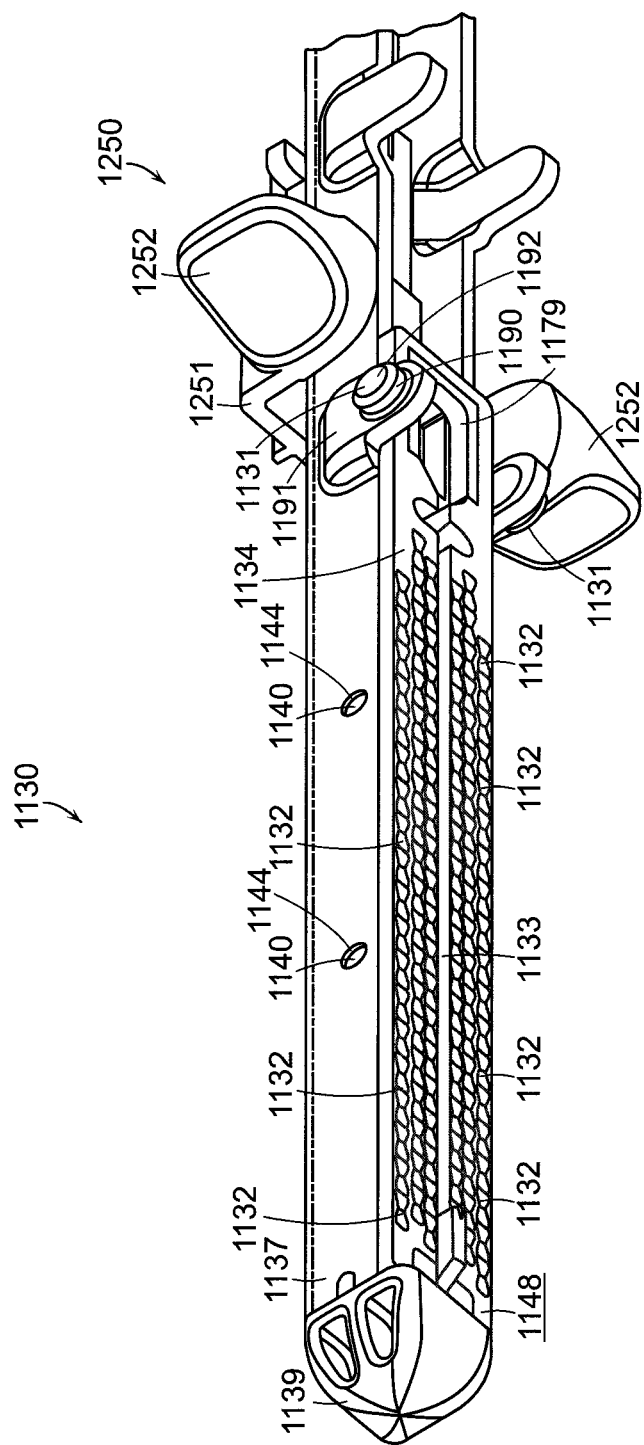
FIG. 71 is a similar perspective view of the surgical stapling instrument of FIG. 34 to that of FIG. 50.

In various embodiments, referring now to FIG. 71, each projection 1131 can comprise a slot, or groove, 1190 positioned intermediate sidewall 1191 and an enlarged end, or head, 1192 of projection 1131, wherein the slot 1190 can be configured to receive at least a portion of latch arm 1188. More particularly, in at least one embodiment, the slot 1190 can have a width which is greater than the width of the latch arm 1188 such that, when the latch arm 1188 is engaged with the projection 1131, the latch arm 1188 can enter into slot 1190. In some circumstances, the width of each slot 1190 may be slightly larger than the width of a latch arm 1188 such that the latch arm is closely received within the slot 1190. In various circumstances, the slot 1190, the sidewall 1191, and the head 1192 of projection 1131 can be sized and configured so as to prevent, or at least limit, relative lateral movement, i.e., movement away from or to the sides of anvil 1130, between latch arm 1188 and projection 1131. Further to the above, however, the latch arms 1188 can slide longitudinally within the grooves 1190 as the latch arms 1188 move the projections 1131 into the recesses 1127 in first portion 1102. Owing to such relative sliding movement between latch arms 1188 and projections 1131, frictional forces can be generated therebetween which can resist the movement of latch arms 1188. In various circumstances, the magnitude of such frictional forces can be significant when the normal, or perpendicular, contact forces between the latch arms 1188 and the sidewalls of groove 1190 are large. In many circumstances, as a result, the operator of the surgical instrument has to overcome these frictional forces when actuating clamping mechanism 1180.

Figure 72:
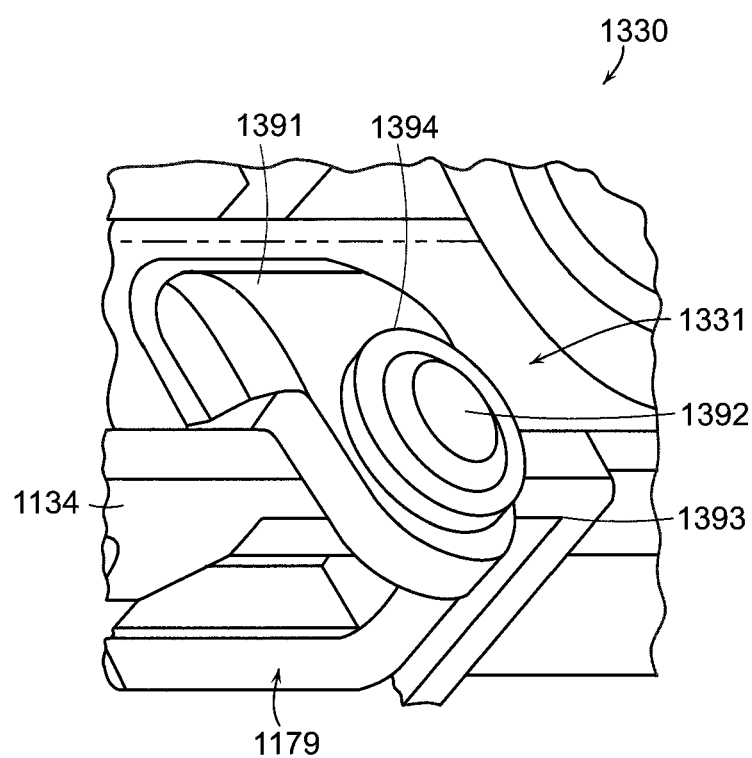
FIG. 72 is a detail view of a latch projection extending from an anvil of a surgical stapling instrument in accordance with at least one alternative embodiment of the present invention.
Figure 73:
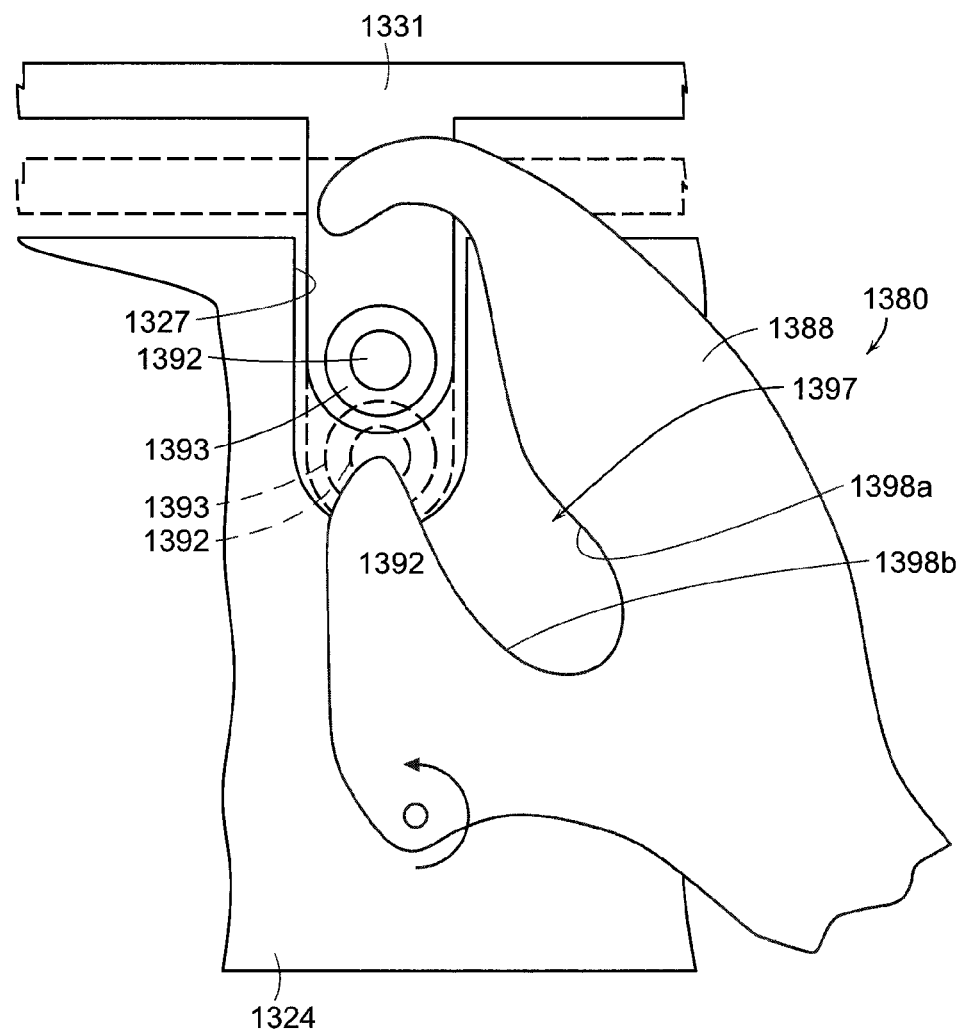
FIG. 73 is a diagram illustrating the latch projection of FIG. 72 and a latch configured to engage the latch projection and move the latch projection into a latch recess.

In various alternative embodiments, referring now to FIGS. 72 and 73, a surgical instrument can comprise one or more latch projections having a rotatable bearing which can reduce the magnitude of the friction forces between the latch arms of a latching mechanism and the latch projections. In at least one embodiment, an anvil 1330, which can be substantially similar to anvil 1130 in many respects, can comprise a latch projection 1331 extending from each side thereof, wherein each latch projection 1331 can comprise a rotatable bearing 1393. In use, the latch arms 1188 of latching mechanism 1180, for example, can contact the rotatable bearings 1393 in order to position the latch projections 1331 in recesses 1127. In various circumstances, the latch arms 1188 can slide across the surface, or outer diameter, of bearings 1393; however, as bearings 1393 can rotate relative to the latch arms 1188, the magnitude of the frictional forces between the latch arms 1188 and projections 1331 can be lower than the magnitude of the frictional forces between latch arms 1188 and projections 1131. Owing to such lower frictional forces, a lower closing, or clamping, force may be required to actuate clamping mechanism 1180, for example.

Figure 74:
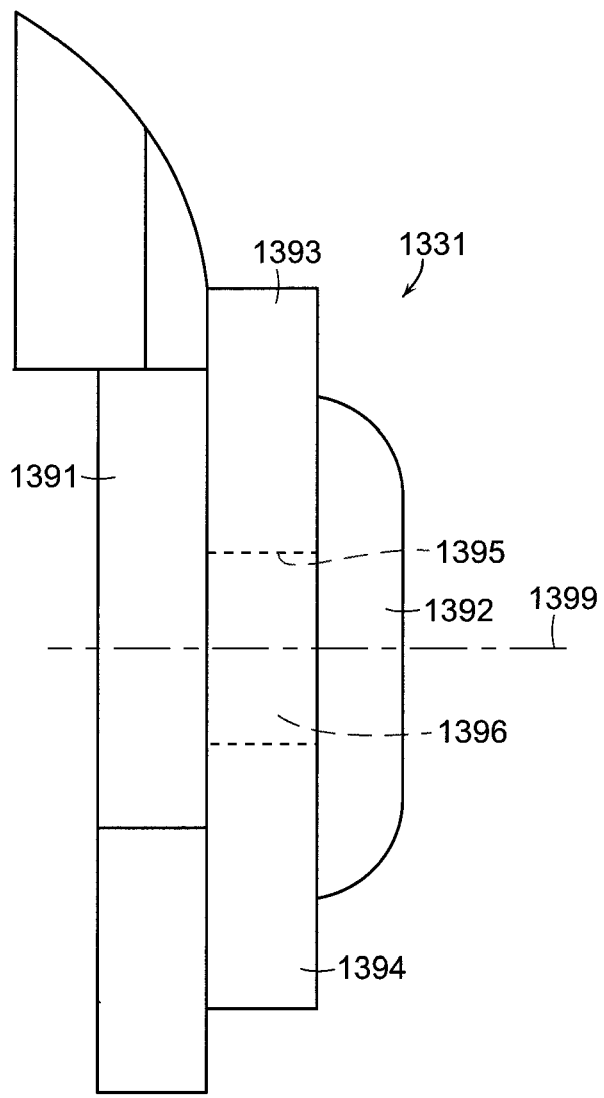
FIG. 74 is an elevational view of the latch projection of FIG. 72.

In various embodiments, referring primarily to FIG. 74, each rotatable bearing 1393 can comprise a circular, or round, outer diameter 1394 and, in addition, a circular, or round, bearing aperture 1395 extending therethrough. In certain embodiments, each projection 1331 can further comprise a shaft portion 1396 extending from sidewall 1391 and an enlarged end, or head, 1392 extending from shaft portion 1396, wherein, as illustrated in FIG. 64, the shaft portion 1396 can extend through the bearing aperture 1395 of rotatable bearing 1393. In various embodiments, the shaft portion 1396 can comprise a circular, or round, outer diameter which can be closely received within bearing aperture 1395 such that there is little, if any, relative radial movement therebetween. The diameter of the bearing aperture 1395, however, may be sufficiently larger than the outer diameter of shaft portion 1396 such that bearing 1393 can rotate relative to shaft portion 1396 about an axis 1399. In various embodiments, the rotatable bearing 1393 can be retained on shaft portion 1396 by the enlarged head 1392. More particularly, in at least one embodiment, the enlarged head 1392 may be larger than, or define a larger diameter than, the diameter of bearing aperture 1395 such that rotatable bearing 1393 cannot slide off the end of shaft portion 1396. In certain embodiments, the sidewall 1391 and the head 1392 can define a gap distance therebetween and, in addition, the bearing 1393 can comprise a width, wherein the gap distance can be larger than the width of bearing 1393. In at least one embodiment, the gap distance may be slightly larger than the width of bearing 1393 such that bearing 1393 does not tilt, or at least substantially tilt, relative to axis 1399, for example.

As discussed above, the latch arms 1188 of latching mechanism 1180 can be configured to engage bearings 1393 and position bearings 1393 within recesses 1127. In various alternative embodiments, referring primarily to FIG. 73, a surgical instrument can comprise a latching mechanism 1380 which can comprise first and second latch arms 1388 extending therefrom on opposite sides of anvil 1331 and staple cartridge channel 1324. In use, similar to the above, the latch arms 1388 can contact bearings 1393 in order to move bearings 1393 into recesses 1327 in staple cartridge channel 1324 and move anvil 1331 toward staple cartridge channel 1324. Such movement is illustrated with phantom lines in FIG. 74. In various embodiments, each latch arm 1388 can at least partially define a groove, or slot, 1397 therein, wherein each slot 1397 can be configured to receive a bearing 1393. In at least one embodiment, a slot 1397 can comprise a first drive surface, or sidewall, 1398*a* which can be positioned against bearing 1393 and, as a closing force is applied to latching mechanism 1380, the latch arm 1388 can apply a closing force to the bearing 1393. In such circumstances, the bearing 1393 can move further into slot 1397 as latching mechanism 1380 is rotated into its closed position. In various circumstances, the slot 1397 can further comprise a second drive surface, or sidewall, 1398*b* which can be positioned against another and/or opposite side of bearing 1393 such that an opening force can be applied to the bearing 1393 via latch arm 1388. As the latching mechanism 1380 is moved into its open position, the bearing 1393 can move out of slot 1397. In any event, the first drive surface 1398*a* and the second drive surface 1398*b* can define a slot width therebetween which can be larger than the outside diameter of bearing 1393 such that bearing 1393 can move within slot 1397. In some embodiments, the slot width may be slightly larger than the outside diameter of bearing 1393. In at least one embodiment, at least portions of the first drive surface 1398*a* and the second drive surface 1398*b* can be parallel, or at least substantially parallel, to one another. In at least one such embodiment, at least portions of the first drive surface 1398*a* can be positioned opposite the second drive surface 1398*b*.

As described above, a surgical stapling instrument can be configured to deform one or more surgical staples between a first, undeployed, configuration and a second, deployed, configuration. In various embodiments, referring now to FIG. 72, a surgical staple, such as staple 1400, for example, can comprise a base 1402, a first leg, or deformable member, 1404 extending from base 1402, and, in addition, a second leg, or deformable member, 1406 extending from base 1402. In certain embodiments, the base 1402, the first leg 1404, and the second leg 1406 can be comprised of a continuous wire, wherein, in at least one embodiment, the first leg 1404 and the second leg 1406 can each be bent in a direction which is perpendicular to the base 1402 prior to staple 1400 being inserted into and deformed by a surgical stapler. More particularly, the staple 1400 can be manufactured such that base 1402 is oriented along a baseline 1401 and such that the legs 1404 and 1406 are oriented along lines 1409 and 1411, respectively, which are perpendicular, or at least substantially perpendicular, to the baseline 1401. In various embodiments, the first leg 1404 can be positioned at a first end of base 1402 and the second end 1406 can be positioned at a second end of base 1402, wherein, in at least one embodiment, a mid-line 1403 can be defined which extends through a midpoint of base 1402 and which extends in a direction which is perpendicular to baseline 1401. The staple 1400 can be configured such that the base 1402, first leg 1404, and second leg 1406 lie, or at least substantially lie, in the same, or common, plane when the staple 1400 is in its first, or undeployed, configuration. In such embodiments, the baseline 1401, along which the base 1402 is oriented, and the perpendicular lines 1409 and 1411, along which the legs 1404 and 1406 are oriented, can lie in the same plane.

In various embodiments, further to the above, the continuous wire comprising the base 1402, the first leg 1404, and the second leg 1406 can be comprised of titanium and/or stainless steel, for example. In at least one embodiment, the first leg 1404 can comprise a first end 1405 and the second leg 1406 can comprise a second end 1407, wherein the ends 1405 and 1407 can each comprise a sharp, or chisel, tip which can be configured to puncture bone and/or tissue. In use, the staple 1400 can be deformed by a surgical stapler in order to capture tissue, for example, within the staple 1400. In various embodiments, the staple 1400 can be deployed from a staple cartridge such that the ends 1405 and 1407 of staple legs 1404 and 1406, respectively, contact an anvil positioned opposite the staple 1400. In such circumstances, a first compressive force $F_1$ can be applied to the first leg 1404 and a second compressive force $F_2$ can be applied to the second leg 1406 while the base 1402 is supported by at least a portion of the staple cartridge. As described in greater detail below, the anvil can comprise a staple pocket which can apply the first compressive force $F_1$ to the first leg 1404 such that the end 1405 of staple leg 1404 is moved toward the base 1402. Similarly, the staple pocket can apply the second compressive force $F_2$ to the second staple leg 1406 such that the end 1407 of staple leg 1404 is also moved toward base 402. In addition to the above, as also discussed in greater detail below, referring now to FIGS. 83-85, the staple pocket can bend the first staple leg 1404 to a first side of base 1402 and the second staple leg 1406 to a second, or opposite, side of base 1402.

Figure 82:
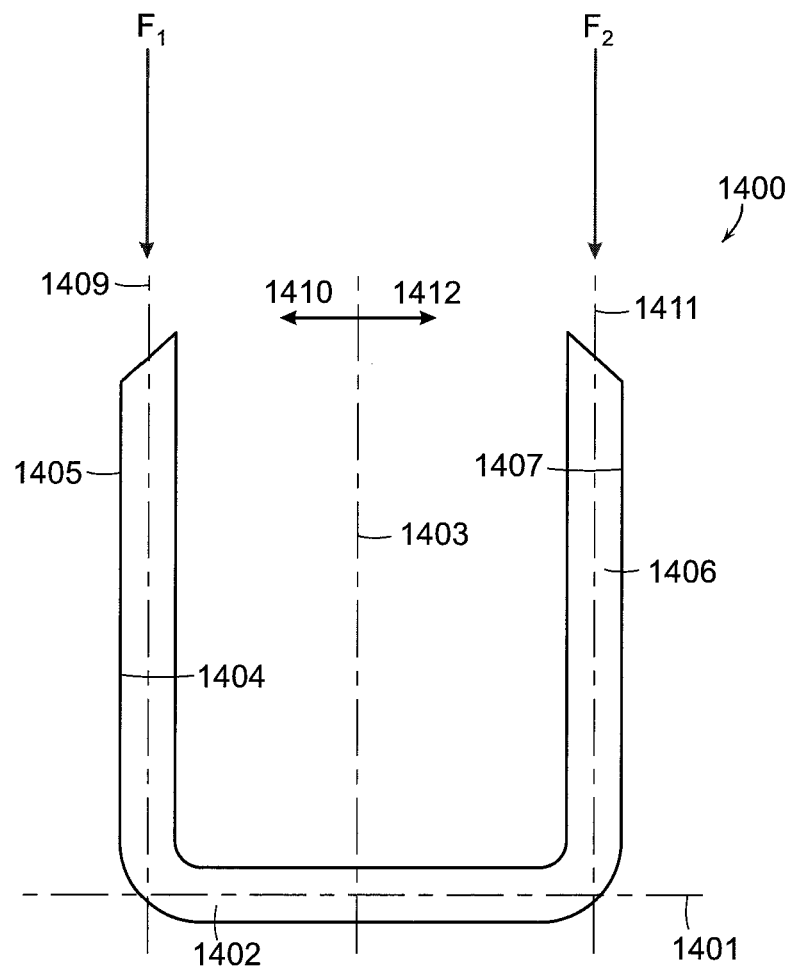
FIG. 82 is an elevational view of a surgical staple in an undeformed shape.

In various embodiments, referring to FIGS. 82 and 83, the first leg 1404 of staple 1400 can be bent such that the end 1405 of the first leg 1404 is moved toward the base 402 and toward the second leg 1406 when the first leg 1404 is deformed by the first compressive force $F_1$. In at least one embodiment, the end 1405 can be moved from a first side 1410 of midline 1403, as illustrated in FIG. 82, to a second side 1412 of midline 1403, as illustrated in FIG. 83. Similarly, the second leg 1406 of staple 1400 can be bent such that the end 1407 of the second leg 1406 is moved toward the base 1402 and toward the first leg 1404 when the second leg 1406 is deformed by the second compressive force $F_2$. In at least one embodiment, the end 1407 can be moved from a second side 1412 of midline 1403, as illustrated in FIG. 82, to a first side 1410 of midline 1403, as illustrated in FIG. 83. In the deployed, or deformed, configuration of staple 1400, as illustrated in FIG. 83, the ends 1405 and 1407 of staple legs 1404 and 1406 can extend across the midline 1403 in such a way that they form an angle therebetween. More particularly, the end 1405 of the first leg 1404, when it is in its deformed configuration, can extend along or with respect to a first axis 1414 and, similarly, the end 1407 of the second leg 1406, when it is in its deformed configuration, can extend along or with respect to a second axis 1416 such that the first axis 1414 and the second axis 1416 define an angle 1417 therebetween. In some embodiments, the angle 1417 may be approximately 90 degrees, for example. In certain embodiments, the angle 1417 may be in a range between approximately 0.1 degrees and approximately 89 degrees, for example. In various embodiments, the angle 1417 may be greater than 90 degrees, while, in at least one embodiment, the angle 1417 may be greater than approximately 90 degrees but less than 180 degrees, for example.

In various embodiments, further to the above, the first axis 1414 and the second axis 1416 can, in various embodiments, be oriented, or crossed, at a transverse angle with respect to each other, i.e., at least when the staple 1400 is viewed from the side or elevational view of FIG. 83. More particularly, upon reviewing FIG. 85, it becomes evident that, although axes 1414 and 1416 extend in transverse directions when viewed from the side (FIG. 83), the axes 1414 and 1416 may not, in at least one embodiment, actually intersect one another. In such embodiments, when viewing the staple 1400 from the top or bottom (FIG. 85), for example, the axes 1414 and 1416 may extend in parallel, or at least substantially parallel, directions. Furthermore, in various embodiments, the reader will note that the first axis 1414 and the second axis 1416 are not perpendicular with baseline 1401. Stated another way, the end 1405 of first staple leg 1404 and the end 1407 of second staple leg 1406 are not pointing directly downwardly toward base 1402 and baseline 1401. In at least one such embodiment, the first axis 1414 and the second axis 1416 can each extend at an acute angle with respect to baseline 1401, for example.

Figure 75:
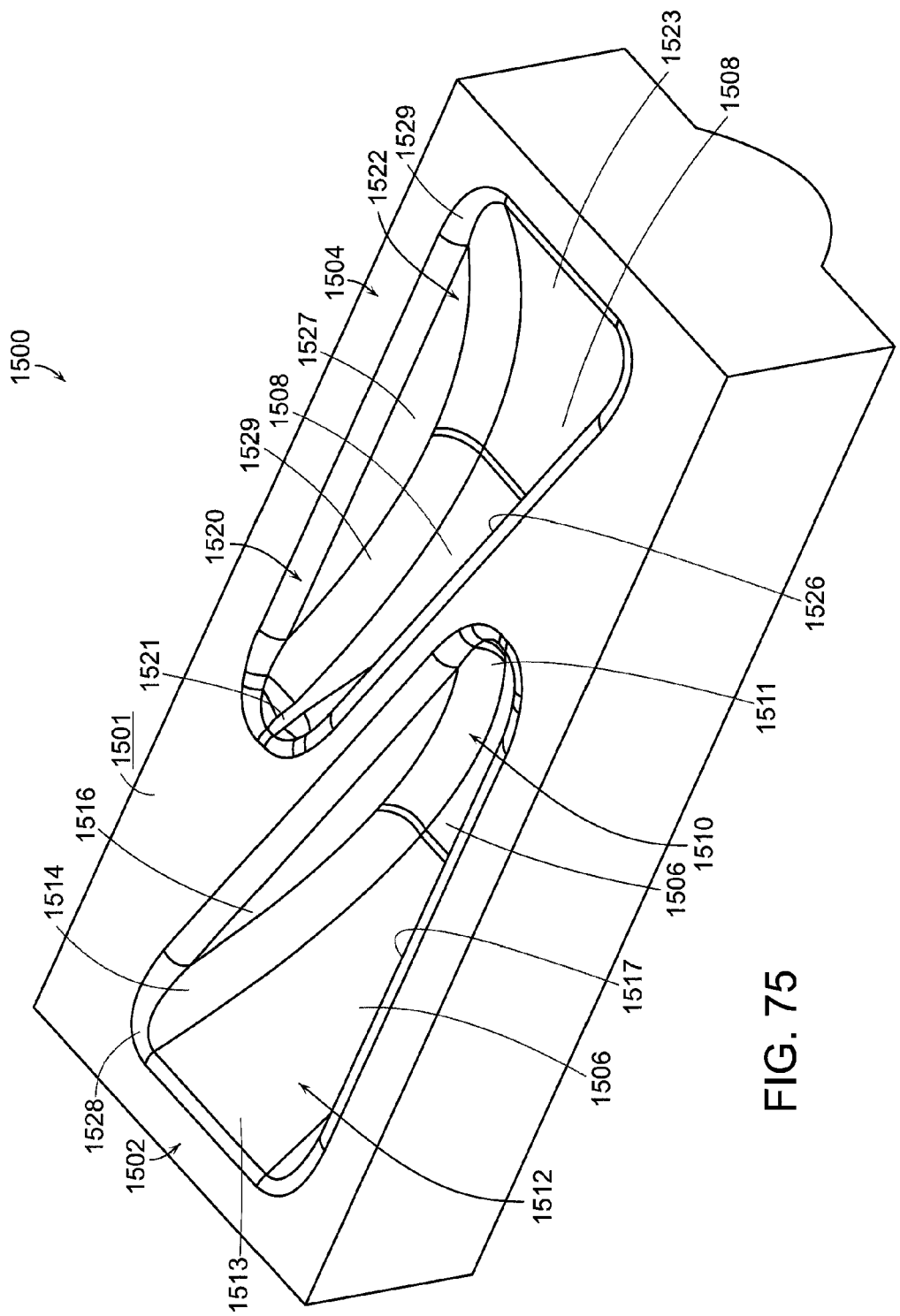
FIG. 75 is a perspective view of a staple pocket in accordance with at least one embodiment of the present invention.

As described above, a surgical instrument can be configured to deform the staple 1400 of FIG. 82, for example, between an undeformed shape (FIG. 82) and a deformed shape (FIG. 83). In various embodiments, as also described above, the surgical instrument can comprise an anvil having a staple pocket configured to receive and deform at least a portion of the staple. In certain embodiments, referring now to FIG. 75, an anvil can comprise a tissue-contacting surface 1501 and a plurality of staple pockets 1500 formed therein, wherein each staple pocket 1500 can be configured to deform a staple 1400. In various embodiments, each staple pocket 1500 can comprise a longitudinal axis 1599 (FIG. 76) and, in addition, a first forming cup 1502 and a second forming cup 1504 positioned relative to the longitudinal axis 1599. In use, the first forming cup 1502 can be configured to receive the first staple leg 1404 of staple 1400 and the second forming cup 1504 can be configured to receive the second staple leg 1406. More particularly, in at least one embodiment, the staple pocket 1500 can be positioned relative to the staple 1400 such that, as the staple 1400 is ejected from a staple cartridge, for example, the end 1405 of first leg 1404 can enter the first forming cup 1502 and the end 1407 of second leg 1406 can enter the second forming cup 1504. Further to the above, the end 1405 of first staple leg 1404 can contact the base 1506 of first forming cup 1502 such that the first compressive force F1 can be applied to the first leg 1404 and, similarly, the end 1407 of second staple leg 1406 can contact the base 1508 of second forming cup 1504 such that the second compressive force F2 can be applied to the second leg 1406.

Figure 80:
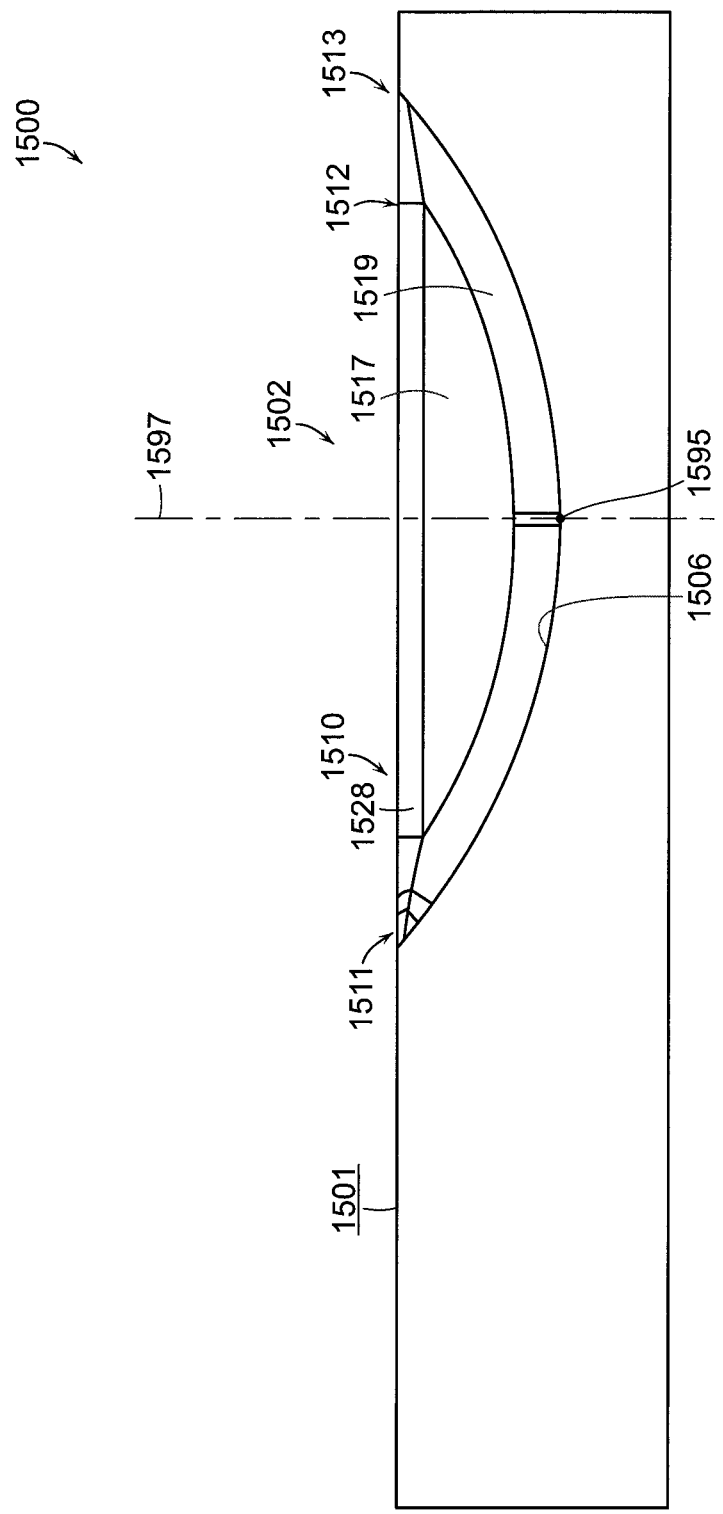
FIG. 80 is a cross-sectional view of the staple pocket of FIG. 75 taken along line 80-80 in FIG. 79.
Figure 81:
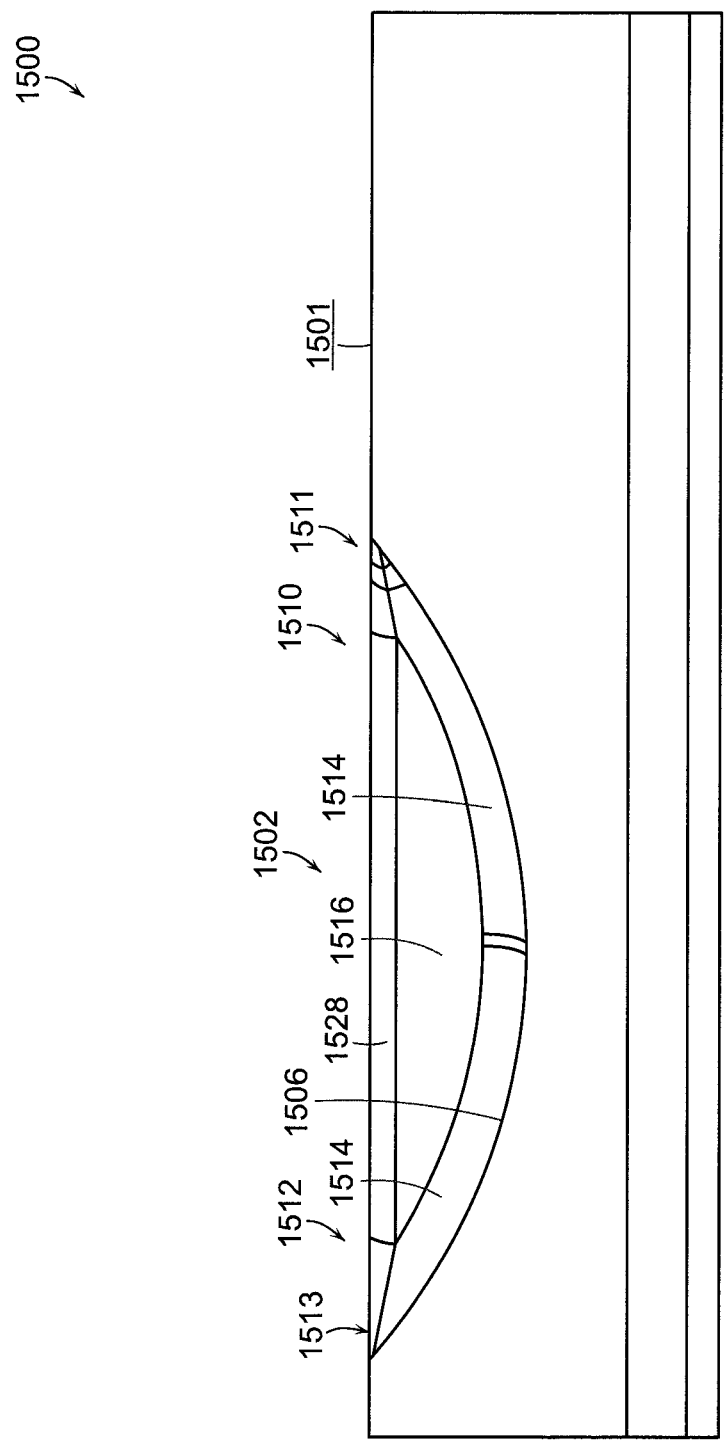
FIG. 81 is a cross-sectional view of the staple pocket of FIG. 75 taken along line 81-81 in FIG. 79.

In various embodiments, further to the above, the first forming cup 1502 can comprise an inside portion 1510 and an outside portion 1512, wherein, when the end 1405 of first staple leg 1404 enters into the first forming cup 1502, the end 1405 can enter into the outside portion 1512. Upon entering into the outside portion 1512 of forming cup 1502, the end 1405 can contact base 1506 and, owing to a concave curve of base 1506, the end 1405 can be directed inwardly toward the inside portion 1510. More particularly, referring now to FIGS. 77-81, the base 1506 can be curved toward tissue-contacting surface 1501 such that, as the staple leg 1404 contacts the base 1506, the end 1405 can be directed downwardly, i.e., away from tissue-contacting surface 1501, and inwardly along the curved concave surface toward an inflection point 1595. In various embodiments, the inflection point 1595 can represent the point in which the concave surface of base 1506 will begin to deflect the end 1405 of first leg 1404 upwardly toward the tissue-contacting surface 1501. In various embodiments, the radius of curvature, r, of the concave surface can be constant, or at least substantially constant, in the longitudinal direction along the length thereof as illustrated in FIGS. 80 and 81. In certain embodiments, the radius of curvature r of the concave surface of base 1506 can be consistent across the width of base 1506 between a first interior sidewall 1516 and a first exterior sidewall 1517. In any event, as the end 1405 of first leg 1404 is advanced into the inside portion 1510 of forming cup 1502, the end 1405 can come into contact with a radius transition 1514 positioned intermediate the base 1506 and the first interior sidewall 1516. In such embodiments, the radius transition 1514 can be configured to direct the end 1405 against the first interior sidewall 1516.

Figure 76:
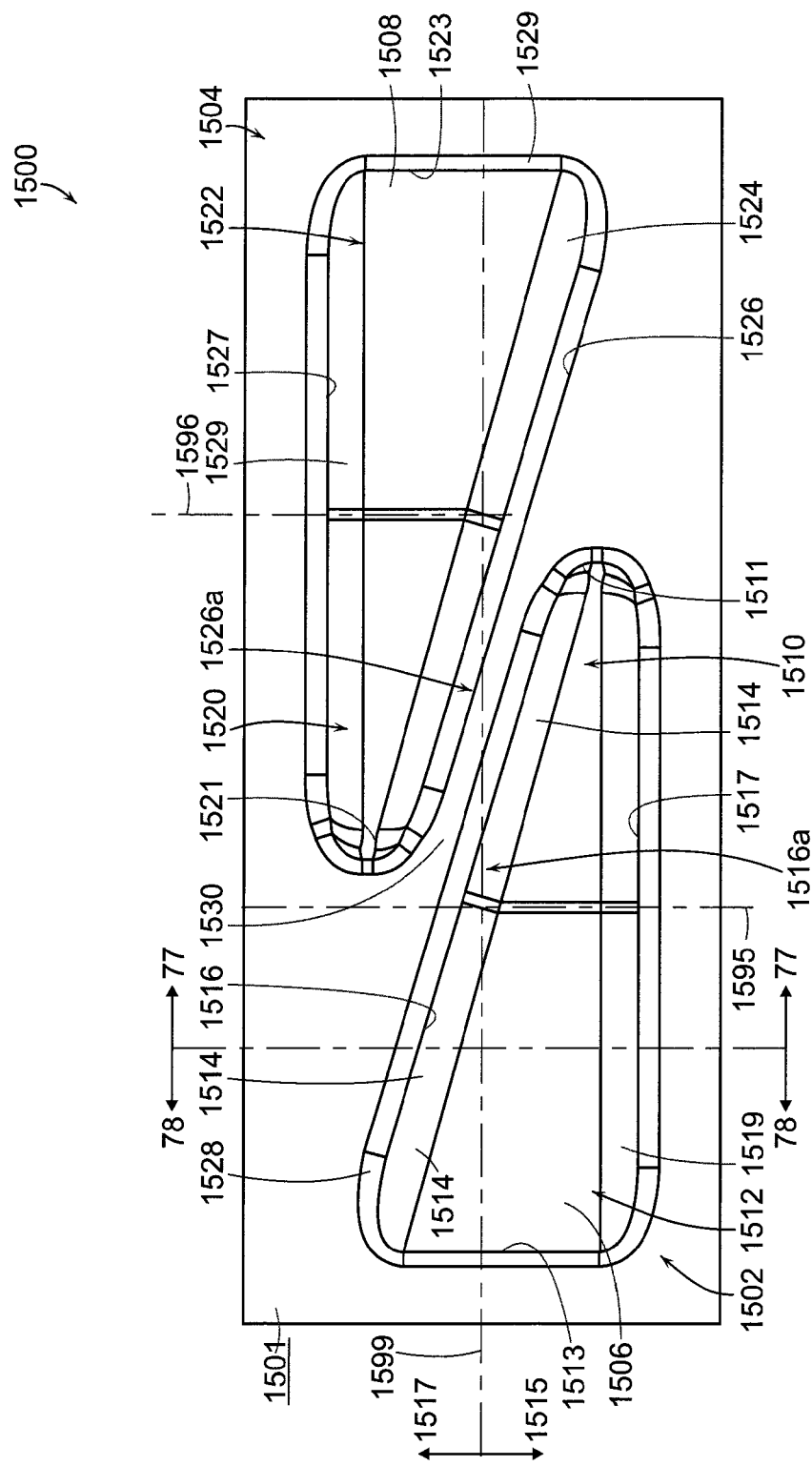
FIG. 76 is a top view of the staple pocket of FIG. 75.
Figure 77:
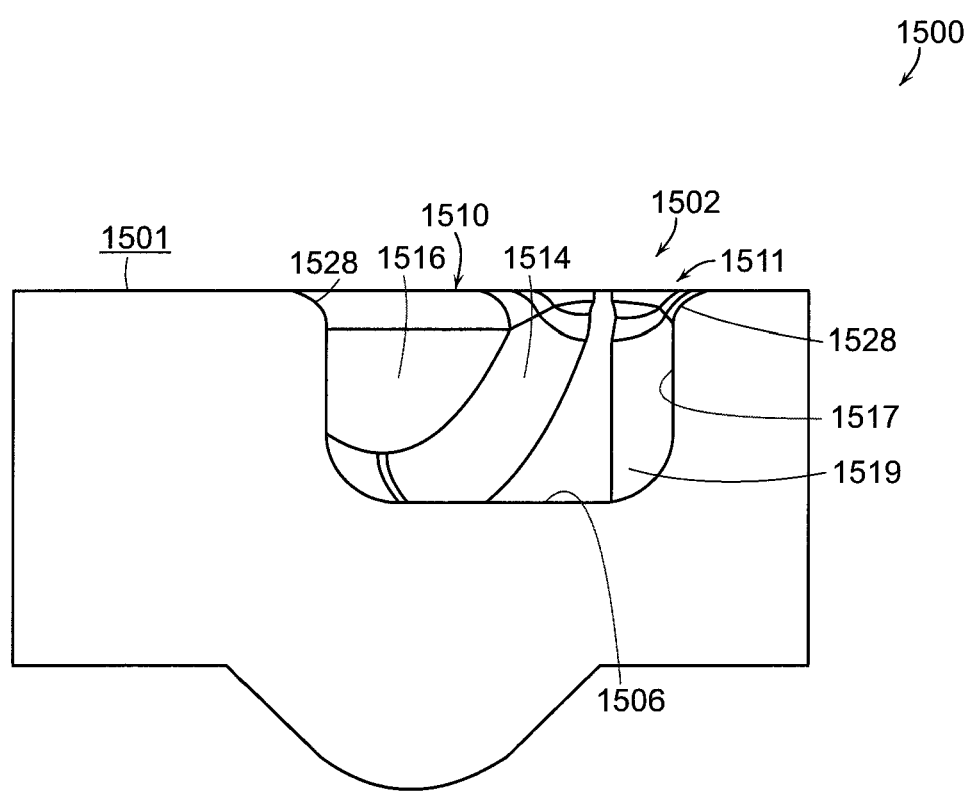
FIG. 77 is a cross-sectional view of the staple pocket of FIG. 75 taken along line 77-77 in FIG. 76.
Figure 78:
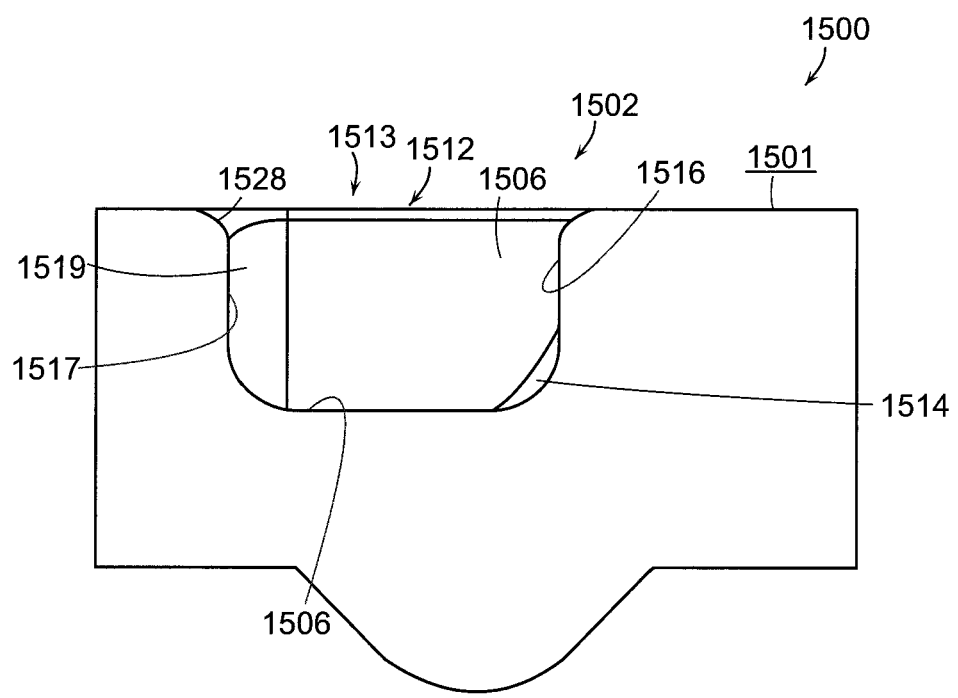
FIG. 78 is a cross-sectional view of the staple pocket of FIG. 75 taken along line 78-78 in FIG. 76.
Figure 79:
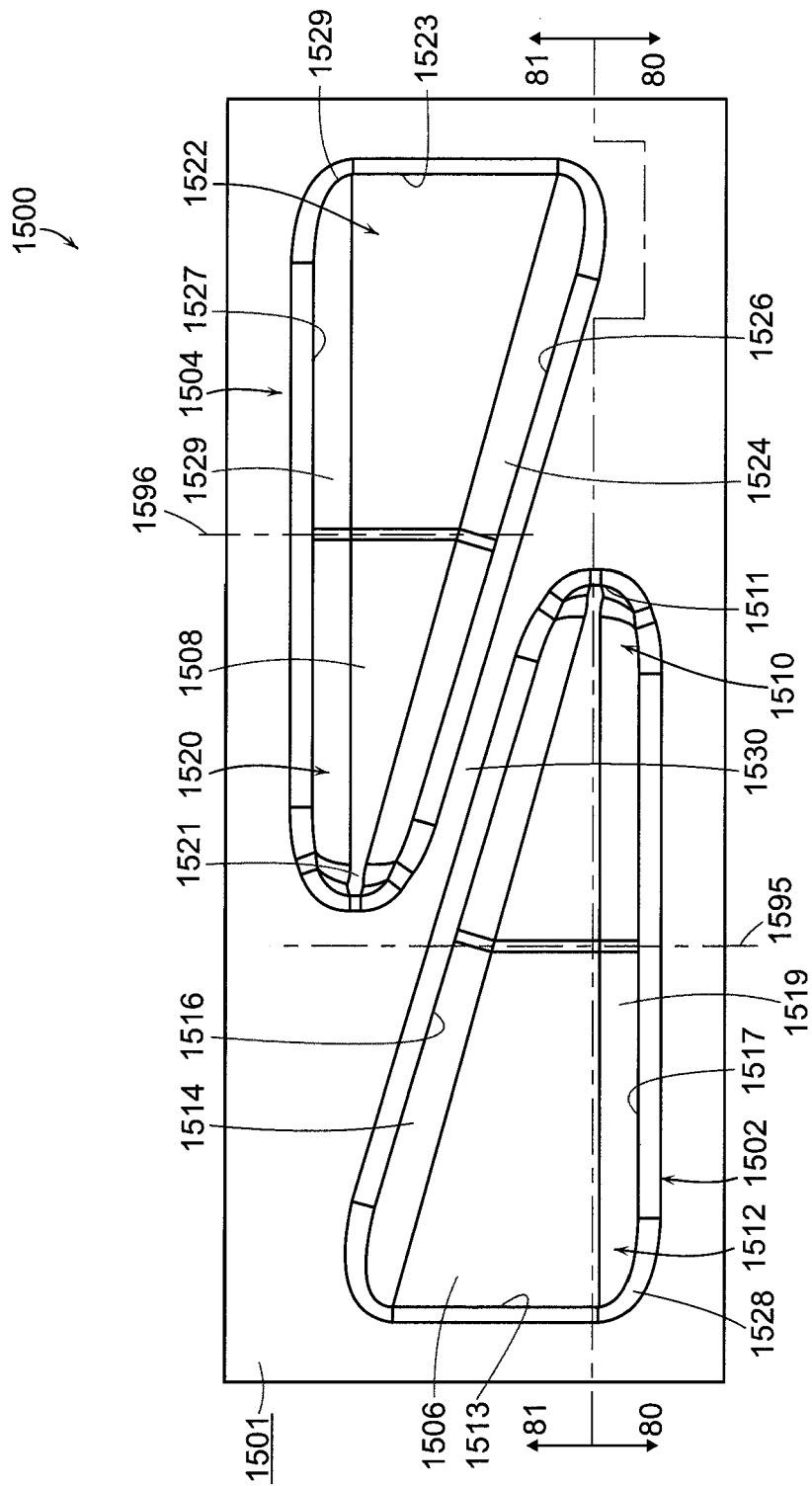
FIG. 79 is another top view of the staple pocket of FIG. 75.

As illustrated in FIG. 76, further to the above, the first interior sidewall 1516 can be oriented at an angle with respect to staple pocket longitudinal axis 1599. In certain embodiments, the first interior sidewall 1516 can be oriented at an acute angle, such as 10 degrees, for example, with respect to longitudinal axis 1599. In various embodiments, the first interior sidewall 1516 and the longitudinal axis 1599 may be neither perpendicular nor parallel to one another. In any event, the first interior sidewall 1516 can extend through the axis 1599 such that a first portion of the first interior sidewall 1516 is positioned on a first side 1515 of axis 1599 and a second portion of the first interior sidewall 1516 is positioned on a second side 1517 of axis 1599. In various embodiments, as a result, the first interior sidewall 1516 can extend between the first outside portion 1512 and the first inside portion 1510. When the end 1405 of first leg 1404 contacts the first interior sidewall 1516, as described above, the end 1405 can be directed along the first interior sidewall 1516 and away from longitudinal axis 1599 such that the staple leg 1404 is bent away from the common plane of staple 1400 toward the first side 1515 of axis 1599. As the end 1405 of first leg 1404 is directed along, or bent by, the first interior sidewall 1516, as described above, the staple leg 1404 can also be directed, or bent, by base 1506. Stated another way, the first sidewall 1516 and the first base 1506 can co-operate to deform the first staple leg 1404 such that end 1405 is re-directed toward the base 1402 and, at the same time, to a first side of the base 1402 as described above. At some point during the insertion of first staple leg 1404 into first forming cup 1502, the end 1405 of first staple leg 1404 can emerge from the first inside portion 1510 of first forming cup 1502 and, as the staple leg 1404 is further deformed by the staple pocket 1500, the end 1405 can be directed along the first axis 1414 (FIG. 83) as described above.

In various embodiments, further to the above, the first interior sidewall 1516 can extend along an interior side of the first base 1506, wherein, in at least one embodiment, the first forming cup 1502 can further comprise a first exterior sidewall 1517 extending along an opposite side of the first base 1506. In certain embodiments, similar to the above, the first forming cup 1502 can further comprise a transition radius 1519 positioned intermediate the base 1506 and the exterior sidewall 1517. In at least one embodiment, referring now to FIG. 76, the exterior sidewall 1517 can extend in a direction which is parallel, or at least substantially parallel, to the staple pocket longitudinal axis 1599. As also illustrated in FIG. 76, the first interior sidewall 1516 and the first exterior sidewall 1517 can extend in directions which are transverse to one another. In at least one embodiment, the interior sidewall 1516 can extend at an acute angle, such as approximately 15 degrees, for example, with respect to the exterior sidewall 1517. In various embodiments, as a result, the outside portion 1512 of first forming cup 1502 can be wider than the inside portion 1510. In at least one such embodiment, the width of the outside portion 1512 and the inside portion 1510 can taper between a first width and a second width.

In various embodiments, referring once again to FIG. 76, the outside portion 1512 of first forming cup 1502 can comprise a first outside wall 1513 which can extend in a direction which is perpendicular to the first exterior wall 1517 and/or the longitudinal axis 1599 and can define the outermost portion of forming cup 1502. In at least one embodiment, further to the above, the width of the first outside wall 1513 can be such that the outside portion 1512 can capture the end 1405 of first leg 1404 and guide it into the inside portion 1510 of cup 1502 as described above. In at least one such embodiment, the first outside wall 1513 can be at least as twice as wide as the diameter of the first leg 1404. In certain embodiments, the first forming cup 1502 can further comprise a channeling surface 1528 surrounding the first inner portion 1510 and the first outer portion 1512 which can be configured to guide the staple leg 1404 into and/or out of the forming cup 1502. In various embodiments, the inside portion 1510 can further comprise an inside wall 1511 which can define the innermost portion of forming cup 1502. Similar to the above, the inside wall 1511 can also define the narrowest portion of forming cup 1502. In at least one embodiment, the width of the inside wall 1511 may be the same, or at least substantially the same, as the diameter of first leg 1404 such that the inside wall 1511 can control the location in which the end 1405 emerges from staple forming cup 1502.

In various embodiments, further to the above, the second forming cup 1504 can comprise an inside portion 1520 and an outside portion 1522, wherein, when the end 1407 of second staple leg 1406 enters into the second forming cup 1504, the end 1407 can enter into the outside portion 1522. Upon entering into the outside portion 1522 of forming cup 1504, the end 1407 can contact base 1508 and, owing to a concave curve of base 1508, the end 1407 can be directed inwardly toward the inside portion 1520. More particularly, similar to the above, the base 1508 can be curved toward tissue-contacting surface 1501 such that, as the staple leg 1406 contacts the base 1508, the end 1407 can be directed downwardly, i.e., away from tissue-contacting surface 1501, and inwardly along the curved concave surface toward an inflection point 1596. In various embodiments, the inflection point 1596 can represent the point in which the concave surface of base 1508 will begin to deflect the end 1407 of second leg 1406 upwardly toward the tissue-contacting surface 1501. In various embodiments, the radius of curvature, r, of the concave surface can be constant, or at least substantially constant, in the longitudinal direction along the length thereof, similar to the base 1506 of first forming cup 1502 illustrated in FIGS. 80 and 81. In any event, as the end 1407 of second leg 1406 is advanced into the inside portion 1520 of forming cup 1504, the end 1407 can come into contact with a radius transition 1524 positioned intermediate the base 1508 and a second interior sidewall 1526. In such embodiments, the radius transition 1524 can be configured to direct the end 1407 against the second interior sidewall 1526.

As illustrated in FIG. 76, further to the above, the second interior sidewall 1526 can be oriented at an angle with respect to staple pocket longitudinal axis 1599. In certain embodiments, the second interior sidewall 1526 can be oriented at an acute angle, such as 10 degrees, for example, with respect to longitudinal axis 1599. In various embodiments, the second interior sidewall 1526 and the longitudinal axis 1599 may be neither perpendicular nor parallel to one another. In any event, the second interior sidewall 1526 can extend through the axis 1599 such that a first portion of the second interior sidewall 1526 is positioned on a first side 1515 of axis 1599 and a second portion of the second interior sidewall 1526 is positioned on a second side 1517 of axis 1599. In various embodiments, as a result, the second interior sidewall 1526 can extend between the second outside portion 1522 and the second inside portion 1520. When the end 1407 of second leg 1406 contacts the interior sidewall 1526, as described above, the end 1407 can be directed along the interior sidewall 1526 such that the staple leg 1406 is bent away from the common plane of staple 1400 toward the second side 1517 of axis 1599. As the end 1407 of second leg 1406 is directed along, and bent by, the interior sidewall 1526, as described above, the staple leg 1406 can also be directed, and bent, by base 1508. Stated another way, the second interior sidewall 1526 and the second base 1508 can co-operate to deform the second staple leg 1406 such that end 1407 is re-directed toward the base 1402 and, at the same time, toward a second, or opposite, side of the base 1402 as described above. At some point during the insertion of second staple leg 1406 into second forming cup 1504, the end 1407 of second staple leg 1406 can emerge from the second inside portion 1520 of second forming cup 1504 and, as the staple leg 1406 is further deformed by the staple pocket 1500, the end 1407 can be directed along the second axis 1416 (FIG. 83) as described above.

In various embodiments, further to the above, the second interior sidewall 1526 can extend along an interior side of the second base 1508, wherein, in at least one embodiment, the second forming cup 1504 can further comprise a second exterior sidewall 1527 extending along an opposite side of the second base 1508. In certain embodiments, similar to the above, the second forming cup 1504 can further comprise a transition radius 1529 positioned intermediate the base 1508 and the exterior sidewall 1527. In at least one embodiment, referring now to FIG. 76, the exterior sidewall 1527 can extend in a direction which is parallel, or at least substantially parallel, to the staple pocket longitudinal axis 1599. As also illustrated in FIG. 76, the second interior sidewall 1526 and the second exterior sidewall 1527 can extend in directions which are transverse to one another. In at least one embodiment, the interior sidewall 1526 can extend at an acute angle, such as approximately 15 degrees, for example, with respect to the exterior sidewall 1527. In various embodiments, as a result, the outside portion 1522 of second forming cup 1504 can be wider than the inside portion 1520. In at least one such embodiment, the width of the outside portion 1522 and the inside portion 1520 can taper between a first width and a second width.

In various embodiments, referring once again to FIG. 76, the outside portion 1522 of second forming cup 1504 can comprise a second outside wall 1523 which can extend in a direction which is perpendicular to the second exterior wall 1527 and/or the longitudinal axis 1599 and can define the outermost portion of forming cup 1504. In at least one embodiment, further to the above, the width of the second outside wall 1523 can be such that the outside portion 1522 can capture the end 1407 of second leg 1406 and guide it into the inside portion 1520 of cup 1504 as described above. In at least one such embodiment, the second outside wall 1523 can be at least as twice as wide as the diameter of the second leg 1406. In certain embodiments, the second forming cup 1504 can further comprise a channeling surface 1529 surrounding the second inner portion 1520 and the second outer portion 1522 which can be configured to guide the staple leg 1406 into and/or out of the forming cup 1504. In various embodiments, the inside portion 1520 can further comprise an inside wall 1521 which can define the innermost portion of forming cup 1504. Similar to the above, the inside wall 1521 can also define the narrowest portion of forming cup 1504. In at least one embodiment, the width of the inside wall 1521 may be the same, or at least substantially the same, as the diameter of second leg 1406 such that the inside wall 1521 can control the location in which the end 1407 emerges from staple forming cup 1504.

As discussed above, referring again to FIGS. 76-78, the first forming cup 1502 can comprise a first interior sidewall 1516 and the second forming cup 1504 can comprise a second interior sidewall 1526. As illustrated in FIG. 76, the first inside portion 1510 of forming cup 1502 can be positioned in close proximity to, or close relation to, the second inside portion 1520 of forming cup 1504 such that the first interior sidewall 1516 can be positioned adjacent to the second interior sidewall 1526. In at least one embodiment, the first interior portion 1510, or at least a substantial portion thereof, can be offset from the staple pocket longitudinal axis 1599 in the first direction 1515 while the second interior portion 1520, or at least a substantial portion thereof, can be offset from the longitudinal axis 1599 in the second direction 1517. In various embodiments, the staple pocket 1500 can comprise a wall 1530 positioned intermediate the first inside portion 1510 and the second inside portion 1520, wherein a first side of wall 1530 can comprise the first interior sidewall 1516 and wherein a second side of wall 1530 can comprise the second interior sidewall 1526. In at least one such embodiment, the first interior sidewall 1516 can be parallel, or at least substantially parallel to, the second interior sidewall 1526. More particularly, in at least one embodiment, the first interior sidewall 1516 can define a first plane and the second interior sidewall 1526 can define a second plane, wherein the first plane and the second plane can be parallel, or at least substantially parallel, to one another. In various embodiments, referring again to FIGS. 77 and 78, the first interior sidewall 1516 can be perpendicular, or at least substantially perpendicular, to the tissue-contacting surface 1501 and, similarly, the second interior sidewall 1526 can be perpendicular, or at least substantially perpendicular, to the tissue-contacting surface 1501.

In various embodiments, further to the above, the first interior sidewall 1516 can comprise a first vertical portion 1516a which is perpendicular, or at least substantially perpendicular, to the tissue-contacting surface 1501. In at least one embodiment, the first vertical portion 1516a can extend through, or transect, the longitudinal axis 1599. In various embodiments, the first vertical portion 1516a can extend along the entirety of, or only a portion of, the first interior sidewall 1516. Similarly, the second interior sidewall 1526 can comprise a second vertical portion 1526a which is perpendicular, or at least substantially perpendicular, to the tissue-contacting surface 1501. In at least one embodiment, such a second vertical portion 1526a can extend through, or transect, the longitudinal axis 1599. In various embodiments, the second vertical portion 1526a can extend along the entirety of, or only a portion of, the second interior sidewall 1526. During the deployment of staple 1400, further to the above, the end 1405 of first leg 1404 can be in contact with the first vertical portion 1516a of first interior sidewall 1516 at the same time the end 1407 of second leg 1406 is in contact with the second vertical portion 1526a of second interior sidewall 1526. In such circumstances, the first vertical portion 1516a and the second vertical portion 1526a can comprise a vertical trap. More particularly, the vertical portions 1516a and 1526a can co-operate to control, deflect, and bend the staple legs 1404 and 1406 in opposite directions, i.e., in directions to the sides of a common plane, as described above, when the legs 1404 and 1406 come into contact with the interior sidewalls 1516 and 1526 of forming cups 1502 and 1504, respectively. For example, referring again to FIG. 75, the first vertical portion 1516a can be configured to deflect and bend the staple leg 1404 to a first side of base 1402 and the second vertical portion 1526a can be configured to deflect and bend the staple leg 1406 to a second, or opposite, side of base 1402.

In various embodiments, further to the above, the vertical trap comprising vertical portions 1516a and 1526a can extend along the entire length of the first and second interior sidewalls 1516 and 1526, while, in other embodiments, the vertical trap may extend along only a portion of the sidewalls 1516 and 1526. In at least one embodiment, the vertical trap can be approximately 0.05 inches long, i.e., the overlap of the first vertical surface 1516a and the second vertical surface 1526a can be approximately 0.05 inches, for example, along the lengths of interior surfaces 1516 and 1526. In various embodiments, the length of the vertical trap can be between approximately 0.03 inches and approximately 0.10 inches, for example. In certain embodiments, the length of the vertical trap can be approximately twice the radius of curvature (r) of the curved concave surface of base 1506, for example. In various embodiments, the length of the vertical trap can be approximately equal to the radius of curvature (r) of base 1506, for example. In at least one embodiment, the length of the vertical trap can be between approximately 0.5*r and approximately 2*r, for example. In various embodiments, further to the above, the vertical trap can extend through the longitudinal axis 1599 of staple pocket 1500 such that, in at least one embodiment, at least a portion of the vertical trap can be positioned on a first side and/or a second side of axis 1599. In certain embodiments, the vertical trap can extend through the central portions of the first and second forming cups 1502 and 1504.

In various embodiments, the first interior sidewall 1516 can further comprise a first angled portion which, in at least one embodiment, can be oriented at an acute angle with respect to the tissue-contacting surface 1501. In at least one such embodiment, the first angled portion can be positioned outwardly with respect to the first vertical portion 1516a. In certain embodiments, the first interior sidewall 1516 can comprise an angled portion positioned toward the outside portion 1512 which can become progressively more perpendicular toward the inside portion 1510 of the first forming cup 1502 until the angled portion transitions into the first vertical portion 1516a. In various embodiments, the second interior sidewall 1526 can further comprise a second angled portion which, in at least one embodiment, can be oriented at an acute angle with respect to the tissue-contacting surface 1501. In at least one such embodiment, the second angled portion can be positioned outwardly with respect to the second vertical portion 1526a. In certain embodiments, the second interior sidewall 1526 can comprise an angled portion positioned toward the outside portion 1522 which can become progressively more perpendicular toward the inside portion 1520 of the second forming cup 1504 until the angled portion transitions into the second vertical portion 1526a.

Figure 85A:
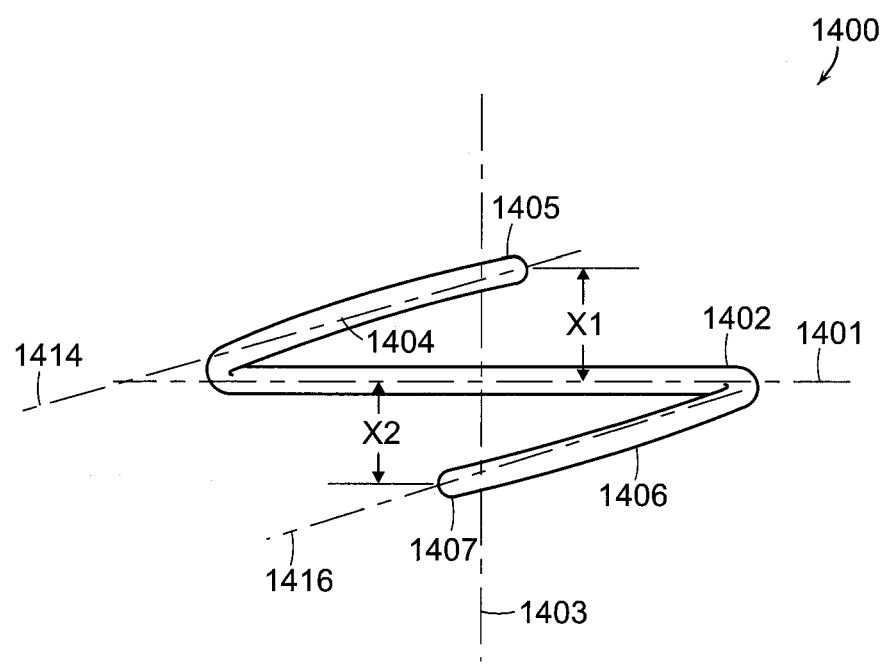
FIG. 85A is another plan view of the surgical staple of FIG. 82 in the deformed shape of FIG. 83.
Figure 87:
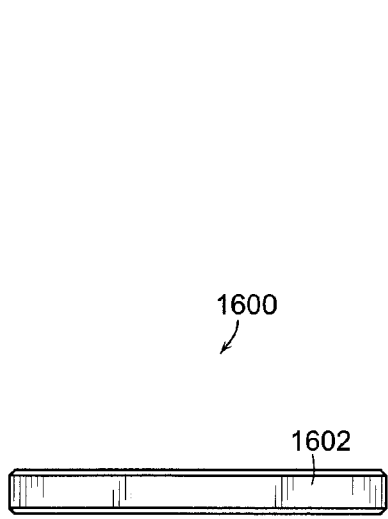
FIG. 87 is a bottom view of the surgical staple of FIG. 86 in an undeformed shape.
Figure 86:
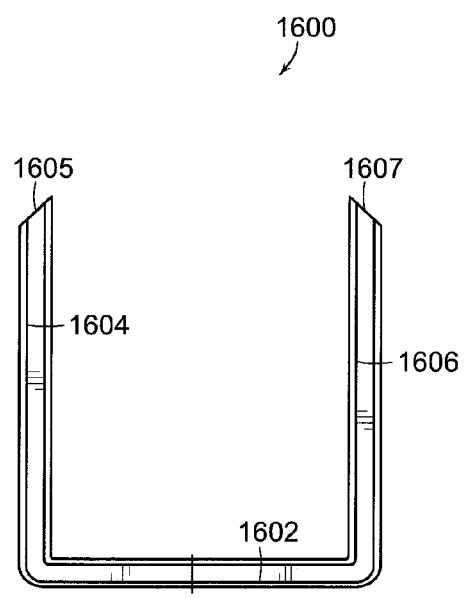
FIG. 86 is an elevational view of a surgical staple in an undeformed shape.

In various embodiments, referring now to FIG. 85A, the staple pocket 1500 can be configured to deform the first staple leg 1404 such that the first end 1405 is deflected a first distance X1 from baseline 1401. Similarly, the second staple leg 1406 can be deformed such that the second end 1407 is deflected a second distance X2 from baseline 1401. In certain embodiments, the distance X1 and the distance X2 can be the same, or at least substantially the same. In various other embodiments, the distances X1 and X2 can be different. In at least one such embodiment, the first leg 1404 can be deformed such that the first end 1405 is positioned closer to base 1402 than the second end 1407, for example. In such embodiments, the first axis 1414 of deformed staple leg 1404 and the second axis 1416 of deformed staple leg 1406 may be non-parallel. More particularly, in at least one embodiment, the first axis 1414 can extend at a first angle with respect to baseline 1401 and the second axis 1416 can extend at a second angle with respect to baseline 1401 wherein the second angle is different than the first angle. In various embodiments, the first leg 1404 and the second leg 1406 can extend across midline 1403 at different angles. In certain other embodiments, the first leg 1404 and the second leg 1406 can be extend at different angles with respect to baseline 1401 although one or both of the legs 1404 and 1406 may not extend across the midline 1403.

In various embodiments, further to the above, a surgical stapler can comprise a staple pocket which can be configured to deform one staple leg of staple 1400 such that it lies within, or substantially within, a common plane with base 1402 and, in addition, deform the other staple leg of staple 1400 to a side of base 1402 as described above. In at least one embodiment, the first leg 1404 can be deformed such that it extends through midline 1403 in a direction which is co-planar, or at least substantially co-planar, with base 1402 and, in addition, the second leg 1406 can be deformed such that it extends through midline 1403 in a direction which is transverse to the plane. Stated another way, in at least one embodiment, axis 1414 and baseline 1401 of staple 1400 can be coplanar, or at least nearly co-planar, with one another while second axis 1416 can extend in a direction which extends through such a plane. In certain embodiments, at least one of the first leg 1404 and the second leg 1406 may not extend through the midline 1403.

In various embodiments, further to the above, the staple pocket 1500 can be configured to deform the staple legs 1404 and 1406 of staple 1400 simultaneously, or at least substantially simultaneously. In at least one embodiment, the base 1506 of first forming cup 1502 can contact end 1405 of first staple leg 1404 at the same time, or at least substantially the same time, that the base 1508 of second forming cup 1504 contacts end 1407 of second staple leg 1406. In certain other embodiments, a staple pocket can be configured to deform the staple legs 1404 and 1406 sequentially. In at least one such embodiment, a first forming cup can be brought into contact with the first staple leg 1404 before a second forming cup is brought into contact with the second staple leg 1406, for example. In various alternative embodiments, although not illustrated, a surgical staple can comprise more than two staple legs, such as three staple legs or four staple legs, for example, and a staple pocket can comprise a corresponding quantity of staple forming cups for deforming the staple legs.

In various embodiments, further to the above, the wire comprising the surgical staple 1400 can comprise a circular, or at least substantially circular, cross-section. In various other embodiments, referring now to FIGS. 86-89, a surgical staple, such as staple 1600, for example, can comprise a non-circular cross-section. In at least one embodiment, the staple 1600 can comprise a base 1602, a first leg 1604, and a second leg 1606, wherein the base 1602 and legs 1604 and 1606 can be comprised of a continuous wire. In various embodiments, the continuous wire can comprise a rectangular cross-section, for example. In at least one embodiment, referring to FIG. 89, the rectangular cross-section can comprise a base (b) and a height (h), wherein the base (b) can be defined relative to a central lateral axis (x), and wherein the height (h) can be defined relative to a central longitudinal axis (y). In various circumstances, the rectangular cross-section can be defined as having two moments of inertia, i.e., a first moment of inertia (Ix) defined with respect to axis (x) and a second moment of inertia (Iy) defined with respect to axis (y). In at least one circumstance, the first moment of inertia (Ix) can be calculated as $(b*h^3)/12$ while the second moment of inertia (Iy) can be calculated as $(h*b^3)/12$. Although staple 1600 comprises a rectangular, or at least substantially rectangular cross-section, any other suitable non-circular cross-section can be utilized, such as oblate, elliptical, and/or trapezoidal cross-sections, for example.

Figure 88:
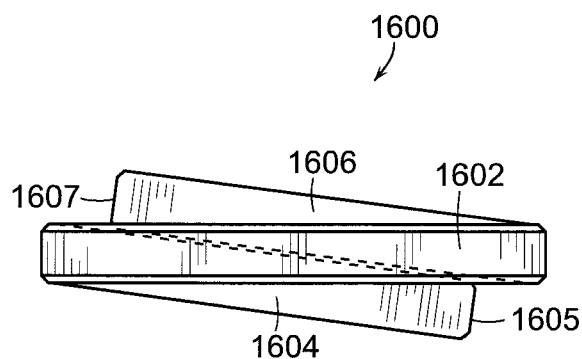
FIG. 88 is a bottom view of the surgical staple of FIG. 86 in a deformed shape in accordance with at least one embodiment of the present invention.
Figure 89:
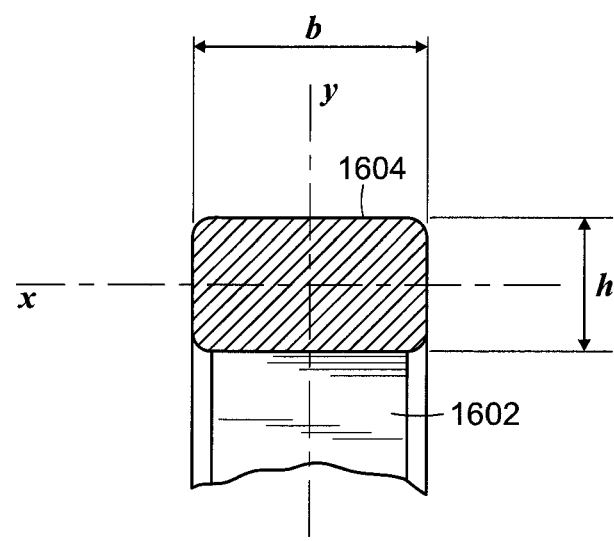
FIG. 89 is a partial cross-sectional view of the surgical staple of FIG. 86.

As illustrated in FIG. 89, the base (b) of surgical staple 1600 is larger than the height (h) and, in view of the above, the moment of inertia (Iy) of the rectangular cross-section is larger than the moment of inertia (Ix). In various embodiments, as a result, the moment of inertia ratio, i.e., Iy/Ix, of the rectangular cross-section can be greater than 1.0. In certain embodiments, the moment of inertia ratio can be between approximately 2.0 and approximately 2.7, for example. In certain other embodiments, the moment of inertia ratio can be between approximately 1.1 and approximately 3.0, for example. As a result of the above, the leg 1604 is more likely to bend about axis (x) than about axis (y) when a force, such as compressive load F1, for example, is applied to the leg 1604. In any event, absent all other considerations, the leg 1604, in such embodiments, is more likely to bend within a common plane defined by the staple 1600 when it is in its undeformed state than bend to a side of staple base 1602. In various embodiments, however, a surgical stapler comprising an anvil and staple pocket in accordance with the embodiments described herein, such as staple pocket 1500, for example, can be utilized to cause the legs 1604 and 1606 of staple 1600 to bend out of their common plane when they are deformed. In such embodiments, this lateral deflection can occur despite the fact that the moment of inertia Iy, which resists such twisting, is greater than the moment of inertia Ix. As illustrated in FIG. 88, the first leg 1604 of staple 1600 can be deformed such that it is bent relative to both axis (x) and axis (y) of its cross-section and, as a result, the first staple leg 1604 can be twisted or deformed such that the end 1605 of first staple leg 1604 is positioned on a first side of base 1602. Similarly, the second leg 1606 can be deformed such that it is bent relative to both axis (x) and axis (y) of its cross-section and, as a result, the second staple leg 1606 can be twisted or deformed such that the end 1607 of second staple leg 1606 is positioned on a second side of base 1602.

Figure 90:
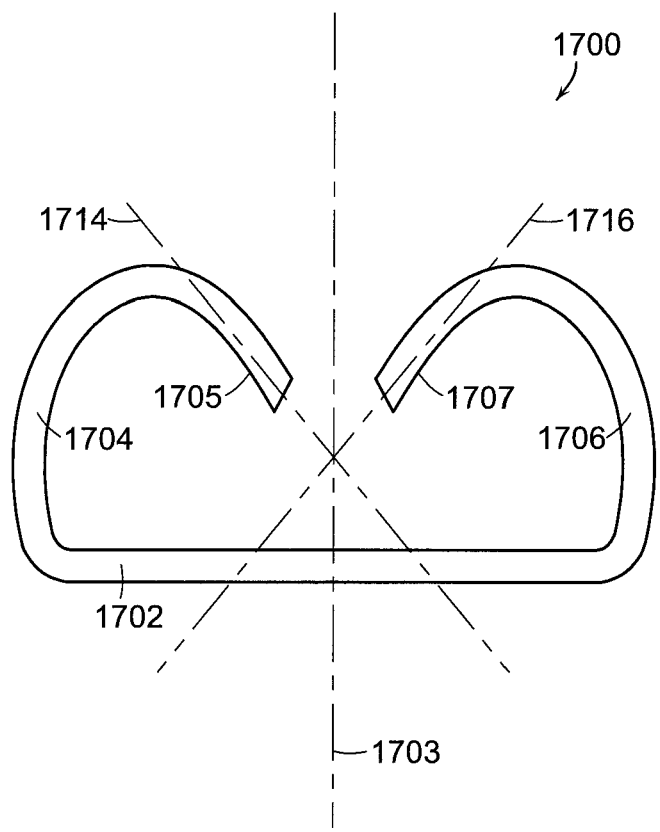
FIG. 90 is an elevational view of a surgical staple in a deformed shape in accordance with at least one embodiment of the present invention.

In various embodiments, referring now to FIG. 90, a surgical staple, such as surgical staple 1700, for example, can comprise a base 1702 and, in addition, a first leg 1704 and a second leg 1706 extending from base 1702. In certain embodiments, similar to the above, the base 1702, the first leg 1704, and the second leg 1706 can lie, or at least substantially lie, in a common plane when the staple 1700 is an undeformed, or undeployed, configuration, i.e., a configuration prior to being deformed by an anvil of a surgical stapler, for example. In the deformed or deployed configuration of staple 1700, as illustrated in FIG. 90, the first leg 1704 can be deformed such that end 1705 points toward base 1702 and second leg 1706. More particularly, in at least one embodiment, the end 1705 can lie along, or with respect to, a first axis 1714 which is oriented at angle with respect to midline 1703. Similarly, the second leg 1706 can be deformed such that end 1707 points toward base 1702 and first leg 1704. More particularly, in at least one embodiment, the end 1707 can lie along, or with respect to, a second axis 1716 which is oriented at angle with respect to midline 1703. In various embodiments, the ends 1705 and 1707 of legs 1704 and 1706 may not cross mid-line 1703. In certain embodiments, similar to the above, the end 1705 of first leg 1704 may be deformed such that it extends to a first side of base 1702 and the end 1707 of second leg 1706 may be deformed such that it extends to a second, or opposite, side of base 1702 such that legs 1704 and 1706 are not entirely positioned in-plane with base 1702 in their deformed configuration, for example.

Figure 91:
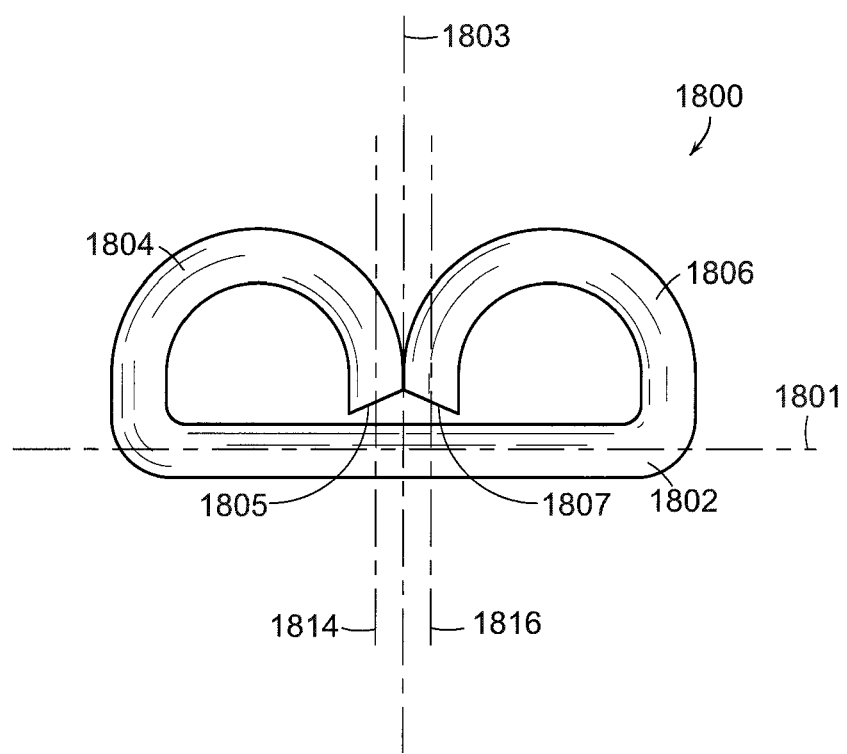
FIG. 91 is an elevational view of a surgical staple in a deformed shape.

In various embodiments, a surgical staple, such as staple 1800 (FIG. 91), for example, can comprise a base 1802, a first leg 1804, and a second leg 1806, wherein the staple 1800 can comprise a substantially U-shaped configuration in its undeformed, or undeployed, configuration. In at least one such embodiment, legs 1804 and 1806 can extend in a perpendicular, or at least substantially perpendicular, direction with respect to base 1802. In various circumstances, the staple 1800 can be deformed into a B-shaped configuration as illustrated in FIG. 91. In at least one such embodiment, the first leg 1804 can be bent downwardly toward base 1802 such that axis 1814 extending through end 1805 is perpendicular, or at least substantially perpendicular, to baseline 1801. Similarly, the second leg 1806 can be bent downwardly toward base 1802 such that axis 1816 extending through end 1807 is perpendicular, or at least substantially perpendicular, to baseline 1801. In at least one such circumstance, the legs 1804 and 1806 can be bent such that axes 1814 and 1816 are parallel, or at least substantially parallel, to one another. In various embodiments, referring again to FIG. 91, the staple legs 1804 and 1806 can be deformed such that they do not cross centerline 1803. The staple legs 1804 and 1806 can be deformed such that they remain in-plane, or at least substantially in-plane, with base 1802.

Various examples described below are envisioned which incorporate one or more aspects of the various embodiments described above. Such examples are exemplary and various aspects of various embodiments described in this application can be combined in a single embodiment. In each of the examples described below, the surgical staple can comprise a base defining a baseline, a first leg and a second leg which extend from the base, and a midline midway between the first leg and the second leg.

Example 1

A surgical staple can be deformed such that:

| First Leg | Second Leg |
| --- | --- |
| Crosses the midline (FIG. 83) | Crosses the midline (FIG. 83) |
| Extends in-plane, or substantially in-plane, with the base (FIG. 91) | Extends out of plane with the base (FIG. 85) |
| The end extends in a non-perpendicular direction with the baseline (FIG. 83) | The end extends in a non-perpendicular direction with the baseline (FIG. 83) |

Example 2

A surgical staple can be deformed such that:

| First Leg | Second Leg |
| --- | --- |
| Crosses the midline (FIG. 83) | Crosses the midline (FIG. 83) |
| Extends out of plane with the base (FIG. 85) to the same side of the base as the second leg, the distance X1 being different than X2 (FIG. 85A) | Extends out of plane with the base (FIG. 85) to the same side of the base as the first leg, the distance X1 being different than X2 (FIG. 85A) |
| The end extends in a non-perpendicular direction with the baseline (FIG. 83) | The end extends in a non-perpendicular direction with the baseline (FIG. 83) |

Example 3

A surgical staple can be deformed such that:

| First Leg | Second Leg |
| --- | --- |
| Does not cross the midline (FIG. 90) | Does not cross the midline (FIG. 90) |
| Extends out of plane with the base (FIG. 85) to a first side of the base, the distance X1 being different than X2 (FIG. 85A) | Extends out of plane with the base (FIG. 85) to a second side of the base, the distance X1 being different than X2 (FIG. 85A) |
| The end extends in a non-perpendicular direction with the baseline (FIG. 83) | The end extends in a non-perpendicular direction with the baseline (FIG. 83) |

Example 4

A surgical staple can be deformed such that:

| First Leg | Second Leg |
| --- | --- |
| Does not cross the midline (FIG. 90) | Does not cross the midline (FIG. 90) |
| Extends out of plane with the base (FIG. 85) to the same side of the base as the second leg, the distance X1 being different than X2 (FIG. 85A) | Extends out of plane with the base (FIG. 85) to the same side of the base as the second leg, the distance X1 being different than X2 (FIG. 85A) |
| The end extends in a non-perpendicular direction with the baseline (FIG. 83) | The end extends in a non-perpendicular direction with the baseline (FIG. 83) |

Example 5

A surgical staple can be deformed such that:

| First Leg | Second Leg |
| --- | --- |
| Does not cross the midline (FIG. 90) | Does not cross the midline (FIG. 90) |
| Extends in-plane, or substantially in-plane, with the base (FIG. 91) | Extends out of plane with the base (FIG. 85) |
| The end extends in a perpendicular direction with the baseline (FIG. 91) | The end extends in a non-perpendicular direction with the baseline (FIG. 83) |

Example 6

A surgical staple can be deformed such that:

| First Leg | Second Leg |
| --- | --- |
| Crosses the midline (FIG. 83) | Does not cross the midline (FIG. 90) |
| Extends out of plane with the base (FIG. 85) to a first side of the base, the distance X1 being different than X2 (FIG. 85A) | Extends out of plane with the base (FIG. 85) to a second side of the base, the distance X1 being different than X2 (FIG. 52A) |
| The end extends in a non-perpendicular direction with the baseline (FIG. 83) | The end extends in a non-perpendicular direction with the baseline (FIG. 83) |

Example 7

A surgical staple can be deformed such that:

| First Leg | Second Leg |
| --- | --- |
| Crosses the midline (FIG. 83) | Does not cross the midline (FIG. 90) |
| Extends out of plane with the base (FIG. 85) to the same side of the base as the second leg, the distance X1 being different than X2 (FIG. 85A) | Extends out of plane with the base (FIG. 85) to the same side of the base as the second leg, the distance X1 being different than X2 (FIG. 85A) |
| The end extends in a non-perpendicular direction with the baseline (FIG. 83) | The end extends in a non-perpendicular direction with the baseline (FIG. 83) |

Example 8

A surgical staple can be deformed such that:

| First Leg | Second Leg |
|---|---|
| Crosses the midline (FIG. 83) | Does not cross the midline (FIG. 90) |
| Extends out of plane with the base (FIG. 85) | Extends in-plane, or substantially in-plane, with the base (FIG. 91) |
| The end extends in a non-perpendicular direction with the baseline (FIG. 83) | The end extends in a perpendicular direction to the baseline (FIG. 91) |

Example 9

A surgical staple can be deformed such that:

| First Leg | Second Leg |
|---|---|
| Crosses the midline (FIG. 83) | Does not cross the midline (FIG. 90) |
| Extends in-plane, or substantially in-plane, with the base (FIG. 91) | Extends out of plane with the base (FIG. 85) |
| The end extends in a non-perpendicular direction with the baseline (FIG. 83) | The end extends in a non-perpendicular direction with the baseline (FIG. 83) |

Several of the deformed staples described above comprise one or more staple legs which cross the mid-line of the staple base. In various embodiments, as a result, the deformed staple legs may at least partially overlap with one another. More particularly, the deformed staple legs, when viewed from the side, may co-operate to traverse the staple base from one end to the other leaving no gap therebetween. Such embodiments can be particularly useful, especially when used to staple vascular tissue. More specifically, the overlapping staple legs can compress blood vessels within the tissue regardless of where the blood vessels extend through the staple. Staples having gaps between the legs, or legs which do not extend along the entire length of the staple base when deformed, may not be able to properly compress every blood vessel in the tissue and, as a result, one or more blood vessels may leak.

In various embodiments, further to the above, a surgical instrument can be configured to deploy a plurality of staples 1400 in the manner described above and illustrated in FIGS. 83-85. In at least one such embodiment, the surgical stapler can deploy the staples 1400 in a sequential manner along a staple path and/or in a simultaneous manner, for example. In certain embodiments, a surgical instrument can be configured to deploy a plurality of staples 1600 in the manner described above and illustrated in FIG. 88. In at least one such embodiment, similar to the above, the surgical stapler can deploy the staples 1600 in a sequential manner along a staple path and/or in a simultaneous manner, for example. In various embodiments, further to the above, a surgical instrument can be configured to deploy a plurality of staples 1700 in the manner described above and illustrated in FIG. 90. In at least one such embodiment, the surgical stapler can deploy the staples 1700 in a sequential manner along a staple path and/or in a simultaneous manner, for example.

In various embodiments, referring now to FIGS. 103-108, a surgical stapling instrument 2100 can comprise, similar to the above, a first housing portion 2102 and a second housing portion 2104 which can be operably connected to one another by a latch 2180. Latch 2180 can comprise a frame 2184 which can be pivotably mounted to a frame 2110 of first housing portion 2102. In use, the latch 2180 can be configured to engage a frame 2114 of second housing portion 2104 and draw the second housing portion 2104 toward the first housing portion 2102 and move the anvil support portion 2130 of second housing portion 2104 toward the staple cartridge support portion 2124 of first housing portion 2102. In various embodiments, the first housing portion 2102, the second housing portion 2104, and the latch 2180 can each comprise one or more contoured outer housings or gripping portions, for example. In at least one such embodiment, the first housing portion 2102 can comprise an outer housing 2108, the second housing portion 2104 can comprise an outer housing 2112, and the latch 2180 can comprise an outer housing 2186. The surgical stapling instrument 2100 can further comprise a firing actuator 2204 which can, similar to the above, be selectively positioned on opposite sides of the surgical stapling instrument. More particularly, further to the above, the actuator 2204 can be selectively positioned on a first side of the housing portions 2102, 2104 such that the actuator 2204 can be moved distally along the first side or selectively positioned on a second side of the housing portions 2102, 2104 such that the actuator 2204 can be moved distally along the second side. In at least one embodiment, the first housing portion 2102 and the second housing portion 2104 can define one or more slots 2118 therebetween which can permit the actuator 2204 to be moved along the first and second sides. In at least one such embodiment, the slots 2118 can be connected by an intermediate slot 2331 which can extend around and/or through the proximal end of the surgical stapling instrument 2100.

Figure 109:
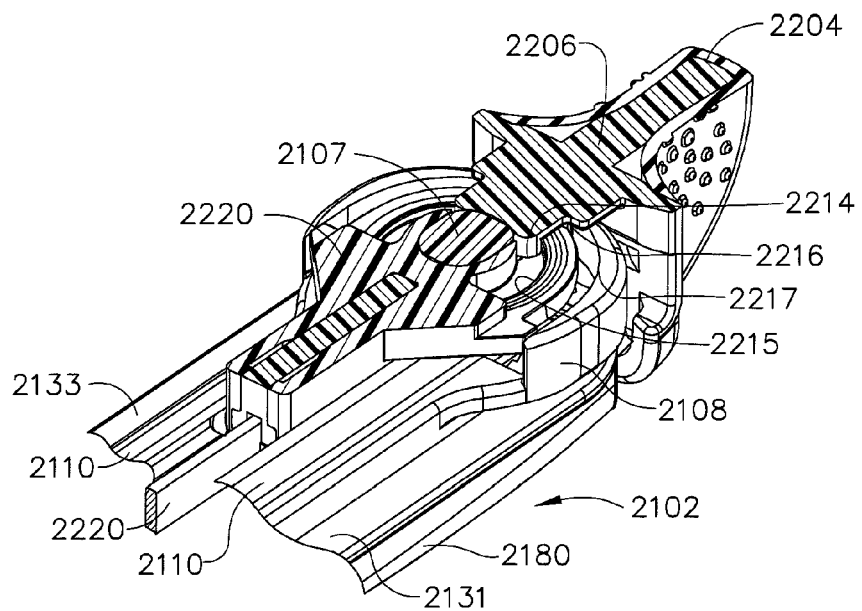
FIG. 109 is a cross-sectional view of the proximal end of the surgical stapling instrument of FIG. 103 illustrating the firing actuator in an unfired position.
Figure 110:
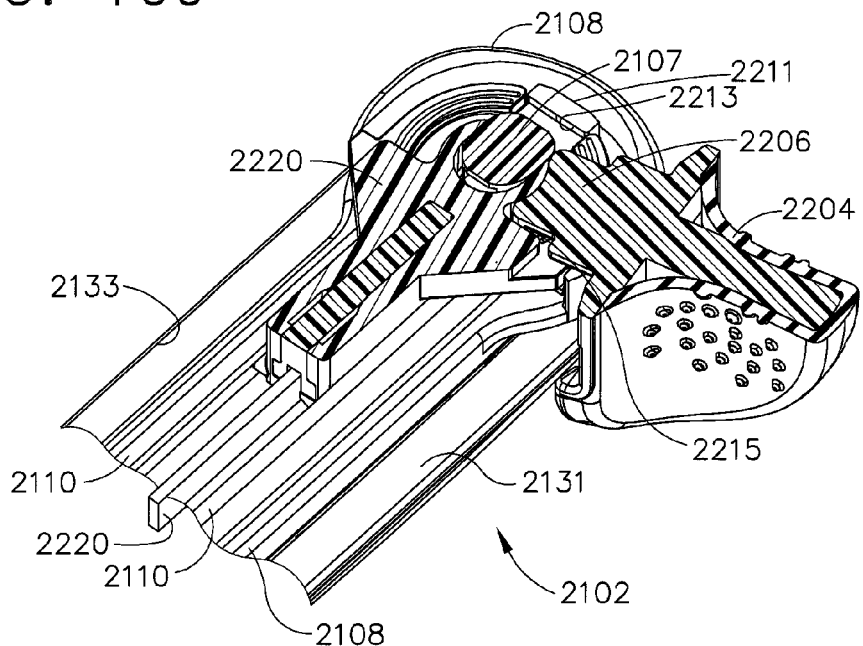
FIG. 110 is a cross-sectional view of the proximal end of the surgical stapling instrument of FIG. 103 illustrating the firing actuator rotated to a first side of the surgical stapling instrument housing.
Figure 111:
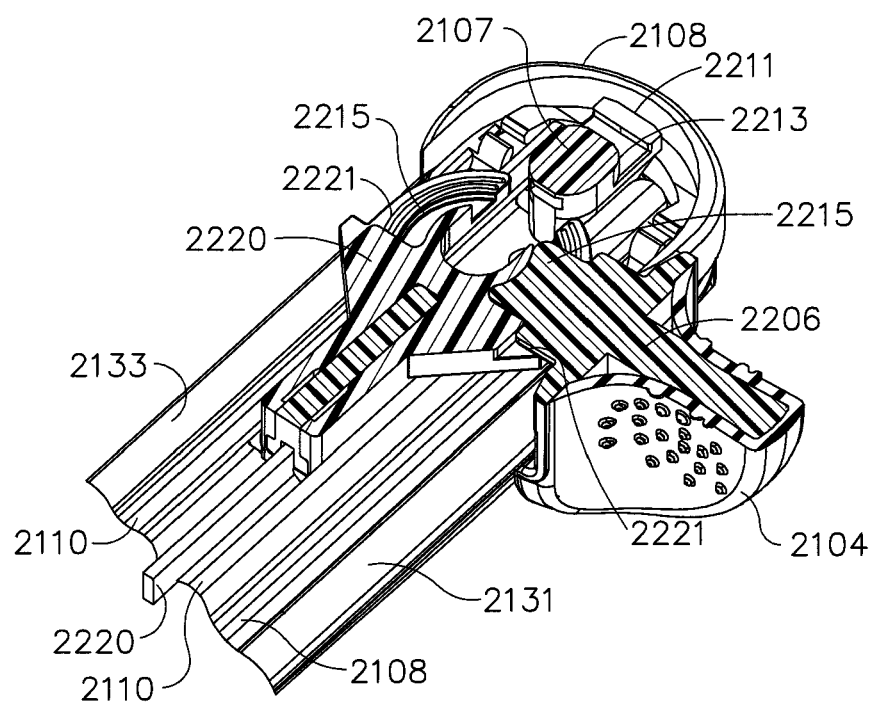
FIG. 111 is a cross-sectional view of the proximal end of the surgical stapling instrument of FIG. 103 illustrating the firing actuator in a partially-fired position.

Further to the above, referring to FIGS. 103-111, the firing actuator 2204 can be rotatably mounted to a drive bar 2220, wherein, in at least one embodiment, the actuator 2204 can be rotatably mounted to the drive bar 2220 via a connecting link 2206. Referring primarily to FIGS. 109-111, the actuator 2204 can be rotated between an intermediate, or neutral, position (FIG. 109) in which the drive bar 2220 is locked in position and cannot be advanced distally and an unlocked position (FIG. 110) in which the drive bar 2220 and the actuator 2204 are ready to be fired distally. Although FIG. 110 illustrates the actuator 2204 in an unlocked position on the first side of the surgical stapling instrument housing, the actuator 2204 can also be moved into an unlocked position on the opposite, or second, side of the surgical stapling instrument housing. The following example, although discussed in connection with the actuator 2204 being moved along the first side of the housing, is also applicable in connection with the actuator 2204 being moved along the second side of the housing. In any event, the actuator 2204 and the first housing portion 2102, for example, can comprise various interlocking features which can prevent, or at least limit, relative movement between the drive bar 2220 and the first housing portion 2102. More particularly, in at least one embodiment, the first housing portion 2102 can comprise one or more slots and/or one or more projections which can be configured to co-operate with one or more slots and/or one or more projections of actuator 2204 such that the drive bar 2220 cannot be advanced distally until the actuator 2204 has been sufficiently rotated out of its neutral position and into an unlocked position. In various embodiments, the proximal end of the first housing portion 2102 can comprise an end post 2107 which can include a retention slot 2213 configured to receive at least a portion of actuator link 2206, such as retention projection 2214, therein. When the actuator 2204 is in its neutral position, the retention projection 2214 is positioned in the retention slot 2213 and neither the actuator 2204 nor the driver bar 2220 can be advanced distally. As the actuator 2204 is rotated toward an unlocked position, the retention projection 2214 can move out of the retention slot 2213 in end post 2107 and into a receiving slot 2215 in driver bar 2220 as illustrated in FIG. 110. In at least one embodiment, the driver bar 2220 and actuator 2204 can remain in a locked condition until the retention projection 2214 has completely exited the retention slot 2213. Thereafter, the actuator 2204 can be advanced distally. In addition to or lieu of the above, the end post 2107 can further comprise a retention wall 2211 which can, similar to the above, impede the distal movement of actuator 2204 and drive bar 2220. More particularly, the actuator link 2206 can further comprise a retention projection 2216 which can be positioned behind, or distally with respect to, the retention wall 2211 when the actuator 2204 is in its neutral position and, owing to such alignment, the retention wall 2211 can provide a bearing surface preventing the distal movement of retention projection 2216. Once actuator 2204 has been sufficiently rotated out of its neutral position toward an unlocked position, the retention projection 2216 can be moved to a position in channel 2217 which is out of longitudinal alignment with the retention wall 2211 thereby permitting relative longitudinal movement therebetween.

Figure 104:
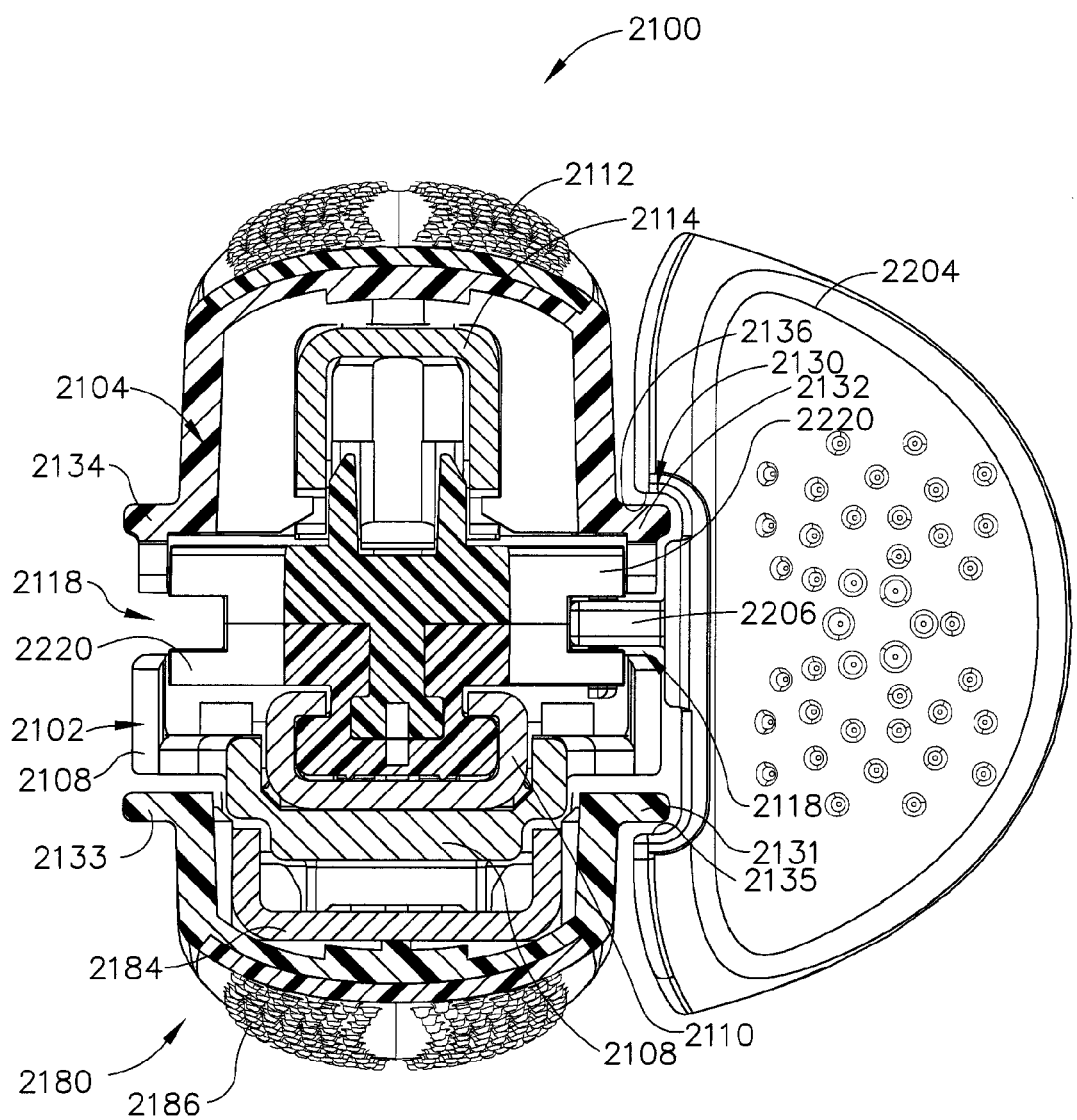
FIG. 104 is a cross-sectional view of the surgical stapling instrument of FIG. 103 illustrating the firing actuator in the partially-advanced position.
Figure 105:
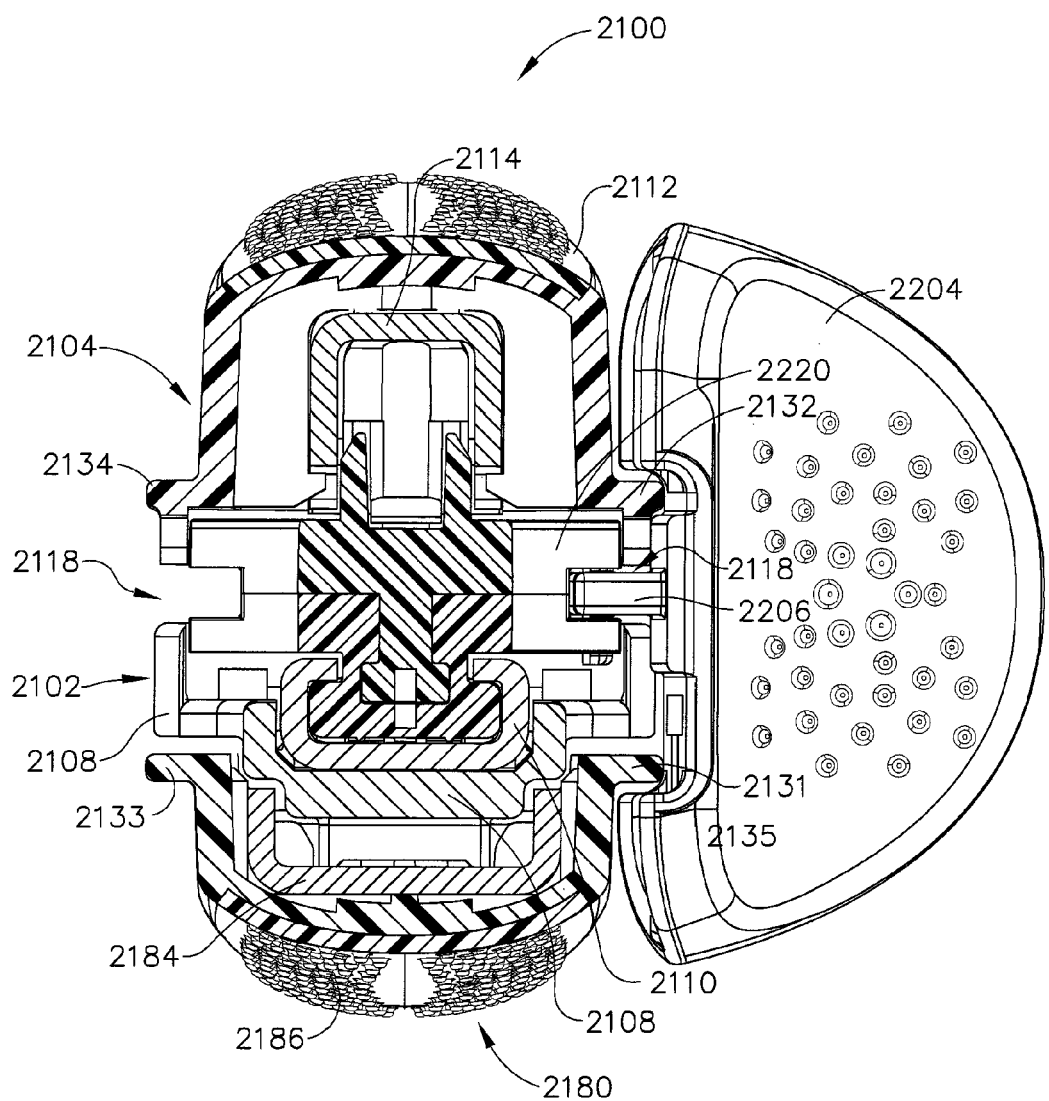
FIG. 105 is a cross-sectional view of the surgical stapling instrument of FIG. 103 illustrating the firing actuator being returned toward an unfired position.
Figure 106:
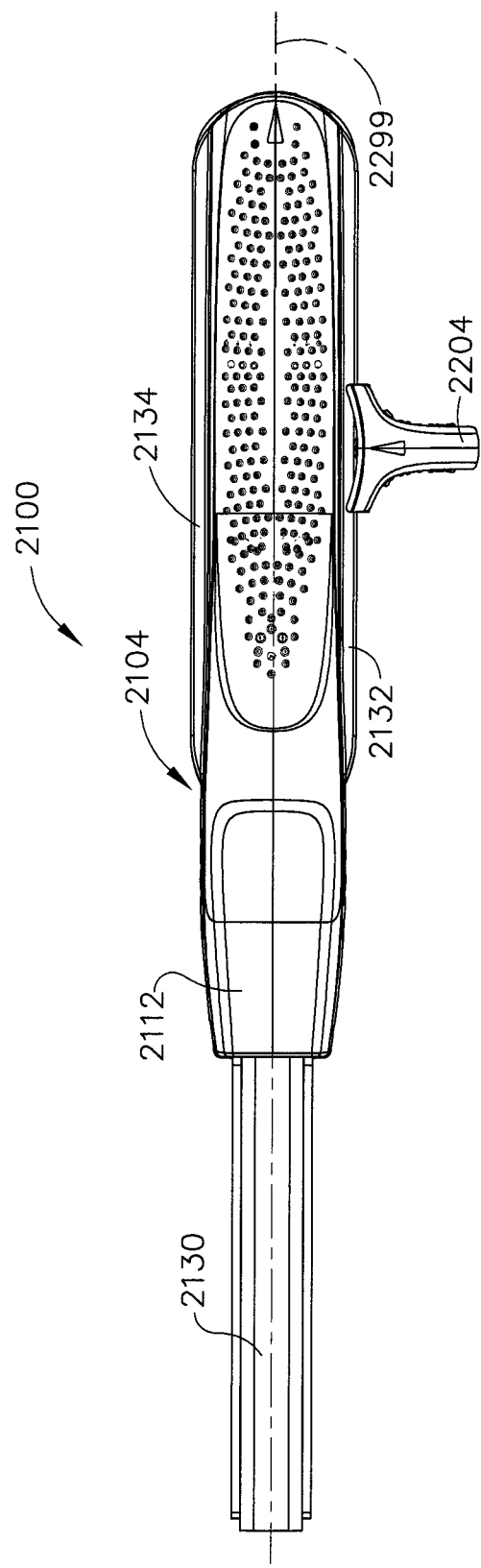
FIG. 106 is a top view of the surgical stapling instrument of FIG. 103 illustrating the firing actuator being moved distally.
Figure 107:
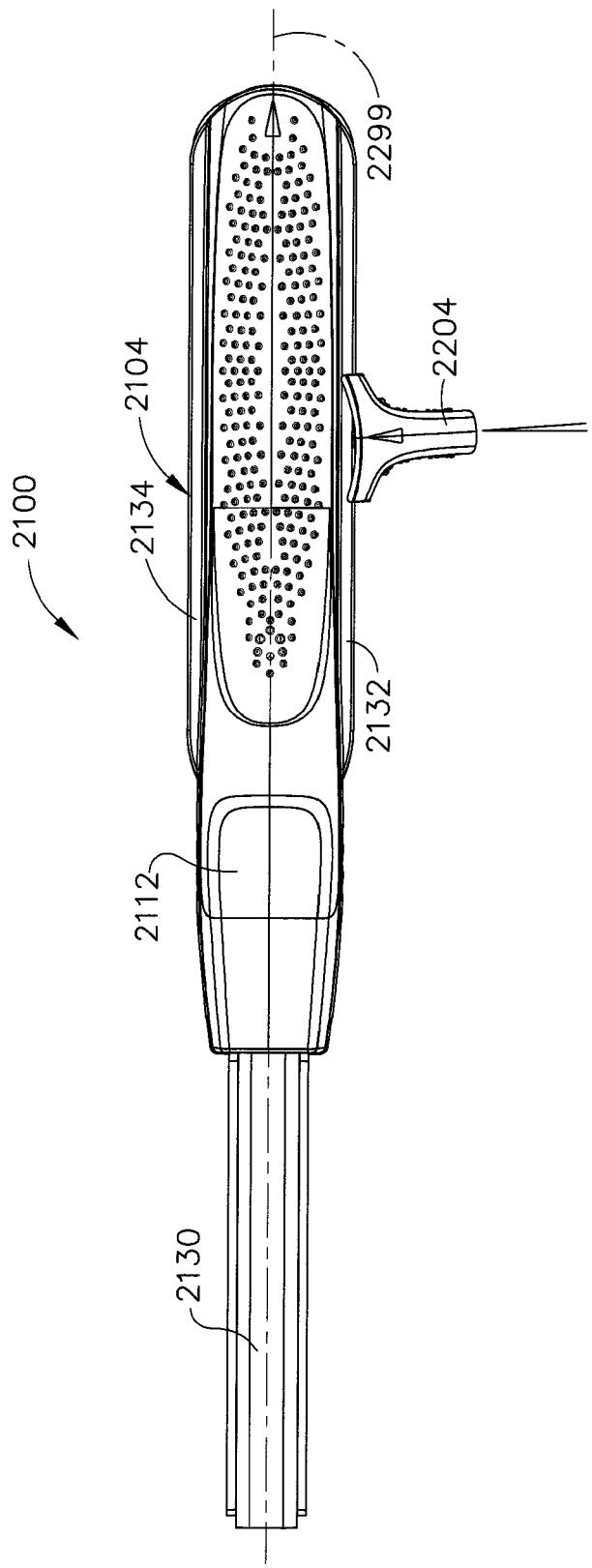
FIG. 107 is a top view of the surgical stapling instrument of FIG. 107 illustrating the firing actuator being moved proximally.
Figure 108:
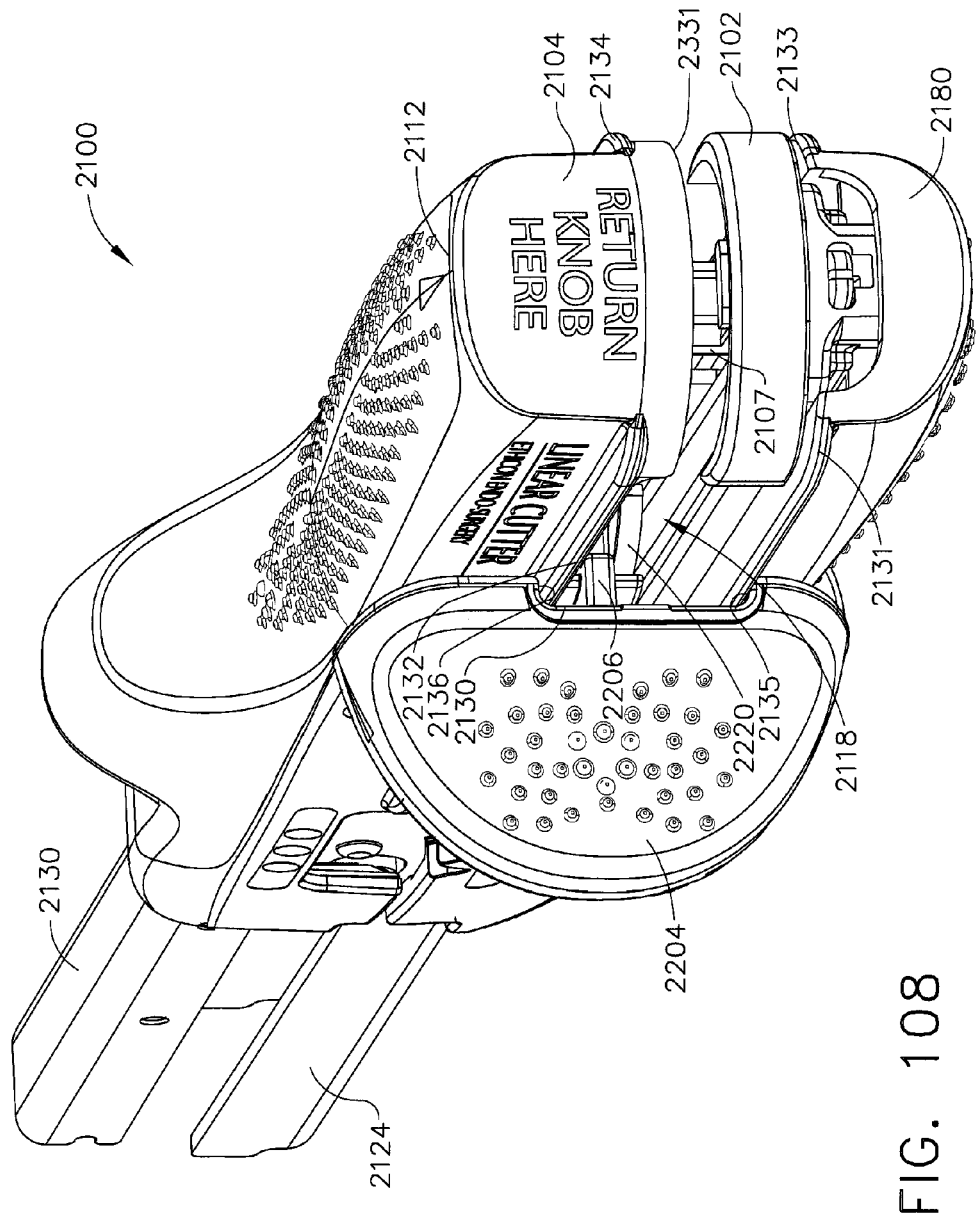
FIG. 108 is another perspective view of the surgical stapling instrument of FIG. 103.

As described above, once the actuator 2204 has been moved into an unlocked position (FIG. 110), the actuator 2204 can be advanced distally into a fired position (FIG. 111). In such circumstances, referring now to FIG. 106, a force can be applied to the actuator 2204 in order to advance drive bar 2220 distally and incise tissue and/or deploy staples from a staple cartridge as described above. In such circumstances, the force can rotate and seat the actuator 2204 in a fully-deployed, or an at least nearly fully-deployed, position. In at least one embodiment, the drive bar 2220 can comprise one or more stops, such as stops 2221 (FIG. 111), for example, which can limit the rotation of the actuator 2204 in the distal direction. In at least one such embodiment, the drive bar 2220 can comprise a first stop 2221 configured to limit the rotation of the actuator 2204 toward the first side of the instrument and a second stop 2221 configured to limit the rotation of the actuator toward the second side of the instrument. In certain embodiments, referring to FIG. 106, the stops 2221 can be configured such that the actuator 2204 is positioned along an axis which is perpendicular, or at least substantially perpendicular, to a longitudinal axis 2299 of the surgical stapling instrument 2100. Such a position of actuator 2204 is also illustrated in FIG. 104. Referring now to FIG. 107, a force can be applied to the actuator 2204 in order to retract the actuator 2204 proximally. In such circumstances, the force can cause the actuator 2204 to rotate proximally until it comes into contact with the first housing portion 2102 and/or the second housing portion 2104. Such a position of actuator 2204 is also illustrated in FIG. 105 wherein the actuator 2204 can be positioned against lock rail 2131 and/or lock rail 2132, for example, in order to prevent any further rotation of the actuator 2204.

In various embodiments, as described above, the latch 2180 can be utilized to lock the first housing portion 2102 and the second housing portion 2104 together. In certain embodiments, the actuator 2204 can be utilized to limit the relative movement between the housing portions 2102, 2104 and/or move the housing portions 2102, 2104 toward one another. In at least one embodiment, referring primarily to FIGS. 103, 104, and 108, the actuator 2204 can comprise a recess, or channel, 2130 which can be configured to receive the lock rails 2131 and 2132 when the actuator 2204 is moved along the first side of the surgical stapling instrument 2100 or, alternatively, receive the lock rails 2133 and 2134 when the actuator 2204 is moved along the second side of the surgical stapling instrument 2100. In either event, the recess 2130 can be configured to capture an opposing set of rails, such as rails 2131 and 2132, for example, and prevent, or at least limit, relative movement therebetween. More particularly, in at least one embodiment, the recess 2130 can comprise a first bearing surface 2135 positioned opposite the first lock rail 2131 and a second bearing surface 2136 positioned opposite the second lock rail 2132 such that the bearing surfaces 2135, 2136 can prevent, or at least limit, the movement of the first housing portion 2102 and the second housing portion 2104 away from one another. In some circumstances, gaps may exist between the bearing surfaces 2135, 2136 and the lock rails 2131, 2132, respectively, when the bearing surfaces 2135, 2136 are adjacent to the lock rails 2131, 2132 while, in other circumstances, the bearing surface 2135 may contact the lock rail 2131 and/or the bearing surface 2136 may contact the lock rail 1232, for example. In use, in various circumstances, the actuator 2204 can be moved from its neutral position (FIG. 109) into an unlocked position (FIG. 110) wherein, in such a position, the recess 2130 can be aligned with either a set of rails 2131, 2132 or a set of rails 2133, 2134 depending on whether the actuator 2204 has been rotated to the first or second side. When the actuator 2204 is advanced distally, in some circumstances, the actuator 2204 may contact the rails and cam, or drive, the rails toward each other. In such circumstances, the first housing portion 2102 and the second housing portion 2104 can be cammed, or driven, toward one another.

In various embodiments, as described above, the actuator 2204 can receive, capture, and/or engage a lock rail extending from each of the first housing portion 2102 and the second housing portion 2104. In various alternative embodiments, the actuator 2204 can be configured to receive, capture, and/or engage two or more lock rails extending from the first housing portion 2102 and/or the second housing portion 2104. In certain embodiments, the first housing portion 2102 and/or the second housing portion 2104 can comprise one or more lock channels which can be configured to receive at least a portion of the actuator. In various embodiments, the housing portions and the actuator of the surgical stapling instrument can comprise any suitable lock portions which can be configured to receive, align, retain, capture, lock, move, cam, and/or limit the movement of the surgical instrument housing portions. In various embodiments, referring primarily to FIGS. 106 and 107, the lock rails 2131, 2132, 2133, and/or 2134 can extend longitudinally along the stapling instrument 2100 such that, in at least one embodiment, they extend in a longitudinal direction from the proximal end of the surgical stapling instrument 2100 toward the distal end of the instrument which is parallel, or at least substantially parallel, to longitudinal axis 2299. Furthermore, in at least one embodiment, the lock rails 2131, 2132, 2133, and/or 2134 can extend in directions which are parallel, or at least substantially parallel, to one another.

Figure 119:
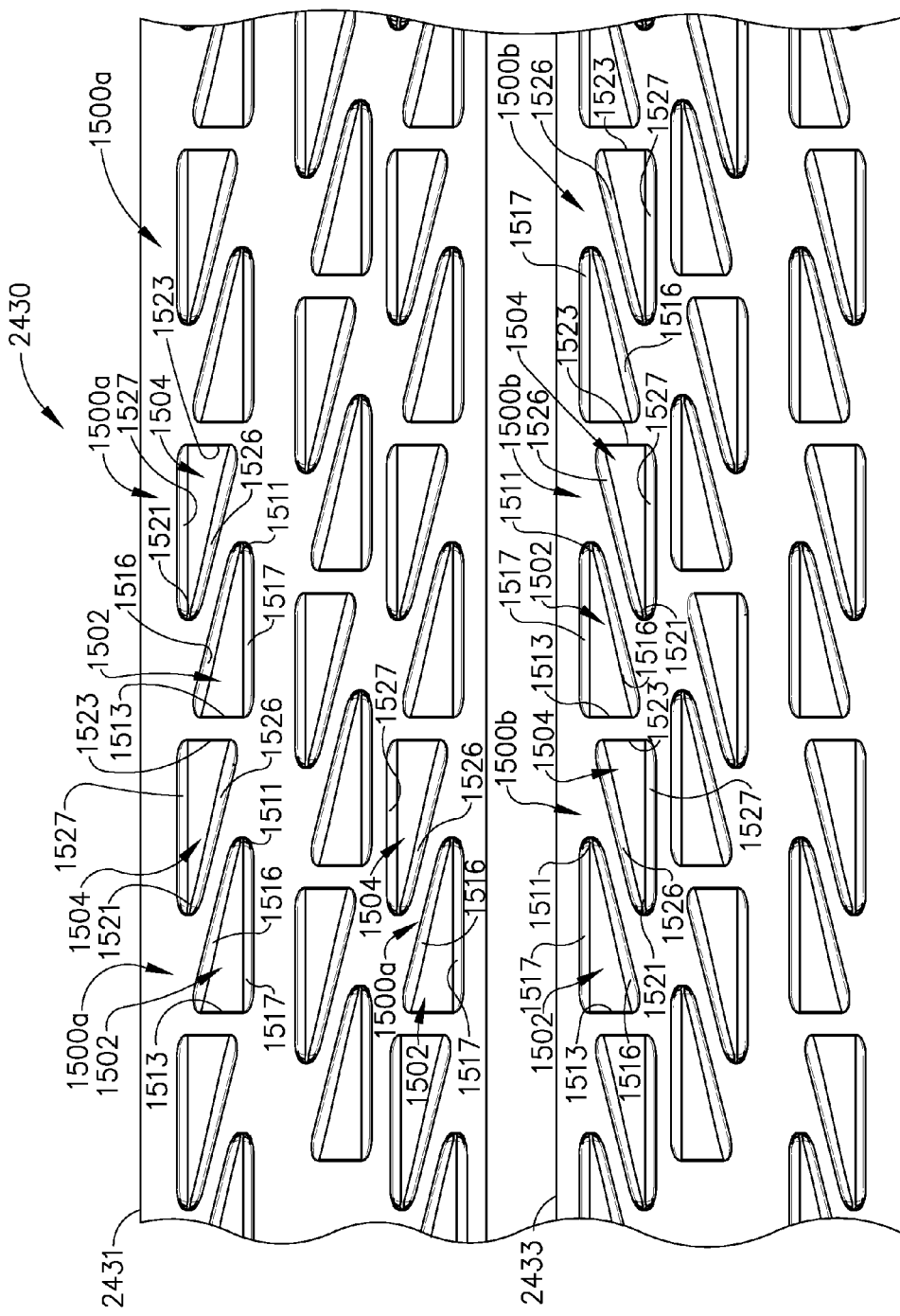

In various embodiments, as discussed above, a surgical stapling instrument can comprise an anvil including a plurality of staple pockets 1500. In certain embodiments, the staple pockets 1500 can be arranged in an end-to-end manner extending between a proximal end and a distal end of the anvil. Referring now to FIG. 119, an anvil can comprise one or more rows of staple pockets 1500 wherein the first forming cup 1502 of each staple pocket 1500 can be positioned distally with respect to its respective second forming cup 1504, for example. In certain other embodiments, the first forming cups 1502 can be positioned proximally with respect to their respective second forming cups 1504. In various embodiments, each first forming cup 1502 can comprise a generally triangular shape comprising a first leg comprising first outer sidewall 1513, a second leg comprising first exterior sidewall 1517 extending perpendicular to, or at least substantially perpendicular to, the first leg, and a hypotenuse extending between the first leg and the second leg comprising first interior sidewall 1516. In at least one such embodiment, the first leg, the second leg, and the hypotenuse of the first forming cup 1502 can form a right, or at least substantially right, triangle. As illustrated in FIG. 119, an anvil, such as anvil 2430, for example, can comprise a first side 2431, a second side 2432, a knife slot 2433 extending between the first side 2431 and the second side 2432, and a plurality of staple pockets 1500. The plurality of staple pockets 1500 can include a first group of staple pockets 1500, hereinafter referred to as first staple pockets 1500a, which each comprise a first configuration and a second group of staple pockets 1500, hereinafter referred to as second staple pockets 1500b, which each comprise a second configuration. With regard to the first staple pockets 1500a, the first forming cups 1502 therein can comprise first exterior sidewalls 1517 which can face toward and/or can be parallel to the knife slot 2433 and first interior sidewalls 1516 which can face toward the first side 2431 of the anvil 2430.

Similar to the above, each second forming cup 1504 can comprise a generally triangular shape comprising a first leg comprising second outer sidewall 1523, a second leg comprising second exterior sidewall 1527 extending perpendicular to, or at least substantially perpendicular to, the first leg, and a hypotenuse extending between the first leg and the second leg comprising second interior sidewall 1526. In at least one such embodiment, the first leg, the second leg, and the hypotenuse of the second forming cup 1504 can form a right, or at least substantially right, triangle. Similarly, the second forming cups 1504 of first staple pockets 1500a comprise second exterior sidewalls 1527 which can face toward and/or can be parallel to the first side 2431 of the anvil 2430 while the second interior sidewalls 1526 can face toward the knife slot 2433. In various embodiments, the second staple pockets 1500b can comprise a geometry which is a minor-image, or substantially a mirror image, of the first staple pockets 1500a. Similar to the first forming cups 1502 of the first staple pockets 1500a, the first forming cups 1502 of the second staple pockets 1500b can comprise first exterior sidewalls 1517 which can face toward and/or can be parallel to the knife slot 2433 and first interior sidewalls 1516 which can face toward the second side 2432 of the anvil 2430. Furthermore, similar to the second forming cups 1504 of the first staple pockets 1500a, the second forming cups of the second staple pockets 1500b can comprise second exterior sidewalls 1527 which can face toward and/or can be parallel to the second side 2432 of the anvil 2430 and second interior sidewalls 1526 which can face toward the knife slot 2433.

In various embodiments, an anvil of a surgical stapler can comprise a row of first staple pockets 1500a and a row of second staple pockets 1500b. Referring again to FIG. 119, anvil 2430 can comprise a plurality of rows including first staple pockets 1500a on a first side of the knife slot 2433 and a plurality of rows including second staple pockets 1500b on the opposite side of the knife slot 2433. In use, in at least one such embodiment, the staple legs that are formed by the first forming cups 1502 can be at least partially bent toward the knife slot 2433 while the staple legs that are formed by the second forming cups 1504 can be at least partially bent away from the knife slot 2433, for example. Such an arrangement of formed staples could be produced on both sides of the knife slot 2433. In certain alternative embodiments, the staple pockets 1500 could be arranged such that the staple legs that are formed by the first forming cups 1502 can be at least partially bent away from the knife slot 2433 while the staple legs that are formed by the second forming cups 1504 can be at least partially bent toward the knife slot 2433, for example. In certain embodiments, an anvil can comprise alternating rows of staple pockets 1500a and 1500b. In at least one embodiment, an anvil can comprise rows of staple pockets including both staple pockets 1500a and staple pockets 1500b, for example. In at least one such embodiment, various patterns of staple legs being formed toward and away from one another could be achieved.

Figure 112:
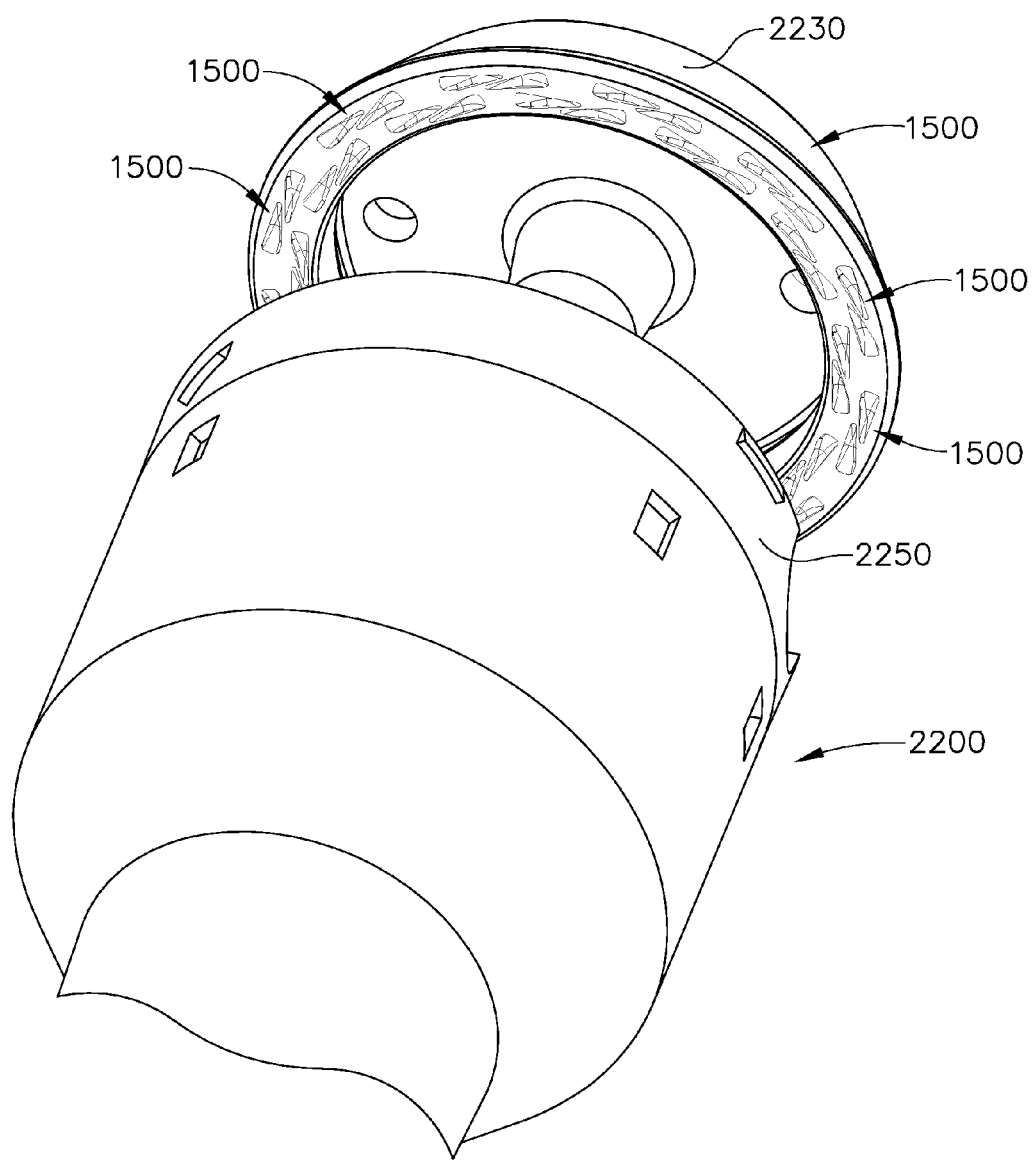
FIG. 112 is a partial perspective view of a surgical stapling instrument comprising a circular anvil and a circular staple cartridge in accordance with at least one embodiment of the present invention.

In various embodiments, further to the above and referring to FIG. 76 once again, the anvil of a surgical stapler can comprise a plurality of staple pockets 1500. In certain embodiments, the staple pockets 1500 can be arranged and positioned along straight, or at least substantially straight, lines such that longitudinal axes 1599 of the staple pockets 1500 are either collinear with, substantially collinear with, parallel to, and/or substantially parallel to one another. In various embodiments, a surgical stapling instrument can comprise a curved anvil. Referring now to FIG. 112, a surgical stapling instrument 2200, for example, can comprise an end effector including a circular, or at least substantially circular, anvil 2230. Anvil 2230 can comprise an inner circular, or at least substantially circular, row of staple pockets 1500 and an outer circular, or at least substantially circular, row of staple pockets 1500, for example. In various embodiments, the inner circular row of staple pockets 1500 and the outer circular row of staple pockets 1500 can be concentric, or at least substantially concentric, with one another. In various other embodiments, an anvil may comprise only one circular row of staple pockets 1500 or more than two circular rows of staple pockets 1500, for example.

In various embodiments, referring again to FIG. 112, the surgical stapling instrument 2200 can further comprise a circular staple cartridge 2250 positioned opposite the anvil 2230. The staple cartridge 2250 can comprise a plurality of staples stored therein wherein, during use, the staples can be ejected from the staple cartridge 2250 and contact the staple pockets 1500. In various embodiments, the staples can be stored in staple cavities defined within the staple cartridge 2250. The staple cavities and the staples can be aligned with the staple pockets 1500 such that the legs of the staples can enter into the first and second forming cups 1502 and 1504 of the staple pockets 1500 as described above. In various embodiments, the surgical stapling instrument can comprise a firing drive which can eject the staples from the staple cartridge and, in addition, move a cutting member relative to the staple cartridge and anvil. Various surgical stapling instruments are disclosed in U.S. Pat. No. 5,285,945, entitled SURGICAL ANASTOMOSIS STAPLING INSTRUMENT, which issued on Feb. 14, 1994, the entire disclosure of which is incorporated by reference herein.

Figure 113:
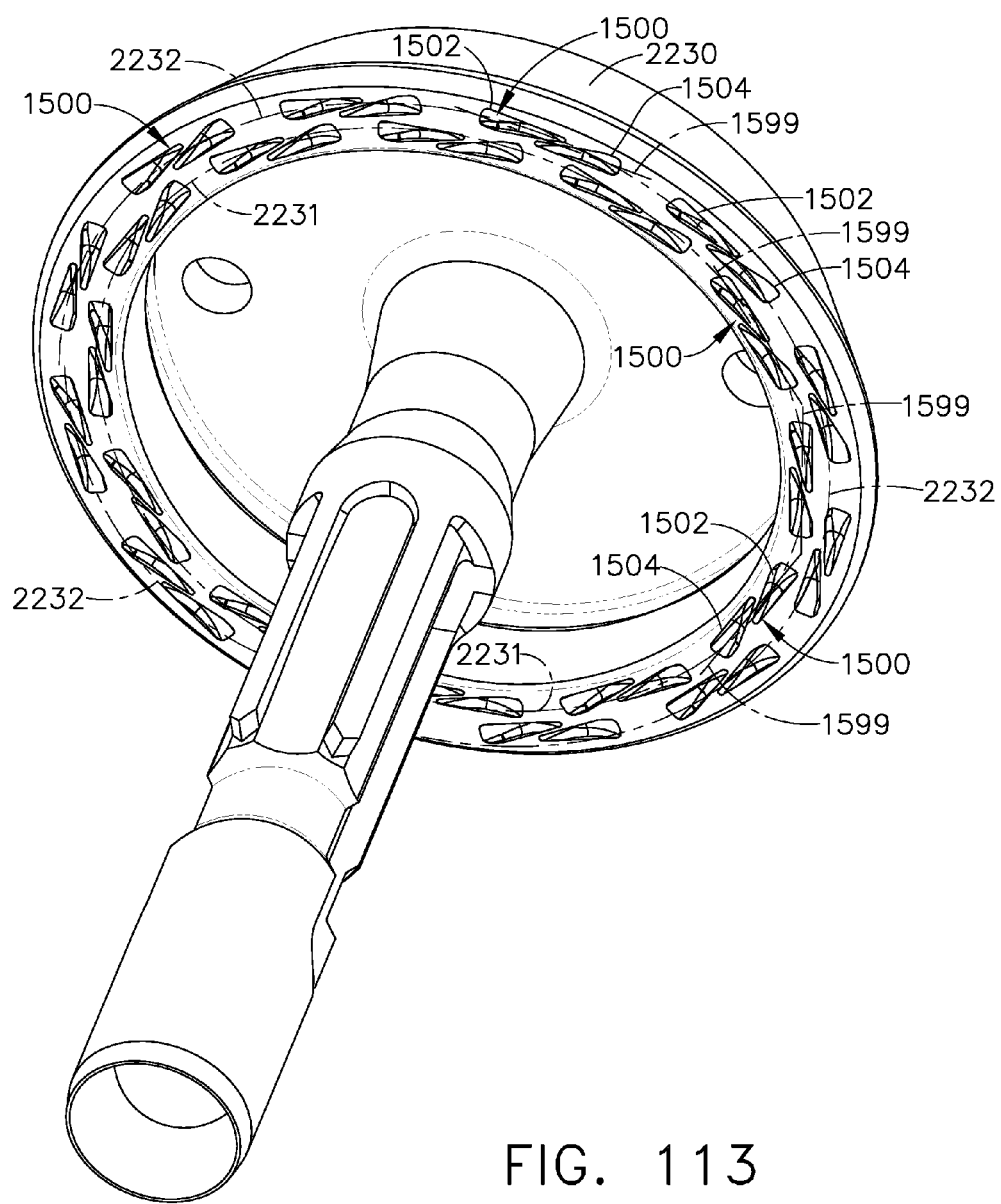
FIG. 113 is a perspective view of the anvil of FIG. 112.

In various embodiments, referring primarily now to FIG. 113, the staple pockets 1500 can be positioned along an inner circular path 2231 and/or an outer circular path 2232, for example. As discussed above, each staple pocket 1500 can comprise a longitudinal axis 1599 which can, in certain embodiments, extend through the center of their respective staple pockets 1500. As illustrated in FIG. 113, each longitudinal axis 1599 can extend transversely through an inner circular path 2231 and/or an outer circular path 2232. In at least one such embodiment, the longitudinal axes 1599 of the inner row of staple pockets 1500 can extend transversely through the inner circular path 2231 and the longitudinal axes 1599 of the outer row of staple pockets 1500 can extend transversely through the outer circular path 2232. In various embodiments, referring to FIG. 76 once again, each staple pocket 1500 can be defined by a longitudinal length extending between the first outside wall 1513 and the second outside wall 1523 wherein, in at least one such embodiment, each longitudinal length can comprise a midpoint. In certain embodiments, the staple cavities 1500 can be positioned and arranged such that the midpoints of the longitudinal lengths are positioned on and/or near the inner circular path 2231 and/or the outer circular path 2232. In at least one embodiment, the midpoints of the longitudinal lengths can be positioned offset with respect to the inner circular path 2231 and/or the outer circular path 2232.

In various embodiments, further to the above, the axes 1599 of the staple pockets 1500 can be tilted with respect to the inner and outer circular paths 2231 and 2232. In at least one such embodiment, each staple pocket 1500 can comprise a first forming cup 1502 at least partially positioned on one side of a circular path and a second forming cup 1504 at least partially positioned on the other side of the circular path. In certain other embodiments, the staple pockets 1500 can be contoured such that the longitudinal centerline of the staple pockets is curved to match, or at least substantially match, the radius of curvature of the inner circular path 2231 and/or the outer circular path 2232, for example. In various embodiments, each circular path can be defined by a constant, or at least substantially constant, radius of curvature, and the staple pockets 1500 can be contoured to match, or at least substantially match, the radius of curvature.

Figure 114:
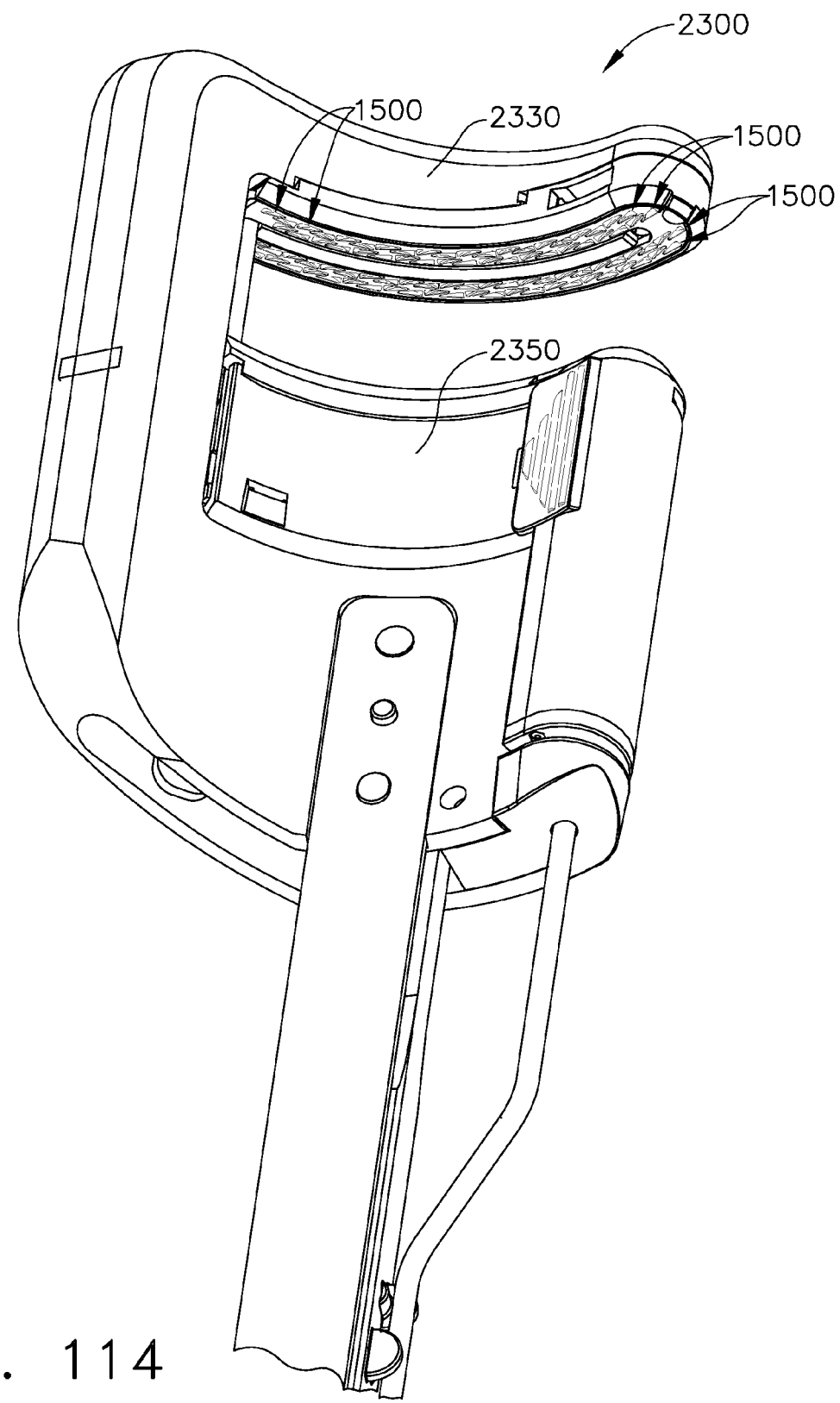
FIG. 114 is a partial perspective view of a surgical stapling instrument comprising a curved anvil and a curved staple cartridge in accordance with at least one embodiment of the present invention.
Figure 115:
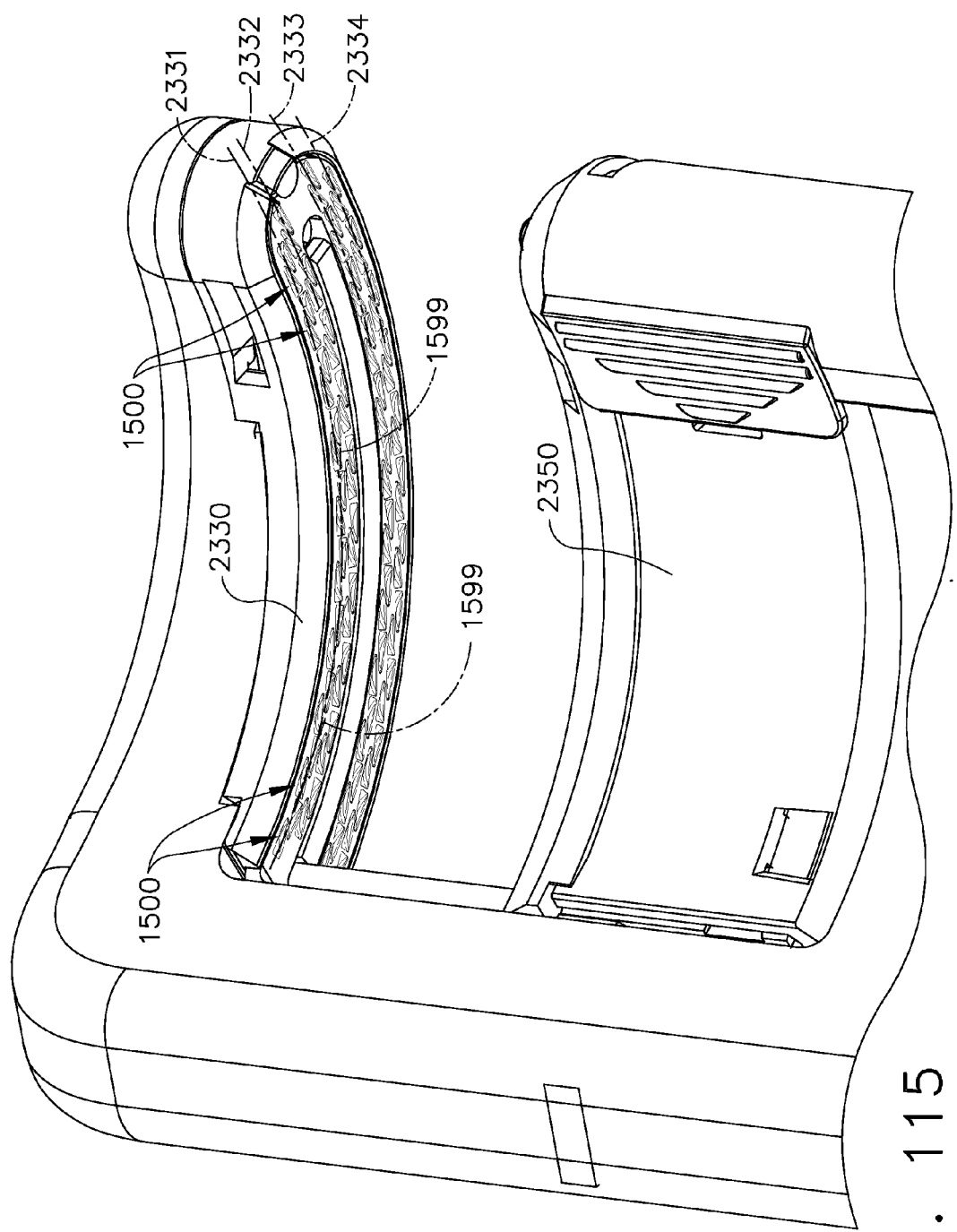
FIG. 115 is a detail view of the curved anvil and the curved staple cartridge of FIG. 114.
Figure 116:
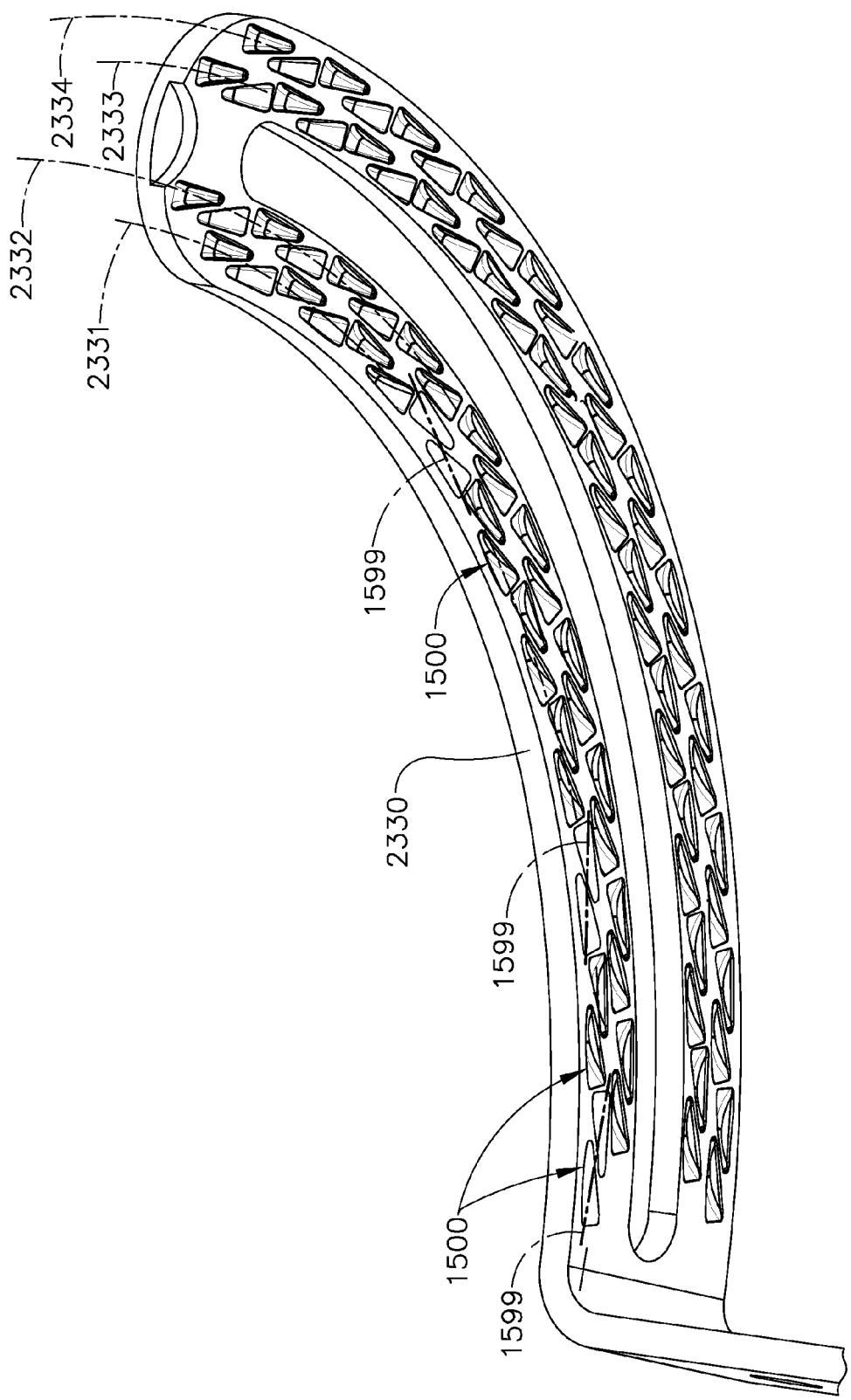
FIG. 116 is a detail view of a curved anvil plate of the curved anvil of FIG. 114.

In various embodiments, referring now to FIG. 114, a surgical instrument, such as surgical instrument 2300, for example, can include a curved anvil 2330. Similar to the above, the curved anvil 2330 can comprise a plurality of staple pockets 1500 positioned along several curved rows. In the illustrated embodiment, the anvil 2330 can comprise four curved rows of pockets 1500, for example, wherein, referring primarily to FIGS. 115 and 116, the staple pockets 1500 can be positioned along a first curved path 2331, a second curved path 2332, a third curved path 2333, and/or a fourth curved path 2334. In at least one such embodiment, each curved path can be defined by a different radius of curvature. In certain embodiments, each curved path can be defined by a constant, or at least substantially constant, radius of curvature. In certain other embodiments, each curved path can be defined by more than one radius of curvature. Similar to the above, the longitudinal axes 1599 of the staple pockets 1500 can extend transversely with respect to the curved paths and, in certain embodiments, the axes 1599 can be centered on the curved paths. In various embodiments, the surgical instrument 2300 can further comprise a staple cartridge 2350 which includes a plurality of staples removably stored therein. The surgical instrument 2300 can further comprise a firing drive which can eject the staples from the staple cartridge and, in addition, move a cutting member, or knife, relative to the staple cartridge 2350 and the anvil 2330. Various surgical stapling instruments are disclosed in U.S. patent application Ser. No. 11/014,910, entitled CURVED CUTTER STAPLER SHAPED FOR MALE PELVIS, filed on Dec. 20, 2004, the entire disclosure of which is incorporated by reference herein.

Figure 118:
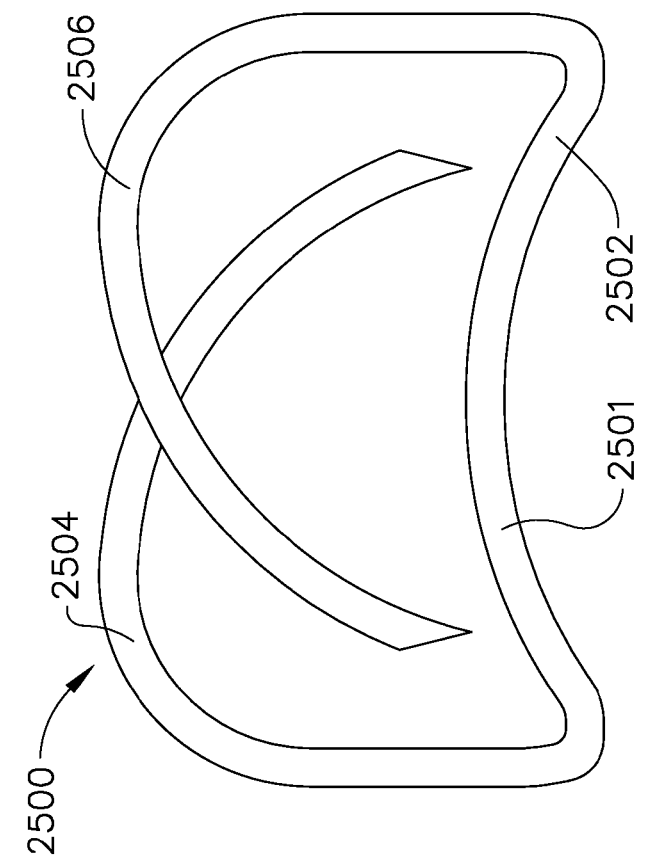
Figure 117:
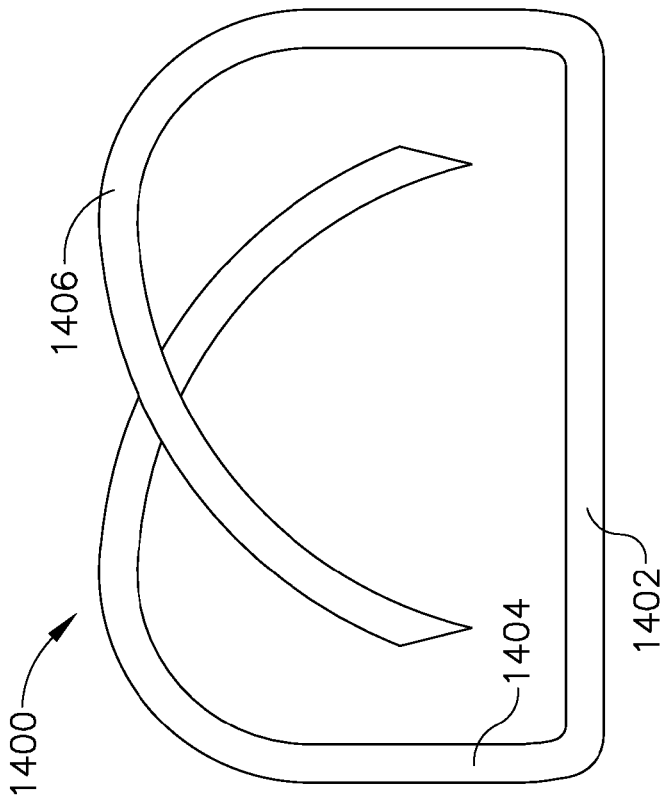
FIG. 117 is an elevational view of a deformed staple in accordance with at least one embodiment of the present invention.

As described above in connection with surgical staple 1400 and FIGS. 82-85, a surgical staple can comprise a flat, or at least substantially flat, base 1402 extending between staple legs 1404 and 1406. In use, in at least one embodiment, a staple cartridge can include a plurality of staple drivers which can be configured to support the bases 1402 of the staples 1400 as the staple drivers eject the staples 1400 out of the staple cartridge. In various embodiments, the staple drivers can comprise one or more flat, or at least substantially flat, support cradles which can support the flat, or at least substantially flat, bases 1402. In various other embodiments, referring now to FIG. 118, a surgical staple, such as staple 2500, for example, can comprise a base 2502, a first leg 2504, and a second leg 2506. Similar to the staple legs 1404 and 1406 of staple 1400, the staple legs 2504 and 2506 can extend upwardly in either a substantially U-shaped configuration and/or a substantially V-shaped configuration when the staples 2500 are in an unformed, or undeployed, condition. As the staples 2500 are ejected from the staple cartridge, similar to staples 1400, the staple legs 2504 and 2506 can contact an anvil positioned opposite the staple cartridge which can be configured to deform the staple legs and curl them toward the base of the staples, as described above. FIG. 118 depicts a staple 2500 in such a deformed, or deployed, condition. As also illustrated in FIG. 118, the base 2502 of the staple 2500 can be curved. In various embodiments, the base 2502 can comprise a curved portion 2501 which can curve upwardly, or inwardly, toward the staple legs 2504 and 2506. More particularly, when comparing a staple 1400 (FIG. 117) and a staple 2500 (FIG. 118) side-by-side, it can be seen that the base 2502 extends above a horizontal plane defined by base 1402. In various embodiments, further to the above, the curved portion 2501 can be defined by a single radius of curvature or more than one radius of curvature. In at least one embodiment, the curved portion 2501 can comprise an arcuate configuration. In various embodiments, the curved portion 2501 can comprise an arched-shaped and/or bow-shaped configuration. In certain embodiments, the curved portion 2501 can comprise a parabolic, or at least substantially parabolic, configuration. Regardless of the configuration, in various embodiments, the curved portion 2501 can comprise a spring which can resiliently apply a spring force to the captured tissue.

In various embodiments, the curved portion 2501 can be configured to apply a compressive force, or pressure, to the tissue captured within the deformed, or deployed, staple 2500. In use, as the staple legs 2504 and 2506 are being deformed against the anvil, the staple legs 2504 and 2506 can begin to compress the tissue against the curved portion 2501 of base 2502 and, as a result, the curved portion 2501 can at least partially deflect from the load being applied thereto. In various circumstances, the curved portion 2501 can deform elastically and/or plastically, wherein the amount of deformation can be a function of the tissue thickness, for example. More particularly, if the tissue captured within the staple 2500 is relatively thin, the curved portion 2501 may deform very little, if at all, and if the tissue captured within the staple 2500 is relatively thick, the deformation can be relatively larger. In certain embodiments, each staple 2500 can be manufactured with a curved portion 2501 such that the bases 2502 of the staples 2500 are pre-curved before they are assembled into a staple cartridge. In at least one embodiment, the staple drivers positioned within the staple cartridge can comprise a curved support cradle which can support the bottom surfaces of the curved portions 2501. In at least one such embodiment, the support cradle can comprise a curved surface which matches, or at least substantially matches, the curvature of a curved portion 2501. In certain embodiments, the bases 2502 of the staples 2500 can be deformed during the staple-forming process to include an upwardly-depending curved portion, such as a curved portion 2501, for example. In at least one such embodiment, the staples 2500 can comprise a flat, or at least substantially flat, base 2502 wherein each of the staple drivers can comprise one or more curved mandrels configured to contact and deform the bases 2502. In certain other embodiments, the staples 2500 can comprise pre-curved bases before they are inserted into the staple cartridge wherein the final shape of the curves can be obtained during the staple-forming process, similar to the process described above.

In various embodiments, further to the above, the curved portion 2501, for example, of the staples 2500 can apply a sufficient pressure to the tissue which can reduce or stop bleeding therefrom. In certain embodiments, the curved portion can extend across the entire distance between the first staple leg 2504 and the second staple leg 2506. In certain other embodiments, the curved portion may only extend across only a portion of the distance between the staple legs 2504 and 2506. In at least one embodiment, the base 2502 may comprise both curved portions and flat portions, for example. In certain embodiments, a compressible material can be positioned on and/or attached to a staple cartridge and/or an anvil, for example, which can be compressed against the tissue and captured within the staples when the staples are deployed. Similar to curved portion 2501, the compressible material can deflect elastically and/or plastically as the legs of the staple are being formed and bent downwardly toward the staple bases. In various circumstances, the amount of deformation can be a function of the tissue thickness, for example, captured within the staples. More particularly, if the tissue captured within a staple is relatively thin, the compressible material may deform very little, if at all, and if the tissue captured within the staple is relatively thick, the deformation of the compressible material can be relatively larger. In any event, the compressible material can comprise a layer of adjunct, haemostatic material, and/or any other suitable therapeutic material which can facilitate in reducing or stopping bleeding from the staple tissue and/or otherwise treat the tissue. As mentioned above, referring now to FIG. 120, the compressible material, such as compressible material 2340, for example, can be attached to the anvil and/or staple cartridge. In certain embodiments, the compressible material can be adhered to the anvil and/or staple cartridge utilizing one or more adhesives, for example. In various embodiments, the compressible material can comprise retention features which can be configured to engage the anvil and/or staple cartridge and retain the compressible material to the anvil and/or staple cartridge. In at least one such embodiment, the compressible material can be at least partially positioned within the staple cavities defined in the staple cartridge and/or the staple pockets defined in the anvil, for example. In certain embodiments, the movement of a cutting member, or knife, relative to the staple cartridge and anvil when the staples are being deployed can dislodge or detach the compressible material from the anvil and/or staple cartridge.

In various embodiments, further to the above, a surgical staple can be comprised of titanium, such as titanium wire, for example. In certain embodiments, a surgical staple can be comprised of an alloy comprising titanium, aluminum, and/or vanadium, for example. In at least one embodiment, the surgical staple can be comprised of surgical stainless steel and/or an alloy comprised of cobalt and chromium, for example. In any event, the surgical staple can be comprised of metal, such as titanium, and a metal oxide outer surface, such as titanium oxide, for example. In various embodiments, the metal oxide outer surface can be coated with a material. In certain embodiments, the coating material can be comprised of polytetrafluoroethylene (PTFE), such as Teflon®, and/or a tetrafluoroethylene (TFE) such as ethylene-tetrafluoroethylene (ETFE), perfluroalkoxyethylene-tetrafluoroethylene (PFA), and/or Fluorinated Ethylene Propylene (FEP), for example. Certain coatings can comprise silicon. In various embodiments, such coating materials can prevent, or at least inhibit, further oxidation of the metal. In certain embodiments, the coating materials can provide one or more lubricious surfaces against which the anvil, or staple pockets, can contact the staples in order to reduce the friction force therebetween. In various circumstances, lower friction forces between the staples and the staple pockets can reduce the force required to deform the staples.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A surgical stapler, comprising:
  a curved anvil assembly, comprising:
    a tissue contacting surface;
    a plurality of staple pockets formed in said tissue contacting surface, wherein said staple pockets are positioned along a curve, and wherein each said staple pocket comprises:
      a staple pocket centerline, wherein a said staple pocket centerline of a first staple pocket is neither parallel to nor collinear with a said staple pocket centerline of a second staple pocket;
      a first forming cup, comprising:
        a first inside portion;
        a first outside portion; and
        a first interior sidewall extending between said first outside portion and said first inside portion, wherein said first interior sidewall comprises a first vertical portion which is substantially perpendicular to said tissue contacting surface; and a second forming cup, comprising:
  a second inside portion;
  a second outside portion, wherein said first inside portion is positioned in close relation to said second inside portion, wherein said first inside portion and said second inside portion are positioned offset with respect to said staple pocket centerline, wherein said first outside portion and said second outside portion are positioned on opposite sides of said first inside portion and said second inside portion, and wherein said first outside portion and said second outside portion are oriented in a direction which is transverse to said staple pocket centerline; and
  a second interior sidewall extending between said second outside portion and said second inside portion, wherein said second interior sidewall comprises a second vertical portion which is substantially perpendicular to said tissue contacting surface.

2. The surgical stapler of claim 1, wherein said first vertical portion of said first interior sidewall is perpendicular to said tissue contacting surface, and wherein said second vertical portion of said second interior sidewall is perpendicular to said tissue contacting surface.

3. The surgical stapler of claim 2, wherein said first interior sidewall further comprises a first angled portion which is oriented at an acute angle relative to said tissue contacting surface, wherein said first angled portion is positioned outwardly with respect to said first vertical portion, wherein said second interior sidewall further comprises a second angled portion which is oriented at an acute angle relative to said tissue contacting surface, and wherein said second angled portion is positioned outwardly with respect to said second vertical portion.

4. The surgical stapler of claim 1, wherein said first vertical portion transects said staple pocket centerline, and wherein said second vertical portion transects said staple pocket centerline.

5. The surgical stapler of claim 1, wherein said first inside portion and said second inside portion are divided by a wall, wherein said wall is defined by said first interior sidewall and said second interior sidewall.

6. The surgical stapler of claim 1, wherein said first inside portion is defined by a first width and said first outside portion is defined by a second width, and wherein said second width is wider than said first width.

7. The surgical stapler of claim 1, wherein said first forming cup further comprises a first exterior sidewall, wherein said second forming cup further comprises a second exterior sidewall, wherein said first interior sidewall and said first exterior sidewall are oriented at an acute angle with one another, and wherein said second interior sidewall and said second exterior sidewall are oriented at an acute angle with one another.

8. The surgical stapler of claim 7, wherein said first forming cup comprises a first elongated base, wherein said first elongated base is curved concavely along said staple pocket centerline, wherein said second forming cup comprises a second elongated base, and wherein said second elongated base is curved concavely along said staple pocket centerline.

9. The surgical stapler of claim 8, wherein said first elongated base is defined by a radius of curvature (r), and wherein said first vertical portion is defined by a length between approximately 0.5*r and approximately 2.0*r.

10. The surgical stapler of claim 1, wherein said first interior sidewall is parallel to said second interior sidewall.

11. A surgical stapler, comprising:
a curved anvil assembly, comprising:
  a tissue contacting surface;
  a plurality of staple pockets formed in said tissue contacting surface, wherein said staple pockets are positioned along a curved path, wherein each said staple pocket comprises:
    a staple pocket midline, wherein a said staple pocket midline of a first staple pocket is neither parallel to nor collinear with a said staple pocket midline of a second staple pocket;
    a first forming cup, comprising:
      a first inside portion;
      a first outside portion; and
      a first interior sidewall extending between said first outside portion and said first inside portion, wherein said first interior sidewall comprises a first vertical portion which is substantially perpendicular to said tissue contacting surface; and
    a second forming cup, comprising:
      a second inside portion;
      a second outside portion, wherein said first inside portion is positioned in close relation to said second inside portion, wherein said first inside portion and said second inside portion are positioned offset with respect to said staple pocket midline, and wherein said first outside portion and said second outside portion are positioned on opposite sides of said first inside portion and said second inside portion; and
      a second interior sidewall extending between said second outside portion and said second inside portion, wherein said second interior sidewall comprises a second vertical portion which is substantially perpendicular to said tissue contacting surface, wherein said first vertical portion and said second vertical portion extend through said staple pocket midline, and wherein said first interior surface and said second interior surface comprise a trap for deforming a first staple leg of a staple to a first side of said staple pocket midline and for deforming a second staple leg of the staple to a second side of said staple pocket midline.

12. The surgical stapler of claim 11, wherein said first vertical portion of said first interior sidewall is perpendicular to said tissue contacting surface, and wherein said second vertical portion of said second interior sidewall is perpendicular to said tissue contacting surface.

13. The surgical stapler of claim 12, wherein said first interior sidewall further comprises a first angled portion which is oriented at an acute angle relative to said tissue contacting surface, wherein said first angled portion is positioned outwardly with respect to said first vertical portion, wherein said second interior sidewall further comprises a second angled portion which is oriented at an acute angle relative to said tissue contacting surface, and wherein said second angled portion is positioned outwardly with respect to said second vertical portion.

14. The surgical stapler of claim 11, wherein said first inside portion and said second inside portion are divided by a wall, wherein said wall is defined by said first interior sidewall and said second interior sidewall.

15. The surgical stapler of claim 11, wherein said first inside portion is defined by a first width and said first outside portion is defined by a second width, and wherein said second width is wider than said first width.

16. The surgical stapler of claim 11, wherein said first forming cup further comprises a first exterior sidewall, wherein said second forming cup further comprises a second exterior sidewall, wherein said first interior sidewall and said first exterior sidewall are oriented at an acute angle with one another, and wherein said second interior sidewall and said second exterior sidewall are oriented at an acute angle with one another.

17. The surgical stapler of claim 16, wherein said first forming cup comprises a first elongated base, wherein said first elongated base is curved concavely along said staple pocket midline, wherein said second forming cup comprises a second elongated base, and wherein said second elongated base is curved concavely along said staple pocket midline.

18. The surgical stapler of claim 17, wherein said first elongated base is defined by a radius of curvature (r), and wherein said first vertical portion is defined by a length between approximately 0.5*r and approximately 2.0*r.

19. The surgical stapler of claim 11, wherein said first interior sidewall is parallel to said second interior sidewall.

20. The surgical stapler of claim 11, further comprising a staple at least partially coated by at least one of polytetrafluoroethylene and silicon.

21. The surgical stapler of claim 11, further comprising at least one piece of compressible material attached to said tissue contacting surface.

\* \* \* \* \*